United States Patent
Lynch et al.

(10) Patent No.: US 11,268,111 B2
(45) Date of Patent: *Mar. 8, 2022

(54) COMPOSITIONS AND METHODS FOR ROBUST DYNAMIC METABOLIC CONTROL OF A BIOFERMENTATION PROCESS

(71) Applicant: DUKE UNIVERSITY, Durham, NC (US)

(72) Inventors: Michael David Lynch, Durham, NC (US); Zhixia Ye, Raleigh, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/487,542

(22) PCT Filed: Feb. 21, 2018

(86) PCT No.: PCT/US2018/019040
§ 371 (c)(1),
(2) Date: Aug. 21, 2019

(87) PCT Pub. No.: WO2018/156646
PCT Pub. Date: Aug. 30, 2018

(65) Prior Publication Data
US 2020/0056211 A1 Feb. 20, 2020

Related U.S. Application Data

(60) Provisional application No. 62/461,436, filed on Feb. 21, 2017.

(51) Int. Cl.
| | | |
|---|---|---|
| C12P 7/42 | (2006.01) | |
| C12N 9/04 | (2006.01) | |
| C12N 9/02 | (2006.01) | |
| C12N 9/06 | (2006.01) | |
| C12N 9/10 | (2006.01) | |
| C12N 15/74 | (2006.01) | |
| C12P 13/06 | (2006.01) | |

(52) U.S. Cl.
CPC .............. *C12P 7/42* (2013.01); *C12N 9/001* (2013.01); *C12N 9/0006* (2013.01); *C12N 9/0008* (2013.01); *C12N 9/0016* (2013.01); *C12N 9/0051* (2013.01); *C12N 9/1025* (2013.01); *C12N 15/746* (2013.01); *C12P 13/06* (2013.01)

(58) Field of Classification Search
None
See application file for complete search history.

(56) References Cited

U.S. PATENT DOCUMENTS

| | | | |
|---|---|---|---|
| 8,916,358 B2 | 12/2014 | Swartz | |
| 10,036,001 B2 | 7/2018 | Swartz | |
| 10,662,426 B2* | 5/2020 | Lynch | ................ C12N 15/63 |
| 2011/0125118 A1 | 5/2011 | Lynch | |
| 2011/0244575 A1 | 10/2011 | Lipscomb | |
| 2012/0214170 A1 | 8/2012 | Moore | |
| 2015/0072399 A1 | 3/2015 | Lynch et al. | |

FOREIGN PATENT DOCUMENTS

| | | |
|---|---|---|
| EP | 2842542 A1 | 3/2015 |
| WO | 2012129450 A1 | 9/2012 |
| WO | 2013176772 A1 | 11/2013 |
| WO | 2014160025 A1 | 10/2014 |
| WO | 2015191638 A1 | 12/2015 |
| WO | 2018156646 A1 | 8/2018 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Kizer et al. Appl Environ Microbiol. May 2008;74(10):3229-41. (Year: 2008).*
Prather et al. CurrOpin Biotechnol. Oct. 2008;19(5):468-74. (Year: 2008).*
Rath et al. Nucleic Acids Res. Jan. 9, 2015; 43(1): 237-246. (Year: 2015).*
Lynch. Into new territory: improved microbial synthesis through engineering of the essential metabolic network. Curr Opin Biotechnol. Apr. 2016;38:106-11. Epub Feb. 10, 2016. (Year: 2016).*
Lee et al. Appl Microbiol Biotechnol. Jul. 2004;65(1):56-60. (Year: 2004).*
Kim et al. Microbiologyopen. Aug. 2015; 4(4): 632-643. (Year: 2015).*
Wang et al. J Ind Microbiol Biotechnol. Dec. 2013;40(12):1449-60. (Year: 2013).*
Vick et al. Appl Environ Microbiol. Feb. 2015; 81(4): 1406-1416. (Year: 2015).*
Jan et al. Biotechnol Prog. Sep.-Oct. 2013;29(5):1124-30. (Year: 2013).*
Luo et al. Nucleic Acids Res. Jan. 9, 2015; 43(1): 674-681. (Year: 2015).*
Yuki Soma et al: "Metabolic flux redirection from a central metabolic pathway toward a synthetic pathway using a metabolic toggle switch", Metabolic Engineering, vol. 23, May 1, 2014, pp. 175-184.
Kathleen E. McGinness et al: "Engineering Controllable Protein Degradation", Molecular Cell., vol. 22, No. 5, Jun. 1, 2006, pp. 701-707.
Levchenko Igor et al:" A specificity-enhancing factor for the ClpXP degradation machine", Science, vol. 289, No. 5488, Sep. 29, 2000, pp. 2354-2356.

(Continued)

*Primary Examiner* — Christian L Fronda
(74) *Attorney, Agent, or Firm* — Benesch, Friedlander, Coplan & Aronoff LLP

(57) ABSTRACT

The present disclosure provides compositions and methods for rapid production of chemicals in genetically engineered microorganisms in a large scale. Also provided herein is a high-throughput metabolic engineering platform enabling the rapid optimization of microbial production strains. The platform, which bridges a gap between current in vivo and in vitro bio-production approaches, relies on dynamic minimization of the active metabolic network.

16 Claims, 117 Drawing Sheets

Specification includes a Sequence Listing.

(56) References Cited

OTHER PUBLICATIONS

Lynch et al., "Standarized two-stage bioprocess development using synthetic metabolic valves and dynamic metabolic control". Abstracts of Papers ; ACS National Meeting & Exposition; 249th National Meeting and Exposition of the American-Chemical-Society (ACS), vol. 249, p. BIOT418.
Brockman et al., "Dynamic knockdown of *E. coli* central metabolism for redirecting fluxes of primary metabolites", Metabolic Engineering, vol. 28., pp. 104-113.
Kim et al., "A genetic strategy to identify targets for the development of drugs that prevent bacterial persistence", Proc. Natl. Acad. Sci USA (2013); vol. 110, pp. 19095-19100.
Qi et al., "Repurposing CRISPR as an RNA-guided platform for sequence-specific control of gene expression," Cell (2013); vol. 152, pp. 1173-1183.

* cited by examiner

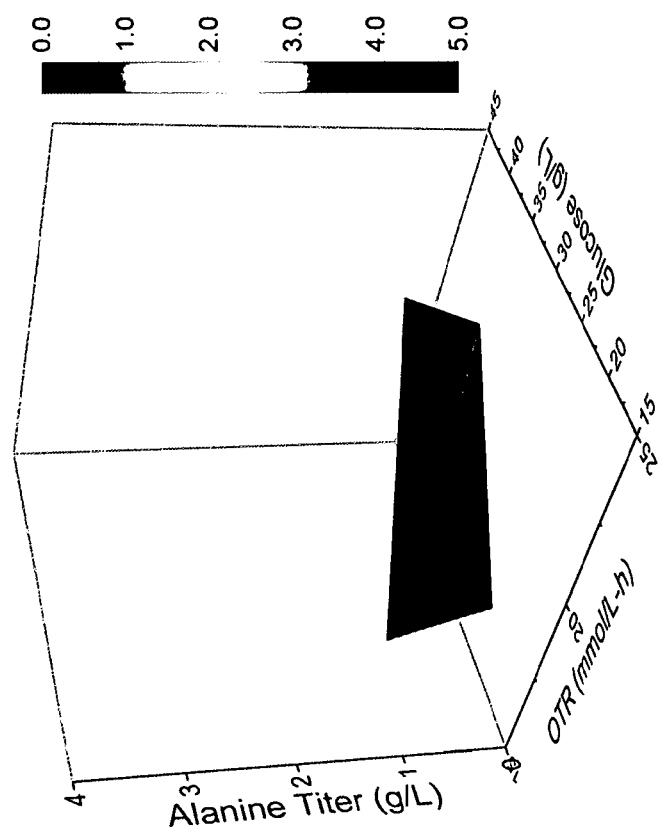

COMPOSITIONS AND METHODS FOR ROBUST DYNAMIC METABOLIC CONTROL OF A BIOFERMENTATION PROCESS

CROSS-REFERENCE

This application is a continuation of U.S. application Ser. No. 16/487,542, filed Aug. 21, 2019, which is a National Stage Entry of PCT/US 18/19040. filed Feb. 21, 2018 which claims the benefit of U.S. Provisional Application No. 62/461,436, filed Feb. 21, 2017, which application is incorporated herein by reference in its entirety.

STATEMENT AS TO FEDERALLY SPONSORED RESEARCH

This invention was made with Government support under Federal Grant Nos. HR0011-14-C-0075 awarded by DOD/DARPA, 12043956 and N00014-16-1-2558 awarded by NAVY/ONR, and 1445726 awarded by NSF. The Government has certain rights to this invention.

REFERENCE TO A SEQUENCE LISTING

The instant application contains a Sequence Listing which has been filed electronically in ASCII format and is hereby incorporated by reference in its entirety. Said ASCII copy, created on Feb. 21, 2018, is named 52240_702_601_SL.txt and is 81,697 bytes in size.

BACKGROUND OF THE INVENTION

Biotechnology-based fermentation processes have been successfully developed to produce everything from biologics and small molecule therapies to specialty, bulk and commodity chemicals, and even next generation biofuels. These processes have made rapid advancements in recent years due to technology developments in the fields of fermentation science and synthetic biology, as well as metabolic and enzyme engineering. Despite these substantial advances, most successful examples of rational and directed engineering approaches have also greatly relied on numerous and often lengthy cycles of trial and error. The present disclosure provides a strategy that simultaneously reduces the complexity of the problem (as well as the size of the relevant design space), while also minimizing metabolic responses to environmental conditions, increasing robustness and scalability of engineered strains.

SUMMARY OF THE INVENTION

The present disclosure provides, in part, a high-throughput engineering platform that enables the rapid development of microbial production strains.

In one aspect, the present disclosure provides a cell for generating a product, wherein the cell comprises: a heterologous polynucleotide for controlled reduction of expression of an enzyme of a metabolic pathway, wherein the controlled reduction of expression of the enzyme induces a stationary phase of the cell; and a heterologous production polynucleotide for mediating controlled increase in expression of a production enzyme for generation of the product; wherein a rate of production of the product during the stationary phase is reduced less in response to a change of an environmental condition as compared to a cell lacking the enzyme.

In some embodiments, the heterologous polynucleotide reduces flux through the metabolic pathway. In some embodiments, the enzyme is selected from the group consisting of enoyl-ACP/CoA reductase, glucose-6-phosphate dehydrogenase, lipoamide dehydrogenase, citrate synthase, soluble transhydrogenase, and NADH-dependent glyceraldehyde-3-phosphate dehydrogenase. In some embodiments, the production enzyme is selected from the group consisting of NADPH-dependent alanine dehydrogenase, an alanine exporter, and NADPH-dependent glyceraldehyde-3-phosphate dehydrogenase. In some embodiments, the change of an environmental condition comprises increasing or decreasing a concentration of a sugar in a culture medium contacting the cell. In some embodiments, the sugar is glucose. In some embodiments, the change of an environmental condition comprises increasing or decreasing oxygenation of a culture medium contacting the cell. In some embodiments, the product comprises 3-hydroxypropionic acid.

In some embodiments, the product comprises an amino acid. In some aspects, the amino acid comprises alanine. In some aspects, the cell is grown in a culture, and a rate of production of the alanine by the culture is at least 0.5 g/L/hour. In some aspects, the rate of production of the alanine is at least 1.0 g/L/hour. In some aspects, the rate of production of the alanine is at least 1.5 g/L/hour. In some aspects, the rate of production of the alanine is at least 1.6 g/L/hour. In some aspects, the culture produces at least 80 g/L of the alanine. In some aspects, the culture produces at least 100 g/L of the alanine. In some aspects, the culture produces at least 120 g/L of the alanine. In some aspects, the culture produces at least 140 g/L of the alanine. In some aspects, the production polynucleotide encodes an alanine exporter. In some aspects, the alanine exporter is alaE.

In some embodiments, the product comprises mevalonic acid. In some embodiments, the cell is grown in a culture, and a rate of production of the mevalonic acid by the culture is at least 0.5 g/L/hour. In some embodiments, the rate of production of the mevalonic acid is at least 1.0 g/L/hour. In some embodiments, the rate of production of the mevalonic acid is at least 1.2 g/L/hour. In some embodiments, the rate of production of the mevalonic acid is at least 1.25 g/L/hour. In some aspects, the cell is grown in a culture, and the culture produces at least 50 g/L of the mevalonic acid. In some embodiments, the culture produces at least 70 g/L of the mevalonic acid. In some embodiments, the culture produces at least 90 g/L of the mevalonic acid. In some embodiments, the culture produces at least 95 g/L of the mevalonic acid. In some embodiments, the heterologous polynucleotide is selected from the group consisting of: a silencing polynucleotide for repressing transcription of a gene encoding the enzyme; and a degradation polynucleotide for mediating cellular degradation of the enzyme.

In some aspects, the heterologous polynucleotide comprises a silencing polynucleotide, and the silencing polynucleotide comprises a guide RNA (gRNA) comprising a gRNA sequence that recognizes a promoter of a gene encoding the enzyme. In some aspects, the heterologous polynucleotide encodes a CRISPR enzyme, and the CRISPR enzyme specifically binds to the promoter sequence when bound to the gRNA. In some aspects, the CRISPR enzyme is catalytically inactive. In some aspects, the heterologous polynucleotide comprises a degradation polynucleotide, wherein the degradation polynucleotide comprises a sequence encoding a degradation tag, wherein the degradation tag mediates degradation of the enzyme. In some embodiments, expression of the heterologous polynucleotide is regulated by phosphate availability in the cell. In some embodiments, expression of the production polynucleotide is regulated by phosphate availability in the cell. In some embodiments, the cell is an *E. coli* cell.

In another aspect, disclosed herein is a method comprising: culturing independently a plurality of strains of a cell, wherein each strain comprises (i) a heterologous polynucleotide for mediating controlled reduction of expression of an enzyme of a metabolic pathway, wherein the controlled reduction of expression of the enzyme induces a stationary phase of the cell; and (ii) a heterologous production polynucleotide for mediating controlled increase in expression of a production enzyme for generation of the product; wherein each strain of the plurality of strains differs from another strain in a sequence of at least one of the heterologous polynucleotide or the heterologous production polynucleotide; growing the plurality of strains to stationary phase; and selecting a strain of the plurality of strains based on a level of the product produced by the selected strain during the stationary phase.

In some embodiments, the method comprises determining the level of the product. In some embodiments, the method comprises growing the selected strain. In some embodiments, the selected strain is grown in a bioreactor. In some embodiments, a culture medium comprising the selected strain has a volume of at least 500 ml. In some embodiments, the culture medium has a volume of at least 1 L. In some embodiments, the heterologous polynucleotide is selected from the group consisting of: a silencing polynucleotide for repressing transcription of a gene encoding the enzyme; and a degradation polynucleotide for mediating cellular degradation of the enzyme. In some embodiments, a first and second strain of the plurality of strains comprises a silencing polynucleotide. In some embodiments, the silencing polynucleotide comprises a guide RNA (gRNA) comprising a gRNA sequence that recognizes a promoter sequence of a gene encoding the enzyme. In some embodiments, the gRNA sequence differs between the first and second strains. In some embodiments, the first and second strain of the plurality of strains comprise a degradation polynucleotide. In some embodiments, the degradation polynucleotide differs between the first and second strains. In some embodiments, the enzyme is selected from the group consisting of enoyl-ACP/CoA reductase, glucose-6-phosphate dehydrogenase, lipoamide dehydrogenase, citrate synthase, soluble transhydrogenase, and NADH-dependent glyceraldehyde-3-phosphate dehydrogenase. In some embodiments, the production enzyme is selected from the group consisting of NADPH-dependent alanine dehydrogenase, an alanine exporter, and NADPH-dependent glyceraldehyde-3-phosphate dehydrogenase. In some embodiments, the product is selected from the group consisting of mevalonic acid, 3-hydroxypropionic acid, and an amino acid.

In some embodiments, the product is an amino acid and the amino acid is alanine. In some embodiments, the cell of the selected strain a rate of production of the product during the stationary phase is reduced less in response to a change of an environmental condition as compared to a cell lacking the heterologous polynucleotide. In some embodiments, the change of an environmental condition comprises a change in concentration of a sugar of a culture medium contacting the cell. In some embodiments, the change of an environmental condition comprises a change in oxygenation of a culture medium contacting the cell.

In another aspect, disclosed herein is a method of generating a cellular product comprising: culturing a heterologous cell in a culture medium, wherein the heterologous cell comprises: (i) a heterologous polynucleotide for mediating controlled reduction of expression of an enzyme of a metabolic pathway, wherein the controlled reduction of expression of the enzyme induces a stationary phase of the cell; and (ii) a heterologous production polynucleotide for mediating controlled increase in expression of a production enzyme for generation of the product; wherein a rate of production of the product during the stationary phase is reduced less in response to a change of an environmental condition as compared to a cell lacking the enzyme.

In one embodiment, the method further comprises changing the environmental condition. In one embodiment, the environmental condition comprises a concentration of a sugar of the culture medium, and changing the environmental condition comprises increasing or decreasing the concentration. In some embodiments, the sugar is glucose. In some embodiments, the environmental condition comprises an oxygen concentration of the culture medium, and changing the environmental condition comprises increasing or decreasing the oxygen concentration. In some embodiments, the culturing is performed in a bioreactor. In some embodiments, the culture medium has a volume of at least 500 ml. In some embodiments, the culture medium has a volume of at least 1 L. In some embodiments, the product comprises 3-hydroxypropionic acid. In some embodiments, the product comprises an amino acid. In some embodiments, the amino acid comprises alanine. In some embodiments, the rate of production of the alanine is at least 0.5 g/L/hour. In some embodiments, the rate of production of the alanine is at least 1.0 g/L/hour. In some embodiments, the rate of production of the alanine is at least 1.5 g/L/hour. In some embodiments, the rate of production of the alanine is at least 1.6 g/L/hour. In some embodiments, the production polynucleotide encodes an alanine exporter. In some embodiments, the alanine exporter is alaE.

In some embodiments, the product comprises mevalonic acid. In some embodiments, the rate of production of the mevalonic acid is at least 0.5 g/L/hour. In some embodiments, the rate of production of the mevalonic acid is at least 1.0 g/L/hour. In some embodiments, the rate of production of the mevalonic acid is at least 1.2 g/L/hour. In some embodiments, the rate of production of the mevalonic acid is at least 1.25 g/L/hour. In some embodiments, the heterologous polynucleotide is selected from the group consisting of: a silencing polynucleotide for repressing transcription of a gene encoding the enzyme; and a degradation polynucleotide for mediating cellular degradation of the enzyme. In some embodiments, the heterologous polynucleotide comprises a silencing polynucleotide, and the silencing polynucleotide comprises a guide RNA (gRNA) comprising a gRNA sequence that recognizes a promoter sequence of a gene encoding the enzyme. In some embodiments, the heterologous polynucleotide encodes a CRISPR enzyme, wherein the CRISPR enzyme specifically binds to the promoter sequence when bound to the gRNA. In some embodiments, the CRISPR enzyme is catalytically inactive. In some embodiments, the heterologous polynucleotide comprises a degradation polynucleotide, wherein the degradation polynucleotide comprises a sequence encoding a degradation tag, wherein the degradation tag mediates degradation of the enzyme. In some embodiments, the expression of the heterologous polynucleotide is regulated by phosphate availability in the cell. In some embodiments, the expression of the production polynucleotide is regulated by phosphate availability in the cell. In some embodiments, the cell is an *E. coli* cell.

In another aspect, disclosed herein is a cell for production of alanine, wherein the cell comprises: (i) a heterologous polynucleotide for controlled reduction of expression of an enzyme of a metabolic pathway, wherein the enzyme is selected from the group consisting of enoyl-ACP/CoA reductase, glucose-6-phosphate dehydrogenase, lipoamide dehydrogenase (lpd), citrate synthase (gltA), soluble transhydrogenase, and NADH-dependent glyceraldehyde-3-phosphate dehydrogenase; and (ii) an alanine exporter, wherein the alanine exporter is expressed at increased levels as compared to a wildtype cell.

In some embodiments, the alanine exporter is encoded by an alaE gene. In some embodiments, the controlled reduction of expression of the enzyme induces a stationary phase of the cell. In some embodiments, the cell further comprises a heterologous production polynucleotide for controlled increase in expression of a production enzyme for generation of the alanine. In some embodiments, the production enzyme is selected from the group consisting of NADPH-dependent alanine dehydrogenase and NADPH-dependent glyceraldehyde-3-phosphate dehydrogenase. In some embodiments, the heterologous polynucleotide is selected from the group consisting of: a silencing polynucleotide for mediating transcriptional repression of a gene encoding the enzyme; and a degradation polynucleotide for mediating cellular degradation of the enzyme. In some embodiments, the heterologous polynucleotide comprises a silencing polynucleotide, and the silencing polynucleotide comprises a guide RNA (gRNA) comprising a gRNA sequence that recognizes a promoter sequence of a gene encoding the enzyme. In some embodiments, the polynucleotide further encodes a CRISPR enzyme, wherein the CRISPR enzyme specifically binds to the promoter sequence when bound to the gRNA. In some embodiments, the CRISPR enzyme is catalytically inactive. In some embodiments, the heterologous polynucleotide comprises a degradation polynucleotide, wherein the degradation polynucleotide comprises a sequence encoding a degradation tag, wherein the degradation tag mediates degradation of the enzyme. In some embodiments, the polynucleotide is regulated by phosphate availability in the cell. In some embodiments, the production polynucleotide is regulated by phosphate availability in the cell. In some embodiments, the cell is an *E. coli* cell.

In some embodiments, a culture comprises the cell. In some embodiments, a rate of production of the alanine by the culture is at least 0.5 g/L/hour. In some embodiments, a rate of production of the alanine by the culture is at least 1.0 g/L/hour. In some embodiments, a rate of production of the alanine by the culture is at least 1.5 g/L/hour. In some embodiments, a rate of production of the alanine by the culture is at least 1.6 g/L/hour. In some embodiments, the culture produces at least 100 g/L of the alanine. In some embodiments, the culture produces at least 120 g/L of the alanine. In some embodiments, the culture produces at least 140 g/L of the alanine.

In some aspects, disclosed herein is a method of production of alanine comprising growing in a culture medium a cell comprising (i) a heterologous polynucleotide for controlled reduction of expression of a enzyme of a metabolic pathway, wherein the enzyme is selected from the group consisting of enoyl-ACP/CoA reductase, glucose-6-phosphate dehydrogenase, lipoamide dehydrogenase, citrate synthase, soluble transhydrogenase, and NADH-dependent glyceraldehyde-3-phosphate dehydrogenase; and (ii) an alanine exporter, wherein the alanine exporter is expressed at increased levels as compared to a wildtype cell.

In some embodiments, the controlled reduction of expression of the enzyme induces a stationary phase of the cell. In some embodiments, the method further comprises decreasing an oxygenation level or a sugar concentration of the culture medium during the stationary phase, wherein a rate of production of the cellular product is reduced less in response to the decreasing as compared to a cell lacking the heterologous polynucleotide. In some embodiments, the sugar is glucose. In some embodiments, the alanine exporter is encoded by an alaE gene. In some embodiments, the cell further comprises a heterologous production polynucleotide for controlled increase in expression of a production enzyme for generation of the alanine. In some embodiments, the production enzyme is selected from the group consisting of: NADPH-dependent alanine dehydrogenase and NADPH-dependent glyceraldehyde-3-phosphate dehydrogenase. In some embodiments, the heterologous polynucleotide is selected from the group consisting of: a silencing polynucleotide for mediating transcriptional repression of a gene encoding the enzyme; and a degradation polynucleotide for mediating cellular degradation of the enzyme. In some embodiments, the heterologous polynucleotide comprises a silencing polynucleotide, and the silencing polynucleotide comprises a guide RNA (gRNA) comprising a gRNA sequence that recognizes a promoter sequence of a gene encoding the enzyme. In some embodiments, the heterologous polynucleotide encodes a CRISPR enzyme, wherein the CRISPR enzyme specifically binds to the promoter sequence when bound to the gRNA. In some embodiments, the CRISPR enzyme is catalytically inactive. In some embodiments, the heterologous polynucleotide comprises a degradation polynucleotide, wherein the degradation polynucleotide comprises a sequence encoding a degradation tag, wherein the degradation tag mediates degradation of the enzyme.

In some embodiments, the expression of the heterologous polynucleotide is regulated by phosphate availability in the cell. In some embodiments, the production polynucleotide is regulated by phosphate availability in the cell. In some embodiments, the cell is an *E. coli* cell. In some embodiments, a rate of production of the alanine is at least 0.5 g/L/hour. In some embodiments, a rate of production of the alanine is at least 1.0 g/L/hour. In some embodiments, a rate of production of the alanine is at least 1.5 g/L/hour. In some embodiments, a rate of production of the alanine is at least 1.6 g/L/hour.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 27A-D depict alanine production in response to different OTR and glucose concentration in micro-fermentation for 4 strains evaluated for robustness.

DETAILED DESCRIPTION OF THE INVENTION

Definitions

Figure 1A:
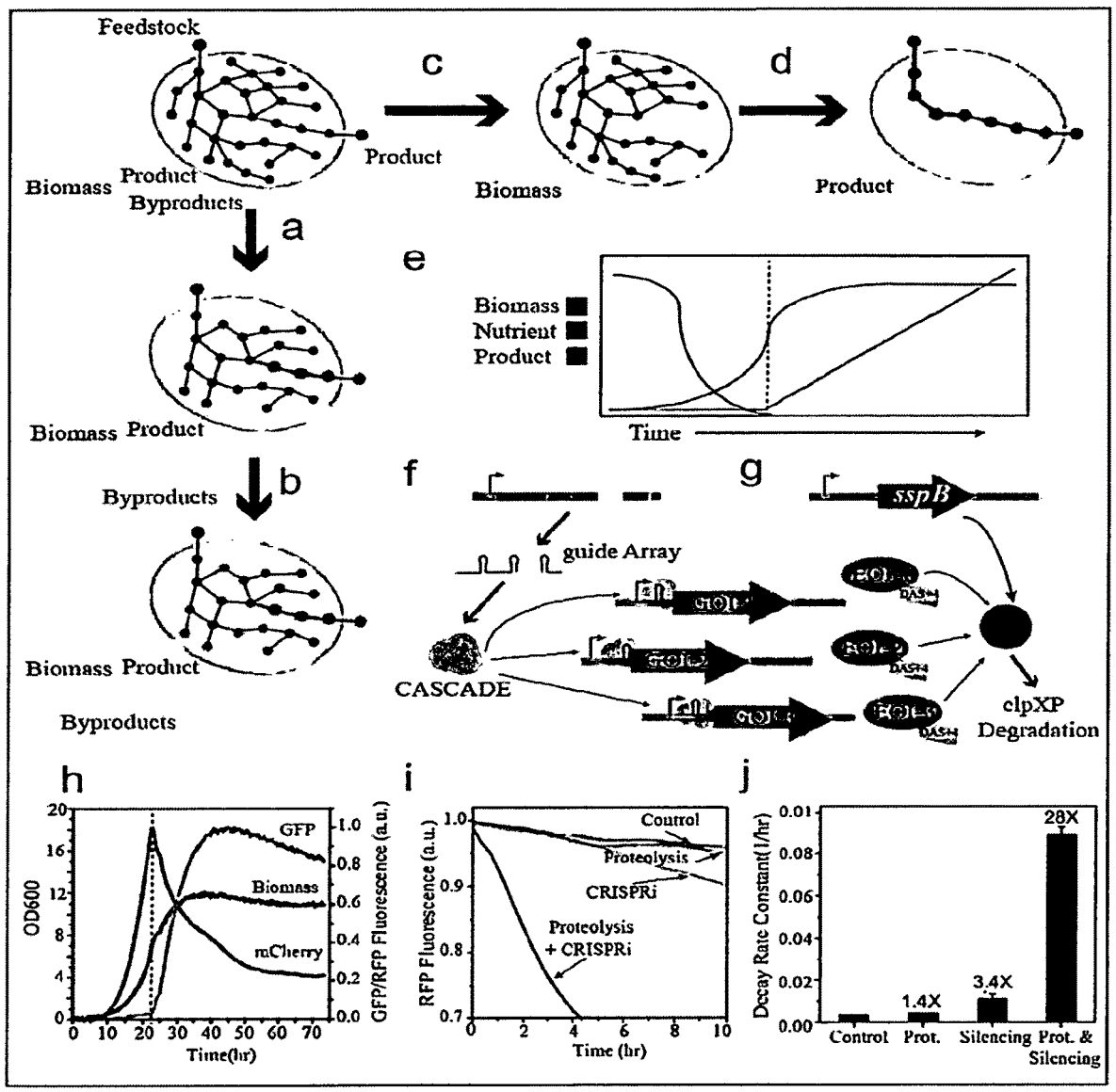
FIG. 1A depicts an overview of dynamic metabolic control in 2-stage fermentations.

As used in the specification and the claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "microorganism" includes a single microorganism as well as a plurality of microorganisms; and the like.

As used herein, "reduced enzymatic activity," "reducing enzymatic activity," and the like is meant to indicate that a microorganism cell's, or an isolated enzyme, exhibits a lower level of activity than that measured in a comparable cell of the same species or its native enzyme. That is, enzymatic conversion of the indicated substrate(s) to indicated product(s) under known standard conditions for that enzyme is at least 10, at least 20, at least 30, at least 40, at least 50, at least 60, at least 70, at least 80, or at least 90 percent less than the enzymatic activity for the same biochemical conversion by a native (non-modified) enzyme under a standard specified condition. This term also can include elimination of that enzymatic activity. A cell having reduced enzymatic activity of an enzyme can be identified using any method known in the art. For example, enzyme activity assays can be used to identify cells having reduced enzyme activity. See, for example, *Enzyme Nomenclature*, Academic Press, Inc., New York 2007.

The term "heterologous DNA," "heterologous nucleic acid sequence," and the like as used herein refers to a nucleic acid sequence wherein at least one of the following is true: (a) the sequence of nucleic acids foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid, such as a nonnative promoter driving gene expression.

The term "synthetic metabolic valve," and the like as used herein refers to either the use of controlled proteolysis, gene silencing or the combination of both proteolysis and gene silencing to alter metabolic fluxes.

The term "heterologous" is intended to include the term "exogenous" as the latter term is generally used in the art. With reference to the host microorganism's genome prior to the introduction of a heterologous nucleic acid sequence, the nucleic acid sequence that codes for the enzyme is heterologous (whether or not the heterologous nucleic acid sequence is introduced into that genome).

As used herein, the term "gene disruption," or grammatical equivalents thereof (and including "to disrupt enzymatic function," "disruption of enzymatic function," and the like), is intended to mean a genetic modification to a microorganism that renders the encoded gene product as having a reduced polypeptide activity compared with polypeptide activity in or from a microorganism cell not so modified. The genetic modification can be, for example, deletion of the entire gene, deletion or other modification of a regulatory sequence required for transcription or translation, deletion of a portion of the gene which results in a truncated gene product (e.g., enzyme) or by any of various mutation strategies that reduces activity (including reducing activities to no detectable activity level) the encoded gene product. A disruption may broadly include a deletion of all or part of the nucleic acid sequence encoding the enzyme, and also includes, but is not limited to other types of genetic modifications, e.g., introduction of stop codons, frame shift mutations, introduction or removal of portions of the gene, and introduction of a degradation signal, those genetic modifications affecting mRNA transcription levels and/or stability, and altering the promoter or repressor upstream of the gene encoding the enzyme.

Bio-production or fermentation, as used herein, may be aerobic, microaerobic, or anaerobic.

When the genetic modification of a gene product, e.g., an enzyme, is referred to herein, including the claims, it is understood that the genetic modification is of a nucleic acid sequence, such as or including the gene, that normally encodes the stated gene product, e.g., the enzyme.

As used herein, the term "metabolic flux" and the like refers to changes in metabolism that lead to changes in product and/or byproduct formation, including production rates, production titers and production yields from a given substrate.

Species and other phylogenic identifications are according to the classification known to a person skilled in the art of microbiology.

Enzymes are listed here within, with reference to a Universal Protein Resource (Uniprot) identification number, which would be well known to one skilled in the art (Uniprot is maintained by and available through the UniProt Consortium).

Where methods and steps described herein indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

The meaning of abbreviations is as follows: "C" means Celsius or degrees Celsius, as is clear from its usage, DCW means dry cell weight, "s" means second(s), "min" means minute(s), "h," "hr," or "hrs" means hour(s), "psi" means pounds per square inch, "nm" means nanometers, "d" means day(s), "μL" or "uL" or "ul" means microliter(s), "mL" means milliliter(s), "L" means liter(s), "mm" means millimeter(s), "nm" means nanometers, "mM" means millimolar, "μM" or "uM" means micromolar, "M" means molar, "mmol" means millimole(s), "μmol" or "uMol" means micromole(s), "g" means gram(s), "μg" or "ug" means microgram(s) and "ng" means nanogram(s), "PCR" means polymerase chain reaction, "OD" means optical density, "$OD_{600}$" means the optical density measured at a photon wavelength of 600 nm, "kDa" means kilodaltons, "g" means the gravitation constant, "bp" means base pair(s), "kbp" means kilobase pair(s), "% w/v" means weight/volume percent, "% v/v" means volume/volume percent, "IPTG" means isopropyl-μ-D-thiogalactopyranoside, "aTc" means anhydrotetracycline, "RBS" means ribosome binding site, "rpm" means revolutions per minute, "HPLC" means high performance liquid chromatography, and "GC" means gas chromatography.

Overview

Provided herein is a high-throughput metabolic engineering platform enabling the rapid optimization of microbial production strains. The platform, which bridges a gap between current in vivo and in vitro bio-production approaches, relies on dynamic minimization of the active metabolic network. Dynamic metabolic network minimization can be accomplished using combinations of CRISPR interference and controlled proteolysis to reduce the activity of multiple enzymes in essential central metabolism. Minimization can be implemented in the context of standardized 2-stage bio-processes. This approach not only can result in a design space with greatly reduced complexity, but also in increased metabolic fluxes and production rates as well as in strains which are robust to environmental conditions. Robustness can lead to predictable scalability from high-throughput small-scale screens, or "micro-fermentations", to fully instrumented bioreactors. Predictive high-throughput approaches may be critical for metabolic engineering programs to truly take advantage of the rapidly increasing throughput and decreasing costs of synthetic biology. The examples provided herein have not only demonstrated proof of principle for this approach in the common industrial microbe: E. coli, and has validated this approach with the rapid optimization of E. coli strains producing two important industrial chemicals: alanine and mevalonic acid, at commercially meaningful rates, titers (147 g/L and 97 g/L, respectively), and yields.

Also provided herein are systems and methods to rapidly optimize a microorganism for chemical productions in a high-throughput fashion.

Also provided herein are microorganisms that can be used with the disclosed platform and/or methods for chemical productions.

Synthetic Metabolic Valves (SMVs)

The current disclosure describes the construction of synthetic metabolic valves (SMVs) comprising one or more or a combination of the following: controlled gene silencing and controlled proteolysis. It is appreciated that one well skilled in the art is aware of several methodologies for gene silencing and controlled proteolysis.

The development of platform microbial strains that utilize SMVs can decouple growth from product formation. These strains enable the dynamic control of metabolic pathways, including those that when altered have negative effects on microorganism growth. Dynamic control over metabolism is accomplished via a combination of methodologies including but not limited to transcriptional silencing and controlled enzyme proteolysis. These microbial strains are utilized in a multi-stage bioprocess encompassing as least two stages, the first stage in which microorganisms are grown and metabolism can be optimized for microbial growth and at least one other stage in which growth can be slowed or stopped, and dynamic changes can be made to metabolism to improve production of desired product, such as a chemical or fuel. The transition of growing cultures between stages and the manipulation of metabolic fluxes can be controlled by artificial chemical inducers or preferably by controlling the level of key limiting nutrients. In addition, genetic modifications may be made to provide metabolic pathways for the biosynthesis of one or more chemical or fuel products. Also, genetic modifications may be made to enable the utilization of a variety of carbon feedstocks including but not limited sugars such as glucose, sucrose, xylose, arabinose, mannose, and lactose, oils, carbon dioxide, carbon monoxide, methane, methanol and formaldehyde.

This approach allows for simpler models of metabolic fluxes and physiological demands during a production phase, turning a growing cell into a stationary phase biocatalyst. These synthetic metabolic valves can be used to turn off essential genes and redirect carbon, electrons and energy flux to product formation in a multi-stage fermentation process. One or more of the following enables these synthetic valves: 1) transcriptional gene silencing or repression technologies in combination with 2) inducible enzyme degradation and 3) nutrient limitation to induce a stationary or non-dividing cellular state. SMVs are generalizable to any pathway and microbial host. These synthetic metabolic valves allow for novel rapid metabolic engineering strategies useful for the production of renewable chemicals and fuels and any product that can be produced via whole cell catalysis.

In various cases, one SMV can refer to the manipulation of one gene (or its protein product). The manipulation can be controlled silencing of the gene and/or controlled degradation of its protein product. In certain cases, combination of SMVs can lead to improved production in yields, rate and/or robustness, which includes manipulation of two genes (or their protein products). In some cases, an engineered microorganism comprises at least one SMV. In some cases, an engineered microorganism comprises more than one SMV. In some cases, an engineered microorganism comprises two, three, four, five, six, seven, eight, nine, or ten, or more SMVs.

Method and Systems for Bio-Production

Provided herein are methods or systems for robust large scale production of molecules from biologics and small molecule therapeutics to specialty, bulk and commodity chemicals, and biofuels. The methods or systems provided herein comprise using engineered microorganism which comprises a limited set of metabolic enzymes. In some embodiments, the engineered microorganism comprises at least one metabolic enzyme that has reduced level or activity. In some embodiments, the engineered microorganism comprises two, three, four, five, six, seven, eight, nine, or ten, or more metabolic enzymes that have reduced level or activity. The methods and systems provided herein can reduce metabolic responses to environmental conditions and can be easily transferred from small scale (e.g. mgs) production to large scale (e.g. kgs) production. The methods and systems provided herein can reduce the time and costs associated with transitioning from small scale (e.g. mgs) to large scale (e.g. kgs) production.

Within the scope of the current disclosure are genetically modified microorganism, wherein the microorganism is capable of producing a product derived from any key metabolic intermediate including but not limited to malonyl-CoA, pyruvate, oxaloacetate, erthyrose-4-phosphate, xylulose-5-phosphate, alpha-ketoglutarate and citrate at a specific rate selected from the rates of greater than 0.05 g/gDCW-hr, 0.08 g/gDCW-hr, greater than 0.1 g/gDCW-hr, greater than 0.13 g/gDCW-hr, greater than 0.15 g/gDCW-hr, greater than 0.175 g/gDCW-hr, greater than 0.2 g/gDCW-hr, greater than 0.25 g/gDCW-hr, greater than 0.3 g/gDCW-hr, greater than 0.35 g/gDCW-hr, greater than 0.4 g/gDCW-hr, greater than 0.45 g/gDCW-hr, or greater than 0.5 g/gDCW-hr.

In various embodiments, the invention includes a culture system comprising a carbon source in an aqueous medium and a genetically modified microorganism, wherein said genetically modified organism is present in an amount selected from greater than 0.05 gDCW/L, 0.1 gDCW/L, greater than 1 gDCW/L, greater than 5 gDCW/L, greater than 10 gDCW/L, greater than 15 gDCW/L or greater than 20 gDCW/L, such as when the volume of the aqueous medium is selected from greater than 5 mL, greater than 100 mL, greater than 0.5 L, greater than 1 L, greater than 2 L, greater than 10 L, greater than 250 L, greater than 1000 L, greater than 10,000 L, greater than 50,000 L, greater than 100,000 L or greater than 200,000 L, and such as when the volume of the aqueous medium is greater than 250 L and contained within a steel vessel.

Carbon Sources

Bio-production media, which is used in the present invention with recombinant microorganisms must contain suitable carbon sources or substrates for both growth and production stages. Suitable substrates may include, but are not limited to glucose, sucrose, xylose, mannose, arabinose, oils, carbon dioxide, carbon monoxide, methane, methanol, formaldehyde and glycerol. It is contemplated that all of the above mentioned carbon substrates and mixtures thereof are suitable in the present invention as a carbon source(s).

Microorganisms

Features as described and claimed herein may be provided in a microorganism selected from the listing herein, or another suitable microorganism, that also comprises one or more natural, introduced, or enhanced product bio-production pathways. Thus, in some embodiments the microorganism(s) comprise an endogenous product production pathway (which may, in some such embodiments, be enhanced), whereas in other embodiments the microorganism does not comprise an endogenous product production pathway.

The examples describe specific modifications and evaluations to certain bacterial and fungal microorganisms. The scope of the invention is not meant to be limited to such species, but to be generally applicable to a wide range of suitable microorganisms.

Suitable host cells or host microorganisms for bio-production can be either prokaryotic or eukaryotic. Suitable host cells or host microorganisms can be bacteria such as *Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacil-*

*lus, Streptomyces*, and *Pseudomonas*. In some embodiments, a host cell or an engineered cell is *E. coli*. In some embodiments, a host cell or an engineered cell is *S. cerevisiae*.

In certain aspects, provided herein is a microorganism genetically modified to comprise: a production pathway comprising at least one enzyme for the biosynthesis of a product, and a combination of multiple synthetic metabolic valves to controllably reduce or eliminate flux through multiple metabolic pathways. In some embodiments, each of the multiple synthetic metabolic valves comprises one or more genes for (i) controlled silencing of gene expression of at least one gene or (ii) the controlled proteolytic inactivation of at least one protein. In some embodiments, a rate of the biosynthesis of the product is increased in a productive stationary phase upon a depletion of a nutrient, wherein the depletion of the nutrient induces the multiple synthetic metabolic valves. In some cases, the controlled silencing of gene expression is accomplished by RNA interference, CRISPR interference or transcriptional repression. In some cases, the controlled proteolytic inactivation is accomplished by protein cleavage by a specific protease or targeted degradation by specific peptide tags. In some cases, the nutrient is phosphate, nitrogen, sulfur, magnesium, or a combination thereof.

In certain aspects, provided herein is a genetically modified microorganism comprising: a production pathway comprising at least one enzyme for the biosynthesis of a product from one of the following metabolites: pyruvate, acetolactate, acetyl-CoA, acetoacetyl-CoA or malonyl-CoA; and a combination of multiple synthetic metabolic valves, wherein each of the multiple synthetic metabolic valves comprises one of a fabI, gltA, lpd, zwf or udhA gene for (i) controlled silencing of gene expression of a corresponding one of said fabI, gltA, lpd, zwf or udhA genes or (ii) controlled proteolytic inactivation of a protein encoded by a corresponding one of said fabI, gltA, lpd, zwf or udhA genes. In some embodiments, a rate of the biosynthesis of the product is increased in a productive stationary phase upon a depletion of a nutrient, wherein the depletion of the nutrient induces the multiple synthetic metabolic valves. In some embodiments, the product is alanine or a derivative thereof. In some embodiments, the product is mevalonate or a derivative thereof. In some embodiments, the product is malonic acid or a derivative thereof. In some embodiments, the nutrient is phosphate, nitrogen, sulfur, magnesium, or a combination thereof.

In certain aspects, provided herein is a genetically modified microorganism comprising: a production pathway to produce alanine from pyruvate; and a combination of multiple synthetic metabolic valves, wherein each of the multiple synthetic metabolic valves comprises one of a fabI, gltA, lpd, zwf or udhA gene for (i) controlled silencing of gene expression of a corresponding one of said fabI, gltA, lpd, zwf or udhA genes or (ii) controlled proteolytic inactivation of a protein encoded by one of said fabI, gltA, lpd, zwf or udhA genes. In some embodiments, a rate of the biosynthesis of alanine is increased in a productive stationary phase upon a depletion of a nutrient, wherein the depletion of the nutrient induces the multiple synthetic metabolic valves. In some embodiments, the nutrient is phosphate, nitrogen, sulfur, magnesium, or a combination thereof.

In some cases, a genetically modified microorganism is a heterologous cell. In some cases, provided herein is a heterologous cell for generating a product. In some cases, a heterologous cell comprises an engineered valve polynucleotide for mediating controlled reduction of expression of a valve enzyme acting in a metabolic pathway. In certain cases, a controlled reduction of expression of a valve enzyme reduces flux through a metabolic pathway, wherein the controlled reduction of expression of the valve enzyme induces a stationary phase of the heterologous cell. In some cases, a heterologous cell further comprises an engineered production polynucleotide for mediating controlled increase in expression of a production enzyme for generation of the product. In some situations, a heterologous cell comprises an engineered valve polynucleotide for mediating controlled reduction of expression of a valve enzyme acting in a metabolic pathway, wherein a rate of production of a product during a stationary phase is reduced less in response to a change of an environmental condition as compared to a cell lacking the controlled reduction of expression of the valve enzyme.

In some cases, provided herein is a heterologous cell for generating a product, wherein said cell comprises: an engineered valve polynucleotide for mediating controlled reduction of expression of a valve enzyme acting in a metabolic pathway, wherein said controlled reduction of expression of said valve enzyme reduces flux through said metabolic pathway, wherein said controlled reduction of expression of said valve enzyme induces a stationary phase of said cell; and an engineered production polynucleotide for mediating controlled increase in expression of a production enzyme for generation of said product; wherein a rate of production of said product during said stationary phase is reduced less in response to a change of an environmental condition as compared to a cell lacking said controlled reduction of expression of said valve enzyme.

In some cases, provided herein is a cell comprising a reduced expression or activity of a valve enzyme, wherein the valve enzyme comprises an enzyme selected from the group consisting of enoyl-ACP/CoA reductase (fabI), glucose-6-phosphate dehydrogenase (zwf), lipoamide dehydrogenase (lpd), citrate synthase (gltA), soluble transhydrogenase (udhA), NADH-dependent glyceraldehyde-3-phosphate dehydrogenase (gapA), and a combination thereof.

In some cases, provided herein is a cell comprising a production enzyme, wherein the production enzyme comprises an enzyme selected from the group consisting of NADPH-dependent alanine dehydrogenase (ald), alanine exporter (alaE), NADPH-dependent glyceraldehyde-3-phosphate dehydrogenase (gapN), and a combination thereof.

Environmental Conditions

Environmental conditions can comprise medium and culture conditions. Environmental factors that may influence production can be temperature, pH, acidity, ethanol, sulfite, and availability of nutrients.

In addition to an appropriate carbon source, such as selected from one of the herein disclosed types, bio-production media may contain suitable minerals, salts, cofactors, buffers and other components, known to those skilled in the art, suitable for the growth of the cultures and promotion of the enzymatic pathway necessary for chemical product bio-production under the present disclosure. Another aspect of the invention regards media and culture conditions that comprise genetically modified microorganisms of the invention and optionally supplements.

Typically cells are grown at a temperature in the range of about 25° C. to about 40° C. in an appropriate medium, as well as up to 70° C. for thermophilic microorganisms. Suitable growth media are well characterized and known in the art.

Suitable pH ranges for the bio-production are between pH 2.0 to pH 10.0, where pH 6.0 to pH 8.0 is a typical pH range for the initial condition. However, the actual culture conditions for a particular embodiment are not meant to be limited by these pH ranges.

Bio-productions may be performed under aerobic, microaerobic or anaerobic conditions with or without agitation.

In some cases, a change of an environmental condition comprises a change in sugar concentration of a culture medium contacting a cell. In some cases, a change in sugar concentration of a culture medium is an increase of sugar concentration. In some other cases, a change in sugar concentration is a decrease of sugar concentration. In some situations, an increase of sugar concentration is from 1% to 2%, from 2% to 3%, from 3% to 4%, from 4% to 5%, from 5% to 10%, from 10% to 15%, from 15% to 20%, from 20% to 30%, from 30% to 40%, from 40% to 50%, from 50% to 60%, from 60% to 70%, from 70% to 80%, from 80% to 90%, or from 90% to 100% more sugar compared with the original sugar concentration in the culture medium. In some situations, a decrease of sugar concentration is from 1% to 2%, from 2% to 3%, from 3% to 4%, from 4% to 5%, from 5% to 10%, from 10% to 15%, from 15% to 20%, from 20% to 30%, from 30% to 40%, from 40% to 50%, from 50% to 60%, from 60% to 70%, from 70% to 80%, from 80% to 90%, or from 90% to 100% less sugar compared with the original sugar concentration in the culture medium.

In some cases, a change of an environmental condition comprises a change in oxygenation of a culture medium contacting a cell. In some cases, a change in oxygenation of a culture medium is an increase of oxygenation. In some other cases, a change in oxygenation of a culture medium is a decrease of oxygenation. In some situations, an increase of oxygenation is the addition of oxygen from 1% to 2%, from 2% to 3%, from 3% to 4%, from 4% to 5%, from 5% to 10%, from 10% to 15%, from 15% to 20%, from 20% to 30%, from 30% to 40%, from 40% to 50%, from 50% to 60%, from 60% to 70%, from 70% to 80%, from 80% to 90%, or from 90% to 100% more than the original amount of oxygen added in a culture medium. In some situations, a decrease of oxygenation is the addition of oxygen from 1% to 2%, from 2% to 3%, from 3% to 4%, from 4% to 5%, from 5% to 10%, from 10% to 15%, from 15% to 20%, from 20% to 30%, from 30% to 40%, from 40% to 50%, from 50% to 60%, from 60% to 70%, from 70% to 80%, from 80% to 90%, or from 90% to 100% less than the original amount of oxygen added in a culture medium.

Bio-Production Reactors and Systems

Fermentation systems utilizing methods and/or compositions according to the invention are also within the scope of the invention.

Any of the recombinant microorganisms as described and/or referred to herein may be introduced into an industrial bio-production system where the microorganisms convert a carbon source into a product in a commercially viable operation. The bio-production system includes the introduction of such a recombinant microorganism into a bioreactor vessel, with a carbon source substrate and bio-production media suitable for growing the recombinant microorganism, and maintaining the bio-production system within a suitable temperature range (and dissolved oxygen concentration range if the reaction is aerobic or microaerobic) for a suitable time to obtain a desired conversion of a portion of the substrate molecules to a selected chemical product. Bio-productions may be performed under aerobic, microaerobic, or anaerobic conditions, with or without agitation. Industrial bio-production systems and their operation are well-known to those skilled in the arts of chemical engineering and bioprocess engineering. The amount of a product produced in a bio-production media generally can be determined using a number of methods known in the art, for example, high performance liquid chromatography (HPLC), gas chromatography (GC), or GC/Mass Spectroscopy (MS).

Genetic Modifications, Nucleotide Sequences, and Amino Acid Sequences

Embodiments of the present disclosure may result from introduction of an expression vector into a host microorganism, wherein the expression vector contains a nucleic acid sequence coding for an enzyme that is, or is not, normally found in a host microorganism.

The ability to genetically modify a host cell is essential for the production of any genetically modified (recombinant) microorganism. The mode of gene transfer technology may be by electroporation, conjugation, transduction, or natural transformation. A broad range of host conjugative plasmids and drug resistance markers are available. The cloning vectors are tailored to the host organisms based on the nature of antibiotic resistance markers that can function in that host. Also, as disclosed herein, a genetically modified (recombinant) microorganism may comprise modifications other than via plasmid introduction, including modifications to its genomic DNA.

More generally, nucleic acid constructs can be prepared comprising an isolated polynucleotide encoding a polypeptide having enzyme activity operably linked to one or more (several) control sequences that direct the expression of the coding sequence in a microorganism, such as E. coli, under conditions compatible with the control sequences. The isolated polynucleotide may be manipulated to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well established in the art.

The control sequence may be an appropriate promoter sequence, a nucleotide sequence that is recognized by a host cell for expression of a polynucleotide encoding a polypeptide of the present disclosure. The promoter sequence may contain transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell. The techniques for modifying and utilizing recombinant DNA promoter sequences are well established in the art.

For various embodiments of the invention the genetic manipulations may be described to include various genetic manipulations, including those directed to change regulation of, and therefore ultimate activity of, an enzyme or enzymatic activity of an enzyme identified in any of the respective pathways. Such genetic modifications may be directed to transcriptional, translational, and post-translational modifications that result in a change of enzyme activity and/or selectivity under selected and/or identified culture conditions and/or to provision of additional nucleic acid sequences such as to increase copy number and/or mutants of an enzyme related to product production. Specific methodologies and approaches to achieve such genetic modification are well known to one skilled in the art.

In various embodiments, to function more efficiently, a microorganism may comprise one or more gene deletions. For example, in *E. coli*, the genes encoding the lactate dehydrogenase (ldhA), phosphate acetyltransferase (pta), pyruvate oxidase (poxB), pyruvateformate lyase (pflB), methylglyoxal synthase (mgsA), acetate kinase (ackA), alcohol dehydrogenase (adhE), the clpXP protease specificity enhancing factor (sspB), the ATPdependent Lon protease (lon), the outer membrane protease (ompT), the arcA transcriptional dual regulator (arcA), and the iclR transcriptional regulator (iclR) may be disrupted, including deleted. Such gene disruptions, including deletions, are not meant to be limiting, and may be implemented in various combinations in various embodiments. Gene deletions may be accomplished by numerous strategies well known in the art, as are methods to incorporate foreign DNA into a host chromosome.

In various embodiments, to function more efficiently, a microorganism may comprise one or more synthetic metabolic valves, composed of enzymes targeted for controlled proteolysis, expression silencing or a combination of both controlled proteolysis and expression silencing. In some embodiments, a microorganism may comprise two, three, four, five, six, seven, eight, nine, or ten, or more synthetic metabolic valves. For example, one enzyme encoded by one gene or a combination of numerous enzymes encoded by numerous genes in *E. coli* may be designed as synthetic metabolic valves to alter metabolism and improve product formation. Representative genes in *E. coli* may include but are not limited to the following: fabI, zwf gltA, ppc, udhA, lpd, sucD, aceA, pfkA, lon, rpoS, tktA or tktB. It is appreciated that it is well known to one skilled in the art how to identify homologues of these genes and or other genes in additional microbial species.

For all nucleic acid and amino acid sequences provided herein, it is appreciated that conservatively modified variants of these sequences are included, and are within the scope of the invention in its various embodiments. Functionally equivalent nucleic acid and amino acid sequences (functional variants), which may include conservatively modified variants as well as more extensively varied sequences, which are well within the skill of the person of ordinary skill in the art, and microorganisms comprising these, also are within the scope of various embodiments of the invention, as are methods and systems comprising such sequences and/or microorganisms.

Accordingly, as described in various sections above, some compositions, methods and systems of the present disclosure comprise providing a genetically modified microorganism that comprises both a production pathway to make a desired product from a central intermediate in combination with synthetic metabolic valves to redistribute flux.

Aspects of the invention also regard provision of multiple genetic modifications to improve microorganism overall effectiveness in converting a selected carbon source into a selected product. Particular combinations are shown, such as in the Examples, to increase specific productivity, volumetric productivity, titer and yield substantially over more basic combinations of genetic modifications. In addition to the above-described genetic modifications, in various embodiments genetic modifications, including synthetic metabolic valves also are provided to increase the pool and availability of the cofactor NADPH and/or NADH which may be consumed in the production of a product.

More generally, and depending on the particular metabolic pathways of a microorganism selected for genetic modification, any subgroup of genetic modifications may be made to decrease cellular production of fermentation product(s) other than the desired fermentation product, selected from the group consisting of acetate, acetoin, acetone, acrylic, malate, fatty acid ethyl esters, isoprenoids, glycerol, ethylene glycol, ethylene, propylene. butylene, isobutylene, ethyl acetate, vinyl acetate, other acetates, 1,4-butanediol, 2,3-butanediol, butanol, isobutanol, sec-butanol, butyrate, isobutyrate, 2-OH-isobutryate, 3-OHbutyrate, ethanol, isopropanol, D-lactate, L-lactate, pyruvate, itaconate, levulinate, glucarate, glutarate, caprolactam, adipic acid, propanol, isopropanol, fusel alcohols, and 1,2-propanediol, 1,3-propanediol, formate, fumaric acid, propionic acid, succinic acid, valeric acid, maleic acid and poly-hydroxybutyrate. Gene deletions may be made as disclosed generally herein, and other approaches may also be used to achieve a desired decreased cellular production of selected fermentation products other than the desired products.

VI.a Gene Silencing

In particular the invention describes the use of controlled gene silencing to help enable the control over metabolic fluxes in controlled multi-stage fermentation processes. There are several methodologies known in the art for controlled gene silencing, including but not limited to mRNA silencing or RNA interference, silencing via transcriptional repressors and CRISPR interference.

In some cases, a valve polynucleotide comprises a polynucleotide selected from the group consisting of: a silencing polynucleotide for repressing transcription of a gene encoding said valve enzyme; a degradation polynucleotide for mediating cellular degradation of said valve enzyme; and a combination thereof.

In some cases, a valve polynucleotide comprises a silencing polynucleotide, and said silencing polynucleotide comprises a guide RNA (gRNA) comprising a gRNA sequence that recognizes a promoter of a gene encoding said valve enzyme.

In some cases, a valve polynucleotide further encodes a CRISPR enzyme, wherein said CRISPR enzyme specifically binds to said promoter sequence when bound to said gRNA. In some cases, a CRISPR enzyme is catalytically inactive.

In some cases, a valve polynucleotide comprises a degradation polynucleotide, wherein said degradation polynucleotide comprises a sequence encoding a degradation tag, wherein said degradation tag mediates degradation of said valve enzyme. In some cases, the expression of a valve polynucleotide is regulated by phosphate availability in a cell. In some cases, the expression of a production polynucleotide is regulated by phosphate availability in a cell. In certain cases, the cell is an *E. coli* cell.

Controlled Proteolysis

In particular the current disclosure describes the use of controlled protein degradation or proteolysis to help enable the control over metabolic fluxes in controlled multi-stage fermentation processes. There are several methodologies known in the art for controlled protein degradation, including but not limited to targeted protein cleavage by a specific protease and controlled targeting of proteins for degradation by specific peptide tags. Systems for the use of the *E. coli* clpXP protease for controlled protein degradation can be used. This methodology relies upon adding a specific C-terminal peptide tag such as a DAS4 (or DAS+4) tag. Proteins with this tag are not degraded by the clpXP protease until the specificity enhancing chaperone sspB is expressed. sspB induces degradation of DAS4 tagged proteins by the clpXP protease. In additional numerous site specific protease systems are well known in the art. Proteins can be engineered to contain a specific target site of a given protease and then cleaved after the controlled expression of the protease. In some embodiments the cleavage can be expected lead to protein inactivation or degradation. For example, an N-terminal sequence can be added to a protein of interest to enable clpS dependent clpAP degradation. In addition, this sequence can further be masked by an additional N-terminal sequence, which can be controllable cleaved such as by a ULP hydrolase. This allows for controlled N-rule degradation dependent on hydrolase expression. It is therefore possible to tag proteins for controlled proteolysis either at the N-terminus or C-terminus.

The preference of using an N-terminal vs. C-terminal tag will largely depend on whether either tag affects protein function prior to the controlled onset of degradation. The invention describes the use of controlled protein degradation or proteolysis to help enable the control over metabolic fluxes in controlled multi-stage fermentation processes, in *E. coli*. There are several methodologies known in the art for controlled protein degradation in other microbial hosts, including a wide range of gram-negative as well as gram-positive bacteria, yeast and even archaea. In particular, systems for controlled proteolysis can be transferred from a native microbial host and used in a non-native host.

Synthetic Metabolic Valve Control

In particular the current disclosure describes the use of synthetic metabolic valves to control metabolic fluxes in multi-stage fermentation processes. There are numerous methodologies known in the art to induce expression that can be used at the transition between stages in multistage fermentations. These include but are not limited to artificial chemical inducers including: tetracycline, anhydrotetracycline, lactose, IPTG (isopropyl-beta-D-1-thiogalactopyranoside), arabinose, raffinose, tryptophan and numerous others. Systems linking the use of these well known inducers to the control of gene expression silencing and/or controlled proteolysis can be integrated into genetically modified microbial systems to control the transition between growth and production phases in multi-stage fermentation processes.

In addition, it may be desirable to control the transition between growth and production in multi-stage fermentations by the depletion of one or more limiting nutrients that are consumed during growth. Limiting nutrients can include but are not limited to: phosphate, nitrogen, sulfur and magnesium. Natural gene expression systems that respond to these nutrient limitations can be used to operably link the control of gene expression silencing and/or controlled proteolysis to the transition between growth and production phases in multi-stage fermentation processes.

Products

In some embodiments, provided herein is a microorganism or a cell for producing a product. In some cases, the product comprises 3-hydroxypropionic acid. In some cases, the product comprises an amino acid. In some cases, the amino acid comprises alanine. In some cases, the alanine is L-alanine. In some cases, the alanine is D-alanine. In some cases, a rate of production of alanine is at least 0.1 g/L/hr, 0.2 g/L/hr, 0.3 g/L/hr, 0.4 g/L/hr, 0.5 g/L/hr, 0.6 g/L/hr, 0.7 g/L/hr, 0.8 g/L/hr, 0.9 g/L/hr, 1.0 g/L/hr, 1.1 g/L/hr, 1.2 g/L/hr, 1.3 g/L/hr, 1.4 g/L/hr, 1.5 g/L/hr, 1.6 g/L/hr, 1.7 g/L/hr, 1.8 g/L/hr, 1.9 g/L/hr, 2.0 g/L/hr, 2.5 g/L/hr, 3.0 g/L/hr, 3.5 g/L/hr, 4.0 g/L/hr, 4.5 g/L/hr, 5.0 g/L/hr, 5.5 g/L/hr, 6.0 g/L/hr, 7.0 g/L/hr, 8.0 g/L/hr, 9.0 g/L/hr, or at least 10 g/L/hr.

In some cases, the alanine titers after 24 hours can be from 0 to 0.5 g/L, 0.5 g/L to 1 g/L, 1 g/L to 1.5 g/L, 1.5 g/L to 2 g/L, 2 g/L to 2.5 g/L, 2.5 g/L to 3 g/L, 3 g/L to 3.5 g/L, 3.5 g/L to 4 g/L, 4 g/L to 4.5 g/L, 4.5 g/L to 5 g/L, or from 5 g/L to 10 g/L. The dynamic range of alanine production offered by SMVs can be up to a 4-fold increase compared to that offered by solely altering the expression level of the production pathway enzymes (by changing the promoter). In some cases, the dynamic range of alanine production offered by SMVs can be up to a 2-fold, 3-fold, 4-fold, 5-fold, 6-fold, 7-fold, 8-fold, 9-fold, or 10-fold increase compared to that offered by solely altering the expression level of the production pathway enzymes.

In some cases, a production polynucleotide in the microorganism encodes an alanine exporter. In some cases, the alanine exporter is alaE.

In some cases, the product comprises mevalonic acid. In some cases, a rate of production of mevalonic acid is at least 0.1 g/L/hr, 0.2 g/L/hr, 0.3 g/L/hr, 0.4 g/L/hr, 0.5 g/L/hr, 0.6 g/L/hr, 0.7 g/L/hr, 0.8 g/L/hr, 0.9 g/L/hr, 1.0 g/L/hr, 1.1 g/L/hr, 1.2 g/L/hr, 1.3 g/L/hr, 1.4 g/L/hr, 1.5 g/L/hr, 1.6 g/L/hr, 1.7 g/L/hr, 1.8 g/L/hr, 1.9 g/L/hr, 2.0 g/L/hr, 2.5 g/L/hr, 3.0 g/L/hr, 3.5 g/L/hr, 4.0 g/L/hr, 4.5 g/L/hr, 5.0 g/L/hr, 5.5 g/L/hr, 6.0 g/L/hr, 7.0 g/L/hr, 8.0 g/L/hr, 9.0 g/L/hr, or at least 10 g/L/hr.

Methods

Provided herein are methods for producing a product in an engineered microorganism in a large scale. Also provided herein are methods for engineering microorganisms for large-scale production of a product in a high-throughput fashion.

In some cases, provided herein is a method, comprising: culturing a plurality of strains of a cell, wherein each strain of said plurality of strains comprises (i) an engineered valve polynucleotide for mediating controlled reduction of expression of a valve enzyme acting in a metabolic pathway, wherein said controlled reduction of expression of said valve enzyme reduces flux through said metabolic pathway; and (ii) an engineered production polynucleotide for mediating controlled increase in expression of a production enzyme for generation of said product; wherein each strain of said plurality of strains differs from another strain in a sequence of at least one of said engineered valve polynucleotide or said engineered production polynucleotide; measuring a level of said product generated by each of said plurality of strains; and selecting a strain based on said level of said product. In some embodiments, the method further comprises growing said selected strain in a bioreactor. In some embodiments, a culture medium comprising said selected strain has a volume of at least 100 ml, 200 ml, 300 ml, 400 ml, 500 ml, 600 ml, 700 ml, 800 ml, 900 ml, or at least 1000 ml. In some embodiments, a culture medium has a volume of at least 1 L.

In some embodiments, a valve polynucleotide comprises a polynucleotide selected from the group consisting of: a silencing polynucleotide for repressing transcription of a gene encoding said valve enzyme; a degradation polynucleotide for mediating cellular degradation of said valve enzyme; and a combination thereof. In some embodiments, a first and a second strain of said plurality of strains comprise a silencing polynucleotide. In some embodiments, a silencing polynucleotide comprises a guide RNA (gRNA) comprising a gRNA sequence that recognizes a promoter of a gene encoding said valve enzyme. In some embodiments, a gRNA sequence differs between said first and second strains. In some embodiments, a promoter recognized by said gRNA differs between said first and second strains. In some embodiments, a first strain comprises said silencing polynucleotide and said degradation polynucleotide, and a second strain comprises said silencing polynucleotide but does not comprise said degradation polynucleotide. In some embodiments, a level of product is greater in said second strain than said first strain. In some embodiments, a level of product is greater in said first strain than said second strain. In some embodiments, a valve enzyme comprises an enzyme selected from the group consisting of enoyl-ACP/CoA reductase (fabI), glucose-6-phosphate dehydrogenase (zwf), lipoamide dehydrogenase (lpd), citrate synthase (gltA), soluble transhydrogenase (udhA), NADH-dependent glyceraldehyde-3-phosphate dehydrogenase (gapA), and a combination thereof. In some embodiments, a production enzyme comprises an enzyme selected from the group consisting of NADPH-dependent alanine dehydrogenase (ald), alanine exporter (alaE), NADPH-dependent glyceraldehyde-3-phosphate dehydrogenase (gapN), and a combination thereof.

In some embodiments, a product is selected from the group consisting of mevalonic acid, 3-hydroxypropionic acid, an amino acid, and a combination thereof. In some embodiments, the amino acid is alanine. In some embodiments, the alanine is L-alanine. In some embodiments, the alanine is D-alanine.

In some embodiments, a rate of production of the product during said stationary phase is reduced less in response to a change of an environmental condition as compared to a cell lacking said controlled reduction of expression of said valve enzyme.

In some embodiments, a change of an environmental condition comprises a change in a sugar concentration of a culture medium contacting said cell.

In some embodiments, a change of an environmental condition comprises a change in oxygenation of a culture medium contacting said cell.

In some cases, provided herein is a method of generating a cellular product comprising: culturing a heterologous cell in a culture medium, wherein said heterologous cell comprises: (i) an engineered valve polynucleotide for mediating controlled reduction of expression of a valve enzyme acting in a metabolic pathway, wherein said controlled reduction of expression of said valve enzyme reduces flux through said metabolic pathway, wherein said controlled reduction of expression of said valve enzyme induces a stationary phase of said cell; and (ii) an engineered production polynucleotide for mediating controlled increase in expression of a production enzyme for generation of said product; wherein a rate of production of said product during said stationary phase is reduced less in response to a change of an environmental condition as compared to a cell lacking said controlled reduction of expression of said valve enzyme. In some embodiments, the method further comprises changing said environmental condition. In some embodiments, the environmental condition comprises a sugar concentration of said culture medium, and changing said environmental condition comprises increasing or decreasing said sugar concentration. In some cases, said sugar is glucose, sucrose, lactose, maltose, xylose, mannitol, or a combination thereof. In some cases, said sugar is glucose. In some cases, the environmental condition comprises an oxygen concentration of said culture medium, and changing said environmental condition comprises increasing or decreasing said oxygen concentration. In some cases, said culturing is performed in a bioreactor.

In some cases, said culture medium has a volume of at least 100 ml, 200 ml, 300 ml, 400 ml, 500 ml, 600 ml, 700 ml, 800 ml, 900 ml, or at least 1000. In some cases, said culture medium has a volume of at least 1 L. In some case, said product comprises 3-hydroxypropionic acid. In some cases, said product comprises an amino acid. In some cases, said amino acid comprises alanine.

In some cases, a rate of production of said alanine is at least 0.1 g/L/hr, 0.2 g/L/hr, 0.3 g/L/hr, 0.4 g/L/hr, 0.5 g/L/hr, 0.6 g/L/hr, 0.7 g/L/hr, 0.8 g/L/hr, 0.9 g/L/hr, 1.0 g/L/hr, 1.1 g/L/hr, 1.2 g/L/hr, 1.3 g/L/hr, 1.4 g/L/hr, 1.5 g/L/hr, 1.6 g/L/hr, 1.7 g/L/hr, 1.8 g/L/hr, 1.9 g/L/hr, 2.0 g/L/hr, 2.5 g/L/hr, 3.0 g/L/hr, 3.5 g/L/hr, 4.0 g/L/hr, 4.5 g/L/hr, 5.0 g/L/hr, 5.5 g/L/hr, 6.0 g/L/hr, 7.0 g/L/hr, 8.0 g/L/hr, 9.0 g/L/hr, or at least 10 g/L/hr. In some cases, said production polynucleotide encodes an alanine exporter. In some cases, said alanine exporter is alaE. In some cases, said culturing occurs for less than 20 hours, 30 hours, 40 hours, 50 hours, 60 hours, 70 hours, 80 hours, 90 hours, or less than 100 hours. In some cases, said culturing occurs for less than 10 hours, 15 hours, 20 hours, 25 hours, 30 hours, 35 hours, 40 hours, or less than 45 hours. In some cases, said culturing occurs for less than 30 hours.

In some cases, said product comprises mevalonic acid. In some cases, a rate of production of said mevalonic acid is at least 0.1 g/L/hr, 0.2 g/L/hr, 0.3 g/L/hr, 0.4 g/L/hr, 0.5 g/L/hr, 0.6 g/L/hr, 0.7 g/L/hr, 0.8 g/L/hr, 0.9 g/L/hr, 1.0 g/L/hr, 1.1 g/L/hr, 1.2 g/L/hr, 1.3 g/L/hr, 1.4 g/L/hr, 1.5 g/L/hr, 1.6 g/L/hr, 1.7 g/L/hr, 1.8 g/L/hr, 1.9 g/L/hr, 2.0 g/L/hr, 2.5 g/L/hr, 3.0 g/L/hr, 3.5 g/L/hr, 4.0 g/L/hr, 4.5 g/L/hr, 5.0 g/L/hr, 5.5 g/L/hr, 6.0 g/L/hr, 7.0 g/L/hr, 8.0 g/L/hr, 9.0 g/L/hr, or at least 10 g/L/hr. In some cases, said culturing occurs for less than 20 hours, 30 hours, 40 hours, 50 hours, 60 hours, 70 hours, 80 hours, 90 hours, or less than 100 hours. In some cases, said culturing occurs for less than 80 hours.

In some embodiments, a valve polynucleotide comprises a polynucleotide selected from the group consisting of: a silencing polynucleotide for repressing transcription of a gene encoding said valve enzyme; a degradation polynucleotide for mediating cellular degradation of said valve enzyme; and a combination thereof. In some cases, a valve polynucleotide comprises a silencing polynucleotide, and said silencing polynucleotide comprises a guide RNA (gRNA) comprising a gRNA sequence that recognizes a promoter of a gene encoding said valve enzyme. In some cases, a valve polynucleotide further encodes a CRISPR enzyme, wherein said CRISPR enzyme specifically binds to said promoter sequence when bound to said gRNA. In some cases, a CRISPR enzyme is catalytically inactive. In some case, a valve polynucleotide comprises a degradation polynucleotide, wherein said degradation polynucleotide comprises a sequence encoding a degradation tag, wherein said degradation tag mediates degradation of said valve enzyme. In some cases, an expression of said valve polynucleotide is regulated by phosphate. In some cases, an expression of said production polynucleotide is regulated by phosphate. In some cases, said cell is an *E. coli* cell.

Optimization of Bio-Production

Biotechnology based fermentation processes have been successfully developed to produce everything from biologics and small molecule therapeutics to specialty, bulk and commodity chemicals, and even next generation biofuels[1-3]. These processes have made rapid advancements in recent years due to numerous technology developments[4, 5]. It has never been easier to produce new molecules using synthetic biology. Despite these advances, a major challenge remains in taking molecules from proof of concept (POC) to commercially meaningful levels. Strain optimization, or overcoming the "mg" to "kg" hurdle has remained a key barrier to the successful commercialization of bio-processes. After the demonstration of POC, successful bio-process development routinely requires lengthy iterations of both microbial strain and fermentation optimization[6-8] (FIG. 1B). These optimization efforts are often specific to the product or host strain of interest. The throughput of synthetic biology has outpaced that of metabolic engineering, partly due to a lack of broadly useful tools to perform meaningful and standardized optimization of engineered microbial strains in a high-throughput manner[9].

There are numerous challenges in strain optimization and moving past POC levels, not the least of which are the size and complexity of the potential design space. In contrast to simpler gene circuits, amenable to electrical circuit models[10-12], metabolic networks are highly interconnected. Each metabolite and/or enzyme can interact with endless others. This combinatorial complexity results in a huge potential design space, which is intractable to the kinds of systematic experimentation required for the development of standardized design principles (Supplemental Materials, Table 1). The challenges in addressing such a large design space have persisted despite the dramatic advances in, and decreased costs of, reading and writing DNA that have led to new high-throughput DNA assembly and microbial strain construction methods[13-16]. It is not surprising that new synthetic biology technologies involving strain engineering are often demonstrated with easily screened or selected phenotypes[13, 17-19]. Most of these are limited to a focus on optimizing a limited set of pathway specific enzymes.

One approach to overcome the complexity of this challenge is the use of in vitro systems for bio-production, which comprise a limited set of metabolic enzymes. However, these approaches have challenges in replicating key advantages of in vivo systems, including cofactor recycling and energy generation[20, 21]. Another approach to deal with this complexity is to develop faster screening methods for strain evaluation[22]. However, increased throughput alone can never evaluate the full complexity of the potential design space. In addition, results obtained from high-throughput studies often do not translate, even in the same microbe, to a different environment[20, 23, 24]. Small scale screens do not readily translate to larger scale production processes, leading to iterations of process optimization on top of strain optimization (FIG. 1B). This is because metabolism is highly regulated and can respond, sometimes dramatically, to changes in environmental conditions[25 20, 26-28]. A lack of environmental robustness is traditionally one factor making the scale up of fermentation based processes difficult. This issue has led to the development of specialized complex micro-reactor systems for scale down offering only modest improvements in throughput[20, 29-31].

There remains a significant need for broadly applicable, rapid and robust approaches to greatly reduce the time and costs transitioning from "mgs" to "kgs". Ideally, approaches should be amenable to multiple products and production hosts. Provided herein is the development of a generalizable, high-throughput strain optimization approach that enables the use of truly scalable, standardized fermentation processes. This approach, as outlined in FIG. 1B, panel b, involves the dynamic minimization of the active metabolic network[32], which combines the benefits of a smaller design space common to in vitro approaches while maintaining the benefits of in vivo biosynthesis[20]. We can isolate and focus on the minimal metabolic networks required for production. Utilizing combinations of synthetic metabolic valves (SMVs)[32, 33] (FIGS. 2A-D) we can dynamically minimize the metabolic network and redirect metabolic flux in the context of a standardized 2-stage fermentation process[20].

This approach can reduce the complexity of the problem and the size of the relevant design space, greatly speeding up optimization. In various embodiments, it is demonstrated herein that dynamic metabolic network minimization can improve pathway fluxes beyond those achievable with production pathway modifications alone (FIGS. 3A-K and 6A-H).

Simultaneously, we demonstrate that dynamic network minimization reduces metabolic responses to environmental conditions, which increases the robustness and scalability of engineered strains (FIGS. 3A-K and 5A-J).

Examples

2-Stage Synthetic Metabolic Valves in E. coli

We first developed improved synthetic metabolic valves (SMVs) in E. coli that are capable of the dynamic reduction of protein levels in a 2-stage process. These SMVs can be used to reduce levels of key metabolic enzymes (or reduce enzymatic activities of key metabolic enzymes) and rely on controlled proteolysis or CRISPR-based gene silencing or both proteolysis and silencing in combination (FIGS. 2A-D)[32-35]. Cell growth and dynamic metabolic control can be implemented using phosphate depletion as an environmental trigger. Phosphate can be an ideal candidate as a trigger, as one of the costliest components of minimal media. In addition, stationary phases induced in E. coli by phosphate depletion have retained glycolytic uptake as well as increased protein expression[31, 36]. Numerous promoter systems responding to phosphate are well characterized in E. coli as well as other microbes including S. cerevisiae[37]. Phosphate responsive promoter variants were evaluated (Supplemental Materials, Section 1) and subsequently used for 2-stage control.

Figure 2A:
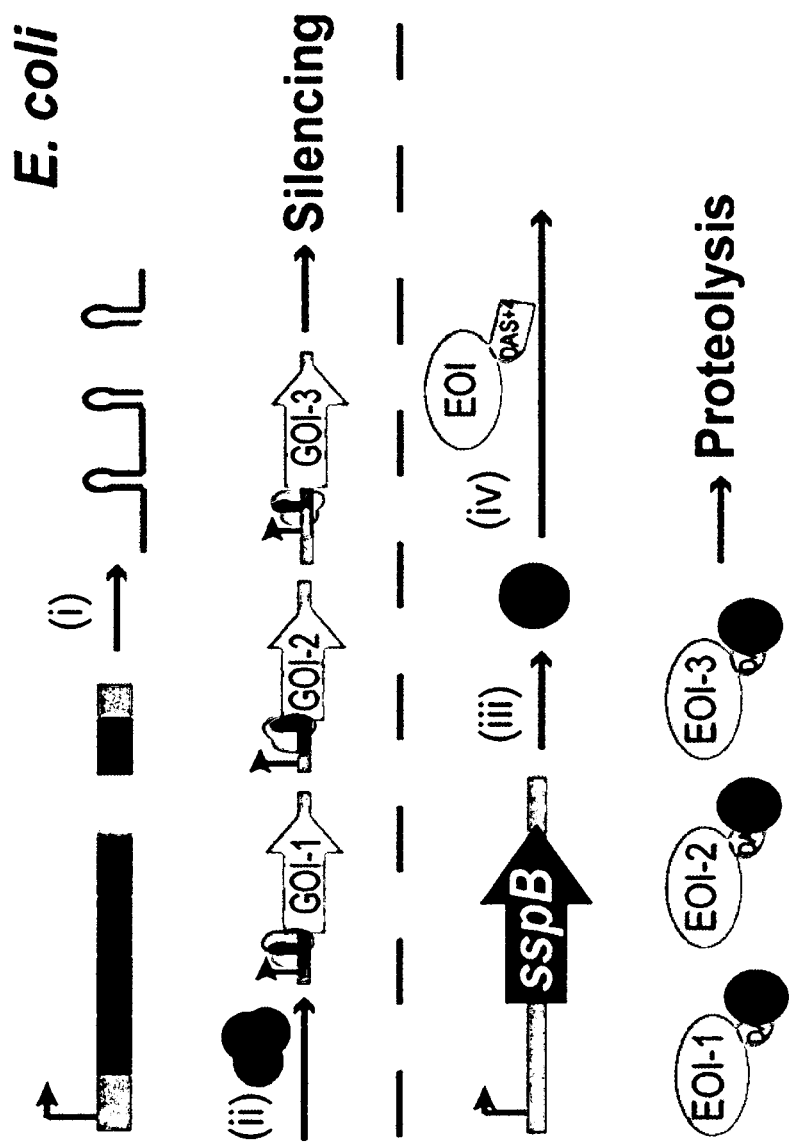
FIGS. 2A-D depict an example of implementation of 2-stage Synthetic Metabolic Valves (SMVs) in *E. coli*.

SMVs were implemented in E. coli using the native Type I-E Cascade CRISPR system for induced gene silencing[34, 38], while controlled proteolysis was induced by incorporating C-terminal degron tags on target proteins, both as previously demonstrated 63,33 (FIG. 2A). These systems were introduced into a host strain initially engineered for minimal byproduct formation and high biomass yields and growth rates (E. coli strain DLF_0025, Supplemental Materials, Section 3)[24, 27, 28 39]. Using this approach, as FIGS. 2A-D demonstrate, protein levels can be controlled in 2-stage processes, as exemplified by turning "ON" GFPuv and "OFF" mCherry fluorescent proteins with phosphate depletion in minimal medium. The combination of gene silencing with proteolysis results in the largest rates of protein degradation (FIGS. 2C-D). The specific impact of gene silencing and proteolysis on decay rates will likely vary depending on the host, target gene/enzyme, and its specific natural turnover rates and expression levels[40, 41].

Metabolic Network Minimization Leads to Improved Fluxes

Figure 3A:
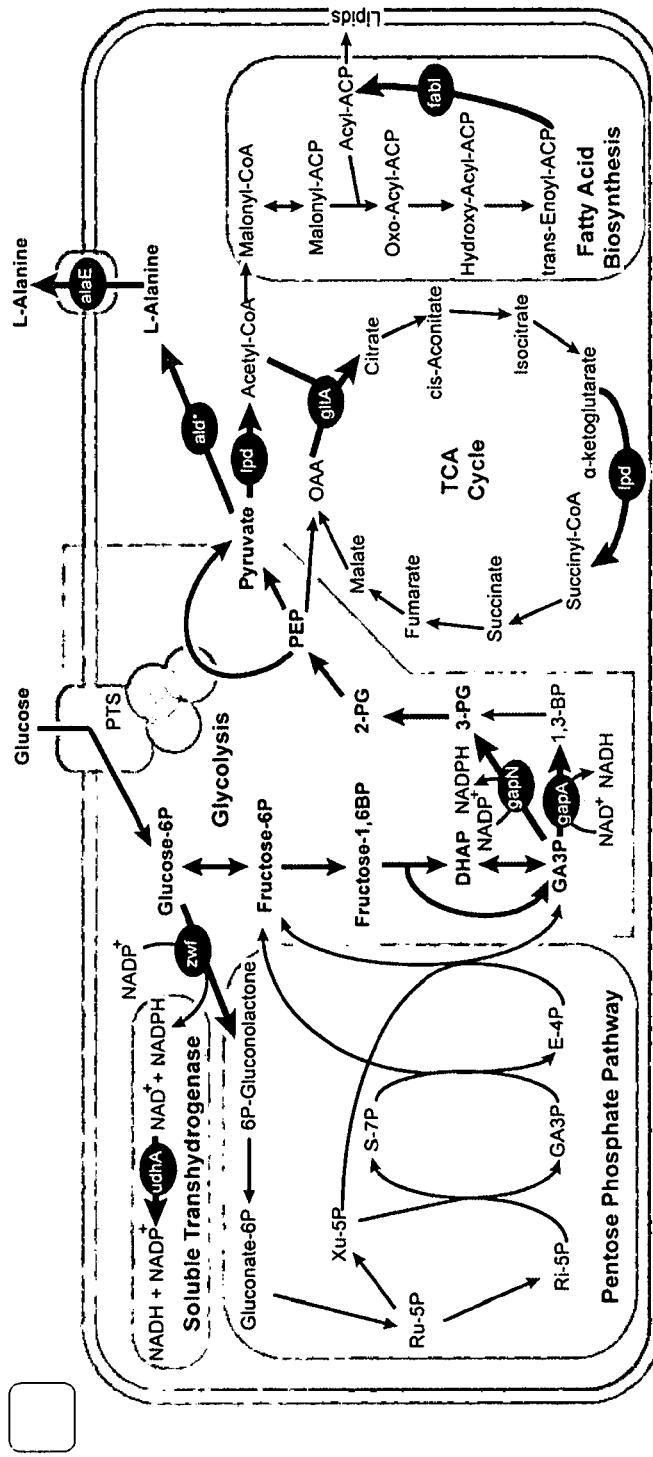
FIGS. 3A-K depict an example of alanine production in *E. coli* utilizing 2-stage dynamic control.
Figure 3B:
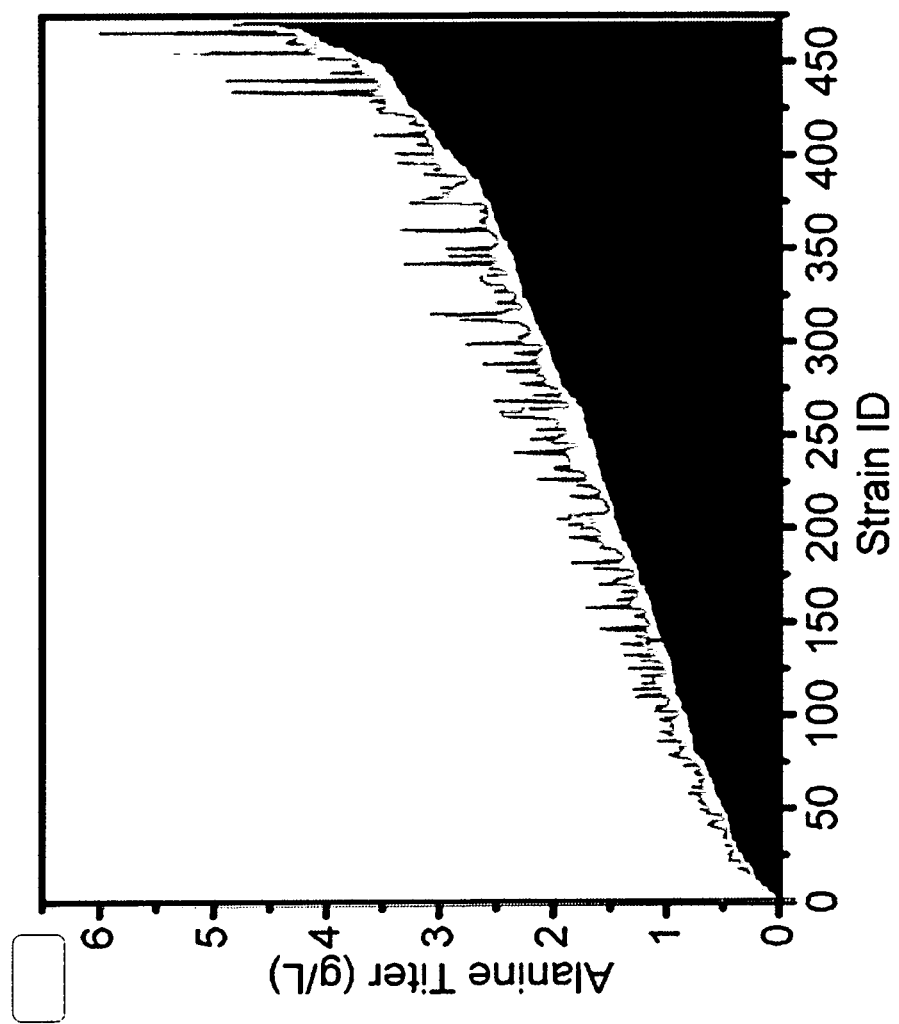
Figure 3C:
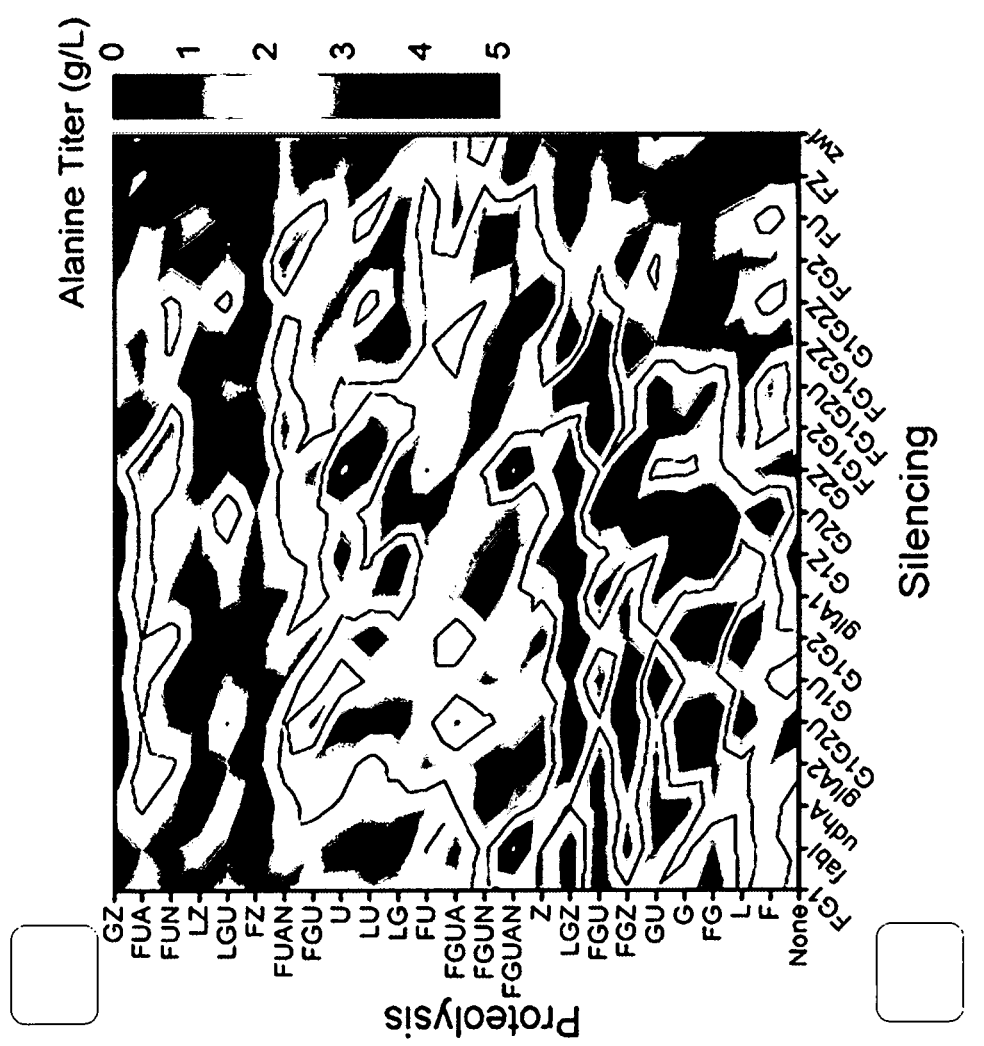
Figure 3D:
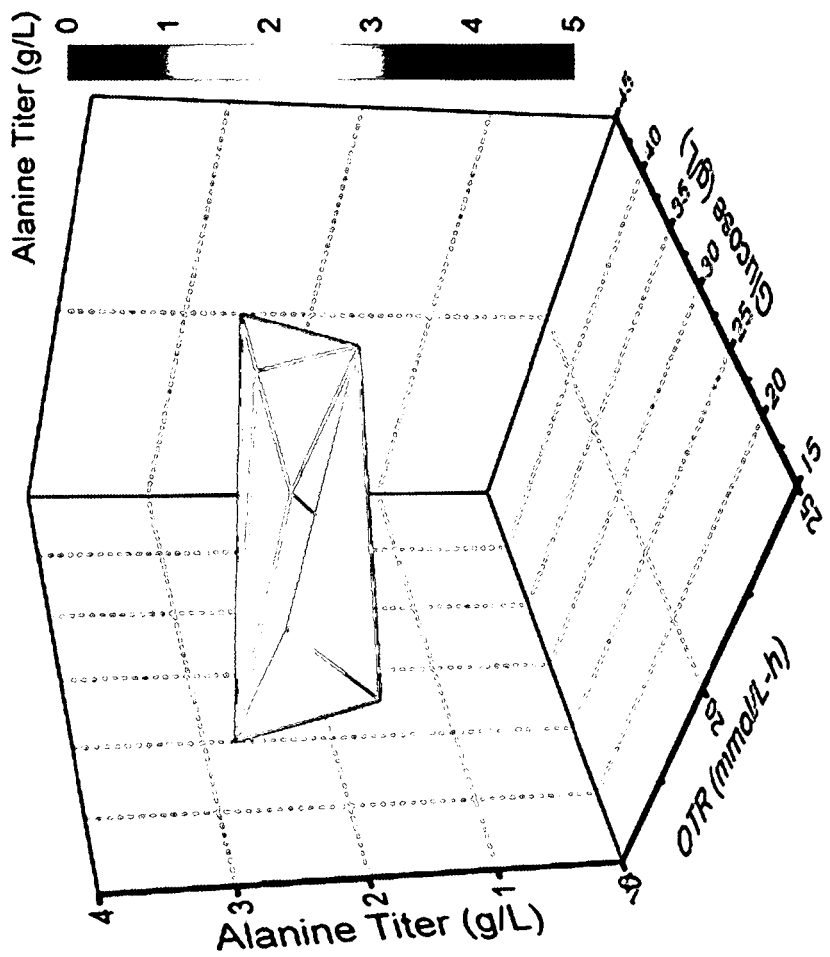

With the successful demonstration of dynamic control of protein levels in a 2-stage process, we turned to investigate the dynamic control of metabolic fluxes in E. coli through controlled reduction of key central metabolic enzymes alone and in combination. Reducing fluxes through thermodynamically favored "committed" reactions in the network is expected to lead to increases in network metabolite pools (Supplemental Materials Section 5), and as a result, changes in pathway fluxes. Enzymes in key committed steps in central metabolic pathways were identified and chosen as initial SMV targets and alanine was chosen as an initial test product (FIGS. 3A-K). A set of strains were constructed for alanine production (FIG. 3A), comprising an NADPH-dependent alanine dehydrogenase (ald*)[42]. Variants with multiple combinations of SMVs in central metabolic enzymes were made, with either modifications to induce proteolysis or gene silencing or both in combination. (Supplemental Materials, Section 3). Together the set of strains having SMVs evaluated in 2-stage processes are identified as "Valve" strains. A panel of alanine "Valve" strains (~500 strains in total) were evaluated for alanine production in standardized, 2-stage, 96-well plate based micro-fermentations (Supplemental Materials, Section 7). Alanine titers after 24 hours of production are given in FIGS. 3B-C. Briefly, alanine titers after 24 hours ranged from ~0 g/L to ~4.7 g/L, and as expected, varied significantly with respect to the number and combination of SMVs; most SMV combinations lead to improved performance when compared to the control with no SMVs and the alanine pathway alone. In some cases, the alanine titers after 24 hours can be from 0 to 0.5 g/L, 0.5 g/L to 1 g/L, 1 g/L to 1.5 g/L, 1.5 g/L to 2 g/L, 2 g/L to 2.5 g/L, 2.5 g/L to 3 g/L, 3 g/L to 3.5 g/L, 3.5 g/L to 4 g/L, 4 g/L to 4.5 g/L, 4.5 g/L to 5 g/L, or from 5 g/L to 10 g/L. The dynamic range of alanine production offered by SMVs can be up to a 4-fold increase compared to that offered by solely altering the expression level of the production pathway enzymes (by changing the promoter) (Supplemental Materials, Section 7). In some cases, the dynamic range of alanine production offered by SMVs can be up to a 2-fold, 3-fold, 4-fold, 5-fold, 6-fold, 7-fold, 8-fold, 9-fold, or 10-fold increase compared to that offered by solely altering the expression level of the production pathway enzymes. Importantly, the use of proteolysis or silencing alone and/or in combination had significant impacts on production, indicating that for each enzyme the fine tuning of activity using SMVs is critical. One of the best performing strains from the micro-fermentations was then evaluated in a minimal medium, 2-stage, 1 L fermentation with 10 gdcw/L of biomass (FIG. 3F), which resulted in 80 g/L 100% L-alanine after 48 hours of production with a yield of 0.8 g/g. Further engineering of this strain by overexpressing an alanine exporter (encoded by the E. coli alaE gene[43]) resulted in 147 g/L 100% L-alanine after 27 hours of production with a yield within error of theoretical yield ~1 g/g, (FIG. 3G).

Micro-Fermentation Robustness

A central hypothesis was that by restricting metabolism in the production stage, strain performance could not only be improved, but would be more robust to environmental (process) conditions. Simply put, carbon flow is restricted through a minimized metabolic network, which can no longer adapt via cellular responses to the environment. To test this hypothesis, strains were evaluated under different "micro-fermentation" process conditions. Glucose concentration and oxygen transfer rate (key process variables impacting strain performance in traditional fermentations[26]) were varied (FIG. 3D, Supplemental Materials, Section 8), and alanine production measured. A robustness score (RS) was developed to quantify environmental robustness. Larger RS scores indicate more robust strains. Whereas relative standard deviation (RSD) is one metric for robustness, we wanted to incorporate a stricter measure of robustness which also incorporates the maximal deviation (Max Dev) a strain has under all process conditions (RS, Equation (1)).

$$RS = 100 - \frac{average(RDS) + max(Dev)}{2} * 100 \quad \text{Equation (1)}$$

Figure 3E:
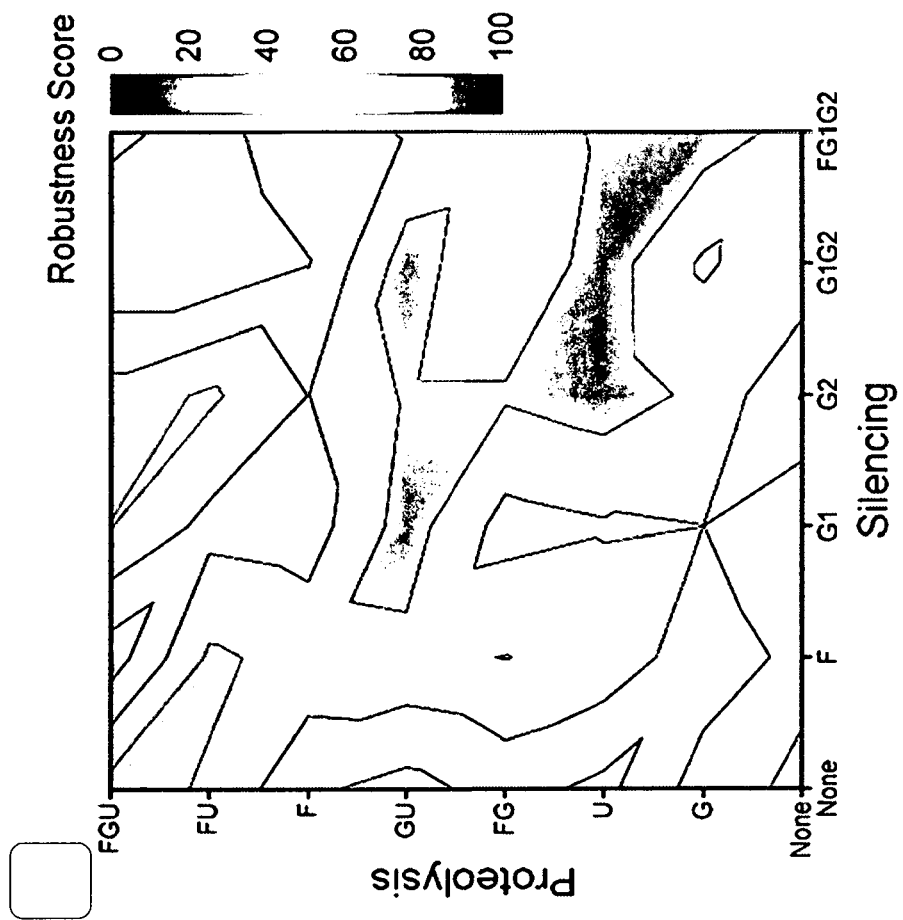
Figure 3G:
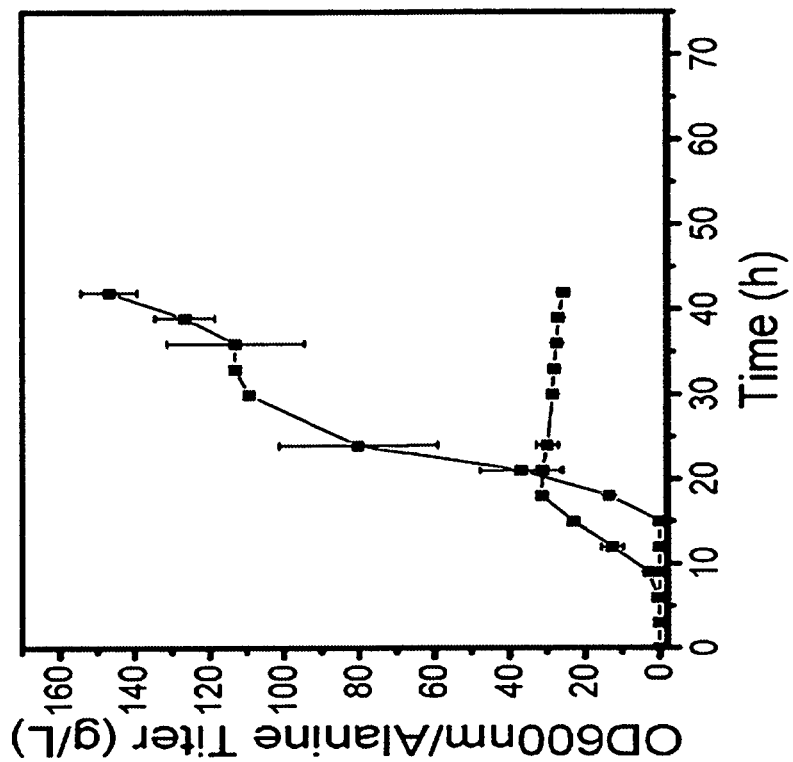

Robustness scores for a subset of 48 alanine "Valve" strains are given in FIG. 3E. Results from these experiments studies are tabulated in Supplemental Materials, Section 8. A Chi$^2$ analysis using a cutoff of RS>0.6 for robustness was used to identify key SMVs which statistically contribute to process robustness. The proteolytic degradation of fabI was a primary contributor to robustness (Chi$^2$=13.85, P$_{value}$<0.001) and as a result, "Valve" strains with proteolytic degradation of fabI were used in further studies. In addition, the "Valve" strains with proteolytic degradation of gltA and/or the combination of the proteolytic degradation of fabI and gltA were found to also be significant contributors of robustness, albeit with a large P$_{value}$.

2-Stage "Valve" Strains Compared to Traditional Growth Associated Strains

To compare the 2-stage approach enabled by SMVs to more traditional growth associated processes, we constructed 5 strains, with constitutively expressed alanine dehydrogenase (ald*), capable of the growth associated production of alanine. These growth associated strains varied in the strength of the promoter used to drive ald* expression[44] (Supplemental Materials, Section 2), yet utilized the same common no-valve control host strain. FIG. 5 illustrates the results of a direct comparison of "Valve" strains in a 2-stage process compared to "Growth Associated (GA)" strains in a traditional fermentation at the microtiter (FIGS. 5A-D) and 1 L (FIGS. 5E-J) scales. In micro-fermentations, 2-stage "Valve" strains outperformed GA strains with respect to titer and process robustness. The most robust GA strain from the micro-fermentation analysis (also with the highest production level) was compared to a robust "Valve" strain in 1 L fermentations with varied process conditions. The "Valve" strains showed consistent performance in all process conditions evaluated (FIG. 5E), consistent with results from micro-fermentations, where the GA strain had significant performance variability dependent on process. We hypothesized that the increased environmental robustness observed in both "micro-" and 1 L scale fermentations for "Valve" strains would lead to predictable scale up, where strains with improved performance in high-throughput micro-fermentations would reliably have improved performance in controlled bioreactors. To evaluate the scalability of the system, "Valve" alanine strains with statistically differentiated performance in micro-fermentations (P-value<0.001) were evaluated in standardized 2-stage 1 L fermentations and compared to all GA strains. Statistically different performances observed in "micro-fermentations" have scaled predictably to 1 L fermentations for 2-stage "Valve" strains. This contrasts with results obtained with GA strains where no correlation between micro-fermentation and 1 L performance was observed (FIGS. 5G-H).

Product Flexibility

Figure 6A:
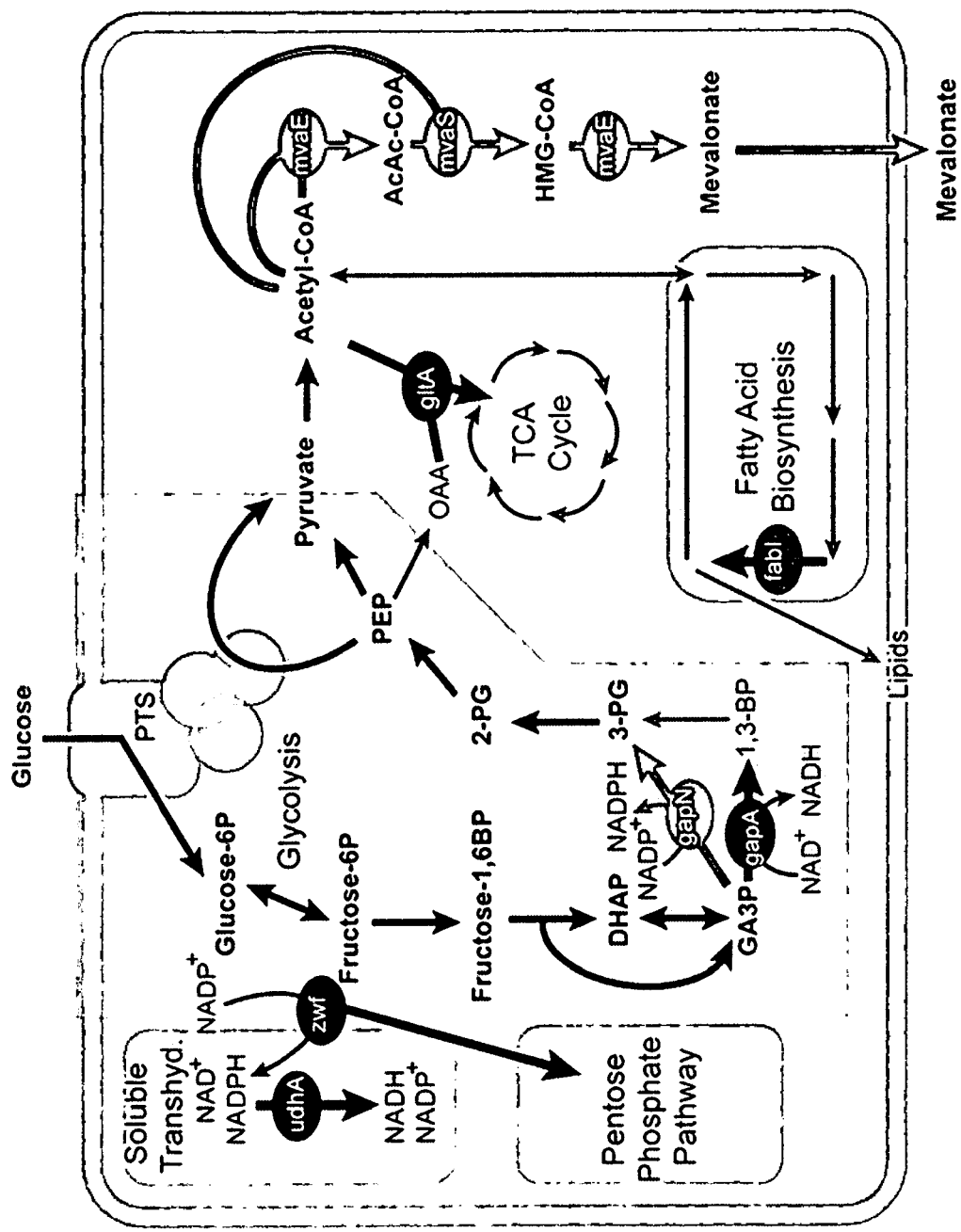
FIG. 6A-H depict an example of mevalonate production in *E. coli* utilizing 2-stage dynamic control.
Figure 6B:
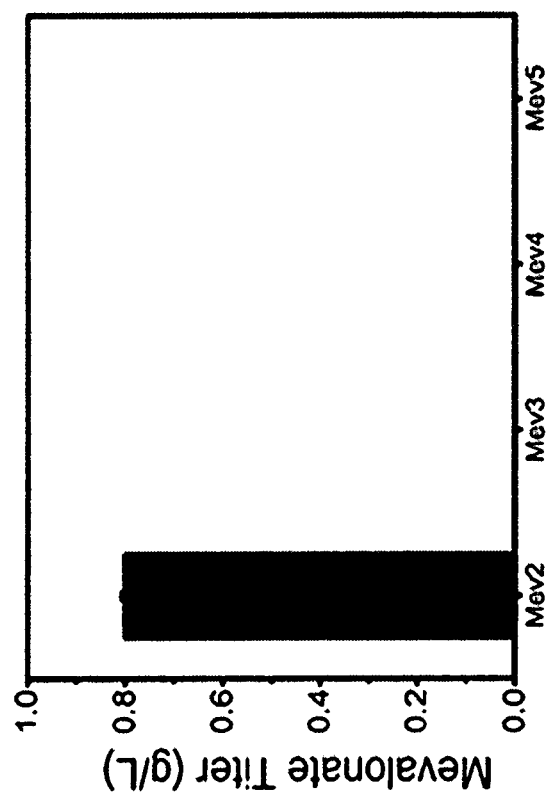
Figure 6C:
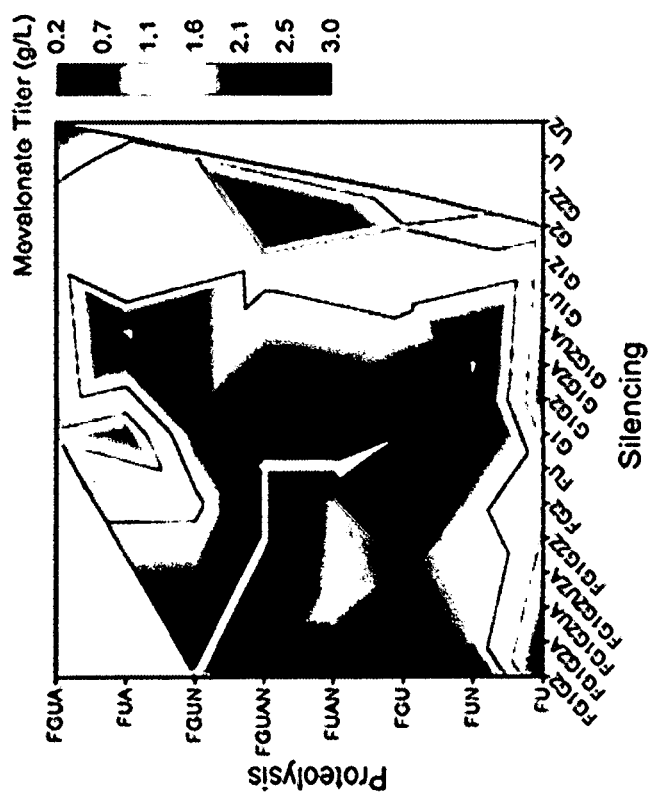

With the successful and predictable scale-up of alanine strains into 1 L fully instrumented fermentations, we moved to validate the technology platform for an additional product: mevalonic acid. To this end, additional dynamic production pathways were constructed for mevalonic acid biosynthesis (FIG. 6A). A set of two-gene production pathway plasmids encoding three enzymatic functions was constructed for mevalonic acid production, consisting of the E. faecalis mvaE and mvaS genes encoding a bifunctional acetyl-CoA acetyltransferase, NADPH dependent HMG-CoA reductase, and HMG-CoA synthase respectively. A mutant mvaS gene, mvaS (A110G) with higher activity was used[45, 46]. Production plasmids were initially evaluated for mevalonate production in the control strain (FIG. 6B). The best producing plasmid was then introduced into a variety of engineered "Valve" strains and evaluated in micro-fermentations (FIG. 6C). A subset of statistically differentiated strains were then evaluated in 1 L fermentations to assess scalability (FIG. 6D), which, as in the case of alanine, was predictive. In some cases, a performing strain produced meaningful titers and yields, 97 g/L in 78 hrs of production with a yield of 0.46 g/g (84% of theoretical yield) (FIG. 6E). Specific productivity for this mevalonate strain is over 4-fold higher than the best previously reported results[47] (Supplemental Materials, Section 9).

Discussion

Historically some of the most successful efforts to metabolically engineer the production of small molecules have leveraged the power of anaerobic metabolism to couple product formation with growth. This has allowed for the classical design and selection of industrial strains to produce many products including ethanol, succinic acid, lactate and isobutanol, which have leveraged the power of evolution and selection to reach optimal metabolic fluxes in engineered networks[48, 49]_ENREF_12. While growth associated production is not strictly linked to anaerobic metabolism, growth association greatly limits the number and variety of different molecules that can be made using synthetic biology. A generic, robust and accessible non-growth associated platform would greatly simplify the optimization and scale up of a diverse number of products.

In contrast to most existing 2-stage processes, which have relied on natural metabolic responses to environmental triggers for production improvement, we have taken the next step in actively minimizing the essential metabolic network and redirecting metabolites to products of interest. Many of the targeted essential central metabolic pathways in this work have traditionally been off limits to engineering strategies, as deleting essential enzymes is incompatible with growth and growth associated production in traditional fermentation. The dynamically minimized metabolic network also results in enhanced robustness to environmental variables enabling the faithful translation of high-throughput small-scale studies to larger instrumented fermentations. A current paradigm in the field is to improve the throughput of relevant strain evaluations by developing small-scale, custom-designed micro-reactors for enhanced process control. In contrast, our approach is a move in a new direction involving engineering microbial metabolism to be less sensitive to process changes, simplifying high-throughput experimentation.

Beyond robustness, we have demonstrated that combinatorial modifications to essential enzymes in minimal metabolic networks can lead to significant improvements in production, particularly when compared to altering production pathway expression levels alone. These large variations in performance are due to changes in a limited subset of key central metabolic nodes, likely resulting in altered metabolite levels. Compared to previous approaches to dynamically control enzyme levels, we demonstrate improved potential for fine tuning of protein levels with a combination of gene silencing and proteolysis[50]. As stationary phase cells cannot dilute existing proteins with cell division, this dual approach makes sense. The specific control of the level of any given enzyme will of course also depend on natural turnover mechanisms. At first glance, it may still be surprising that the combination of both gene silencing and proteolysis together does not always result in improved performance, i.e. "more is not always better". Future efforts may be needed to explain these results, which could either be due to a requirement of maintaining minimal fluxes in the larger network or a consequence of changes in the levels of key regulatory metabolites that are not part of the minimal network, yet influence network activity.

While the approach as demonstrated can address many issues common to most bio-production processes, many product specific challenges remain. The toxicity of a product or pathway metabolite may limit titers or production rates. A minimal network that may be optimal at a low titer, may not be optimal at elevated titers. In addition, the engineering of improved enzymes is often a challenge in many "mg" to "kg" projects.

Feasibility of adapting this approach to other microbial hosts is expected. Key requirements for new hosts include a rapid and robust growth phase, the ability to engineer dynamic control over protein levels, and a metabolically active stationary phase. Numerous microbes have well characterized nutrient triggers for productive stationary phase metabolism[36], for example nitrogen limitation in Ralstonia species, Yarrowia species and others[51, 52]. Even when these requirements are not naturally met, they can be engineered into the host such as S. cerevisiae or other microbes, with each potential host presenting unique challenges and corresponding solutions.

Future efforts can be aimed at applying this platform for molecules with more complex production pathways. This approach can offer a tractable route for rapid optimization to metabolic engineers and synthetic biologists, who wish to move past POC levels and begin to tackle problems at more industrially relevant rates, titers and yields.

Methods

Reagents and Media

Unless otherwise stated, all materials and reagents were of the highest grade possible and purchased from Sigma (St. Louis, Mo.). C13 labeled Alanine (2,3-13C2, 99%) (Item #CLM-2734-PK) was purchased from Cambridge Isotope Laboratories, Inc. (Tewksbury, Mass.). Luria Broth was used for routine strain and plasmid propagation and construction. Working antibiotic concentrations were as follows: ampicillin (100 µg/mL), kanamycin (35 µg/mL), chloramphenicol (35 µg/mL), spectinomycin (100 µg/mL), zeocin (50 µg/mL), gentamicin (10 µg/mL), blasticidin (100 µg/mL), puromycin (150 µg/mL), tetracycline (5 µg/mL). Luria broth with low salt (Lennox formulation) was used to select for zeocin, blasticidin and puromycin resistant clones. In addition, for puromycin selection, phosphate buffer (pH=8.0) was added to LB Lennox to a final concentration of 50 mM. Media formulations including stock solutions are described in Supplemental Materials, Section 7.

E. coli Strain Construction

Oligonucleotides and synthetic linear DNA (Gblocks™) used for strain construction and confirmation are all given in Supplemental Materials, Section 3, and they were obtained from Integrated DNA Technologies (IDT, Coralville, Iowa). Strain BW25113 was obtained from the Yale Genetic Stock Center (CGSC http://cgsc.biology.yale.edu/). Strain BWapldf was a kind gift from George Chen (Tsinghua University)[62]. Chromosomal modifications were made using standard recombineering methodologies[63] either with direct antibiotic cassette integration in the case of C-terminal DAS+4 tags carrying antibiotic resistance cassettes, or through scarless tet-sacB selection and counterselection, strictly following the protocols of Li et al[64]. The recombineering plasmid pSIM5 and the tet-sacB selection/counterselection marker cassette were kind gifts from Donald Court (NCI, https://redrecombineering.ncifcrfigov/courtlab.html). Briefly, the tet-sacB selection/counterselection cassette was amplified using the appropriate oligos supplying ~50 bp flanking homology sequences using Econotaq (Lucigen Middleton, Wis.) according to manufacturer's instructions, with an initial 10 minutes denaturation at 94° C., followed by 35 cycles of 94° C., for 15 seconds, 52° C. for 15 seconds, and 72° C. for 5 minutes. Cassettes used for "curing" of the tet-sacB cassette or direct integration (when an antibiotic marker is present) were obtained as gBlocks from IDT. In the case of the sspB gene deletion, the open reading frame deletion replaced with a kanamycin resistance was amplified from the Keio Collection strain, JW3197-1[65], and moved to the appropriate background strain using standard methodologies. The kanamycin resistance cassette was cured using the pCP20 plasmid, leaving an frt scar[63, 65]. Chromosomal modifications were confirmed by PCR amplification and sequencing (Eton Biosciences) using paired oligonucleotides, either flanking the entire region, or in the case of DAS+4 tag insertions an oligo 5' of the insertion and one internal to the resistance cassette.

*E. coli* Plasmid Construction

Primers used for the design and construction of CAS-CADE guides arrays were listed in Supplemental Materials, Section 6. Gene silencing guide arrays were expressed from a series of pCASCADE plasmids. The pCASCADE-control plasmid was prepared by swapping the pTet promoter in perRNA. Tet[73] with an insulated low phosphate induced ugpB promoter[74]. Promoter sequences for all genes were obtained from EcoCyc database (https://ecocyc.org/). In order to design CASCADE guide array, CASCADE PAM sites near the −35 or −10 box of the promoter of interest were identified, 30 bp at the 3' end of PAM site was selected as the guide sequence and cloned into pCASCADE plasmid using Q5 site-directed mutagenesis (NEB, MA) following manufacturer's protocol, with the modification that 5% v/v DMSO was added to the Q5 PCR reaction. PCR cycles were as follows: amplification involved an initial denaturation step at 98° C. for 30 second followed by cycling at 98° C. for 10 second, 72° C. for 30 second, and 72° C. for 1.5 min (the extension rate was 30 second/kb) for 25 cycles, then a final extension for 2 min at 72° C. 2 μL of PCR mixture was used for 10 μL KLD reaction, which proceeded under room temperature for 1 hour, after which, 1 μL KLD mixture was used for electroporation.

The pCASCADE guide array plasmids were prepared by sequentially amplifying complementary halves of each smaller guide plasmid by PCR, followed by subsequent DNA assembly. The pCASCADE-control vector was used as template. pCASCADE plasmids with arrays of two or more guides were prepared using Q5 High-Fidelity 2× Master Mix (NEB, MA). PCR cycles were as follows: amplification involved an initial denaturation step at 98° C. for 30 second followed by cycling at 98° C. for 10 second, 66° C. for 30 second, and 72° C. for 45 second (the extension rate was 30 second/kb) for 35 cycles, then a final extension for 2 min at 72° C. PCR product was purified by gel-extraction, 20 μL ultrapure water was used to elute 50 μL PCR reaction purification. 1 μL of each eluted PCR product was used for 10 μL of Gibson Assembly (NEB, MA), which was completed by incubation at 50° C. for 15 min. 1 μL Gibson Assembly mix was used for electroporation.

Production pathways enzymes were expressed from high copy plasmids via low phosphate inducible promoters. Production pathway gene sequences were codon optimized using the Codon Optimization Tool from the IDT website, phosphorylated G-Blocks™ were designed and purchased from IDT for each pathway. Plasmids were assembled using NEBuilder® HiFi DNA Assembly Master Mix following manufacturer's protocol (NEB, MA). pSMART-HC-Kan (Lucigen, Wis.) was used as backbone for all pathway plasmids. All plasmid sequences were confirmed by DNA sequencing (Eton Bioscience, NC) and deposited with Addgene.

*E. coli* BioLector

Single colonies of each strain were inoculated into 5 mL LB with appropriate antibiotics and cultured at 37° C., 220 rpm for 9 hours or until OD600 reached >2. 500 μL of the culture was inoculated into 10 mL SM10 medium with appropriate antibiotics, and cultured in a square shake flask (CAT #: 25-212, Genesee Scientific, Inc. San Diego, Calif.) at 37° C., 220 rpm for 16 hours. Cells were pelleted by centrifugation and the culture density was normalized to OD600=5 using FGM3 media. Growth and fluorescence measurements were obtained in a Biolector (m2p labs, Baesweiler, Germany) using a high mass transfer Flower-Plate (CAT #: MTP-48-B, m2p-labs, Germany). 40 μL of the OD normalized culture was inoculated into 760 μL of FGM3 medium with appropriate antibiotics. Biolector settings were as follows: RFP gain=100, GFP gain=20, Biomass gain=20, shaking speed=1300 rpm, temperature=37° C., humidity=85%. Every strain was analyzed in triplicate.

*E. coli* Micro-Fermentations

Plasmids were transformed into host strains by electroporation using ECM 630 High Throughput Electroporation System (Harvard Apparatus, Inc. Holliston, Mass.) following manufacturer's protocol or using individual electroporation cuvettes. Glycerol stocks were prepared for each transformation plate by adding equal volume of sterile 20% glycerol, and 3 μL were used to inoculate overnight culture in 150 μL SM10++ medium with appropriate antibiotics. Plates were covered with sandwich covers (Model #CR1596 obtained from EnzyScreen, Haarlam, The Netherlands). These covers ensured minimal evaporative loss during incubation. Unless otherwise stated, 96 well plates were cultured at 37° C., 400 rpm for 16 hours, shaker orbit is 25 mm. This combination of orbit and minimal shaking speed is required to obtain needed mass transfer coefficient and enable adequate culture oxygenation.

After 16 hours of growth, cells were pelleted by centrifugation, excess media was removed and cells were resuspended in 150 μL of FGM3 Wash solution. Subsequently cells were once again pelleted and again excess media was removed, pellet was resuspended in 50 μL, FGM3 No Phosphate media containing appropriate antibiotics. 5 μL, of the resuspended culture was added to 195 μL, of water for OD600 measurement using standard flat bottom 96 well plate. OD600 for production was normalized to OD600=1, using FGM3 No Phosphate media containing appropriate antibiotics, in a total volume of 150 μL, using standard 96 well plate. Plates were covered with sandwich covers (Model #CR1596 obtained from EnzyScreen, Haarlam, The Netherlands) and 96 well plate cultures were incubated at 37° C., 400 rpm for 24 hours. After 24 hours of production, all samples from each well were pelleted by centrifugation and the supernatant collected for subsequent analytical measurement. Triplicate micro-fermentations were performed for each strain.

For growth associated alanine micro-fermentations, glycerol stock preparation and 16 hour overnight culture in SM10++ proceeded as described above. After 16 hours of growth in SM10++ medium, 5 μL of overnight culture was inoculated into 150 μL, FGM3 with 40 mM phosphate containing appropriate antibiotic. Plates were covered with sandwich covers (Model #CR1596 obtained from Enzy-Screen, Haarlam, The Netherlands) and 96 well plate cultures were incubated at 37° C., 400 rpm for 24 hours. After 24 hours of production, OD600 was recorded, all samples from each well were then pelleted by centrifugation and the supernatant collected for subsequent analytical measurement. Triplicate micro-fermentations were performed for each strain.

Micro-fermentation robustness evaluations were conducted as described in Supplemental Materials, Section 8.

1 L Fermentation Seeds

Single colony from transformation plate was inoculated into 5 mL LB with appropriate antibiotics and cultured at 37° C., 220 rpm for 16 hours. 500 µL, of the LB culture was inoculated into 50 mL SM10 media with appropriate antibiotics in square shake flask (CAT #: 25-214, Genesee Scientific, Inc. San Diego, Calif.), the culture was incubated at 37° C. with a shaking speed of 220 rpm for 24 hours, at which time OD600 is usually between 3 and 10, the culture was harvested by centrifugation at 4000 rpm for 15 min, supernatant was discarded and cell culture was normalized to OD600=10 using SM10 media. For 1 L fermentation seed, 6 mL of normalized OD600=10 culture was added to 1.5 mL of 50% glycerol in cryovials, and stored at −80° C.

1 L Fermentations

An Infors-HT Multifors (Laurel, Md., USA) parallel bioreactor system was used to perform 1 L fermentations, including three gas connection mass flow controllers configured for air, oxygen and nitrogen gases. Vessels used had a total volume of 1400 mL and a working volume of up to 1 L. Online pH and pO2 monitoring and control were accomplished with Hamilton probes. Offgas analysis was accomplished with a multiplexed Blue-in-One BlueSens gas analyzer (BlueSens. Northbrook, Ill., USA). Culture densities were continually monitored using Optek 225 mm OD probes, (Optek, Germantown, Wis., USA). The system used was running IrisV6.0 command and control software and integrated with a Seg-flow automated sampling system (Flownamics, Rodeo, Calif., USA), including FISP cell free sampling probes, a Segmod 4800 and FlowFraction 96 well plate fraction collector.

For the standardized 2-stage process with ~10 gcdw/L biomass, tanks were filled with 800 mL of FGM10 medium, with enough phosphate to target a final *E. coli* biomass concentration ~10 gcdw/L. Antibiotics were added as appropriate. Frozen seed vials were thawed on ice and 7.5 mL of seed culture was used to inoculate the tanks. After inoculation, tanks were controlled at 37° C. and pH 6.8 using 5 M ammonium hydroxide and 1 M hydrochloric acid as titrants. 10 M ammonium hydroxide was used for FIG. 3G fermentation run. The following oxygen control scheme was used to maintain the desired dissolved oxygen set point. First gas flow rate was increased from a minimum of 0.3 L/min of air to 0.8 L/min of air, subsequently, if more aeration was needed, agitation was increased from a minimum of 300 rpm to a maximum of 1000 rpm. Finally, if more oxygen was required to achieve the set point, oxygen supplementation was included using the integrated mass flow controllers. Starting glucose concentration was 25 g/L. A constant concentrated sterile filtered glucose feed (500 g/L) was added to the tanks at specified rate, i.e. 2 g/h, once agitation reached 800 rpm. In cases where feed rate or dissolved oxygen content needed to be varied for robustness study, changes were made after cells entered stationary phase. Fermentation runs were extended for up to ~50 hours after entry into stationary phase and samples automatically withdrawn every 3 hours. Samples were saved for subsequent analytical measurement.

In the case of growth associated fermentation processes, tanks were filled with 800 mL of FGM10 medium with 40 mM phosphate, which was in great excess and ensured phosphate depletion doesn't happen for growth associated fermentation processes. Antibiotics were added as appropriate. Frozen seed vials were thawed on ice and 7.5 mL of seed culture was used to inoculate the tanks. After inoculation, tanks were controlled at 37° C. and pH 6.8 using 5 M ammonium hydroxide and 1 M hydrochloric acid as titrants. The following oxygen control scheme was used to maintain the desired dissolved oxygen set point. First gas flow rate was increased from a minimum of 0.3 L/min of air to 0.8 L/min of air, subsequently, if more aeration was needed, agitation was increased from a minimum of 300 rpm to a maximum of 1000 rpm. Finally, if more oxygen was required to achieve the set point, oxygen supplementation was included using the integrated mass flow controllers. Starting glucose concentration was 25 g/L. A constant concentrated sterile filtered glucose feed (500 g/L) was added to the tanks at specified rate, i.e. 2 g/h, once agitation reached 800 rpm. Feed rate and dissolved oxygen concentration was set to desired values in the beginning, and maintained throughout the fermentation process. Fermentation runs were continued for up to ~50 hours and samples automatically withdrawn every 3 hours. Samples were saved for subsequent analytical analysis.

Analytical Methods

Sample standard curves for all compounds quantified are shown in Supplemental Materials, Section 10.

Glucose and Ethanol Quantification: A UPLC-RI method was developed for the simultaneous quantification of glucose and ethanol concentrations, using an Acquity H-Class UPLC integrated with a Waters 2414 Refractive Index (RI) detector (Waters Corp., Milford, Mass. USA). Chromatographic separation was performed using a Bio-Rad Fast Acid Analysis HPLC Column (100×7.8 mm, 9 µm particle size; CAT #: #1250100, Bio-Rad Laboratories, Inc., Hercules, Calif.) at 65° C. 5 mM sulfuric acid was used as the eluent. The isocratic elution was as follows: 0-0.1 min, flow rate increased from 0.4 mL/min to 0.42 mL/min, 0.1-12 min flow rate at 0.48 mL/min. Sample injection volume was 10 µL. UPLC method development was carried out using standard aqueous stock solutions of analytes. Peak integration and further analysis was performed using MassLynx v4.1 software. The linear range used for glucose was 1-10 g/L, for ethanol was 1-20 g/L. Samples were diluted as needed to be within the accurate linear range. Dilution was performed using ultrapure water.

Alanine Quantification: A reverse phase UPLC-MS/MS method was developed for alanine. Chromatographic separation was performed using a Restek Ultra AQ C18 column (150 mm×2.1 i.d., 3 µm; CAT #: 9178362, Restek Corporation, Bellefonte, Pa.) at 70° C. The following eluents were used: solvent A: $H_2O$, 0.2% formic acid and 0.05% ammonium (v/v); solvent B: MeOH, 0.2% formic acid and 0.05% ammonium (v/v). The gradient elution was as follows: 0-0.1 min isocratic 5% B, flow rate increased from 0.65 mL/min to 0.75 mL/min; 0.1-0.3 min, linear from 5% to 95% B at 0.75 mL/min; 0.3-0.9 min isocratic 95% B at 0.75 mL/min; and 0.9-1.2 min linear from 95% to 5% B at 0.75 mL/min; 1.2-1.3 min isocratic 5% B at 0.75 mL/min. Sample injection volume was 5 µL. UPLC method development was carried out using standard aqueous stock solutions of analyte. Separations were performed using an Acquity H-Class UPLC integrated with a Xevo™ TQD Mass spectrometer (Waters Corp., Milford, Mass. USA). MS/MS parameters including MRM transitions were tuned for each analyte and are listed in Table 22. Alanine (2,3-13C2, 99%) was used as internal standard for alanine at a concentration of 5 mg/L.

Peak integration and further analysis was performed using MassLynx v4.1 software. The linear range for alanine was 1-100 mg/L. Samples were diluted as needed to be within the accurate linear range. Dilution was performed using ultrapure water, and the final 10-fold dilution was performed using solvent A, with 5 mg/L of C13 alanine (2,3-13C2, 99%).

Mevalonic Acid Quantification: A reverse phase UPLC-TUV method was developed for the simultaneous quantification of mevalonic acid and mevalonolactone. Chromatographic separation was performed using a Restek Ultra AQ C18 column (150 mm×2.1 i.d., 3 µm; CAT #: 9178362, Restek Corporation, Bellefonte, Pa.) at 30° C. 20 mM phosphoric acid was used as the eluent. The isocratic elution was as follows: 0-3 min isocratic at 1 mL/min. Sample injection volume was 10 µL. Absorbance was monitored at 210 nm. UPLC method development was carried out using standard aqueous stock solutions of analytes. Separations were performed using an Acquity H-Class UPLC (Waters Corp., Milford, Mass. USA). Peak integration and further analysis was performed using MassLynx v4.1 software. The linear range for mevalonic acid and mevalonolactone were 0.01-0.1 g/L. Samples were diluted as needed to be within the accurate linear range. Mevalonic acid diluted in 20 mM phosphoric acid would spontaneously convert to mevalonolactone[80], thus, quantification of both mevalonic acid and mevalonolactone was necessary for fermentation samples. Mevalonic acid and mevalonolactone standards were prepared fresh each time, and ran immediately on UPLC. Dilution was performed using ultrapure water, and the final 10-fold dilution was performed using 20 mM phosphoric acid.

Alanine Stereoisomer Quantification: A reverse phase UPLC-TUV method was developed for the simultaneous quantification and differentiation of L-/D-alanine. Chromatographic separation was performed using a Chirex 3126 (D)-penicillamine column (150×4.6 mm, 5 µm; Phenomenex Inc., Torrance, Calif.) at 50° C. 2 mM Copper Sulfate was used as the eluent. The isocratic elution was as follows: 0-10 min at 0.75 mL/min. Sample injection volume was 10 µL. Absorbance was monitored at 254 nm. UPLC method development was carried out using standard aqueous stock solutions of analytes. Separations were performed using an Acquity H-Class UPLC (Waters Corp., Milford, Mass. USA). Peak integration and further analysis was performed using MassLynx v4.1 software. The linear range for L-/D-alanine was 0.1-1 g/L. Samples were diluted as needed to be within the accurate linear range. Dilution was performed using ultrapure water.

Supplemental Materials

TABLE 1

Combinatorial complexity of metabolic networks.

| Combination # | Entire E. coli Gene Network | Reduced Central Metabolism Network |
|---|---|---|
| | Number of Experiments | |
| 1 | 4500 | ~45 (Glycolysis, TCA, PPP and ETC genes only) |
| 2 | $1.0 \times 10^6$ | 990 |
| 3 | $1.5 \times 10^{10}$ | 14,190 |
| 4 | $1.7 \times 10^{13}$ | 148,995 |
| 5 | $1.5 \times 10^{16}$ | $1.2 \times 10^6$ |

Section 1: Phosphate Promoters

Figure 7:
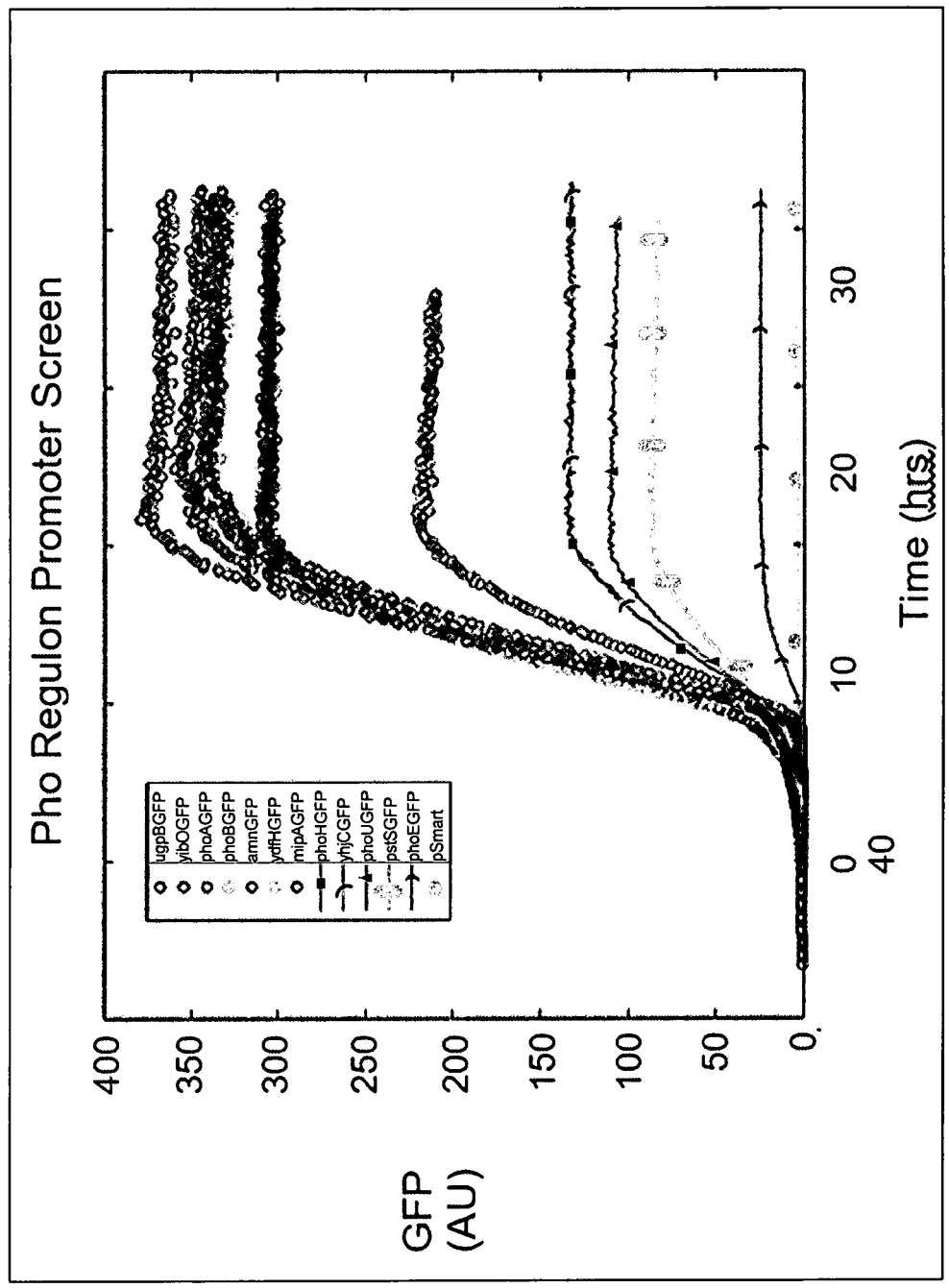
FIG. 7 depicts an example of phosphate depletion promoter characterization.

Phosphate promoter sequences were obtained from the EcoCyc database[81] for PhoB regulated promoters (https://ecocyc.org/, Table 2). We sought to evaluate not only the relative strength of promoters previously characterized to respond to phosphate depletion, but in addition the relative leakiness in phosphate rich conditions. To this aim we constructed a set of fluorescent reporter plasmids. We cloned the ultraviolet excitable GFPuv gene behind a set of 12 phosphate dependent promoters, in the pSMART-HC-Kan (Lucigen, Wis.) backbone. These reporter strains were evaluated in a 2-stage micro-fermentation protocol in an m2p-labs Biolector™. Results are illustrated in FIG. 7. The ugpB gene promoter was often chosen for high level tightly controlled expression when expression cassettes were chromosomally integrated or for the inducible expression of guide arrays.

Figure 8:
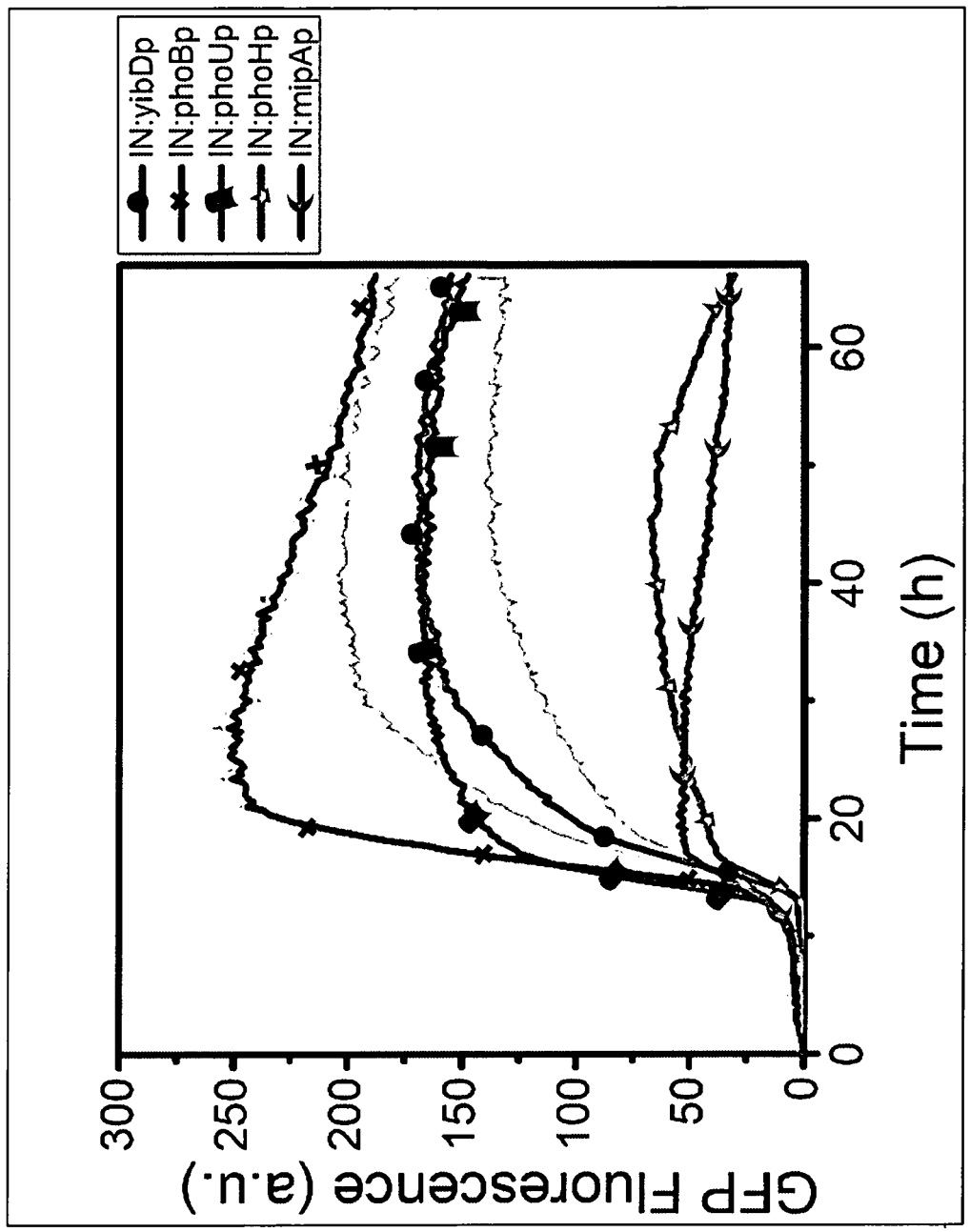
FIG. 8 depicts an example of insulated phosphate depletion promoter characterization.

Insulators[82] were added to both 5' and 3' end of a subset of phosphate promoters (Table 3) to help with consistent performance in different sequence contexts. To reduce read-through transcription, a unique terminator was added to the 5' end of each insulated promoter. Terminator sequences were from http://parts.igem.org/Terminators/Catalog. Insulated phosphate promoters were similarly characterized using GFPuv expression in a m2p-labs Biolector™ (FIG. 8).

TABLE 2

Phosphate inducible promoter sequences evaluated, the ribosomal binding site is underlined, and the start codon of the gene (GFPuv) is shown in bold text.

| Promoter Name | Sequence | SEQ ID NO |
|---|---|---|
| ugpBp | TCTTTCTGACACCTTACTATCTTACAAATGTA ACAAAAAAGTTATTTTTCTGTAATTCGAGCAT GTCATGTTACCCCGCGAGCATAAAACGCGTGT GT<u>AGGAGGA</u>TAATCTATG | 1 |
| yibDp | GTGCGTAATTGTGCTGATCTCTTATATAGCTG CTCTCATTATCTCTCTACCCTGAAGTGACTCT CTCACCTGTAAAAATAATATCTCACAGGCTTA ATAGTTTCTTAATACAAAGCCTGTAAAACGTC AGGATAACTTCTGTGT<u>AGGAGGA</u>TAATCTATG | 2 |
| phoAp | CGATTACGTAAAGAAGTTATTGAAGCATCCTC GTCAGTAAAAAGTTAATCTTTTCAACAGCTGT CATAAAGTTGTCACGGCCGAGACTTATAGTCG CTTTGTTTTTATTTTTAATGTATTTGTAGTG TAGGAGGATAATCTATGGCTAGCAAAGG<u>AGAA GAA</u>CTTTTCACATG | 3 |
| phoBp | GCCACGGAAATCAATAACCTGAAGATATGTGC GACGAGCTTTTCATAAATCTGTCATAAATCTG ACGCATAATGACGTCGCATTAATGATCGCAAC CTATTTATTGTGTAGGAGGATAATCTATGGCT AGCAAAG<u>GAGAAGAA</u>CTTTTCACATG | 4 |
| amnp | AGACAGTCAACGCGCTTGATAGCCTGGCGAAG ATCATCCGATCTTCGCCTTACACTTTTGTTTC ACATTTCTGTGACATACTATCGGATGTGCGGT AATTGTAT<u>AGGAGGA</u>TAATCTATG | 5 |
| ydfHp | GCTATGCCGGACTGAATGTCCACCGTCAGTAA TTTTTATACCCGGCGTAACTGCCGGGTTATTG CTTGTCACAAAAAAGTGGTAGACTCATGCAGT TAACTCACTGTGT<u>AGGAGGA</u>TAATCTATG | 6 |
| mipAp | CATCCATAAATTTTGCATAATTAATGTAAAGA CCAGGCTCGCCAGTAACGCTAAATTCATTTGG CTGTAAGCGCGGTGTCATCCGCGTCAGGAAAA TTAAACAGTTACTTTAAAAAATGAAAACGTAA AAAGGTTGGGTTTCGATGTATTGACGGGTAAA CTTTGTCGCCCGCTAAACATTTGTTTGTGT<u>AG GAGGA</u>TAATCTATG | 7 |

TABLE 2-continued

Phosphate inducible promoter sequences evaluated, the ribosomal binding site is underlined, and the start codon of the gene (GFPuv) is shown in bold text.

| Promoter Name | Sequence | SEQ ID NO |
|---|---|---|
| phoHp | AATCCTGCTGAAAGCACACAGCTTTTTTCATC ACTGTCATCACTCTGTCATCTTTCCAGTAGAA ACTAATGTCACTGAAATGGTGTTTTATAGTTA AATATAAGTAAATATATTGTTGCAATAAATGC GAGATCTGTTGTACTTATTAAGTAGCAGCGGA AGTTCGTGT<u>AGGAGGA</u>TAATCTATG | 8 |
| yhjCp | CTACAGAGATGACGTGTAGAAAATAGTTACCG ATATAAATAGTTACAGCTAAACGCCTGAAATT ACATGTCGAGGGCACTATTTAAAACAATTTTG AGGATTTCCTTATATTGGTGGTTAGTACGCAT GCAATTAAAAATGAAATTCCGCGACCACAAGC CAAAATAACAAACGGCAAGGAGACAAAAATAA GCACAAATAGCCAACACGTCCTCTGTTCACTT TAAAGGGAATCGCTGAAAAATACGCTCTGTTT AAGGGGATTCACCTTTCTCAGAAAGCTATTCC GCCCTTTTCCTGCTGAGAAATCGCCACATTCG GCATGACAACATTGTGAAAGTGT<u>AGGAGGA</u>TA ATCATG | 9 |
| phoUp | ACCGAACTGAAGCAGGATTACACCGTGGTGAT CGTCACCCACAACATGCAGCAGGCTGCGCGTT GTTCCGACCACACGGCGTTTATGTACCTGGGC GAATTGATTGAGTTCAGCAACACGGACGATCT GTTCACCAGTGT<u>AGGAGGA</u>TAATCTATG | 10 |
| pstSp | AAGACTTTATCTCTCTGTCATAAAACTGTCAT ATTCCTTACATATAACTGTCACCTGTTTGTCC TATTTTGCTTCTCGTAGCCAACAAACAATGCT TTATGAGTGTAGGAGGATAATCTATGGCTAGC AAAGG<u>AGAAGAA</u>CTTTTCACATG | 11 |
| phoEp | AGCATGGCGTTTTGTTGCGCGGGATCAGCAAG CCTAGCGGCAGTTGTTTACGCTTTTATTACAG ATTTAATAAATTACCACATTTTAAGAATATTA TTAATCTGTAATATATCTTTAACAATCTCAGG TTAAAAACTTTCCTGTTTTCAACGGGACTCTC CCGCTGGTGT<u>AGGAGGA</u>TAATCTATG | 12 |

TABLE 3

Insulated promoter sequences. Insulator sequences are italicized. -35 and -10 boxes are highlighted in bold and underlined.

| Insulated Promoter | Sequence | SEQ ID NO |
|---|---|---|
| BBa_B0015_IN_yibDp | CCAGGCATCAAATAAAACGAAAGGCTCAGTCGAAAGACTGGGCCTT TCGTTTTATCTGTTGTTTGTCGGTGAACGCTCTCTACTAGAGTCAC *ACTGGCTCACCTTCGGGTGGGCCTTTCTGCGTTTATACACAGCTAA CACCACGTCGTCCCTATCTGCTGCCCTAGGTCTATGAGTGGTTGCT* GGATAACGTGCGTAATTGTGCTGATCTCTTATATAGCTGCTCTCAT TATCTCTCTACCCTGAA<u>GTGACT</u>CTCTCACCTGTAAAATAATATC TCACAGGCT<u>TAATA</u>GTTTCTTAATACAAAGCCTGTAAAACGTCAGG ATAACTT*CTATATTCAGGGAGACCACAACGGTTTCCCTCTACAAAT AATTTTGTTTAACTTT* | 13 |
| BBa_B1002_IN_phoBp | *CGCAAAAAACCCCGCTTCGGCGGGGTTTTTTCGCACGTCTCCATCG CTTGCCCAAGTTGTGAAGCACAGCTAACACCACGTCGTCCCTATCT GCTGCCCTAGGTCTATGAGTGGTTGCTGGATAACGCCACGGAAATC* AATAACCTGAAGATATGTGCGACGAGCT<u>TTTCATA</u>AATCTGTCATA AATCTGACG<u>CATAAT</u>GACGTCGCATTAATGATCGCAACCTATTTAT TATATT*CAGGGAGACCACAACGGTTTCCCTCTACAAATAATTTTGT TTAACTTT* | 14 |
| BBa_B1004_IN_mipAp | *CGCCGAAAACCCCGCTTCGGCGGGGTTTTGCCGCACGTCTCCATCG CTTGCCCAAGTTGTGAAGCACAGCTAACACCACGTCGTCCCTATCT GCTGCCCTAGGTCTATGAGTGGTTGCTGGATAACCATCCATAAATT* TTGCATAATTAATGTAAAGACCAGGCTCGCCAGTAACGCTAAATTC ATTTGGCTGTAAGCGCGGTGTCATCCGCGTCAGGAAAATTAAACAG TTACTTTAAAAAATGAAAACGTAAA<u>AAGGTT</u>GGGTTTCGATGTATT GACGG<u>GTAAAC</u>TTTGTCGCCCGCTAAACATTTGTTTATATT*CAGGG AGACCACAACGGTTTCCCTCTACAAATAATTTTGTTTAACTTT* | 15 |
| BBa_B1006_IN_phoUp | *AAAAAAAACCCCGCCCCTGACAGGGCGGGGTTTTTTTACGTCTCTC CATCGCTTGCCCAAGTTGTGAAGCACAGCTAACACCACGTCGTCCC TATCTGCTGCCCTAGGTCTATGAGTGGTTGCTGGATAACACCGAAC TGAAGCAGGATTACACCGTGGTGATCGTCACCCACAACATGCAGCA GGCTGCGCGTTGTTCCGACCACA*<u>CGGCGT</u>TTATGTACCTGGGCGAA TT<u>GATTGA</u>GTTCAGCAACACGGACGATCTGTTCACCAATATT*CAGG GAGACCACAACGGTTTCCCTCTACAAATAATTTTGTTTAACTTT* | 16 |
| BBa_B1010_IN_phoHp | *CGCCGCAAACCCCGCCCCTGACAGGGCGGGGTTTCGCCGCACGTCT CCATCGCTTGCCCAAGTTGTGAAGCACAGCTAACACCACGTCGTCC CTATCTGCTGCCCTAGGTCTATGAGTGGTTGCTGGATAACAATCCT* GCTGAAAGCACACAGCTTTTTTCATCACTGTCATCACT<u>CTGTCA</u>TC TTTCCAGTAGAAA<u>TAATGT</u>CACTGAAATGGTGTTTTATAGTTAAA | 17 |

TABLE 3-continued

Insulated promoter sequences.
Insulator sequences are italicized. -35 and -10
boxes are highlighted in bold and underlined.

| Insulated Promoter | Sequence | SEQ ID NO |
|---|---|---|
|  | TATAAGTAAATATATTGTTGCAATAAATGCGAGATCTGTTGTACTT ATTAAGTAGCAGCGGAAGTT*CATATTCAGGGAGACCACAACGGTTT CCCTCTACAAATAATTTTGTTTAACTTT* |  |

Section 2: Constitutive Promoters

Figure 9:
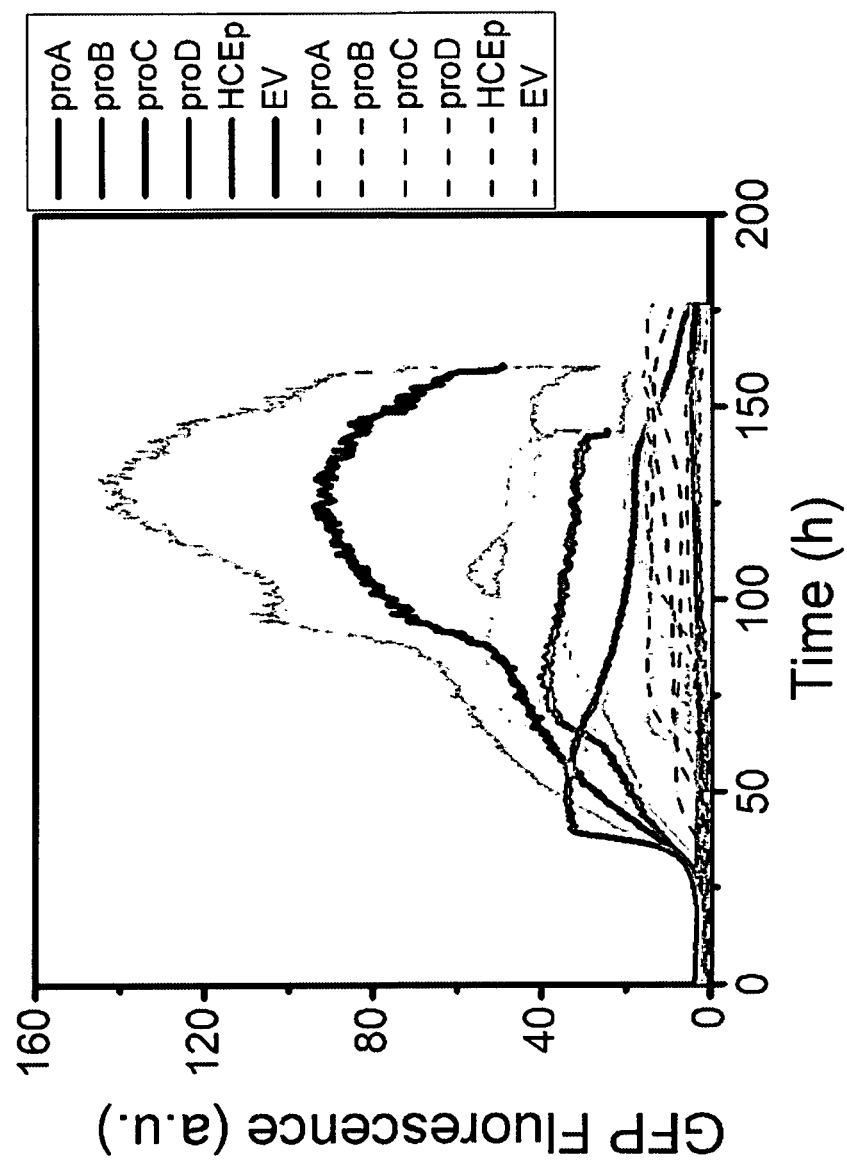
FIG. 9 depicts an example of insulated constitutive promoter characterization.

A set of constitutive insulated promoters of varying strength were used for constitutive expression and taken directly from Davis et al., including the proA, proB, proC, proD promoters[82] and HCEp promoter[83]. Insulator was added to 5' and 3' of HCEp promoter. Similar to insulated phosphate promoters, a unique terminator was added to the 5' end of constitutive promoters. These were used to drive constitutive pathway expression in growth associated production strains as well as to make strain modifications where constitutive heterologous gene expression was appropriate. These promoter sequences are given in Table 4 below and promoter characterized using GFPuv expression (FIG. 9).

TABLE 4

Constitutive promoter sequences.

| Promoter | Sequence | SEQ ID NO |
|---|---|---|
| BBa_B1004_proA | CGCCGAAAACCCCGCTTCGGCGGG GTTTTGCCGCACGTCTCCATCGCT TGCCCAAGTTGTGAAGCACAGCTA ACACCACGTCGTCCCTATCTGCTG CCCTAGGTCTATGAGTGGTTGCTG GATAACTTTACGGGCATGCATAAG GCTCGTAGGCTATATTCAGGGAGA CCACAACGGTTTCCCTCTACAAAT AATTTTGTTTAACTTT | 18 |
| BBa_B1006_proB | AAAAAAAAACCCCGCCCCTGACAG GGCGGGGTTTTTTTACGTCTCCA TCGCTTGCCCAAGTTGTGAAGCAC AGCTAACACCACGTCGTCCCTATC TGCTGCCCTAGGTCTATGAGTGGT TGCTGGATAACTTTACGGGCATGC ATAAGGCTCGTAATATATATTCAG GGAGACCACAACGGTTTCCCTCTA CAAATAATTTTGTTTAACTTT | 19 |
| BBa_B1010_proC | CGCCGCAAACCCCGCCCCTGACAG GGCGGGGTTTCGCCGCACGTCTCC ATCGCTTGCCCAAGTTGTGAAGCA CAGCTAACACCACGTCGTCCCTAT CTGCTGCCCTAGGTCTATGAGTGG | 20 |

TABLE 4-continued

Constitutive promoter sequences.

| Promoter | Sequence | SEQ ID NO |
|---|---|---|
|  | TTGCTGGATAACTTTACGGGCATG CATAAGGCTCGTATGATATATTCA GGGAGACCACAACGGTTTCCCTCT ACAAATAATTTTGTTTAACTTT |  |
| BBa_B1002_proD | CGCAAAAAACCCCGCTTCGGCGGG GTTTTTTCGCACGTCTCCATCGCT TGCCCAAGTTGTGAAGCACAGCTA ACACCACGTCGTCCCTATCTGCTG CCCTAGGTCTATGAGTGGTTGCTG GATAACTTTACGGGCATGCATAAG GCTCGTATAATATATTCAGGGAGA CCACAACGGTTTCCCTCTACAAAT AATTTTGTTTAACTTT | 21 |
| BBa_B0015_IN_HCEp | CCAGGCATCAAATAAAACGAAAGG CTCAGTCGAAAGACTGGGCCTTTC GTTTTATCTGTTGTTTGTCGGTGA ACGCTCTCTACTAGAGTCACACTG GCTCACCTTCGGGTGGGCCTTTCT GCGTTTATACACAGCTAACACCAC GTCGTCCCTATCTGCTGCCCTAGG TCTATGAGTGGTTGCTGGATAACC TCCTTCACAGATTCCCAATCTCTT GTTAAATAACGAAAAAGCATCAAT TAAAACCCATGTCTTTCTATATTC CAGCAATGTTTTATAGGGGACATA TTGATGAAGATGGGTATCACCTTA GTGAATTGCTATAAGCTGCTCTTT TTTGTTCGTGATATACTGATAAAT TGAATTTTCACACTTCATATTCAG GGAGACCACAACGGTTTCCCTCTA CAAATAATTTTGTTTAACTTT | 22 |

Section 3: Chromosomally Modified Host Strains

Figure 11:
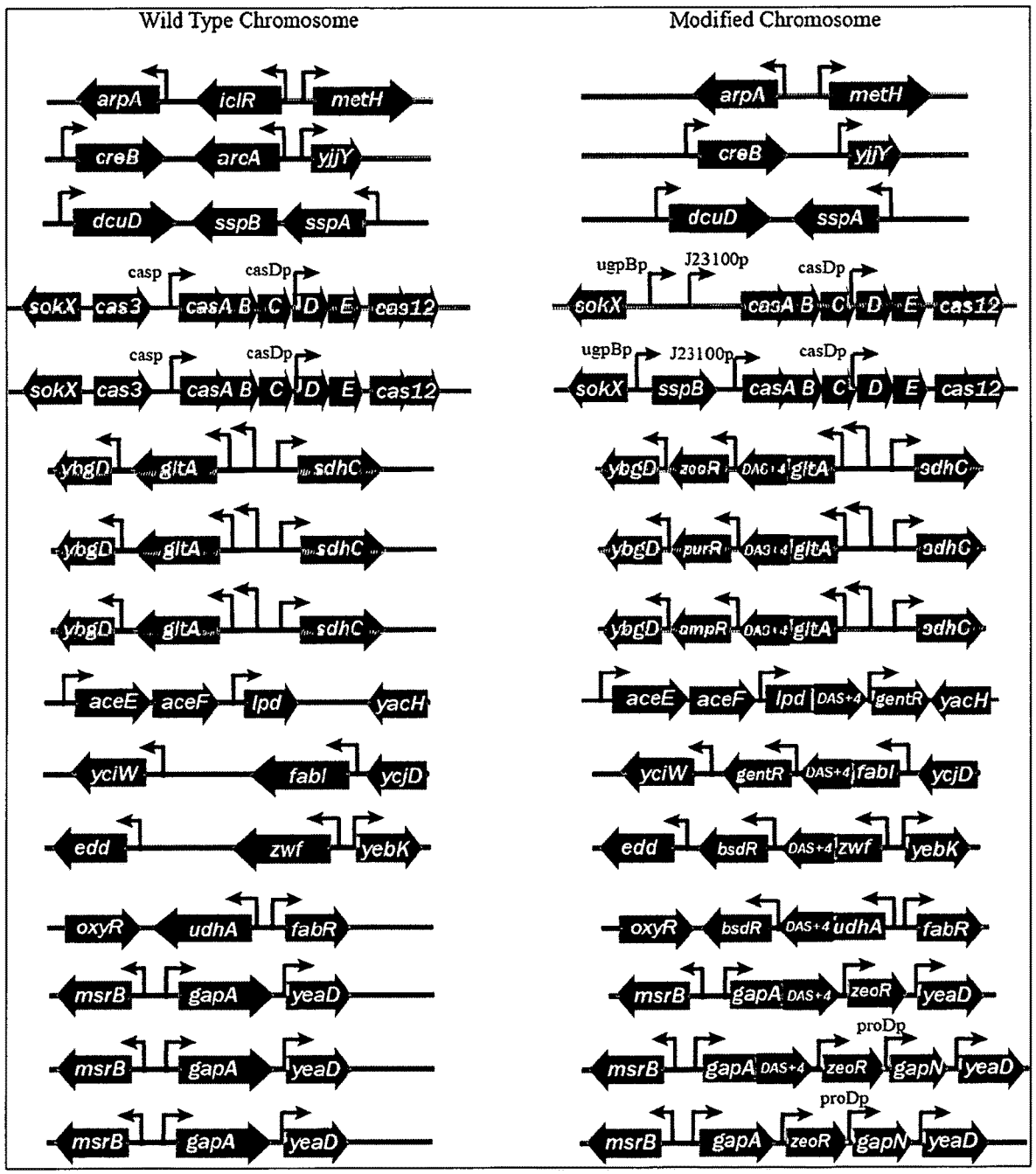
FIG. 11 depicts examples of chromosomal modifications.

FIG. 11 depicts each chromosomal modification. Strains utilized and/or constructed for this study are listed in Table 5. Tables 6 and 7 lists oligonucleotides and synthetic DNA sequences used for strain construction and/or confirmation. FIG. 12 and FIG. 13A-E show growth rates and glucose distribution during growth for control strains in 1 L fermentation.

TABLE 5

List of chromosomally modified strains.

| Strain | Genotype | Source |
|---|---|---|
| BW25113 (wt) | F-, λ-, Δ(araD-araB)567, lacZ4787(del)(::rrnB-3), rph-1, Δ(rhaD-rhaB)568, hsdR514 | CGSC |
| JW3197-1 | BW25113, sspB756(del)::kan | 53 |
| Bwapldf | BW25113, ΔackA-pta, ΔpoxB, ΔpflB, ΔldhA, ΔadhE | 39 |
| DLF_0001 | BWapldf, ΔiclR, ΔarcA | this study |
| DLF_0002 | BWapldf, ΔiclR, ΔarcA, ΔsspB:frt | this study |
| DLF_0025 | DLF_0002, Δcas3::tm-ugpb-sspB-pro-casA(N2S) | this study |
| DLF_0028 | DLF_0025, fabI-DAS + 4-gentR | this study |

TABLE 5-continued

List of chromosomally modified strains.

| Strain | Genotype | Source |
|---|---|---|
| DLF_0031 | DLF_0025, lpd-DAS + 4-gentR | this study |
| DLF_0038 | DLF_0025, fabI-DAS + 4-gentR, udhA-DAS + 4-bsdR | this study |
| DLF_0039 | DLF_0025, fabI-DAS + 4-gentR, gltA-DAS + 4-zeoR | this study |
| DLF_0040 | DLF_0025, fabI-DAS + 4-gentR, zwf-DAS + 4-bsdR | this study |
| DLF_0041 | DLF_0025, lpd-DAS + 4-gentR, gltA-DAS + 4-zeoR | this study |
| DLF_0042 | DLF_0025, lpd-DAS + 4-gentR, udhA-DAS + 4-bsdR | this study |
| DLF_0043 | DLF_0025, gltA-DAS + 4-zeoR | this study |
| DLF_0044 | DLF_0025, gltA-DAS + 4-zeoR, zwf-DAS + 4-bsdR | this study |
| DLF_0045 | DLF_0025, gltA-DAS + 4-zeoR, udhA-DAS + 4-bsdR | this study |
| DLF_0046 | DLF_0025, fabI-DAS + 4-gentR, gltA-DAS + 4-zeoR, zwf-DAS + 4-bsdR | this study |
| DLF_0047 | DLF_0025, fabI-DAS + 4-gentR, gltA-DAS + 4::zeoR, udhA-DAS + 4-bsdR | this study |
| DLF_0048 | DLF_0025, lpd-DAS + 4-gentR, gltA-DAS + 4-zeoR, zwf-DAS + 4-bsdR | this study |
| DLF_0049 | DLF_0025, lpd-DAS + 4-gentR, gltA-DAS + 4-zeoR, udhA-DAS + 4-bsdR | this study |
| DLF_0165 | DLF_0025, lpd-DAS + 4-gentR, zwf-DAS + 4-bsdR | this study |
| DLF_0763 | DLF_0025, udhA-DAS + 4-bsdR | this study |
| DLF_01002 | DLF_0025 zwf-DAS + 4-bsdR | this study |
| DLF_01517 | DLF_0012, Δcas3::pro-casA(N2S) | this study |
| DLF_01530 | DLF_0025, fabI-DAS + 4-gentR, udhA-DAS + 4-bsdR, zeoR-proDp-gapN-zeoR | this study |
| DLF_01531 | DLF_0025, fabI-DAS + 4-gentR, udhA-DAS + 4-bsdR, gltA-DAS + 4-purR | this study |
| DLF_01532 | DLF_0025, fabI-DAS + 4-gentR, udhA-DAS + 4-bsdR, gapA-DAS + 4-zeoR-proDp-gapN | this study |
| DLF_01533 | DLF_0025, fabI-DAS + 4-gentR, udhA-DAS + 4-bsdR, gapA-DAS + 4-zeoR-proDp-gapN, gltA-DAS + 4-purR | this study |
| DLF_01536 | DLF_0025, fabI-DAS + 4-gentR, udhA-DAS + 4-bsdR, zeoR-proDp-gapN, gltA-DAS + 4-purR | this study |
| DLF_01537 | DLF_0025, fabI-DAS + 4-gentR, udhA-DAS + 4-bsdR, gapA-DAS + 4-zeoR | this study |
| DLF_01538 | DLF_0025, fabI-DAS + 4-gentR, gltA-DAS + 4-zeoR, udhA-DAS + 4-bsdR, gapA-DAS + 4-zeoR | this study |

TABLE 6

Oligonucleotides utilized for strain construction.

| Oligo | Sequence | SEQ ID NO |
|---|---|---|
| ilcR_tetA_F | TAACAATAAAAATGAAAATGATTTCCACGATACAGAAAAAAGAGACTGTCATCCTAATTTTTGTTGACACTCTATC | 23 |
| ilcR_sacB_R | TGCCACTCAGGTATGATGGGCAGAATATTGCCTCTGCCCGCCAGAAAAAGATCAAAGGGAAAACTGTCCATATGC | 24 |
| iclR_500up | CCGACAGGGATTCCATCTG | 25 |
| iclR_500dn | TATGACGACCATTTGTCTACAGTTC | 26 |
| arcA_tetA_F | GGACTTTTGTACTTCCTGTTTCGATTTAGTTGGCAATTTAGGTAGCAAACTCCTAATTTTTGTTGACACTCTATC | 27 |
| arcA_sacB_R | ATAAAACGGCGCTAAAAAGCGCCGTTTTTTTGACGGTGGTAAAGCCGAATCAAAGGGAAAACTGTCCATATGC | 28 |
| arcA_500up | CCTGACTGTACTAACGGTTGAG | 29 |
| arcA_500dn | TGACTTTTATGGCGTTCTTTGTTTTTG | 30 |
| sspB_kan_F | CTGGTACACGCTGATGAACACC | 31 |
| sspB_kan_R | CTGGTCATTGCCATTTGTGCC | 32 |
| sspB_conf_F | GAATCAGAGCGTTCCGACCC | 33 |
| sspB_conf_R | GTACGCAGTTTGCCAACGTG | 34 |
| cas3_tetA_F | AATAGCCCGCTGATATCATCGATAATACTAAAAAAACAGGGAGGCTATTATCCTAATTTTTGTTGACACTCTATC | 35 |
| cas3_sacB_R | TACAGGGATCCAGTTATCAATAAGCAAATTCATTTGTTCTCCTTCATATGATCAAAGGGAAAACTGTCCATATGC | 36 |
| cas3_conf_F | CAAGACATGTGTATATCACTGTAATTC | 37 |
| cas3_500dn | GCGATTGCAGATTTATGATTTGG | 38 |
| fabI_conf_F | GCAAAATGCTGGCTCATTG | 39 |
| gapA_conf_F | GAACTGAATGGCAAACTGACTG | 40 |
| gapA_500dn | TGGGGATGATCGACCACA | 41 |

TABLE 6-continued

Oligonucleotides utilized for strain construction.

| Oligo | Sequence | SEQ ID NO |
|---|---|---|
| gltA_conf_F | TATCATCCTGAAAGCGATGG | 42 |
| lpd_conf_F | ATCTCACCGTGTGATCGG | 43 |
| udhA_conf_F | CAAAAGAGATTCTGGGTATTCACT | 44 |
| zwf_conf_F | CTGCTGGAAACCATGCG | 45 |
| zwf_500dn | AGAGCATGTCGTTATAGGAGGTGAT | 46 |
| ampR_intR | AGTACTCAACCAAGTCATTCTG | 47 |
| bsdR_intR | GAGCATGGTGATCTTCTCAGT | 48 |
| gentR_intR | GCGATGAATGTCTTACTACGGA | 49 |
| purR_intR | GTCGCTGGGTAATCTGCAA | 50 |
| tetA_intR | ATCAACGCATATAGCGCTAGCAG | 51 |
| zeoR_intR | ACTGAAGCCCAGACGATC | 52 |

TABLE 7

Synthetic DNA utilized for strain construction.

| | SEQ ID NO |
|---|---|
| tetA-sacB Cassette | |
| TCCTAATTTTTGTTGACACTCTATCATTGATAGAGTTATT<br>TTACCACTCCCTATCAGTGATAGAGAAAGTGAAATGAAT<br>AGTTCGACAAAGATCGCATTGGTAATTACGTTACTCGATG<br>CCATGGGGATTGGCCTTATCATGCCAGTCTTGCCAACGTT<br>ATTACGTGAATTTATTGCTTCGGAAGATATCGCTAACCAC<br>TTTGGCGTATTGCTTGCACTTTATGCGTAATGCAGGTTA<br>TCTTTGCTCCTTGGCTTGGAAAATGTCTGACCGATTTGG<br>TCGGCGCCCAGTGCTGTTGTTGTCATTAATAGGCGCATCG<br>CTGGATTACTTATTGCTGGCTTTTTCAAGTGCGCTTTGGA<br>TGCTGTATTTAGGCCGTTTGCTTTCAGGGATCACAGGAGC<br>TACTGGGGCTGTCGCGGCATCGGTCATTGCCGATACCACC<br>TCAGCTTCTCAACGCGTGAAGTGGTTCGGTTGGTTAGGGG<br>CAAGTTTTGGGCTTGGTTTAATAGCGGGGCCTTATTATTGG<br>TGGTTTTGCAGGAGAGATTTCACCGCATAGTCCCTTTTTT<br>ATCGCTGCGTTGCTAAATATTGTCACTTTCCTTGTGGTTA<br>TGTTTTGGTTCCGTGAAACCAAAAATACACGTGATAATAC<br>AGATACCGAAGTAGGGGTTGACGCAATCGAATTCGGTA<br>TACATCACTTTATTTAAAACGATGCCCATTTTGTTGATTA<br>TTTATTTTCAGCGCAATTGATAGGCCAAATTCCCGCAAC<br>GGTGTGGGTGCTATTTACCGAAAATCGTTTTGGATGGAAT<br>AGCATGATGGTTGGCTTTTCATTAGCGGGTCTTGGTCTTT<br>TACACTCAGTATTCCAAGCCTTTGTGGCAGGAAGAATAGC<br>CACTAAATGGGCGAAAAACGGCAGTACTGCTCGGATTT<br>ATTGCAGATAGTAGTGCATTTGCCTTTTTAGCGTTTATAT<br>CTGAAGGTTGGTTAGTTTTCCCTGTTTTAATTTTATTGGC<br>TGGTGGTGGGGATCGCTTTACCTGCATTACAGGGAGTGATG<br>TCTATCCAAACAAAGAGTCATCAGCAAGGTGCTTTACAGG<br>GATTATTGGTGAGCCTTACCAATGCAACCGGTGTTATTGG<br>CCCATTACTGTTTGCTGTTATTTATAATCATTCACTACCA<br>ATTTGGGATGGCTGGATTTGGATTATTGGTTTAGCGTTTT<br>ACTGTATTATTATCCTGCTATCGATGACCTTCATGTTAAC<br>CCCTCAAGCTCAGGGGAGTAAACAGGAGACAAGTGCTTAG<br>TTATTTCGTCACCAAATGATTTATTCCGCGAAATATAAT<br>GACCCTCTTGATAACCCAAGCATCACATATACCTGCCG<br>TTCACTATTATTAGTGAAATGAGATATTATGATATTTC<br>TGAATTGTGATTAAAAAGGCAACTTTATGCCCATGCAACA<br>GAAACTATAAAAAATACAGAGAATGAAAGAAACAGATAG<br>ATTTTTTAGTTCTTTAGGCCCGTAGTCTGCAAATCCTTTT | 53 |

TABLE 7-continued

Synthetic DNA utilized for strain construction.

| | SEQ ID NO |
|---|---|
| ATGATTTTCTATCAAACAAAAGAGGAAAATAGACCAGTTG<br>CAATCCAAACGAGAGTCTAATAGAATGAGGTCGAAAAGTA<br>AATCGCGCGGGTTGTTACTGATAAAGCAGGCAAGACCTA<br>AAATGTGTAAAGGGCAAAGTGTATACTTTGGCGTCACCCC<br>TTACATATTTTAGGTCTTTTTTTATTGTGCGTAACTAACT<br>TGCCATCTTCAAACAGGAGGGCTGGAAGAAGCAGACCGCT<br>AACACAGTACATAAAAAAGGAGACATGAACGATGAACATC<br>AAAAAGTTTGCAAACAAGCAACAGTATTAACCTTTACTA<br>CCGCACTGCTGGCAGGAGGCGCAACTCAAGCGTTTGCGAA<br>AGAAACGAACCAAAAGCCATATAAGGAAACATACGGCATT<br>TCCCATATTACACGCCATGATATGCTGCAAATCCCTGAAC<br>AGCAAAAAAATGAAAAATATCAAGTTCCTGAGTTCGATTC<br>GTCCACAATTAAAAATATCTCTTCTGCAAAAGGCCTGGAC<br>GTTTGGGACAGCTGGCCATTACAAAACGCTGACGGCACTG<br>TCGCAAACTATCACGGCTACCACATCGTCTTTGCATTAGC<br>CGGAGATCCTAAAAATGCGGATGACACATCGATTTACATG<br>TTCTATCAAAAAGTCGGCGAAACTTCTATTGACAGCTGGA<br>AAAACGCTGGCCGCGTCTTTAAAGACAGCGACAAATTCGA<br>TGCAAATGATTCTATCCTAAAAGACCAAACACAAGAATGG<br>TCAGGTTCAGCCACATTTACATCTGACGGAAAAATCCGTT<br>TATTCTACACTGATTTCTCCGGTAAACATTACGGCAAACA<br>AACACTGACAACTGCACAAGTTAACGTATCAGCATCAGAC<br>AGCTCTTTGAACATCAACGGTGTAGAGGATTATAAATCAA<br>TCTTTGACGGTGACGGAAAAACGTATCAAATGTACAGCA<br>GTTCATCGATGAAGGCAACTACAGCTCAGGCGACAACCAT<br>ACGCTGAGAGATCCTCACTACGTAGAAGATAAAGGCCACA<br>AATACTTAGTATTTGAAGCAAACACTGGAACTGAAGATGG<br>CTACCAAGGCGAAGAATCTTATTTAACAAAGCATACTAT<br>GGCAAAAGCACATCATTCTTCCGTCAAGAAAGTCAAAAAC<br>TTCTGCAAAGCGATAAAAAACGCACGGCTGAGTTAGCAAA<br>CGGCGCTCTCGGTATGATTGAGCTAAACGATGATTACACA<br>CTGAAAAAAGTGATGAAACGCTGATTGCATCTAACACAG<br>TAACGATGAAATTGAACGCGCGAACGTCTTTAAAATGAA<br>CGGCAAATGGTACCTGTTCACTGACTCCCGCGGATCAAAA<br>ATGACGATTGACGGCATTACGTCTAACGATATTTACATGC<br>TTGGTTATGTTTCTAATTCTTTAACTGGCCCATACAAGCC<br>GCTGAACAAACTGGCCTTGTGTTAAAATGGATCTTGAT<br>CCTAACGATGTAACCTTTACTTACTCACACTTCGCTGTAC<br>CTCAAGCGAAAGGAAACAATGTCGTGATTACAAGCTATAT<br>GACAAACAGAGGATTCTACGCAGACAAACAATCAACGTTT<br>GCGCCAAGCTTCCTGCTGAACATCAAAGGCAAGAAAACAT<br>CTGTTGTCAAAGACAGCATCCTTGAACAAGGACAATTAAC<br>AGTTAACAAATAAAAACGCAAAGAAAATGCCGATATTGA<br>CTACCGGAAGCAGTGTGACCGTGTGCTTCTCAAATGCCTG<br>ATTCAGGCTGCTATGTGACTGTTGAGCTGTAACAAGT<br>TGTCTCAGGTGTTCAATTTCATGTTCTAGTTGCTTTGTTT<br>TACTGGTTTCACCTGTTCTATTAGGTGTTACATGCTGTTC<br>ATCTGTTACATTGTCGATCTGTTCATGGTGAACAGCTTTA<br>AATGCACCAAAAACTCGTAAAAGCTCTGATGTATCTATCT<br>TTTTTACACCGTTTTCATCTGTGCATATGGACAGTTTTCC<br>CTTTGAT | |
| ΔiclR-cure | |
| AAATGATTTCCACGATACAGAAAAAAGAGACTGTCATGGG<br>CAGAATATTGCCTCTGCCCGCCAGAAAAAG | 54 |
| ΔarcA-cure | |
| CTGTTTCGATTTAGTTGGCAATTTAGGTAGCAAACTCGGC<br>TTTACCACCGTCAAAAAAAACGGCGCTTTT | 55 |
| Δcas3-pro-casA | |
| CAAGACATGTGTATATCACTGTAATTCGATATTTATGAGC<br>AGCATCGAAAAATAGCCCGCTGATATCATCGATAATACTA<br>AAAAACAGGGAGGCTATTACCAGGCATCAAATAAAACGA<br>AAGGCTCAGTCGAAAGACTGGGCCTTTCGTTTTATCTGTT<br>GTTTGTCGGTGAACGCTCTCTACTAGAGTCACACTGGCTC<br>ACCTTCGGGTGGGCCTTTCTGCGTTTATATCTTTCTGACA<br>CCTTACTATCTTCAAATGTAACAAAAAAGTTATTTTTCT<br>GTAATTCGAGCATGTCATGTTACCCCGCGAGCATAAAACG<br>CGTGTGTAGGAGGATAATCTTTGACGGCTAGCTCAGTCCT<br>AGGTACAGTGCTAGCCATATGAAGGAGAACAAATGAATTT | 56 |

TABLE 7-continued

Synthetic DNA utilized for strain construction.

| | SEQ ID NO |
|---|---|
| GCTTATTGATAACTGGATCCCTGTACGCCCGCGAAACGGG
GGGAAAGTCCAAATCATAAATCTGCAATCGCTATAC | |

Δcas3::ugBp-sspB-pro-casA

| | |
|---|---|
| CAAGACATGTGTATATCACTGTAATTCGATATTTATGAGC
AGCATCGAAAAATAGCCCGCTGATATCATCGATAATACTA
AAAAAACAGGGAGGCTATTACCAGGCATCAAATAAAACGA
AAGGCTCAGTCGAAAGACTGGGCCTTTCGTTTTATCTGTT
GTTTGTCGGTGAACGCTCTCTACTAGAGTCACACTGGCTC
ACCTTCGGGTGGGCCTTTCTGCGTTTATATCTTTCTGACA
CCTTACTATCTTACAAATGTAACAAAAAAGTTATTTTTCT
GTAATTCGAGCATGTCATGTTACCCCGCGAGCATAAAACG
CGTGTGTAGGAGGATAATCTATGGATTTGTCACAGCTAAC
ACCACGTCGTCCCTATCTGCTGCGTGCATTCTATGAGTGG
TTGCTGGATAACCAGCTCACGCCCGCACCTGGTGGTGGATG
TGACGCTCCCTGGCGTGCAGGTTCCTATGGAATATGCGCG
TGACGGGCAAATCGTACTCAACATTGCGCCGCGTGCTGTC
GGCAATCTGGAACTGGCGAATGATGAGGTGCGCTTTAACG
CGCGCTTTGGTGGCATTCGCGCTCAGGTTTCTGTGCCGCT
GGCTGCCGTGCTGGCTATCTACGCCCGTGAAAATGGCGCA
GGCACGATGTTTGAGCCTGAAGCTGCCTACGATGAAGATA
CCAGCATCATGAATGATGAAGAGGCATCGGCAGACAACGA
AACCGTTATGTCGGTTATTGATGGCGACAAGCCAGATCGC
GATGATGACACTCATCCTGACGATGAACCTCCGCAGCCAC
CACGCGGTGGTCGACCGGCATTACGCGTTGTGAAGTAATT
GACGGCTAGCTCAGTCCTAGGTACAGTGCTAGCCATATGA
AGGAGACAAATGAATTTGCTTATTGATAACTGGATCCCT
GTACGCCCGCGAAACGGGGGGAAAGTCCAAATCATAAATC
TGCAATCGCTATAC | 57 | fabI-DAS+4-gentR

| | |
|---|---|
| CTATTGAAGATGTGGGTAACTCTGCGGCATTCCTGTGCTC
CGATCTCTCTGCCGGTATCTCCGGTGAAGTGGTCCACGTT
GACGGCGGTTTCAGCATTGCTGCAATGAACGAACTCGAAC
TGAAAGCGGCCAACGATGAAAACTATTCTGAAAACTATGC
GGATGCGTCTTAATAGGAAGTTCCTATTCTCTAGAAAGTA
TAGGAACTTCCGAATCCATGTGGGAGTTTATTCTTGACAC
AGATATTTATGATAATAACTGAGTAAGCTTAACATAAG
GAGGAAAAACATATGTTACGCAGCAGCAACGATGTTACGC
AGCAGGGCAGTCGCCCTAAAACAAAGTTAGGTGGCTCAAG
TATGGGCATCATTCGCACATGTAGGCTCGGCCCTGACCAA
GTCAAATCCATGCGGGCTGCTCTTGATCTTTTCGGTCGTG
AGTTCGGAGACGTAGCCACCTACTCCCAACATCAGCCGGA
CTCCGATTACCTCGGGAACTTGCTCCGTAGTAAGACATTC
ATCGCGCTTGCTGCCTTCGACCAAGAAGCGGTTGTTGGCG
CTCTCGCGGCTTACGTTCTGCCCAAGTTTGAGCAGCCGCG
TAGTGAGATCTATATCTATGATCTCGCAGTCTTCCGGCGAG
CACCGGAGGCAGGGCATTGCCACCGCGCTCATCAATCTCC
TCAAGCATGAGGCCAACGCGCTTGGTGCTTATGTGATCTA
CGTGCAAGCAGATTACGGTGACGATCCCGCAGTGGCTCTC
TATACAAAGTTGGGCATACGGGAAGAAGTGATTGCACTTTG
ATATCGACCCAAGTACCGCCACCTAAGAAGTTCCTATTCT
CTAGAAAGTATAGGAACTTCCGTTCTGTTGGTAAAGATGG
GCGGCGTTCTGCCGCCCGTTATCTCTGTTATACCTTTCTG
ATATTTGTTATCGCCGATCCGTCTTTCTCCCCTTCCCGCC
TTGCGTCAGG | 58 | gapA-DAS+4-zeoR-proDp-gapN

| | |
|---|---|
| TCTCCAAAGCGGCCAACGATGAAAACTATTCTGAAAACTA
TGCGGATGCGTCTTGATTGACAGCTAGCTCAGTCCTAGGT
ATAATGCTAGCAACTTTAAAATTAAAGAGGTATATATTAA
TGACTAAGCAATATAAGAATTACGTAAATGGGGAGTGGAA
GCTTTCGGAGAATGAAATTAAGATCTATGAACCAGCCAGT
GGGGCGGAATTGGGGTCAGTCCCGGCAATGTCCACTGAAG
AAGTTGACTATGTCTACGCCTCGGCCAAAAAAGCGCAGCC
AGCATGGCGCTCGCTTTCCTATATTGAGCGTGCGGCTTAT
TTGCACAAAGTCGCAGACATCCTGATGCGTGACAAGGAGA
AAATTGGAGCGGTATTGTCCAAGGAAGTAGCGAAAGGCTA
CAAATCCGCAGTATCGGAGGTCGTCCGCACCGCCGAGATT
ATTAATTATGCGGCCGAAGAAGGGCTTCGCATGGAGGGTG
AGGTCTTGGAGGGCGGCAGTTTTGAGGCGGCATCCAAGAA
AAAAATCGCTGTCGTCCGTCGCGAGCCGGTGGGACTTGTG | 59 | gapA-zeoR-proDp-gapN

| | |
|---|---|
| ACGAAACCGGTTACTCCAACAAAGTTCTGGACCTGATCGC
TCACATCTCCAATGATTGACAGCTAGCTCAGTCCTAGGT
ATAATGCTAGCAACTTTAAAATTAAAGAGGTATATATTAA
TGACTAAGCAATATAAGAATTACGTAAATGGGGAGTGGAA
GCTTTCGGAGAATGAAATTAAGATCTATGAACCAGCCAGT
GGGGCGGAATTGGGGTCAGTCCCGGCAATGTCCACTGAAG
AAGTTGACTATGTCTACGCCTCGGCCAAAAAAGCGCAGCC
AGCATGGCGCTCGCTTTCCTATATTGAGCGTGCGGCTTAT
TTGCACAAAGTCGCAGACATCCTGATGCGTGACAAGGAGA
AAATTGGAGCGGTATTGTCCAAGGAAGTAGCGAAAGGCTA
CAAATCCGCAGTATCGGAGGTCGTCCGCACCGCCGAGATT
ATTAATTATGCGGCCGAAGAAGGGCTTCGCATGGAGGGTG
AGGTCTTGGAGGGCGGCAGTTTTGAGGCGGCATCCAAGAA
AAAAATCGCTGTCGTCCGTCGCGAGCCGGTGGGACTTGTG
CTTGCTATTAGTCCGTTCAATTACCCCGTGAATCTGGCCG
GCTCCAAGATTGCCCCTGCACTGATCGCGGGCAATGTAAT
CGCTTTTAAACCACCGACCCAAGGATCGATTAGTGGACTT
CTTTTAGCGGAGGCGTTTGCGGAGGCAGGTCTTCCAGCCG
GCGTATTCAATACCATCACGGGGCGTGGAAGTGAAATCGG
GGATTACATCGTGGAGCACCAGGCAGTAAATTTCATCAAC
TTCACGGGTTCCACGGGGATCGGGGAGCGTATCGGTAAGA
TGGCTGGGATGCGTCCGATCATGTTGGAACTTGGCGGCAA
GGATAGTGCGATTGTGCTGGAAGACGCAGACTTGGAATTG
ACAGCTAAAACATTATCGCTGGAGCCTTCGGGTATAGTG
GTCAACGTTGCACGGCAGTTAAGCGCGTTCTTGTTATGGA
AAGTGTCGCGGATGAATTGGTCGAGAAGATTCGCGAGAAA
GTGTTAGCTCTTACGATTGGAAATCCAGAGGACGATGCTG
ACATCACTCCATTGATCGACACGAAATCCGCGGATTACGT
CGAGGGGCTGATCAACGACGCGAACGATAAGGGAGCAGCG
GCTTTGACCGAGATCAAACGCGAGGGGAACCTGATCTGCC
CGATTCTTTTTGACAAAGTCACAACTGACATGCGCTTGGC
ATGGGAAGAACCCTTCGGCCCAGTCTTGCCTATTATCCGC
GTTACTAGCGTAGAGGAAGCAATTGAAATTTCCAATAAAT
CCGAATATGGGTTGCAAGCGAGTATCTTTACTAACGATTT
TCCACGTGCCTTTGGTATTGCGAACAGTTAGAAGTCGGG
ACAGTTCACATCAACAACAAGACGCAGCGCGGGACAGATA
ACTTCCCCTTTTTGGGAGCAAAGAAGTCTGGGCTGGAAT
CCAAGGGTGAAATACTCCATCGAAGCATGACGACGGTG
AAGAGCGTTGTTTTTGACATCAAGTAAAACATAAGGAGGA
AAAACAGATGGCGAAACTGACCTCGGCGGTTCCGGTTCTG
ACGGCACGTGATGTGGCGGGCGCGGTTGAATTTTGGACGG
ATCGTCTGGGCTTCAGTCGTGATTTTGTGGAAGATGACTT
CGCAGGCGTGGTTCGCGATGACGTCACCCTGTTTATTTCC
GCAGTTCAGGATCAAGTCGTGCCGGACAACACGCTGGCTT
GGGTGTGGGTTCGTGGCCTGGATGAACTGTATGCGGAATG
GAGCGAAGTTGTCTCTACCAATTTCCGTGACGCGAGCGGT
CCGGCCATGACGGAAATCGGCGAACGCGTGGGCTGCG
AATTTGCTCTGCGTGACCCGGCTGGCAACTGTGTCCATTT
CGTGGCTGAAGAACAAGATTGAGTTGAGATGACACTGTGA
TCTAAAAGAGCGACTTCGGTCGCTCTTTTTTTTACCTGA | 60 |

TABLE 7-continued

Synthetic DNA utilized for strain construction.

| | SEQ ID NO |
|---|---|
| ACTTCCCCTTTTTGGGAGCAAAGAAGTCTGGGGCTGGAAT CCAAGGGGTGAAATACTCCATCGAAGCCATGACGACGGTG AAGAGCGTTGTTTTTGACATCAAGTAAAACATAAGGAGGA AAAACAGATGGCGAAACTGACCTCGGCGGTTCCGGTTCTG ACGGCACGTGATGTGGCGGGCGCGGTTGAATTTTGGACGG ATCGTCTGGGCTTCAGTCGTGATTTTGTGGAAGATGACTT CGCAGGCGTGGTTCGCGATGACGTCACCCTGTTTATTTCC GCAGTTCAGGATCAAGTCGTGCCGGACAACACGCTGGCTT GGGTGTGGGTTCGTGGCCTGGATGAACTGTATGCGGAATG GAGCGAAGTTGTCTCTACCAATTTCCGTGACGCGAGCGGT CCGGCCATGACGGAAATCGGCGAACAGCCGTGGGGTCGCG AATTTGCTCTGCGTGACCCGGCTGGCAACTGTGTCCATTT CGTGGCTGAAGAACAAGATTGAGTTGAGATGACACTGTGA TCTAAAAAGAGCGACTTCGGTCGCTCTTTTTTTTACCTGA | |
| gapA-DAS+4-zeoR | |
| TCTACCGATTTCAACGGCGAAGTTTGCACTTCCGTGTTCG ATGCTAAAGCTGGTATCGCTCTGAACGACAACTTCGTGAA ACTGGTATCCTGGTACGACAACGAAACCGGTTACTCCAAC AAAGTTCTGGACCTGATCGCTCACATCTCCAAAGCGGCCA ACGATGAAAACTATTCTGAAAACTATGCGGATGCGTCTTG ATCCTGACGGATGGCCTTTTTGCGTTTCTACAAACTCTTT TTGTTTATTTTTCTAAATACATTCAAATATGTATCCGCTC ATGAGACAATAACCCTGATAAATGCTTCAATAATATTGAA AAAGGAAGAGTAATGGCGAAACTGACCTCGGCGGTTCCGG TTCTGACGGCACGTGATGTGGCGGGCGCGGTTGAATTTTG GACGGATCGTCTGGGCTTCAGTCGTGATTTTGTGGAAGAT GACTTCGCAGGCGTGGTTCGCGATGACGTCACCCTGTTTA TTTCCGCAGTTCAGGATCAAGTCGTGCCGGACAACACGCT GGCTTGGGTGTGGGTTCGTGGCCTGGATGAACTGTATGCG GAATGGAGCGAAGTTGTCTCTACCAATTTCCGTGACGCGA GCGGTCCGGCCATGACGGAAATCGGCGAACAGCCGTGGGG TCGCGAATTTGCTCTGCGTGACCCGGCTGGCAACTGTGTC CATTTCGTGGCTGAAGAACAAGATTGAGTTGAGATGACAC TGTGATCTAAAAGAGCGACTTCGGTCGCTCTTTTTTTTA CCTGATAAATGAAGTTAAAGGACTGCGTCATGATTAAGA AAATTTTTGCCCTTCCGGTCATCGAACAAATCTCCCCTGT CCTCTCCCGTCGTAAACTGGATGAACTGGACCTCATTGTG GTCGATCATCCCCAGGTAAAAGCCTCT | 61 |
| gltA-DAS+4-ampR | |
| GTATTCCGTCTTCCATGTTCACCGTCATTTTCGCAATGGC ACGTACCGTTGGCTGGATCGCCCACTGGAGCGAAATGCAC AGTGACGGTATGAAGATTGCCCGTCCGCGTCAGCTGTATA CAGGATATGAAAACGCGACTTTAAAAGCGATATCAAGCG TGCGGCCAACGATGAAAACTATTCTGAAAACTATGCGGAT GCGTCTTAATAGTCCTGACGGATGGCCTTTTTGCGTTTCT ACAAACTCTTTTTGTTTATTTTTCTAAATACATTCAAATA TGTATCCGCTCATGAGACAATAACCCTGATAAATGCTTCA ATAATATTGAAAAAGGAAGAGTATGAGTATTCAACATTTC CGTGTCGCCCTTATTCCCTTTTTTGCGGCATTTTGCCTTC CTGTTTTTGCTCACCCAGAAACGCTGGTGAAAGTAAAAGA TGCTGAAGATCAGTTGGGTGCACGAGTGGGTTACATCGAA CTGGATCTCAACAGCGGTAAGATCCTTGAGAGTTTTCGCC CCGAAGAACGTTTTCCAATGATGAGCACTTTTAAAGTTCT GCTATGTGGCGCGGTATTATCCCGTGTTGACGCCGGGCAA GAGCAACTCGGTCGCCGCATACACTATTCTCAGAATGACT TGGTTGAGTACTCACCAGTCACAGAAAAGCATCTTACGGA TGGCATGACAGTAAGAGAATTATGCAGTGCTGCCATAACC ATGAGTGATAACACTGCGGCCAACTTACTTCTGACAACGA TCGGAGGACCGAAGGAGCTAACCGCTTTTTTGCACAACAT GGGGGATCATGTAACTCGCCTTGATCGTTGGGAACCGGAG CTGAATGAAGCCATACCAAACGACGAGCGTGACACCACGA TGCCTACAGCAATGGCAACAACGTTGCGCAAACTATTAAC TGGCGAACTACTTACTCTAGCTTCCCGGCAACAATTAATA GACTGGATGGAGGCGGATAAAGTTGCAGGACCACTTCTGC GCTCGGCCCTTCCGGCTGGCTGGTTTATTGCTGATAAATC TGGAGCCGGTGAGCGTGGGTCTCGCGGTATCATTGCAGCA CTGGGGCCAGATGGTAAGCCCTCCCGTATCGTAGTTATCT ACACGACGGGGAGTCAGGCAACTATGGATGAACGAAATAG ACAGATCGCTGAGATAGGTGCCTCACTGATTAAGCATTGG TAACTGTCAGACTAATGGTTGATTGCTAAGTTGTAAATAT TTTAACCCGCCGTTCATATGGCGGGTTGATTTTTATATGC | 62 |
| | SEQ ID NO |
|---|---|
| CTAAACACAAAAAATTGTAAAAATAAAATCCATTAACAGA CCTATATAGATATTTAAAAAGAATAGAACAGCTCAAATTA TCAGCAACCCAATACTTTCAATTAAAAACTTCATGGTAGT CGCATTTATAACCCTATGAAA | |
| gltA-DAS+4-purR | |
| ACCGTCATTTTCGCAATGGCACGTACCGTTGGCTGGATCG CCCACTGGAGCGAAATGCACAGTGACGGTATGAAGATTGC CCGTCCGCGTCAGCTGTATACAGGATATGAAAAACGCGAC TTTAAAAGCGATATCAAGCGTGCGGCCAACGATGAAAACT ATTCTGAAAACTATGCGGATGCGTCTTAATCCTGACGGAT GGCCTTTTTGCGTTTCTACAAACTCTTTTTGTTTATTTTT CTAAATACATTCAAATATGTATCCGCTCATGAGACAATAA CCCTGATAAATGCTTCAATAATATTGAAAAAGGAAGAGTA TGACTGAATACAAGCCCACGGTACGCTTGGCGACGCGCGA CGATGTTCCCCGCGCTGTTCGTACATTAGCTGCGGCCTTT GCAGATTACCCAGCGACGCGCCATACGGTCGATCCGGACC GCCATATCGAGCGTGTCACAGAATTGCAGGAACTTTTCTT AACTCGTGGGCTTGACATCGGAAAGGTCTGGGTGGCT GACGATGGCTGCAGTGGCTGTTTGGACCACTCCGGAGA GTGTAGAGGCTGGTGCAGTGTTCGCCGAAATTGGTCCTCG TATGGCCGAATTAAGTGGAAGTCGTCTGGCAGCCCAACAA CAAATGGAAAGGGTTGCTTGCGCCCCACCGTCCGAAAGAAC CCGCGTGGTTCCTTGCCACCGTTGGAGTAAGCCCAGATCA CCAGGGGAAGGGTTTAGGATCTGCCGTAGTTTTACCAGGT GTGGAGGCAGCAGAACGTGCGGGAGTTCCGGCCTTCCTTG AGACGTCGGCGCCGCGCAATTTACCGTTTTACGAACGTCT TGGATTCACCGTTACGGCGGACGTGGAGGTGCCGGAGGGA CCCCGTACTTGGTGTATGACTCGTAAACCGGGAGCCTGAT AATGGTTGATTGCTAAGTTGTAAATATTTTAACCCGCCGT TCATATGGCGGTTGATTTTTATATGCCTAAACACAAAAA ATTGTAAAAATAAAATCCATTAACAGACCTATATAGATAT TTAAAAAGAATAGAACAGCTCAAATTATCAGCAACCCA | 63 |
| gltA-DAS+4-zeoR | |
| GTATTCCGTCTTCCATGTTCACCGTCATTTTCGCAATGGC ACGTACCGTTGGCTGGATCGCCCACTGGAGCGAAATGCAC AGTGACGGTATGAAGATTGCCCGTCCGCGTCAGCTGTATA CAGGATATGAAAAACGCGACTTTAAAAGCGATATCAAGCG TGCGGCCAACGATGAAAACTATTCTGAAAACTATGCGGAT GCGTCTTAATAGTTGACAATTAATCATCGGCATAGTATAT CGGCATAGTATAATACGACTCACTATAGGAGGGCCATCAT GGCCAAGTTGACCAGTGCCGTTCCGGTGCTCACCGCGCG CGACGTCGCCGGAGCGGTCGAGTTCTGGACCGACCGGCTCG GGTTCTCCCGGGACTTCGTGGAGGACGACTTCGCCGGTGT GGTCCGGGACGACGTGACCCTGTTCATCAGCGCGGTCCAG GACCAGGTGGTGCCGGACAACACCCTGGCCTGGGTGTGGG TGCGCGGCCTGGACGAGCTGTACGCCGAGTGGTCGGAGGT CGTGTCCACGAACTTCCGGGACGCCTCCGGGCCGGCCATG ACCGAGATCGGCGAGCAGCCGTGGGGGCGGGAGTTCGCCC TGCGCGACCCGGCCGGCAACTGCGTGCACTTTGTGGCAGA GGAGCAGGACTGAGGATAAGTAATGGTTGATTGCTAAGTT GTAAATATTTTAACCCGCCGTTCATATGGCGGGTTGATTT TTATATGCCTAAACACAAAAAATTGTAAAAATAAAATCCA TTAACAGACCTATATAGATATTTAAAAAGAATAGAACAGC TCAAATTATCAGCAACCCAATACTTTCAATTAAAAACTTC ATGGTAGTCGCATTTATAACCCTATGAAA | 64 |
| lpd-DAS+4-gentR | |
| GCGGCGAGCTGCTGGGTGAAATCGGCCTGCAATCGAAAT GGGTTGTGATGCTGAAGCAATCGCACTGACCATCCACGCG CACCCGACTCTGCACGAGTCTGTGGGCCTGGCGGCAGAAG TGTTCGAAGGTAGCATTACCGACCTGCCGAACCCGAAGG GAAGAAGAAGGCGGCCAACGATGAAAACTATTCTGAAAAC TATGCGGATGCGTCTTAATAGCGAATCCATGTGGGAGTTT ATTCTTGACACAGATATTTATGATATAATAACTGAGTAAG CTTAACATAAGGAGGAAAACATATGTTACGCAGCAGCAAC CGATGTTACGCAGCAGGGCAGTCGCCCTAAAACAAAGTTA GGTGGCTCAAGTATGGGCATCATTCGCACATGTAGGCTCG GCCCTGACCAAGTCAAATCCATGCGGGCTGCTCTTGATCT TTTCGGTCGTGAGTTCGGAGACGTAGCCACCTACTCCCAA CATCAGCCGGACTCCGATTACCTCGGGAACTTGCTCCGTA | 65 |

TABLE 7-continued

Synthetic DNA utilized for strain construction.

| Sequence | SEQ ID NO |
|---|---|
| GTAAGACATTCATCGCGCTTGCTGCCTTCGACCAAGAAGC<br>GGTTGTTGGCGCTCTCGCGGCTTACGTTCTGCCCAAGTTT<br>GAGCAGCCGCGTAGTGAGATCTATATCTATGATCTCGCAG<br>TCTCCGGCGAGCACCGGAGGCAGGGCATTGCCACCGCGCT<br>CATCAATCTCCTCAAGCATGAGGCCAACGCGCTTGGTGCT<br>TATGTGATCTACGTGCAAGCAGATTACGGTGACGATCCG<br>CAGTGGCTCTCTATACAAAGTTGGGCATACGGGAAGAAGT<br>GATGCACTTTGATATCGACCCAAGTACCGCCACCTAATTT<br>TTCGTTTGCCGGAACATCCGGCAATTAAAAAAGCGGCTAA<br>CCACGCCGCTTTTTTTACGTCTGCAATTTACCTTTCCAGT<br>CTTCTTGCTCCACGTTCAGAGAGACGTTCGCATACTGCTG<br>ACCGTTGCTCGTTATTCAGCCTGACAGTATGGTTACTGTC | |
| udhA-DAS+4-bsdR | |
| TCTGGGTATTCACTGCTTTGGCGAGCGCGCTGCCGAAATT<br>ATTCATATCGGTCAGGCGATTATGGAACAGAAAGGTGGCG<br>GCAACACTATTGAGTACTTCGTCAACACCACCTTTAACTA<br>CCCGACGATGGCGGAAGCCTATCGGGTAGCTGCGTTAAAC<br>GGTTTAAACCGCTGTTTGCGGCCAACGATGAAAACTATT<br>CTGAAAACTATGCGGATGCGTCTTAATAGTTGACAATTAA<br>TCATCGGCATAGTATATCGGCATAGTATAATACGACTCAC<br>TATAGGAGGGCCATCATGAAGACCTTCAACATCTCTCAGC<br>AGGATCTGGAGCTGGTGGAGGTCGCCACTGAGAAGATCAC<br>CATGCTCTATGAGGACAACAAGCACCATGTCGGGGCGGCC<br>ATCAGGACCAAGACTGGGGAGATCATCTCTGCTGTCCACA<br>TTGAGGCCTACATTGGCAGGGTCACTGTCTGTGCTGAAGC<br>CATTGCCATTGGGTCTGCTGTGAGCAACGGGCAGAAGGAC<br>TTTGACACCATTGTGGCTGTCAGGCACCCCTACTCTGATG<br>AGGTGGACAGATCCATCAGGGTGGTCAGCCCCTGTGGCAT<br>GTGCAGAGAGCTCATCTCTGACTATGCTCCTGACTGCTTT<br>GTGCTCATTGAGATGAATGGCAAGCTGGTCAAAACCACCA<br>TTGAGGAACTCATCCCCCTCAAGTACACCAGGAACTAAAG<br>TAAAACTTTATCGAAATGGCCATCCATTCTTGCGCGGATG<br>GCCTCTGCCAGCTGCTCATAGCGGCTGCGCAGCGGTGAGC<br>CAGGACGATAAACCAGGCCAATAGTGCGGCGTGGTTCCGG<br>CTTAATGCACGG | 66 |
| zwf-DAS+4-bsdR | |
| GAAGTGGAAGAAGCCTGGAAATGGGTAGACTCCATTACTG<br>AGGCGTGGGCGATGGACAATGATGCGCCGAAACCGTATCA<br>GGCCGGAACCTGGGGACCCGTTGCCTCGGTGGCGATGATT<br>ACCCGTGATGGTCGTTCCTGGAATGAGTTTGAGGCGGCCA<br>ACGATGAAAACTATTCTGAAAACTATGCGGATGCGTCTTA<br>ATAGTTGACAATTAATCATCGGCATAGTATATCGGCATAG<br>TATAATACGACTCACTATAGGAGGGCCATCATGAAGACCT<br>TCAACATCTCTCAGCAGGATCTGGAGCTGGTGGAGGTCGC<br>CACTGAGAAGATCACCATGCTCTATGAGGACAACAAGCAC<br>CATGTCGGGGCGGCCATCAGGACCAAGACTGGGGAGATCA<br>TCTCTGCTGTCCACATTGAGGCCTACATTGGCAGGGTCAC<br>TGTCTGTGCTGAAGCCATTGCCATTGGGTCTGCTGTGAGC<br>AACGGGCAGAAGGACTTTGACACCATTGTGGCTGTCAGGC<br>ACCCCTACTCTGATGAGGTGGACAGATCCATCAGGGTGGT<br>CAGCCCCTGTGGCATGTGCAGAGAGCTCATCTCTGACTAT<br>GCTCCTGACTGCTTTGTGCTCATTGAGATGAATGGCAAGC<br>TGGTCAAAACCACCATTGAGGAACTCATCCCCCTCAAGTA<br>CACCAGGAACTAAAGTAATATCTGCGCTTATCCTTTATGG<br>TTATTTTACCGGTAACATGATCTTGCGCAGATTGTAGAAC<br>AATTTTTACACTTTCAGGCCTCGTGCGGATTCACCCACGA<br>GGCTTTTTTTATTACACTGACTGAAACGTTTTTGCCCTAT<br>GAGCTCCGGTTACAGGCGTTTCAGTCATAAATCCTCTGAA<br>TGAAACGCGTTGTGAATC | 67 |
| dadX-DAS+4-purR | |
| GCGTGCGCACCATGACGGTGGGGACCGTCTCGATGGATAT<br>GCTAGCGGTCGATTTAACGCCTTGCCCGCAGGCGGGTATT<br>GGTACGCCGGTTGAGCTGTGGGCAAGGAGATCAAAATTG<br>ATGATGTCGCCGCCGCTGCCGGAACGGTGGGCTATGAGTT<br>GATGTGCGCGCTGGCGCTACGCGTCCCGGTTGTGACGGTG<br>GCGGCCAACGATGAAAACTATTCTGAAAACTATGCGGATG<br>CGTCTTAATCCTGACGGATGGCCTTTTTGCGTTTCTACAA<br>ACTCTTTTGTTTATTTTTCTAAATACATTCAAATATGTA<br>TCCGCTCATGAGACAATAACCCTGATAAATGCTTCAATAA | 68 |

TABLE 7-continued

Synthetic DNA utilized for strain construction.

| Sequence | SEQ ID NO |
|---|---|
| TATTGAAAAAGGAAGAGTATGACTGAATACAAGCCCACGG<br>TACGCTTGGCGACGCGCGACGATGTTCCCCGCGCTGTTCG<br>TACATTAGCTGCGGCCTTTGCAGATTACCCAGCGACGCGC<br>CATACGGTCGATCCGGACCGCCATATCGAGCGTGTCACAG<br>AATTGCAGGAACTTTTCTTAACTCGCGTGGGCCTTGACAT<br>CGGAAAGGTCTGGGTGGCTGACGATGGCGCTGCAGTGGCT<br>GTTTGGACCACTCCGGAGAGTGTAGAGGCTGGTGCAGTGT<br>TCGCCGAAATTGGTCCTCGTATGGCCGAATTAAGTGGAAG<br>TCGTCTGGCAGCCCAACAACAAATGGAAGGGTTGCTTGCG<br>CCCCACCGTCCGAAAGAACCCGCGTGGTTCCTTGCCACCG<br>TTGGAGTAAGCCCAGATCACCAGGGGAAGGGTTTAGGATC<br>TGCCGTAGTTTTACCAGGTGTGGAGGCAGCAGAACGTGCG<br>GGAGTTCCGGCCTTCCTTGAGACGTCGGCGCCGCGCAATT<br>TACCGTTTTACGAACGTCTTGGATTCACCGTTACGGCGGA<br>CGTGGAGGTGCCGGAGGGACCCCGTACTTGGTGTATGACT<br>CGTAAACCGGGAGCCTGATAACTTGTTGTAAGCCGGATCG<br>GAGGCAACGTCTTCTGGGTGCAAAAAAATCATCCATCCGG<br>CTGGTCAGCAACTGTAGTTGTTAATGTGACAGAGCCATTG<br>CCCATGATAGTGTCCATTAAAAGGATGGACACTATTTCCC<br>CGGAACCTGAACTCACCGCACAGGCGTTCTACATAAAACG<br>CTTACGCTTCATTGTTGACTC | |

Section 4: Dynamic Control Over Protein Levels.

Plasmids expressing fluorescent proteins and silencing guides were transformed into the corresponding hosts strain listed in Table 8. Strains were evaluated in triplicate in an m2p-labs Biolector™, which simultaneously measures fluorescence including GFPuv and mCherry levels, as well as biomass levels.

TABLE 8

Strains used for Dynamic Control over protein levels

| Microbe | Synthetic Metabolic Valves | Plasmid | Host Strain |
|---|---|---|---|
| E. coli | RFP-control | pCDF-mcherry1 + pSMART-IN: yibDp-GFPuv | DLF_0002 |
| | Proteolysis | pCDF-mcherry2 + pSMART-IN: yibDp-GFPuv | DLF_0025 |
| | Silencing | pCDF-mcherry1 + pCASCADE-proD + pSMART-IN: yibDp-GFPuv | DLF_01517 |
| | Proteolysis + Silencing | pCDF-mcherry2 + pCASCADE-proD + pSMART-IN: yibDp-GFPuv | DLF_0025 |

OD600 readings were corrected using the formula below, where OD600 refers to an offline measurement, OD600* refers to Biolector biomass reading, t0 indicates the start point, and tf indicates the final point.

$$OD600_t = (OD600_t^* - OD600_{t0}^*) * \frac{(OD600_{tf} - OD600_{t0})}{(OD600_{tf}^* - OD600_{t0}^*)} + 0.25 \quad \text{Equation S1}$$

Section 5: Metabolic Control
Near Equilibrium Reactions

The impact of Valves on metabolite pools for near equilibrium reactions is illustrated using the G6P node as an example. Abbreviations: Gluc, glucose; G6P, glucose-6-phosphate; F6P, fructose-6-phosphate; 6PGl, 6-phosphate-gluconolactone.

G6P Node without Valves

Equation S2: Steady State Mass balance $J_2 = J_2 + J_3$

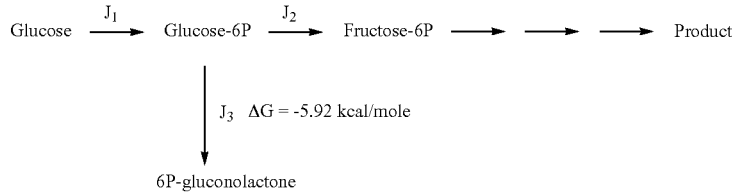

$\Delta G = -14.80$ kcal/mole   $\Delta G = 1.30$ kcal/mole

Glucose $\xrightarrow{J_1}$ Glucose-6P $\xrightarrow{J_2}$ Fructose-6P $\longrightarrow \longrightarrow \longrightarrow$ Product $J_3$  $\Delta G = -5.92$ kcal/mole $\downarrow$ 6P-gluconolactone Net Flux $= J_i = e^{\frac{-dG}{RT}} - 1$  (Equation S3)

$e^{\frac{-dG1}{RT}} - 1 = e^{\frac{-dG2}{RT}} - 1 + e^{\frac{-dG3}{RT}} - 1$  (Equation S4)

$e^{\frac{-dG1}{RT}} = e^{\frac{-dG2}{RT}} + e^{\frac{-dG3}{RT}} - 1$  (Equation S5)

$Keq1 = Keq2 + Keq3 - 1$  (Equation S6)

$Keq1 + 1 = Keq2 + Keq3$  (Equation S7)

$\frac{[G6P]}{[Gluc]} + 1 = \frac{[F6P]}{[G6P]} + \frac{[6PGl]}{[G6P]}$  (Equation S8)

$\frac{[G6P]}{[Gluc]} + 1 = \frac{[F6P] + [6PGl]}{[G6P]}$  (Equation S9)

$\frac{[G6P]^2}{[Gluc]} + [G6P] = [F6P] + [6PGl]$  (Equation S10)

$[F6P] = \frac{[G6P]^2}{[Gluc]} + [G6P] - [6PGl]$  (Equation S11)

G6P Node with Valves

When zwf valve is in effect, $J_3 \approx 0$.

$\Delta G = -14.80$ kcal/mole   $\Delta G = 1.30$ kcal/mole

Glucose $\xrightarrow{J_1}$ Glucose-6P $\xrightarrow{J_2}$ Fructose-6P $\longrightarrow \longrightarrow \longrightarrow$ Product Steady State Mass balance $J_1 = J_2$  (Equation S12)

Net Flux $= J_i = e^{\frac{-dG}{RT}} - 1$  (Equation S13)

$e^{\frac{-dG1}{RT}} - 1 = e^{\frac{-dG2}{RT}} - 1$  (Equation S14)

$Keq1 = Keq2$  (Equation S15)

$\frac{[G6P]}{[Gluc]} = \frac{[F6P]}{[G6P]}$  (Equation S16)

$[F6P] = \frac{[G6P]^2}{[Gluc]}$  (Equation S17)

Impact of Valves $[F6P]\text{network} = \frac{[G6P]^2}{[Gluc]} + [G6P] - [6PGl]$  (Equation S11)

$[F6P]\text{valve} = \frac{[G6P]^2}{[Gluc]}$  (Equation S17)

Since close to equilibrium $[6PGl] > [G6P]$
$[F6P]\text{valve} >= [F6P]\text{network}$ The removal of thermodynamically favored reactions near equilibrium from the network will result in increased metabolite pools.

Section 6: Gene Silencing Arrays & Pathway Expression Constructs

The design and construction of CASCADE guides and guide arrays is illustrated below in FIG. 14 and FIG. 15A-B. The pCASCADE-control plasmid was prepared by swapping the pTet promoter in perRNA.Tet[88] with an insulated low phosphate induced ugpB promoter[82]. Two promoters were responsible for regulating gltA gene, and sgRNA was designed for both promoters, resulting in guide gltA1 (G1) and gltA2 (G2).[89] Four promoters were responsible for regulating gapA gene, and sgRNA was designed for the first promoter, since during exponential phase of growth, gapA mRNAs were mainly initiated at the highly efficient gapA P1 promoter and remained high during stationary phase compared to the other three gapA promoters.[90] Multiple promoters upstream of lpd gene were involved in lpd regulation (https://ecocyc.org/gene?orgid=ECOLI&id=EG10543#tab=showAll), thus design of unique and effective sgRNA for lpd only was not possible. Promoter sequences for fabI, udhA and zwf were obtained from EcoCyc database (https://ecocyc.org/). To design CASCADE guide array, CASCADE PAM sites near the −35 or −10 box of the promoter of interest were identified, 30 bp at the 3' end of PAM site was selected as the guide sequence and cloned into pCASCADE plasmid using Q5 site-directed mutagenesis (NEB, MA) following manufacturer's protocol, with the modification that 5% v/v DMSO was added to the Q5 PCR reaction. The pCASCADE-control vector was used as template. pCASCADE plasmids with arrays of two or more guides were prepared as illustrated in FIG. 15A-B. The pCASCADE guide array plasmid was prepared by sequentially amplifying complementary halves of each smaller guide plasmid by PCR, followed by subsequent DNA assembly. Table 9 lists sgRNA guide sequences and primers used to construct them. All pCASCADE silencing plasmids are listed in Table 10 below and are available at Addgene.

Table 9: List of sgRNA guide sequences and primers used to construct them. Spacers are italicized.

TABLE 9

List of sgRNA guide sequences and primers used to construct them. Spacers are italicized.

| sgRNA/Primer Name | Sequence | SEQ ID NO | Template |
|---|---|---|---|
| fabI | *TCGAGTTCCCCGCGCCAGCGGG GATAAACCGTTGATTATAATAA CCGTTTATCTGTTCGTA*TCGAG TTCCCCGCGCCAGCGGGGATAA ACCG | 69 | |
| fabI-FOR | GTTTATCTGTTCGTA*TCGAGTT CCCCGCGCCAGCGGGGATAAAC CGAAAAAAAAACCCC* | 70 | pCASCADE control |
| fabI-REV | GGTTATTATAATCAACGGTTTA TCCCCGCTGGCGCGGGGAACT CGAGGTGGTACCAGATC | 71 | |
| gapAP1 | *TCGAGTTCCCCGCGCCAGCGGG GATAAACCGGTTTTTGTAATTTT ACAGGCAACCTTTTATT*TCGAGT TCCCCGCGCCAGCGGGGATAAA CCG | 72 | |
| gapAP1-FOR | CAGGCAACCTTTTATT*TCGAGTT CCCCGCGCCAGCGGGGATAAAC CGAAAAAAAAAACCCC* | 73 | pCASCADE control |
| gapAP1-REV | TAAAATTACAAAAACCGGTTT ATCCCCGCTGGCGCGGGGAAC TCGAGGTGGTACCAGATC | 74 | |
| gltA1 | *TCGAGTTCCCCGCGCCAGCGGG GATAAACCGAAAAGCATATAAT GCGTAAAAGTTATGAAGT*TCG AGTTCCGGGCGCCAGCGGGGAT AAACCG | 75 | |
| gltA1-FOR | GCGTAAAAGTTATGAAGTTCG AGTTCCCCGCGCCAGCGGGGAT AAACCGAAAAAAAAACCCC | 76 | pCASCADE control |
| gltA1-REV | ATTATATGCTTTTCGGTTTATC CCCGCTGGCGCGGGGAACTCG AGGTGGTACCAGATCT | 77 | |
| gltA2 | *TCGAGTTCCCCGCGCCAGCGGG GATAAACCGTATTGACCAATTC ATTCGGGACAGTTATTAGT*TCG AGTTCCCCGCGCCAGCGGGGAT AAACCG | 78 | |
| gltA2-FOR | GGGACAGTTATTAGT*TCGAGTT CCCCGCGCCAGCGGGGATAAAC CGAAAAAAAAAACCCC* | 79 | pCASCADE control |
| gltA2-REV | GAATGAATTGGTCAATACGGT TTATCCCCGCTGGCGCGGGGA ACTCGAGGTGGTACCAGATC | 80 | |
| proD | *TCGAGTTCCCCGCGCCAGCGGG GATAAACCGAGTGGTTGCTGGA TAACTTTACGGGCATGC*TCGAG TTCCCCGCGCCAGCGGGGATAA ACCG | 81 | |
| proD-FOR | AACTTTACGGGCATGCT*CGAGT TCCCCGCGCCAGCGGGGATAAA CCGAAAAAAAAACCCC* | 82 | pCASCADE control |
| proD-REV | ATCCAGCAACCACTCGGTTTAT CCCCGCTGGCGCGGGGAACTC GAGGTGGTACCAGATCT | 83 | |
| udhA | *TCGAGTTCCCCGCGCCAGCGGG GATAAACCGTTACCATTCTGTT GCTTTTATGTATAAGAA*TCGAG TTCCCCGCGCCAGCGGGGATAA ACCG | 84 | |
| udhA-FOR | TTTTATGTATAAGAATCGAGTT *CCCCGCGCCAGCGGGGATAAAC CGAAAAAAAAAACCCC* | 85 | pCASCADE control |
| udhA-REV | GCAACAGAATGGTAACGGTTT ATCCCCGCTGGCGCGGGGAAC TCGAGGTGGTACCAGATC | 86 | |
| zwf | *TCGAGTTCCCCGCGCCAGCGGG GATAAACCGCTCGTAAAAGCAG TACAGTGCACCGTAAGATCGA*GTTCCCCGCGCCAGCGGGGATA AACCG | 87 | |
| zwf-FOR | CAGTGCACCGTAAGATCGAGTT *CCCCGCGCCAGCGGGGATAAAC CGAAAAAAAAAACCCC* | 88 | pCASCADE control |
| zwf-REV | TACTGCTTTTACGAGCGGTTTA TCCCCGCTGGCGCGGGGAACT CGAGGTGGTACCAGATC | 89 | |
| FG1 | *TCGAGTTCCCCGCGCCAGCGGG GATAAACCGTTGATTATAATAA CCGTTTATCTGTTCGTA*TCGAG TTCCCCGCGCCAGCGGGGATAA ACCGAAAAGCATATAATGCGT AAAAGTTATGAAGT*TCGAGTTC CCCGCGCCAGCGGGGATAAACC G | 90 | |
| gltA1-FOR | GCGCCAGCGGGGATAAACCGA AAAGCATATAATGCG | 91 | pCASCADE-gltA1 |
| pCASCADE-REV | CTTGCCCGCCTGATGAATGCTC ATCCGG | 92 | |
| pCASCADE-FOR | CCGGATGAGCATTCATCAGGC GGGCAAG | 93 | pCASCADE-fabI |
| fabI-REV | CGGTTTATCCCCGCTGGCGCG GGGAACTCGATACGAACAGAT AAACGGTTATTATAATC | 94 | |
| FG2 | *TCGAGTTCCCCGCGCCAGCGGG GATAAACCGTTGATTATAATAA CCGTTTATCTGTTCGTA*TCGAG TTCCCCGCGCCAGCGGGGATAA ACCGTATTGACCAATTCATTCG GGACAGTTATTAGT*TCGAGTTC CCCGCGCCAGCGGGGATAAACC G | 95 | |
| gltA2-FOR | GCGCCAGCGGGGATAAACCGT ATTGACCAATTCATTC | 96 | pCASCADE-gltA2 |
| pCASCADE-REV | CTTGCCCGCCTGATGAATGCTC ATCCGG | 97 | |
| pCASCADE-FOR | CCGGATGAGCATTCATCAGGC GGGCAAG | 98 | pCASCADE-fabI |
| fabI-REV | CGGTTTATCCCCGCTGGCGCG GGGAACTCGATACGAACAGAT AAACGGTTATTATAATC | 99 | |

TABLE 9-continued

List of sgRNA guide sequences and primers used to construct them. Spacers are italicized.

| sgRNA/Primer Name | Sequence | SEQ ID NO | Template |
|---|---|---|---|
| FU | *TCGAGTTCCCCGCGCCAGCGGG GATAAACCGTTGATTATAATAA CCGTTTATCTGTTCGTATCGAG TTCCCCGCGCCAGCGGGGATAA ACCGTTACCATTCTGTTGCTTT TATGTATAAGAATCGAGTTCCC CGCGCCAGCGGGATAAACCG* | 100 | |
| udhA-FOR | GCGCCAGCGGGGATAAACCGT TACCATTCTGTTG | 101 | pCASCADE-udhA |
| pCASCADE-REV | CTTGCCCGCCTGATGAATGCTC ATCCGG | 102 | |
| pCASCADE-FOR | CCGGATGAGCATTCATCAGGC GGGCAAG | 103 | pCASCADE-fabI |
| fabI-REV | CGGTTTATCCCCGCTGGCGCG GGGAACTCGATACGAACAGAT AAACGGTTATTATAATC | 104 | |
| FZ | *TCGAGTTCCCCGCGCCAGCGGG GATAAACCGTTGATTATAATAA CCGTTTATCTGTTCGTATCGAG TTCCCCGCGCCAGCGGGGATAA ACCGCTCGTAAAAGCAGTACA GTGCACCGTAAGATCGAGTTCC CCGCGCCAGCGGGGATAAACCG* | 105 | |
| zwf-FOR | GCGCCAGCGGGGATAAACCGC TCGTAAAAG | 106 | pCASCADE-zwf |
| pCASCADE-REV | CTTGCCCGCCTGATGAATGCTC ATCCGG | 107 | |
| pCASCADE-FOR | CCGGATGAGCATTCATCAGGC GGGCAAG | 108 | pCASCADE-fabI |
| fabI-REV | CGGTTTATCCCCGCTGGCGCG GGGAACTCGATACGAACAGAT AAACGGTTATTATAATC | 109 | |
| G1G2 | *TCGAGTTCCCCGCGCCAGCGGG GATAAACCGAAAAGCATATAAT GCGTAAAAGTTATGAAGTTCG AGTTCCCCGCGCCAGCGGGGAT AAACCGTATTGACCAATTCATT CGGGACAGTTATTAGTTCGAGT TCCCCGCGCCAGCGGGGATAAA CCG* | 110 | |
| gltA2-FOR | GCGCCAGCGGGGATAAACCGT *ATTGACCAATTCATTC* | 111 | pCASCADE-gltA2 |
| pCASCADE-REV | CTTGCCCGCCTGATGAATGCTC ATCCGG | 112 | |
| pCASCADE-FOR | CCGGATGAGCATTCATCAGGC GGGCAAG | 113 | pCASCADE-gltA1 |
| gltA1-REV | CGGTTTATCCCCGCTGGCGCG GGGAACTCGAACTTCATAACT TTTAC | 114 | |
| G1U | *TCGAGTTCCCCGCGCCAGCGGG GATAAACCGAAAAGCATATAATG CGTAAAAGTTATGAAGTTCGA GTTCCCCGCGCCAGCGGGGATA AACCGTTACCATTCTGTTGCTT TTATGTATAAGAATCGAGTTCC CCGCGCCAGCGGGGATAAACCG* | 115 | |
| udhA-FOR | GCGCCAGCGGGGATAAACCGT TACCATTCTGTTG | 116 | pCASCADE-udhA |
| pCASCADE-REV | CTTGCCCGCCTGATGAATGCTC ATCCGG | 117 | |
| pCASCADE-FOR | CCGGATGAGCATTCATCAGGC GGGCAAG | 118 | pCASCADE-gltA1 |
| gltA1-REV | CGGTTTATCCCCGCTGGCGCG GGGAACTCGAACTTCATAACT TTTAC | 119 | |
| G1Z | *TCGAGTTCCCCGCGCCAGCGGG GATAAACCGAAAAGCATATAAT GCGTAAAAGTTATGAAGTTCG AGTTCCCCGCGCCAGCGGGGAT AAACCGCTCGTAAAAGCAGTA CAGTGCACCGTAAGATCGAGTT CCCCGCGCCAGCGGGGTAAAC CG* | 120 | |
| zwf-FOR | GCGCCAGCGGGGATAAACCGC TCGTAAAAG | 121 | pCASCADE-zwf |
| pCASCADE-REV | CTTGCCCGCCTGATGAATGCTC ATCCGG | 122 | |
| pCASCADE-FOR | CCGGATGAGCATTCATCAGGC GGGCAAG | 123 | pCASCADE-gltA1 |
| gltA1-REV | CGGTTTATCCCCGCTGGCGCG GGGAACTCGAACTTCATAACT TTTAC | 124 | |
| GZU | *TCGAGTTCCCCGCGCCAGCGGG GATAAACCGTATTGACCAATTCA TTCGGGACAGTTATTAGTTCGA GTTCCCCGCCAGCGGGGATA AACCGTTACCATTCTGTTGCTT TTATGTATAAGAATCGAGTTCC CCGCGCCAGCGGGGATAAACCG* | 125 | |
| udhA-FOR | GCGCCAGCGGGGATAAACCGT TACCATTCTGTTG | 126 | pCASCADE-udhA |
| pCASCADE-REV | CTTGCCCGCCTGATGAATGCTC ATCCGG | 127 | |
| pCASCADE-FOR | CCGGATGAGCATTCATCAGGC GGGCAAG | 128 | pCASCADE-gltA2 |
| gltA2-REV | CGGTTTATCCCCGCTGGCGCG GGGAACTCGAACTAATAACTG TC | 129 | |
| G2Z | *TCGAGTTCCCCGCGCCAGCGGG GATAAACCGTATTGACCAATTCA TTCGGGACAGTTATTAGTTCGA GTTCCCCGCCAGCGGGGATA AACCGCTCGTAAAAGCAGTAC AGTGCACCGTAAGATCGAGTTC CCCGCGCCAGCGGGGATAAACC G* | 130 | |
| zwf-FOR | GCGCCAGCGGGGATAAACCGC TCGTAAAAG | 131 | pCASCADE-zwf |
| pCASCADE-REV | CTTGCCCGCCTGATGAATGCTC ATCCGG | 132 | |

TABLE 9-continued

List of sgRNA guide sequences and primers used to construct them. Spacers are italicized.

| sgRNA/Primer Name | Sequence | SEQ ID NO | Template |
|---|---|---|---|
| pCASCADE-FOR | CCGGATGAGCATTCATCAGGCGGGCAAG | 133 | pCASCADE-gltA2 |
| gltA2-REV | CGGTTTATCCCCGCTGGCGCGGGGAACTCGAACTAATAACTGTC | 134 | |
| UZ | *TCGAGTTCCCCGCGCCAGCGGGGATAAACCGTTACCATTCTGTTGCTTTTATGTATAAGAATCGAGTTCCCCGCGCCAGCGGGGATAAACCGCTCGTAAAAGCAGTACAGTGCACCGTAAGATCGAGTTCCCCGCGCCAGCGGGGATAAACCG* | 135 | |
| zwf-FOR | GCGCCAGCGGGGATAAACCGCTCGTAAAAG | 136 | pCASCADE-zwf |
| pCASCADE-REV | CTTGCCCGCCTGATGAATGCTCATCCGG | 137 | |
| pCASCADE-FOR | CCGGATGAGCATTCATCAGGCGGGCAAG | 138 | pCASCADE-udhA |
| udhA-REV | CGGTTTATCCCCGCTGGCGCGGGGAACTCGATTCTTATACATAAAAGC | 139 | |
| FG1G2 | *TCGAGTTCCCCGCGCCAGCGGGGATAAACCGTTGATTATAATAACCGTTTATCTGTTCGTATCGAGTTCCCCGCGCCAGCGGGGATAAACCGAAAAGCATATAATGCGTAAAAGTTATGAAGTTCGAGTTCCCCGCGCCAGCGGGGATAAACCGTATTGACCAATTCATTCGGGACAGTTATTAGTTCGAGTTCCCCGCGCCAGCGGGGATAAACCG* | 140 | |
| gltA2-FOR | GCGCCAGCGGGGATAAACCGTATTGACCAATTCATTC | 141 | pCASCADE-gltA2 |
| pCASCADE-REV | CTTGCCCGCCTGATGAATGCTCATCCGG | 142 | |
| pCASCADE-FOR | CCGGATGAGCATTCATCAGGCGGGCAAG | 143 | pCASCADE-FG1 |
| gltA1-REV | CGGTTTATCCCCGCTGGCGCGGGGAACTCGAACTTCATAACTTTTAC | 144 | |
| G1G2A | *TCGAGTTCCCCGCGCCAGCGGGGATAAACCGAAAAGCATATAATGCGTAAAAGTTATGAAGTTCGAGTTCCCCGCGCCAGCGGGGATAAACCGTATTGACCAATTCATTCGGGACAGTTATTAGTTCGAGTTCCCCGCGCCAGCGGGGATAAACCGGTTTTGTAATTT TACAGGCAACCTTTTATTCGAGTTCCCCGCGCCAGCGGGGATAAACCG* | 145 | |
| gapAP1-FOR | GCGCCAGCGGGGATAAACCGGTTTTGTAATTT TACAGGC | 146 | pCASCADE-gapAP1 |
| pCASCADE-REV | CTTGCCCGCCTGATGAATGCTCATCCGG | 147 | |
| pCASCADE-FOR | CCGGATGAGCATTCATCAGGCGGGCAAG | 148 | pCASCADE-G1G2 |
| gltA2-REV | CGGTTTATCCCCGCTGGCGCGGGGAACTCGAACTAATAACTGTC | 149 | |
| G1G2U | *TCGAGTTCCCCGCGCCAGCGGGGATAAACCGAAAAGCATATAATGCGTAAAAGTTATGAAGTTCGAGTTCCCCGCGCCAGCGGGGATAAACCGTATTGACCAATTCATTCGGGACAGTTATTAGTTCGAGTTCCCCGCGCCAGCGGGGATAAACCGTTACCATTCTGTTGCTTTTATGTATAAGAATCGAGTTCCCCGCGCCAGCGGGGATAAACCG* | 150 | |
| udhA-FOR | GCGCCAGCGGGGATAAACCGTTACCATTCTGTTG | 151 | pCASCADE-udhA |
| pCASCADE-REV | CTTGCCCGCCTGATGAATGCTCATCCGG | 152 | |
| pCASCADE-FOR | CCGGATGAGCATTCATCAGGCGGGCAAG | 153 | pCASCADE-G1G2 |
| gltA2-REV | CGGTTTATCCCCGCTGGCGCGGGGAACTCGAACTAATAACTGTC | 154 | |
| G1G2Z | *TCGAGTTCCCCGCGCCAGCGGGGATAAACCGAAAAGCATATAATGCGTAAAAGTTATGAAGTTCGAGTTCCCCGCGCCAGCGGGGATAAACCGTATTGACCAATTCATTCGGGACAGTTATTAGTTCGAGTTCCCCGCGCCAGCGGGGATAAACCGCTCGTAAAAGCAGTACAGTGCACCGTAAGATCGAGTTCCCCGCGCCAGCGGGGATAAACCG* | 155 | |
| zwf-FOR | GCGCCAGCGGGGATAAACCGCTCGTAAAAG | 156 | pCASCADE-zwf |
| pCASCADE-REV | CTTGCCCGCCTGATGAATGCTCATCCGG | 157 | |
| pCASCADE-FOR | CCGGATGAGCATTCATCAGGCGGGCAAG | 158 | pCASCADE-G1G2 |
| gltA2-REV | CGGTTTATCCCCGCTGGCGCGGGGAACTCGAACTAATAACTGTC | 159 | |
| FG1G2A | *TCGAGTTCCCCGCGCCAGCGGGGATAAACCGTTGATTATAATAACCGTTTATCTGTTCGTATCGAGTTCCCCGCGCCAGCGGGGATAAACCGAAAAGCATATAATGCGTAAAAGTTATGAAGTTCGAGTTCCCCGCGCCAGCGGGGATAAACCGTATTGACCAATTCATTCGGGACAGTTATTAGTTCGAGTTCCCCGCGCCAGCGGGGATAAACCGTTTTTGTAATTT TACAGGCAACCTTTTATTCGAGTTCCCCGCGCCAGCGGGGATAAACCG* | 160 | |
| gapAP1-FOR | GCGCCAGCGGGGATAAACCGGTTTTGTAATTT TACAGGC | 161 | pCASCADE-gapAP1 |
| pCASCADE-REV | CTTGCCCGCCTGATGAATGCTCATCCGG | 162 | |

TABLE 9-continued

List of sgRNA guide sequences and primers used to construct them. Spacers are italicized.

| sgRNA/Primer Name | Sequence | SEQ ID NO | Template |
|---|---|---|---|
| pCASCADE-FOR | CCGGATGAGCATTCATCAGGCGGGCAAG | 163 | pCASCADE-FG1G2 |
| gltA2-REV | CGGTTTATCCCCGCTGGCGCGGGGAACTCGAACTAATAACTGTC | 164 | |
| FG1G2U | *TCGAGTTCCCCGCGCCAGCGGGGATAAACCGTTGATTATAATAACCGTTTATCTGTTCGTATCGAGTTCCCCGCGCCAGCGGGGATAAACCGAAAAGCATATAATGCGTAAAAGTTATGAAGTTCGAGTTCCCCGCGCCAGCGGGGATAAACCGTATTGACCAATTCATTCGGGACAGTTATTAGTTCGAGTTCCCCGCGCCAGCGGGGATAAACCGTTACCATTCTGTTGCTTTTATGTATAAGAATCGAGTTCCCCGCGCCAGCGGGGATAAACCG* | 165 | |
| gltA2-FOR | GCGCCAGCGGGGATAAACCGT*ATTGACCAATTCATTC* | 166 | pCASCADE-udhA |
| pCASCADE-REV | CTTGCCCGCCTGATGAATGCTCATCCGG | 167 | |
| pCASCADE-FOR | CCGGATGAGCATTCATCAGGCGGGCAAG | 168 | pCASCADE-FG1G2 |
| gltA1-REV | CGGTTTATCCCCGCTGGCGCGGGGAACTCGAACTTCATAACTTTTAC | 169 | |
| FG1G2Z | *TCGAGTTCCCCGCGCCAGCGGGGATAAACCGTTGATTATAATAACCGTTTATCTGTTCGTATCGAGTTCCCCGCGCCAGCGGGGATAAACCGAAAAGCATATAATGCGTAAAAGTTATGAAGTTCGAGTTCCCCGCGCCAGCGGGGATAAACCGTATTGACCAATTCATTCGGGACAGTTATTAGTTCGAGTTCCCCGCGCCAGCGGGGATAAACCGCTCGTAAAAGCAGTACAGTGCACCGTAAGATCGAGTTCCCCGCGCCAGCGGGGATAAACCG* | 170 | |
| gltA2-FOR | GCGCCAGCGGGGATAAACCGT*ATTGACCAATTCATTC* | 171 | pCASCADE-zwf |
| pCASCADE-REV | CTTGCCCGCCTGATGAATGCTCATCCGG | 172 | |
| pCASCADE-FOR | CCGGATGAGCATTCATCAGGCGGGCAAG | 173 | pCASCADE-FG1G2 |
| gltA1-REV | CGGTTTATCCCCGCTGGCGCGGGGAACTCGAACTTCATAACTTTTAC | 174 | |
| G1G2UA | *TCGAGTTCCCCGCGCCAGCGGGGATAAACCGAAAAGCATATAATGCGTAAAAGTTATGAAGTTCGAGTTCCCCGCGCCAGCGGGGATAAACCGTATTGACCAATTCATTCGGGACAGTTATTAGTTCGAGTTCCCCGCGCCAGCGGGGATAAACCGTTACCATTCTGTTGCTTTTATGTATAAGAATCGAGTTCCCCGCGCCAGCGGGGATAAACCGTTTTGTAATTTTACAGGCAAC* | 175 | |
| | *CTTTTATTCGAGTTCGCCGCGCCAGCGGGGATAAACCG* | | |
| gapAP1-FOR | GCGCCAGCGGGGATAAACCGTTTTTGTAATTT TACAGGC | 176 | pCASCADE-gapAP1 |
| pCASCADE-REV | CTTGCCCGCCTGATGAATGCTCATCCGG | 177 | |
| pCASCADE-FOR | CCGGATGAGCATTCATCAGGCGGGCAAG | 178 | pCASCADE-G1G2U |
| udhA-REV | CGGTTTATCCCCGCTGGCGCGGGGAACTCGATTCTTATACATAAAAGC | 179 | |
| G1G2UZ | *TCGAGTTCCCCGCGCCAGCGGGGATAAACCGAAAAGCATATAATGCGTAAAAGTTATGAAGTTCGAGTTCCCCGCGCCAGCGGGGATAAACCGTATTGACCAATTCATTCGGGACAGTTATTAGTTCGAGTTCCCCGCGCCAGCGGGGATAAACCGTTACCATTCTGTTGCTTTTATGTATAAGAATCGAGTTCCCCGCGCCAGCGGGGATAAACCGCTCGTAAAAGCAGTACAGTGCACCGTAAGATCGAGTTCCCCGCGCCAGCGGGGATAAACCG* | 180 | |
| zwf-FOR | GCGCCAGCGGGGATAAACCGCTCGTAAAAG | 181 | pCASCADE-zwf |
| pCASCADE-REV | CTTGCCCGCCTGATGAATGCTCATCCGG | 182 | |
| pCASCADE-FOR | CCGGATGAGCATTCATCAGGCGGGCAAG | 183 | pCASCADE-G1G2U |
| udhA-REV | CGGTTTATCCCCGCTGGCGCGGGGAACTCGATTCTTATACATAAAAGC | 184 | |
| FG1G2UA | *TCGAGTTCCCCGCGCCAGCGGGGATAAACCGTTGATTATAATAACCGTTTATCTGTTCGTATCGAGTTCCCCGCGCCAGCGGGGATAAACCGAAAAGCATATAATGCGTAAAAGTTATGAAGTTCGAGTTCCCCGCGCCAGCGGGGATAAACCGTATTGACCAATTCATTCGGGACAGTTATTAGTTCGAGTTCCCCGCGCCAGCGGGGATAAACCGTTACCATTCTGTTGCTTTTATGTATAAGAATCGAGTTCCCCGCGCCAGCGGGGATAAACCGTTTTGTAATTTTACAGGCAACCTTTTATTCGAGTTCCCCGCGCCAGCGGGGATAAACCG* | 185 | |
| gapAP1-FOR | GCGCCAGCGGGGATAAACCGTTTTTGTAATTT TACAGGC | 186 | pCASCADE-gapAP1 |
| pCASCADE-REV | CTTGCCCGCCTGATGAATGCTCATCCGG | 187 | |
| pCASCADE-FOR | CCGGATGAGCATTCATCAGGCGGGCAAG | 188 | pCASCADE-FG1G2U |
| udhA-REV | CGGTTTATCCCCGCTGGCGCGGGGAACTCGATTCTTATACATAAAAGC | 189 | |

TABLE 9-continued

List of sgRNA guide sequences and primers used to construct them. Spacers are italicized.

| sgRNA/Primer Name | Sequence | SEQ ID NO | Template |
|---|---|---|---|
| FG1G2UZ | *TCGAGTTCCCCGCGCCAGCGGG GATAAACCGTTGATTATAATAA CCGTTTATCTGTTCGTATCGAG TTCCCCGCGCCAGCGGGGATAA ACCGAAAAGCATATAATGCGT AAAAGTTATGAAGTTCGAGTTC CCCGCGCCAGCGGGGATAAACC GTATTGACCAATTCATTCGGG ACAGTTATTAGTTCGAGTTCCC CGCGCCAGCGGGGATAAACCGT TACCATTCTGTTGCTTTTATGT ATAAGAATCGAGTTCCCCGCGC CAGCGGGGATAAACCGCTCGTA AAAGCAGTACAGTGCACCGTA AGATCGAGTTCCCCGCGCCAGC GGGGATAAACCG* | 190 | |
| zwf-FOR | GCGCCAGCGGGGATAAACCGC TCGTAAAAG | 191 | pCASCADE-zwf |
| pCASCADE-REV | CTTGCCCGCCTGATGAATGCTC ATCCGG | 192 | |
| pCASCADE-FOR | CCGGATGAGCATTCATCAGGC GGGCAAG | 193 | pCASCADE-FG1G2U |
| udhA-REV | CGGTTTATCCCCGCTGGCGCG GGGAACTCGATTCTTATACAT AAAAGC | 194 | |
| FG1G2UZA | *TCGAGTTCCCCGCGCCAGCGG GATAAACCGTTGATTATAATAA CCGTTTATCTGTTCGTATCGAG TTCCCCGCGCCAGCGGGGATAA ACCGAAAAGCATATAATGCGT AAAAGTTATGAAGTTCGAGTTC CCCGCGCCAGCGGGGATAAACC GTATTGACCAATTCATTCGGG ACAGTTATTAGTTCGAGTTCCC CGCGCCAGCGGGGATAAACCGT TACCATTCTGTTGCTTTTATGT ATAAGAATCGAGTTCCCCGCGC CAGCGGGGATAAACCGCTCGTA AAAGCAGTACAGTGCACCGTA AGATCGAGTTCCCCGCGCCAGC GGGGATAAACCGGTTTTTGTAA TTT TACAGGCAACCTTTTATTC GAGTTCCCCGCGCCAGCGGGGA TAAACCG* | 195 | |
| gapAP1-FOR | GCGCCAGCGGGGATAAACCGG TTTTTGTAATTT TACAGGC | 196 | pCASCADE-gapAP1 |
| pCASCADE-REV | CTTGCCCGCCTGATGAATGCTC ATCCGG | 197 | |
| pCASCADE-FOR | CCGGATGAGCATTCATCAGGC GGGCAAG | 198 | pCASCADE-FG1G2UZ |
| zwf-REV | CGGTTTATCCCCGCTGGCGCG GGGAACTCGATCTTACGGTGC ACTGTAC | 199 | |
| UZ | *TCGAGTTCCCCGCGCCAGCGGG GATAAACCGTTACCATTCTGTT GCTTTTATGTATAAGAATCGAG TTCCCCGCGCCAGCGGGGATAA ACCGCTCGTAAAAGCAGTACA GTGCACCGTAAGATCGAGTTCC CCGCGCCAGCGGGGATAAACCG* | 200 | |
| zwf-FOR | GCGCCAGCGGGGATAAACCGC TCGTAAAAG | 201 | pCASCADE-zwf |
| pCASCADE-REV | CTTGCCCGCCTGATGAATGCTC ATCCGG | 202 | |
| pCASCADE-FOR | CCGGATGAGCATTCATCAGGC GGGCAAG | 203 | pCASCADE-udhA |
| udhA-REV | CGGTTTATCCCCGCTGGCGCG GGGAACTCGATTCTTATACAT AAAAGC | 204 | |

TABLE 10

List of plasmids used in this study.

Plasmid Utilized in this Study

| Plasmid | Purpose | Source |
|---|---|---|
| pSIM5 | Recombineering and Strain Construction | Court Lab[54] |
| pCP20 | FRT kanamycin cassette curing | Court Lab[54] |
| pSMART-HC-Kan | Backbone Vector | Lucigen |
| pcrRNA.Tet | pCASCADE-control backbone | Beisel Lab[34] |

Plasmid Constructed in this Study

| Plasmid | Plasmid Name | Addgene ID |
|---|---|---|
| pSMART-Ala2 | pSMART-HCKan-IN: yibDp-ald* | 71326 |
| pSMART-Ala3 | pSMART-HCKan-IN: phoBp-ald* | 71327 |
| pSMART-Ala4 | pSMART-HCKan-IN: phoHp-ald* | 71328 |
| pSMART-Ala5 | pSMART-HCKan-IN: mipAp-ald* | 71329 |
| pSMART-Ala11 | pSMART-HCKan-proA-ald* | 87172 |
| pSMART-Ala12 | pSMART-HCKan-proC-ald* | 87173 |
| pSMART-Ala13 | pSMART-HCKan-proD-ald* | 87174 |
| pSMART-Ala14 | pSMART-HCKan-proB-ald* | 101079 |
| pSMART-Ala15 | pSMART-HCKan-HCEp-ald* | 101080 |
| pSMART-Mev2 | pSMART-IN: yibDp1-mvaE-IN: phoBp2-mvaS(A110G) | 66642 |
| pSMART-Mev3 | pSMART-IN: yibDp1-mvaE-IN: mipAp2-mvaS(A110G) | 102761 |

TABLE 10-continued

List of plasmids used in this study.

| | | |
|---|---|---|
| pSMART-Mev4 | pSMART-IN: yibDp1-mvaE-IN: phoHp2-mvaS(A110G) | 102762 |
| pSMART-Mev5 | pSMART-IN: mipAp1-mvaE-IN: yibD2-mvaS(A110G) | 102763 |
| pSMART-3HP | pSMART-3HP-NADPH-rhtA | 87143 |
| pCDF-mcherry1 | pCDF-proD-mcherry | 87144 |
| pCDF-mcherry2 | pCDF-proD-mcherry-DAS4 | 87145 |
| pSMART-GFPuv | pSMART-IN: yibDp-GFPuv | 65822 |
| pSMART-GFPuv2 | pSMART-IN: phoBp-GFPuv | 71517 |
| pSMART-GFPuv3 | pSMART-IN: phoUp-GFPuv | 71518 |
| pSMART-GFPuv4 | pSMART-IN: phoHp-GFPuv | 71519 |
| pSMART-GFPuv5 | pSMART-IN: mipAp-GFPuv | 71520 |
| pCASCADE-control | pCASCADE | 65821 |
| pCASCADE-proD | pCASCADE-proD | 65820 |
| pCASCADE-gapAP1 | pCASCADE-gapAP1 | 87146 |
| pCASCADE-fabI | pCASCADE-fabI | 66635 |
| pCASCADE-FG1 | pCASCADE-fabI-gltA1 | 71340 |
| pCASCADE-FG1G2 | pCASCADE-fabI-gltA1-gltA2 | 71342 |
| pCASCADE-FG1G2A | pCASCADE-fabI-gltA1-gltA2-gapA | 87147 |
| pCASCADE-FG1G2U | pCASCADE-fabI-gltA1-gltA2-udhA | 66637 |
| pCASCADE-FG1G2UA | pCASCADE-fabI-gltA1-gltA2-udhA-gapA | 87154 |
| pCASCADE-FG1G2UZ | pCASCADE-fabI-gltA1-gltA2-udhA-zwf | 87148 |
| pCASCADE-FG1G2UZA | pCASCADE-fabI-gltA1-gltA2-udhA-zwf-gapA | 87149 |
| pCASCADE-FG1G2Z | pCASCADE-fabI-gltA1-gltA2-zwf | 66638 |
| pCASCADE-FG2 | pCASCADE-fabI-gltA2 | 71341 |
| pCASCADE-FU | pCASCADE-fabI-udhA | 66636 |
| pCASCADE-FZ | pCASCADE-fabI-zwf | 71335 |
| pCASCADE-G1G2 | pCASCADE-gltA1-gltA2 | 71348 |
| pCASCADE-G1G2A | pCASCADE-gltA1-gltA2-gapA | 87150 |
| pCASCADE-G1G2U | pCASCADE-gltA1-gltA2-udhA | 71343 |
| pCASCADE-G1G2UA | pCASCADE-gltA1-gltA2-udhA-gapA | 87151 |
| pCASCADE-G1G2UZ | pCASCADE-gltA1-gltA2-udhA-zwf | 87152 |
| pCASCADE-G1G2Z | pCASCADE-gltA1-gltA2-zwf | 71347 |
| pCASCADE-G1U | pCASCADE-gltA1-udhA | 71339 |
| pCASCADE-G1Z | pCASCADE-gltA1-zwf | 71337 |
| pCASCADE-G2U | pCASCADE-gltA2-udhA | 65819 |
| pCASCADE-G2Z | pCASCADE-gltA2-zwf | 71338 |
| pCASCADE-gltA1 | pCASCADE-gltA1 | 71334 |
| pCASCADE-gltA2 | pCASCADE-gltA2 | 65817 |
| pCASCADE-udhA | pCASCADE-udhA | 65818 |
| pCASCADE-UZ | pCASCADE-udhA-zwf | 87153 |
| pCASCADE-zwf | pCASCADE-zwf | 65825 |

Section 7: 2-Stage Micro-Fermentations

E. coli Media Stock Solutions

10× concentrated Ammonium-Citrate 30 salts (1L), mix 30 g of $(NH_4)_2SO_4$ and 1.5 g citric acid in water with stirring, adjust pH to 7.5 with 10 M NaOH. Autoclave and store at room temperature (RT).

10× concentrated Ammonium-Citrate 90 salts (1L), mix 90 g of $(NH_4)_2SO_4$ and 2.5 g citric acid in water with stirring, adjust pH to 7.5 with 10 M NaOH. Autoclave and store at RT.

1 M Potassium 3-(N-morpholino) propanesulfonic Acid (MOPS), adjust to pH 7.4 with 50% KOH. Filter sterilize (0.2 μm) and store at RT.

0.5 M potassium phosphate buffer, pH 6.8, mix 248.5 mL of 1.0 M $K_2HPO_4$ and 251.5 mL of 1.0 M $KH_2PO_4$ and adjust to a final volume of 1000 mL with ultrapure water. Filter sterilize (0.2 μm) and store at RT.

2 M $MgSO_4$ and 10 mM $CaSO_4$ solutions. Filter sterilize (0.2 μm) and store at RT.

50 g/L solution of thiamine-HCl. Filter sterilize (0.2 μm) and store at 4° C.

500 g/L solution of glucose, dissolve by stirring with heat. Cool, filter sterilize (0.2 μm), and store at RT.

100 g/L yeast extract, autoclave, and store at RT.

100 g/L casamino acid, autoclave, and store at RT.

500× Trace Metal Stock: Prepare a solution of micronutrients in 1000 mL of water containing 10 mL of concentrated $H_2SO_4$, 0.6 g $CoSO_4 \cdot 7H_2O$, 5.0 g $CuSO_4 \cdot 5H_2O$, 0.6 g $ZnSO_4 \cdot 7H_2O$, 0.2 g $Na_2MoO_4 \cdot 2H_2O$, 0.1 g $H_3BO_3$, and 0.3 g $MnSO_4 \cdot H_2O$. Filter sterilize (0.2 μm) and store at RT in the dark.

Prepare a fresh solution of 40 mM ferric sulfate heptahydrate in water, filter sterilize (0.2 μm) before preparing media each time.

Media Components

Prepare the final working medium by aseptically mixing stock solutions based on the following tables in the order written to minimize precipitation, then filter sterilize (with a 0.2 μm filter).

TABLE 11

Seed Media, pH 6.8:

| Ingredient | Unit | SM10 | SM10++ |
|---|---|---|---|
| $(NH_4)_2SO_4$ | g/L | 9 | 9 |
| Citric Acid | g/L | 0.25 | 0.25 |

TABLE 11-continued

Seed Media, pH 6.8:

| Ingredient | Unit | SM10 | SM10++ |
|---|---|---|---|
| Potassium Phosphate | mM | 5 | 5 |
| $CoSO_4 \cdot 7H_2O$ | g/L | 0.0048 | 0.0048 |
| $CuSO_4 \cdot 5H_2O$ | g/L | 0.04 | 0.04 |
| $ZnSO_4 \cdot 7H_2O$ | g/L | 0.0048 | 0.0048 |
| $Na_2MoO_4 \cdot 2H_2O$ | g/L | 0.0016 | 0.0016 |
| $H_3BO_3$ | g/L | 0.0008 | 0.0008 |
| $MnSO_4 \cdot H_2O$ | g/L | 0.0024 | 0.0024 |
| $FeSO_4 \cdot 7H_2O$ | g/L | 0.044 | 0.044 |
| $MgSO_4$ | mM | 2.5 | 2.5 |
| $CaSO_4$ | mM | 0.06 | 0.06 |
| Glucose | g/L | 45 | 45 |
| MOPS | mM | 200 | 200 |
| Thiamine-HCl | g/L | 0.01 | 0.01 |
| Yeast Extract | g/L | 1 | 2.5 |
| Casamino Acids | g/L | 0 | 2.5 |

TABLE 12

Production/Wash Media, pH 6.8:

| Ingredient | Unit | FGM3 | FGM3 No Phosphate | FGM3 Wash | FGM3 + 40 mM phosphate | FGM10 |
|---|---|---|---|---|---|---|
| $(NH_4)_2SO_4$ | g/L | 3 | 3 | 3 | 3 | 9 |
| Citric Acid | g/L | 0.15 | 0.15 | 0.15 | 0.15 | 0.25 |
| Potassium Phosphate | mM | 1.8 | 0 | 0 | 40 | 5 |
| $CoSO_4 \cdot 7H_2O$ | g/L | 0.0024 | 0.0024 | 0 | 0.0024 | 0.0048 |
| $CuSO_4 \cdot 5H_2O$ | g/L | 0.02 | 0.02 | 0.00 | 0.02 | 0.04 |
| $ZnSO_4 \cdot 7H_2O$ | g/L | 0.0024 | 0.0024 | 0 | 0.0024 | 0.0048 |
| $Na_2MoO_4 \cdot 2H_2O$ | g/L | 0.0008 | 0.0008 | 0 | 0.0008 | 0.0016 |
| $H_3BO_3$ | g/L | 0.0004 | 0.0004 | 0 | 0.0004 | 0.0008 |
| $MnSO_4 \cdot H_2O$ | g/L | 0.0012 | 0.0012 | 0 | 0.0012 | 0.0024 |
| $FeSO_4 \cdot 7H_2O$ | g/L | 0.022 | 0.022 | 0 | 0.022 | 0.044 |
| $MgSO_4$ | mM | 2 | 2 | 0 | 2 | 2.5 |
| $CaSO_4$ | mM | 0.05 | 0.05 | 0 | 0.05 | 0.06 |
| Glucose | g/L | 45 | 25 | 0 | 45 | 25 |
| MOPS | mM | 200 | 200 | 0 | 200 | 0 |
| Thiamine-HCl | g/L | 0.01 | 0.01 | 0 | 0.01 | 0.01 |

Micro-Fermentations

Figure 16A:
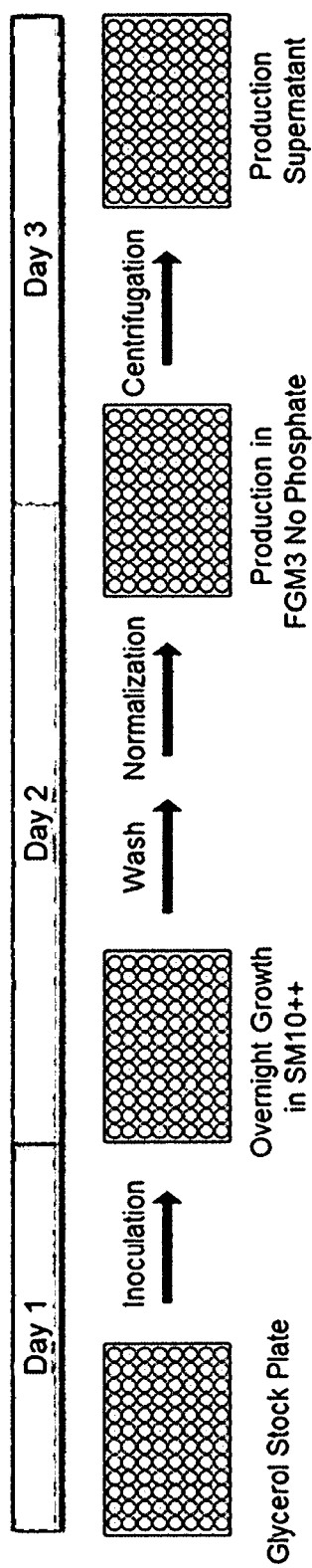
FIGS. 16A-C depict an overview of micro-fermentation process.
Figure 16B:
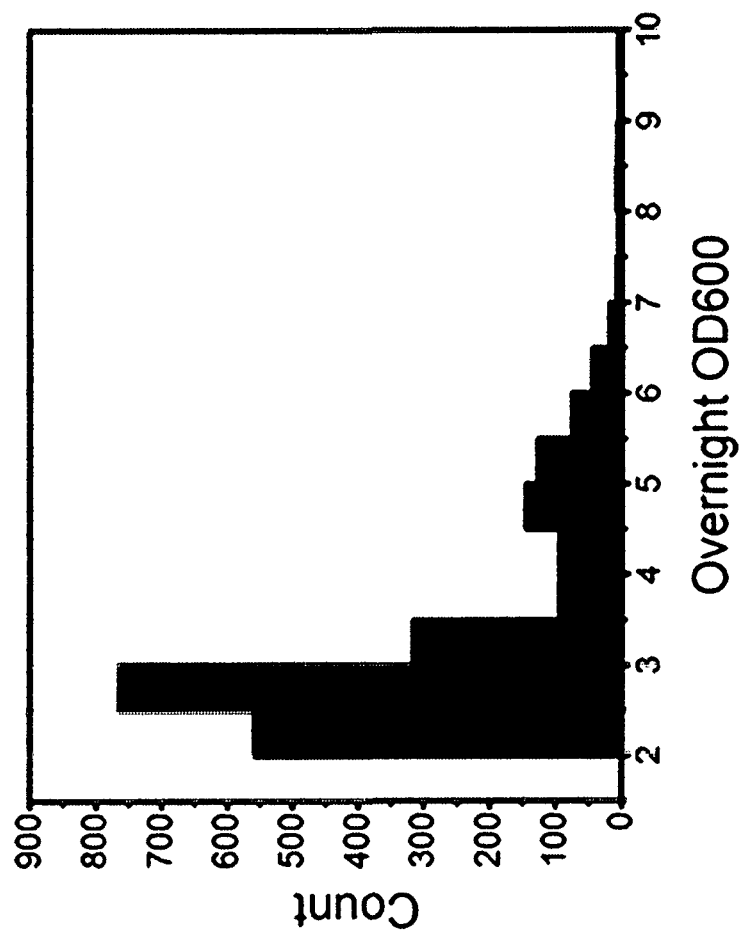
Figure 16C:
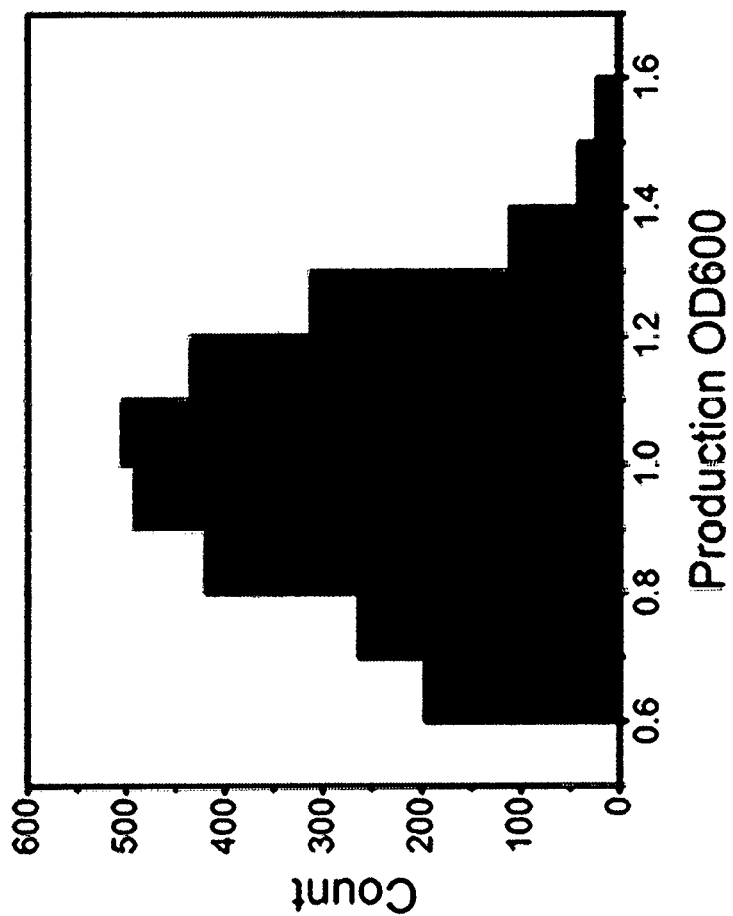
Figure 17:
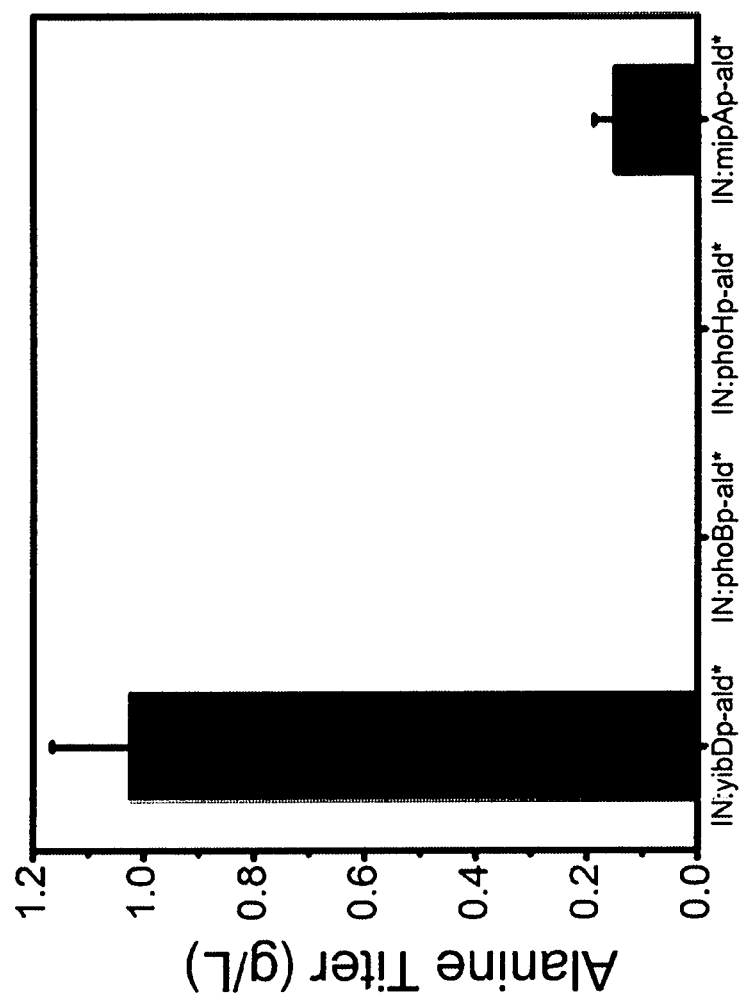
FIG. 17 depicts micro-fermentation for L-alanine production using different insulated phosphate promoters in DLF_0025 strain.

An overview of the micro-fermentation protocol is illustrated in FIG. 16A-C. Strains were evaluated for production in 96 well plate micro-fermentations, wherein cells were initially grown to mid-log phase, harvested, washed, resuspended and normalized in a phosphate free production medium to an OD600=1, for a 24 hour production stage. The success of the micro-fermentations required: (1) syncing strains up by harvesting all strains in exponential phase; (2) the use of low biomass levels, so that batch sugar could be kept low while enabling significant potential product accumulation; and (3) a method to supply adequate mixing and aeration, while minimizing evaporative losses. To address the final requirement, commercially available microplate sandwich covers and clamps from EnzyScreen™ was used, which greatly reduce evaporative losses while enabling high levels of mixing and aeration in standard 25 mm orbit shakers operating at 400 rpm[92-93]. Micro-fermentation results for alanine production with different insulated phosphate promoters are shown in FIG. 17. Micro-fermentation results for strains evaluated with gapA and gapN gene alterations are given in FIG. 18.

Section 8: Micro-Fermentations Robustness Evaluation

During micro-fermentation oxygen robustness studies, production culture volume was varied to achieve desired oxygen transfer rate (OTR) values as previously reported (http://www.enzyscreen.com/oxygen_transfer_rates.htm)[92-93], and as listed below in Table 14. Batch glucose levels during the production stage were altered to assess robustness to glucose. Strains utilized in the robustness experiments at the micro-fermentation scale are listed in Table 15. Results from the micro-fermentation robustness studies are given in FIGS. 19A-D, FIGS. 20A-D, FIGS. 21A-D, FIGS. 22A-D, FIGS. 23A-D, FIGS. 24A-D, FIGS. 25A-D, FIGS. 26A-D, FIGS. 27A-D, FIGS. 28A-D, FIGS. 29A-D, FIGS. 30A-D, FIGS. 31A-D, and FIG. 32.

TABLE 14

Culture conditions for different OTR values. 25 mm orbit shaker

| Max OTR (mmol/L-hr) | Shaking Speed (rpm) | Fill Volume (μL) |
|---|---|---|
| 25 | 400 | 100 |
| 20 | 400 | 150 |
| 15 | 400 | 200 |

TABLE 15

List of strains used for micro-fermentation robustness evaluations and their RS scores.

| Strain # | Silencing | Proteolysis | Plasmid | RS |
|---|---|---|---|---|
| 1 | gltA1 | FU | pSMART-Ala2 | 89.6 |
| 2 | gltA1 | F | pSMART-Ala2 | 89.5 |
| 3 | gltA1 | GU | pSMART-Ala2 | 89.4 |
| 4 | FG1G2 | None | pSMART-Ala2 | 89.3 |
| 5 | G1G2 | GU | pSMART-Ala2 | 88.8 |
| 6 | FG1G2 | G | pSMART-Ala2 | 88.2 |
| 7 | G1G2 | F | pSMART-Ala2 | 83.4 |
| 8 | gltA2 | FGU | pSMART-Ala2 | 83.4 |
| 9 | gltA1 | FGU | pSMART-Ala2 | 83.1 |

TABLE 15-continued

List of strains used for micro-fermentation robustness evaluations and their RS scores.

| Strain # | Silencing | Proteolysis | Plasmid | RS |
|---|---|---|---|---|
| 10 | G1G2 | FGU | pSMART-Ala2 | 82.3 |
| 11 | gltA2 | U | pSMART-Ala2 | 82.2 |
| 12 | gltA2 | F | pSMART-Ala2 | 80.6 |
| 13 | FG1G2 | FG | pSMART-Ala2 | 80.5 |
| 14 | None | G | pSMART-Ala2 | 79.9 |
| 15 | gltA2 | GU | pSMART-Ala2 | 77.9 |
| 16 | fabI | FGU | pSMART-Ala2 | 75.7 |
| 17 | None | FG | pSMART-Ala2 | 75.4 |
| 18 | G1G2 | FU | pSMART-Ala2 | 75.3 |
| 19 | None | FGU | pSMART-Ala2 | 73.4 |
| 20 | None | FU | pSMART-Ala2 | 73.3 |
| 21 | gltA1 | U | pSMART-Ala2 | 72.9 |
| 22 | fabI | FG | pSMART-Ala2 | 69.1 |
| 23 | FG1G2 | FU | pSMART-Ala2 | 67.6 |
| 24 | gltA2 | FU | pSMART-Ala2 | 67.5 |
| 25 | None | F | pSMART-Ala2 | 65.6 |
| 26 | gltA2 | FG | pSMART-Ala2 | 62.1 |
| 27 | FG1G2 | F | pSMART-Ala2 | 61.1 |
| 28 | fabI | GU | pSMART-Ala2 | 59.9 |
| 29 | fabI | F | pSMART-Ala2 | 59.6 |
| 30 | gltA1 | FG | pSMART-Ala2 | 58.1 |
| 31 | gltA1 | None | pSMART-Ala2 | 57.1 |
| 32 | None | None | pSMART-Ala2 | 55.5 |
| 33 | G1G2 | None | pSMART-Ala2 | 54.1 |
| 34 | fabI | U | pSMART-Ala2 | 53.9 |
| 35 | gltA2 | G | pSMART-Ala2 | 52.8 |
| 36 | fabI | None | pSMART-Ala2 | 50.3 |
| 37 | fabI | FU | pSMART-Ala2 | 48.4 |
| 38 | gltA2 | None | pSMART-Ala2 | 47.8 |
| 39 | FG1G2 | FGU | pSMART-Ala2 | 44.6 |
| 40 | None | GU | pSMART-Ala2 | 42.9 |
| 41 | None | U | pSMART-Ala2 | 39.3 |
| 42 | fabI | G | pSMART-Ala2 | 39.2 |
| 43 | gltA1 | G | pSMART-Ala2 | 34.7 |
| 44 | G1G2 | FG | pSMART-Ala2 | 32.8 |
| 45 | FG1G2 | U | pSMART-Ala2 | 29.4 |
| 46 | FG1G2 | GU | pSMART-Ala2 | 24.3 |
| 47 | G1G2 | G | pSMART-Ala2 | 24.1 |
| 48 | G1G2 | U | pSMART-Ala2 | −25.3 |
| 49 | None | None | pSMART-Ala13 | 55.7 |
| 50 | None | None | pSMART-Ala12 | −31.5 |
| 51 | None | None | pSMART-Ala15 | −103.2 |
| 52 | None | None | pSMART-Ala11 | −114.1 |
| 53 | None | None | pSMART-Ala14 | −441.5 |

Section 9: Standardized 2-Stage Fermentations

Figure 33A:
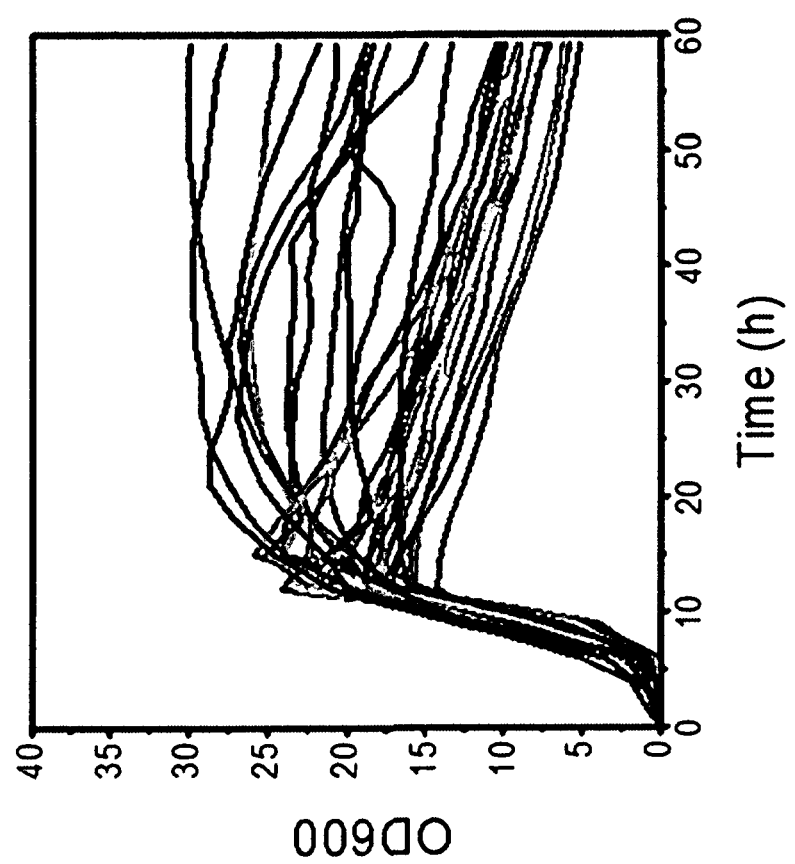
FIGS. 33A-B depict growth profile for all valve and growth associated strains at 1 L scale evaluated in this paper.

A standardized phosphate limited 2-stage fermentation protocol was utilized for evaluation of all valve strains. This protocol yields highly reproducible growth stage results, with minimal strain to strain variability even with strains making different products. More significant variability was observed during the production stage as a result of differing feed rates and base utilization by different strains. FIG. 33A gives the growth curves for all valve strains with a 10 g·cdw/L biomass level in 1 L fermentations performed in this study. This consistency is contrasted to the more variable growth of growth associated production strains, given in FIG. 33B.

TABLE 16

Strains used for mevalonic acid scalability.

| Strain # | Silencing | Proteolysis | Plasmid |
|---|---|---|---|
| 1 | FG1G2 | FU | pSMART-Mev2 |
| 2 | G2Z | FGUA | pSMART-Mev2 |
| 3 | FG1G2A | FUN | pSMART-Mev2 |
| 4 | UZ | FGUA | pSMART-Mev2 |

Section 10: Analytical Methods

TABLE 17

| | UPLC-MS/MS parameters | | | | |
|---|---|---|---|---|---|
| Analyte | Retention Time (min) | ESI Mode | MRM Transition(s) | Cone Voltage | Collision Energy |
| Alanine | 0.5 | + | 89.95→44.08 | 15 | 9 |
| C13-Alanine | 0.5 | + | 91.95→46.08 | 15 | 9 |

DETAILED DESCRIPTION OF FIGURES

Figure 1B:
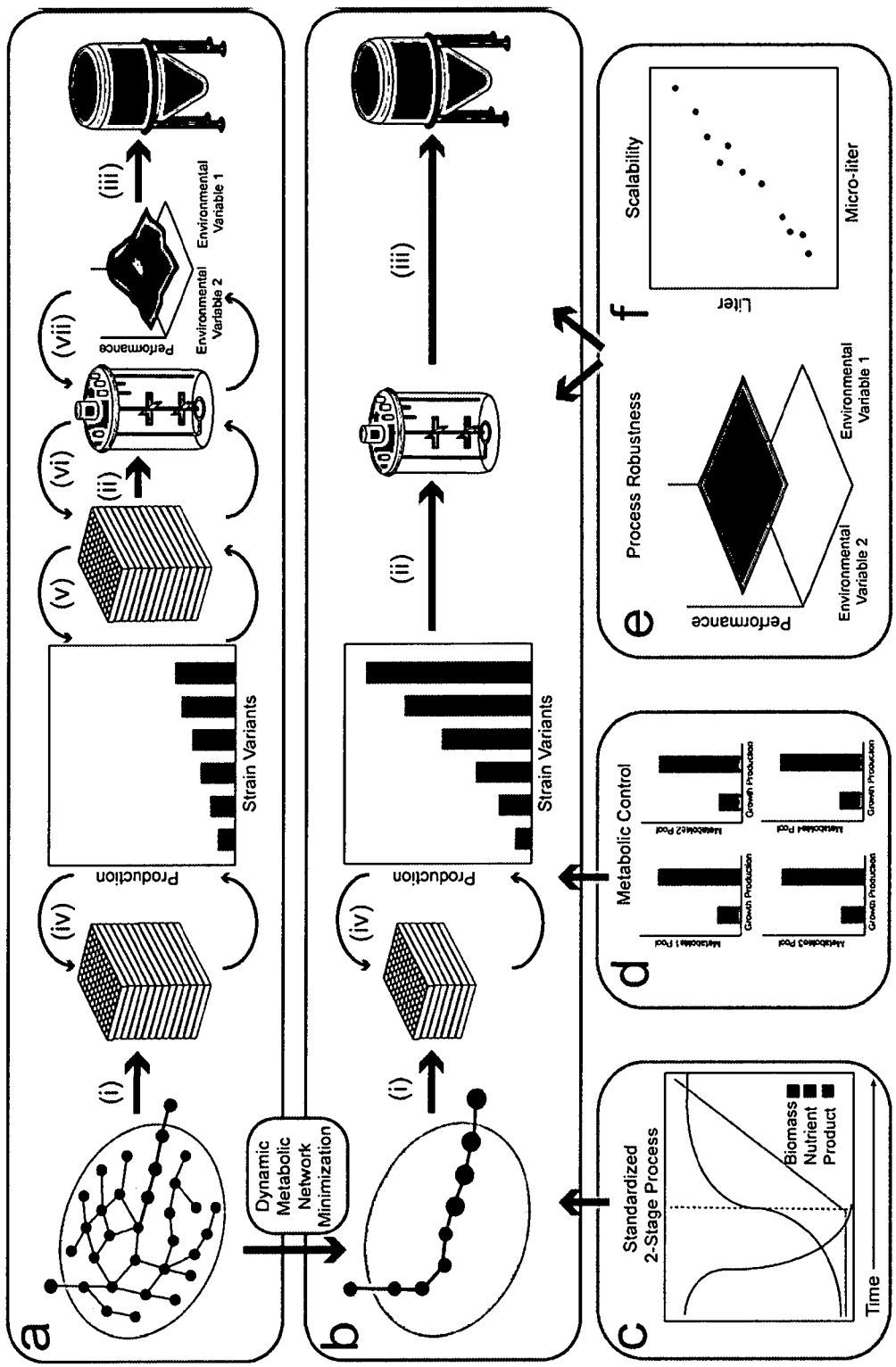
FIG. 1B depicts strain and bioprocess optimization.

FIG. 1A: An Overview of Dynamic Metabolic Control in 2-Stage Fermentations. Metabolic engineering involves optimizing a metabolic pathway to a desired product to the existing metabolic network of a host, converting feedstocks to a desired product. Filled circles indicate metabolites and lines indicate enzymatic reactions. Traditional optimization in metabolic engineering, often involves three key steps (a) the deletion of competing non-essential metabolic pathways including those leading to undesired byproducts and the overexpression of enzymes in the pathway converting feedstock molecules to the product (indicated by thicker lines) and potentially (b) attenuating enzymes in essential metabolism (indicated by orange lines) to further increase production. This process is iterated to optimize the yield to the desired product (pie charts). By contrast, dynamic metabolic network minimization can be used to fully unlock the potential of commonly used 2-stage fermentation processes (c-d). In the first stage of these processes (c) biomass growth and yield are optimized, while in the second stage (d) product formation is optimized, which is well suited for a 2-stage process (e) in which biomass levels accumulate and consume a limiting nutrient (in this case inorganic phosphate), which when depleted triggers entry into a productive stationary phase. Synthetic metabolic valves utilizing CRISPRi based gene silencing and/or controlled proteolysis can be used (f and g) to greatly reduce the pertinent metabolic network upon the transition to the production stage, (f) and array of silencing guides can be induced, processed by the CASCADE complex into individual guides and used to silencing target multiple genes of interest (GOI). (g) If C-terminal DAD+4 lags are added to enzymes of interest (EOI) through chromosomal modification, they can be inducibly degraded by the clpXP protease in the present of and inducible sspB chaperone. (h) Dynamic control over protein levels in *E. coli* using 2 stage dynamic control with inducible proteolysis and CRISPRi silencing. As cells grow phosphate is depleted, and cells "turn off mCherry and "turn on" GFPuv. Shaded areas represent one standard deviation from the mean, n=3. (i) Relative impact of proteolysis and gene silencing alone and in combination on mCherry degradation, with (j) decays rates.

FIG. 1B: Strain and Bioprocess Optimization. (a) Conventional approaches for strain and process optimization in metabolic engineering often involves deletion of competing non-essential metabolic pathways and overexpression of pathway enzymes (Filled circles: metabolites; lines: enzymatic reactions. green indicated a production pathway). (a-i) Strain variants are evaluated at screening scale (microtiter plates, shake flasks, etc), (a-ii) the best strains are assessed in larger scale instrumented bioreactors. Numerous design-build-test cycles (a-vi-vii) are used to iteratively optimize both the production strain and process, including the often-critical optimization of environmental (process) variables (a-vii). (a-iii) The best performing strains and associated optimized process conditions are scaled to industrially relevant levels. (b) Rapid strain and bioprocess optimization using 2-stage dynamic metabolic control. The metabolic network in the cell is dynamically minimized to only the steps essential for product formation. This is accomplished in a standardized 2-stage bioprocess (c), where a biomass accumulating growth stage is followed by a production stage, with only a minimal metabolic network. The limitation of a macronutrient can be used to "switch" cellular metabolism from growth to production. The approach results in a smaller subset of potential strain variants for screening (b-i). Metabolic network minimization helps increase relevant metabolite levels (d) and thus production levels, it also enhances process robustness (e), and as a result process and strain scalability (f). The best producers identified from screening are predictably and rapidly scaled to (b-ii) larger instrumented bioreactors, and (b-iii) subsequently to industrially relevant levels. If needed, limited design-build-test cycles (b-iv) are incorporated to guide improvements. Product independent, standardized protocols are followed for strain evaluation at all scales, eliminating the need for intensive process optimization.

Figure 2B:
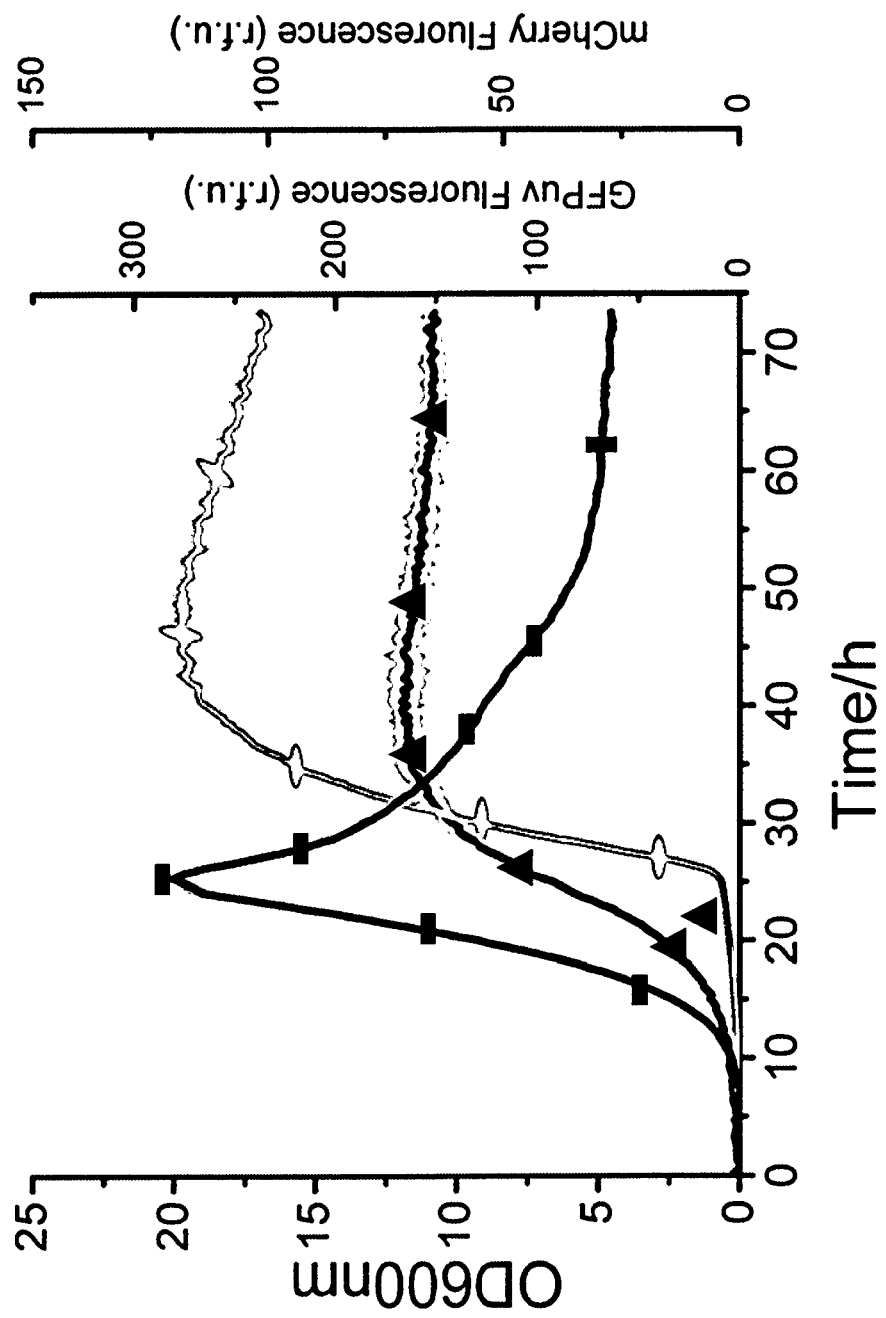
Figure 2C:
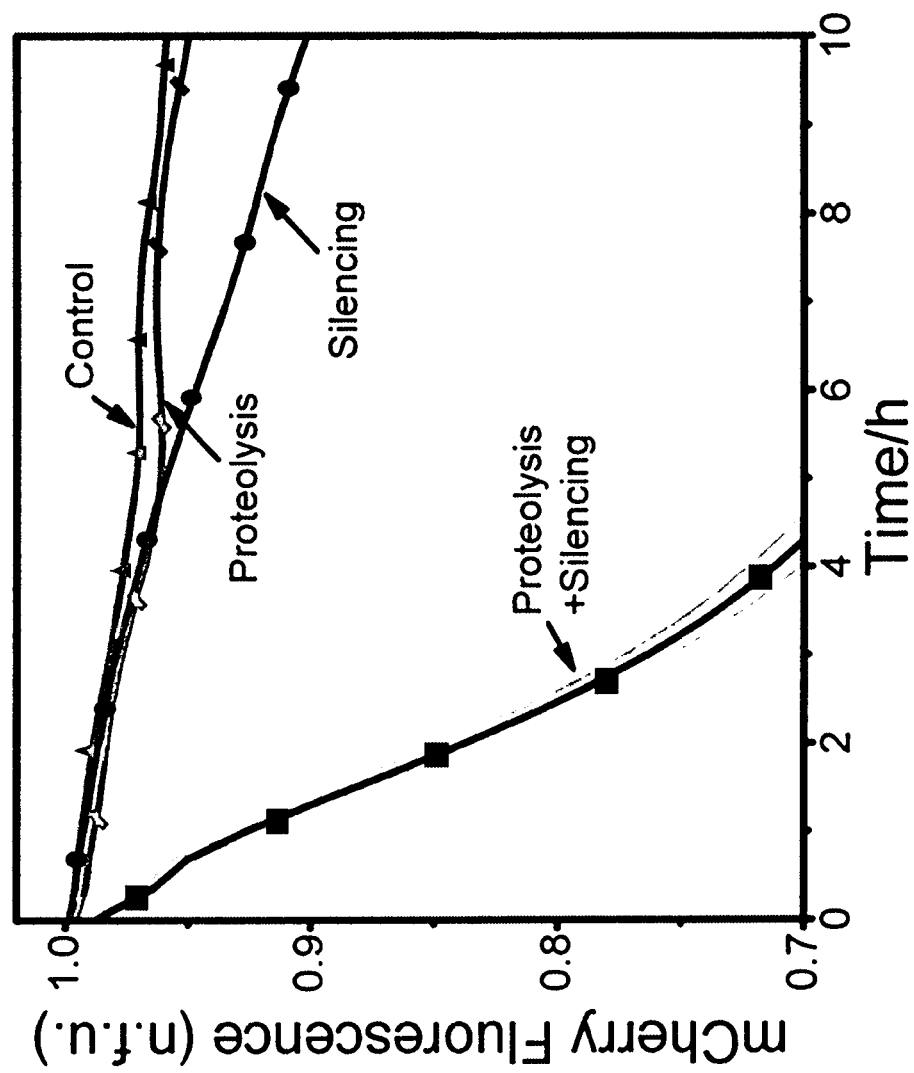
Figure 2D:
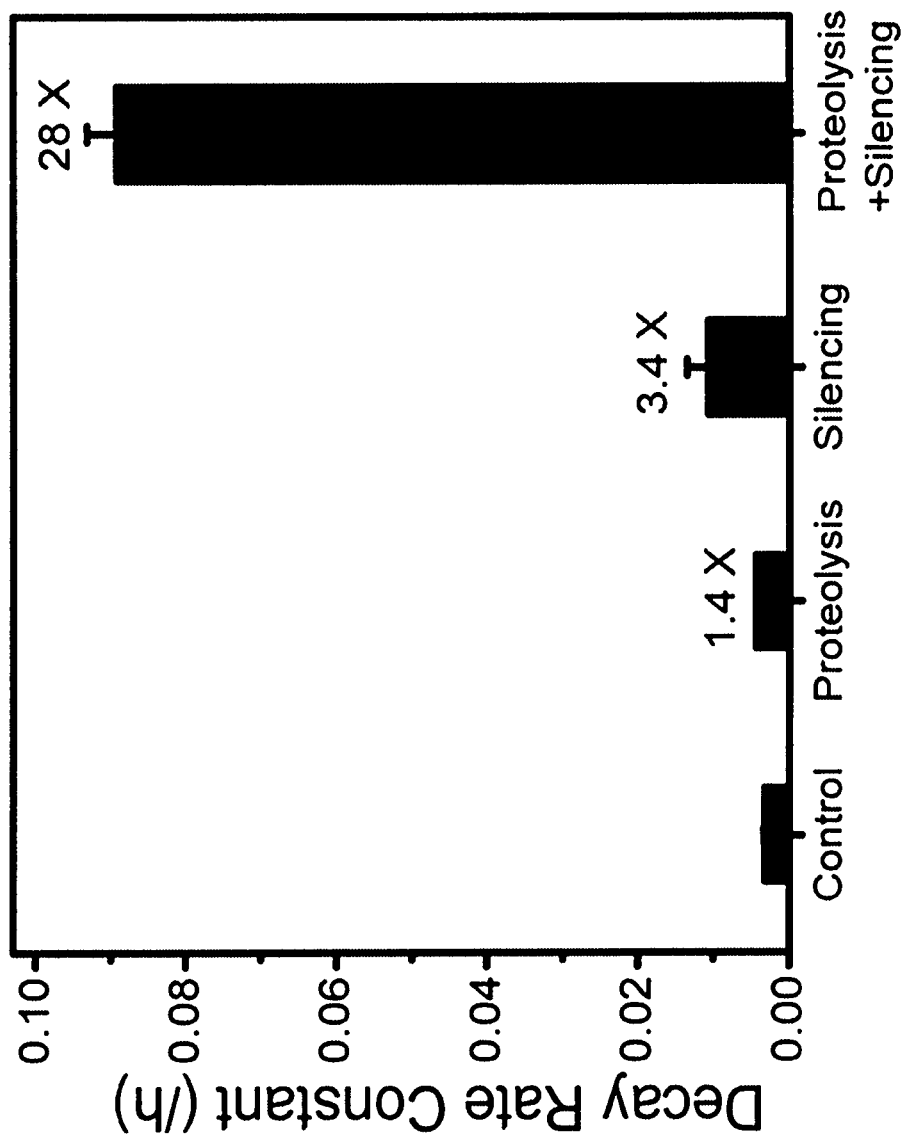

FIGS. 2A-D: Implementation of 2-stage Synthetic Metabolic Valves (SMVs) in *E. coli*. FIG. 2A depicts SMVs utilizing CRISPRi based gene silencing and/or controlled proteolysis were constructed. (Top) Silencing: An array of inducible silencing guide RNAs (i) can be used to silence expression of multiple genes of interest (GOI) when the native *E. coli* CRISPR/Cascade machinery is expressed, which can process guide arrays into individual guides (ii). (Bottom) Proteolysis: When C-terminal DAS+4 tags are added to enzymes of interest (EOI) (through chromosomal modification), they can be degraded by the clpXP protease (iv) upon the controlled induction of the sspB chaperone (iii). FIG. 2B depicts dynamic control over protein levels in *E. coli* using inducible proteolysis and CRISPRi silencing. As cells grow phosphate is depleted, cells "turn OFF" mCherry and "turn ON" GFPuv. Shaded areas represent one standard deviation from the mean, u, relative fluorescence units. FIG. 2C depicts relative impact of proteolysis and gene silencing alone and in combination on mCherry degradation, n.f.u. normalized fluorescence units (normalized to maximal fluorescence). FIG. 2D depicts relative impact of proteolysis and gene silencing alone and in combination on observed mCherry fluorescence decays rates (per hour).

Figure 3F:
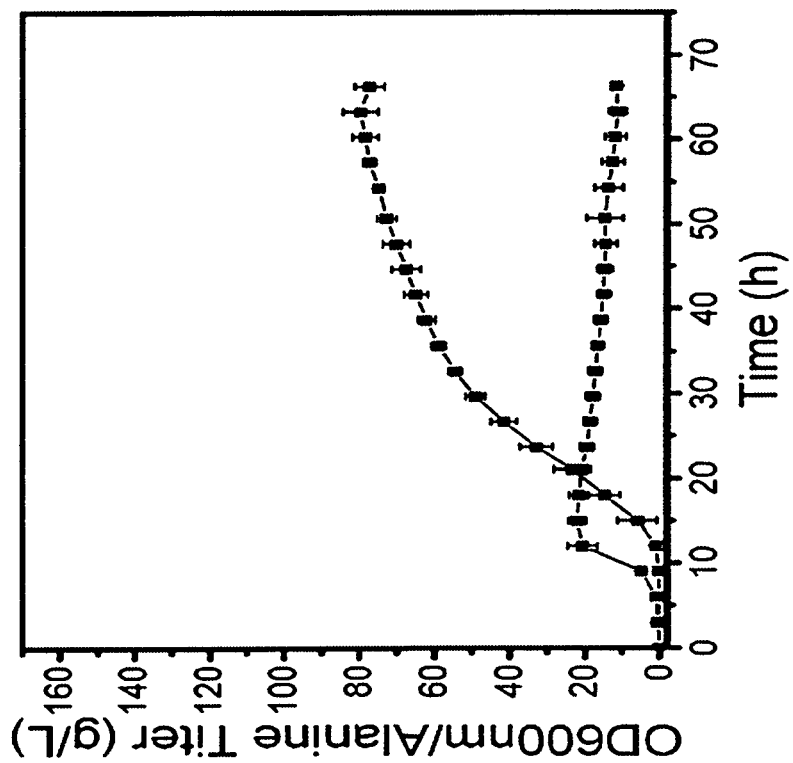
Figure 3H:
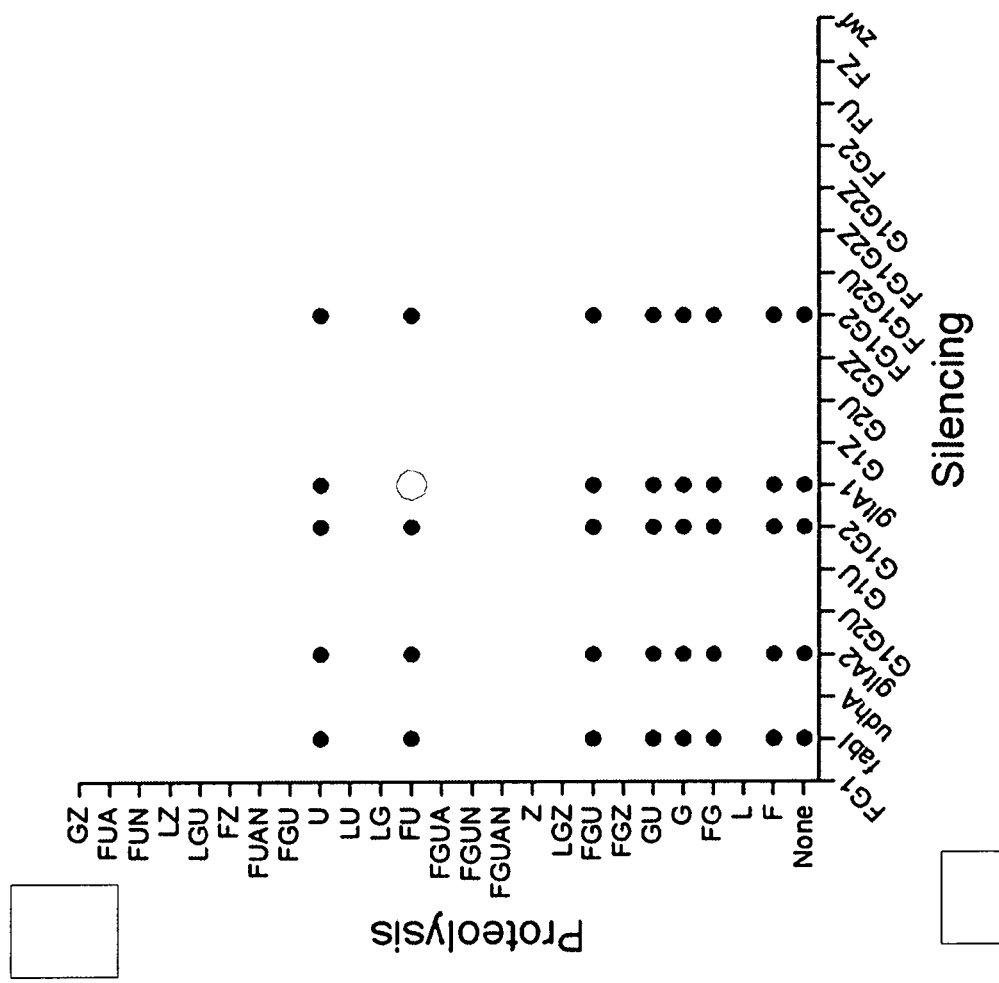
Figure 3I:
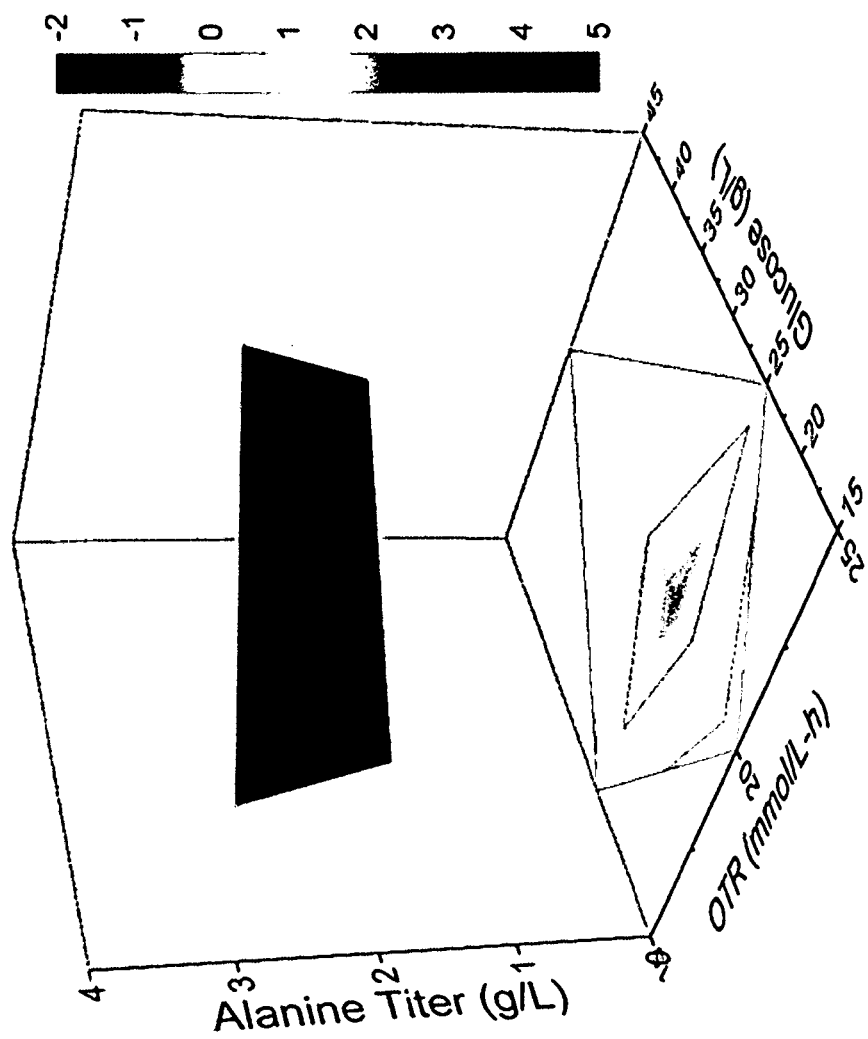
Figure 3K:
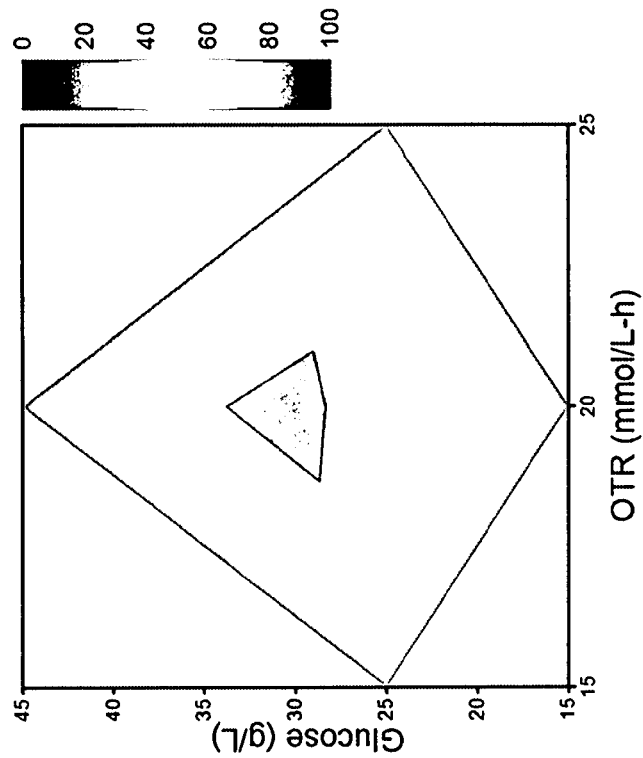
Figure 3J:
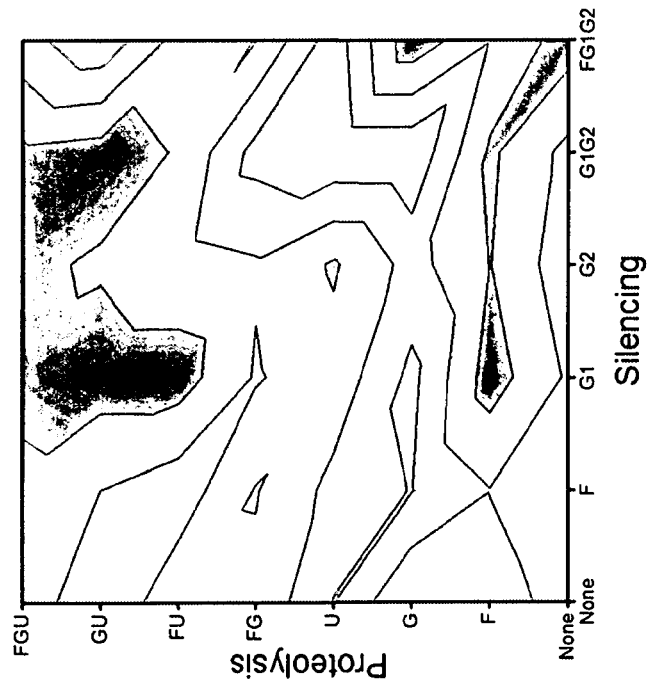

FIGS. 3A-K: Alanine Production in *E. coli* utilizing 2-stage Dynamic Control. FIG. 3A depicts strain variant design. Primary pathways in central metabolism are shown including: Glycolysis, the Pentose Phosphate Pathway, the Citric Acid Cycle (TCA), Fatty Acid Biosynthesis, and the Soluble Transhydrogenase. Key valve candidate enzymes/genes that are "turned OFF" to reduce flux through central metabolism can include: glucose-6-phosphate dehydrogenase (zwf-"Z"), lipoamide dehydrogenase (lpd-"L"), citrate synthase (gltA-"G"), enoyl-ACP reductase (fabI-"F"), and the soluble transhydrogenase (udhA-"U"). Importantly, dynamic elimination of fabI has been previously demonstrated to increase intracellular malonyl-CoA pools as well as malonyl-CoA flux[55]. Enzymes that are dynamically "turned ON" can include the metabolic pathways to produce the products of interest, in this case alanine. Specific pathway enzymes include an NADPH-dependent alanine dehydrogenase (ald*) and an alanine exporter (alaE). Additionally, as the alanine production pathway utilizes NADPH as a cofactor, the NADPH-dependent glyceraldehyde-3-phosphate dehydrogenase encoded by the gapN gene[56] from *S. mutans* was turned on alone and in combination with turning off the native gapA-"A" gene (NADH dependent glyceraldehyde dehydrogenase). Abbreviation: PTS—glucose phosphotransferase transport system, P—phosphate, BP-bisphosphate, OAA—oxaloacetate, DHAP—dihydroxyacetone phosphate, GA3P—glyceraldehyde-3-phosphate, 1,3-BPG—1,3 bisphosphoglycerate, 3-PG—3-phosphoglycerate, 2-PG—2-phosphoglycerate, PEP—phosphoenolpyruvate, MSA—malonate semialdehyde, ACP—acyl carrier protein, Ru—ribulose, Xu—xylulose, E—erthryose, Ri—ribose, S—sedoheptulose. Strains were engineered with SMVs for the dynamic control of all combinations of valve genes/enzymes, either through gene silencing alone, proteolysis alone, or the combination of both. These strains were evaluated for alanine production in standardized micro-fermentations. FIG. 3B depicts rank order plot for average alanine titer (black) of all valve strains examined in 2-stage micro-fermentation, grey area represents standard deviation. Alanine production in the control strain was colored in red. FIG. 3C depicts average alanine titer in 2-stage production in response to different proteolysis and silencing combinations, from 0 g/L (purple) to 5 g/L (red). FIG. 3D depicts average alanine titer in response to different oxygen transfer rates (OTR) and glucose concentrations evaluated for a single "Valve" alanine strain (Silencing of gltA1 ("G1"), Proteolysis of fabI and udhA ("FU")). The results of this surface were used to calculate a strain-specific robustness score (RS) (refer to text), this strain has the highest RS score. FIG. 3E depicts a heat map of the robustness score for a subset of 48 "Valve" strains evaluated across multiple process conditions. FIG. 3F depicts scale up of one of the best producing strain from micro-fermentations (Silencing of fabI-gltA1-gltA2 ("FG1G2"), Proteolysis of fabI, gltA and udhA ("FGU")) to 1 L bioreactors results in a titer of 80 g/L after 48 hrs of production, with a yield of 0.8 g/g. FIG. 3G depicts overexpression of the alaE alanine exporter in this strain (Panel 0 results in significantly improved production, reaching 147 g/L in 27 hrs of production, with a yield of ~1 g/g. (Refer to Supplemental Materials, Section 3 for additional details). FIG. 3H depicts strains selected for robustness evaluation in micro-fermentations. FIG. 3I depicts robustness and titer for the most robust "Valve" alanine strain (Silencing_gltA1, Proteolysis_FU). Bottom surface shows heat map for the alanine titer normalized to the median of all process conditions assessed, upper surface shows alanine tiler under all process conditions, the same color scale (alanine titer in g/L) was used for both panels. FIG. 3J depicts RS3 scores for the selected strains. FIG. 3K depicts process reproducibility heat map for all conditions evaluated, the same grayscale was used for FIG. 3J and FIG. 3K.

Figure 4A:
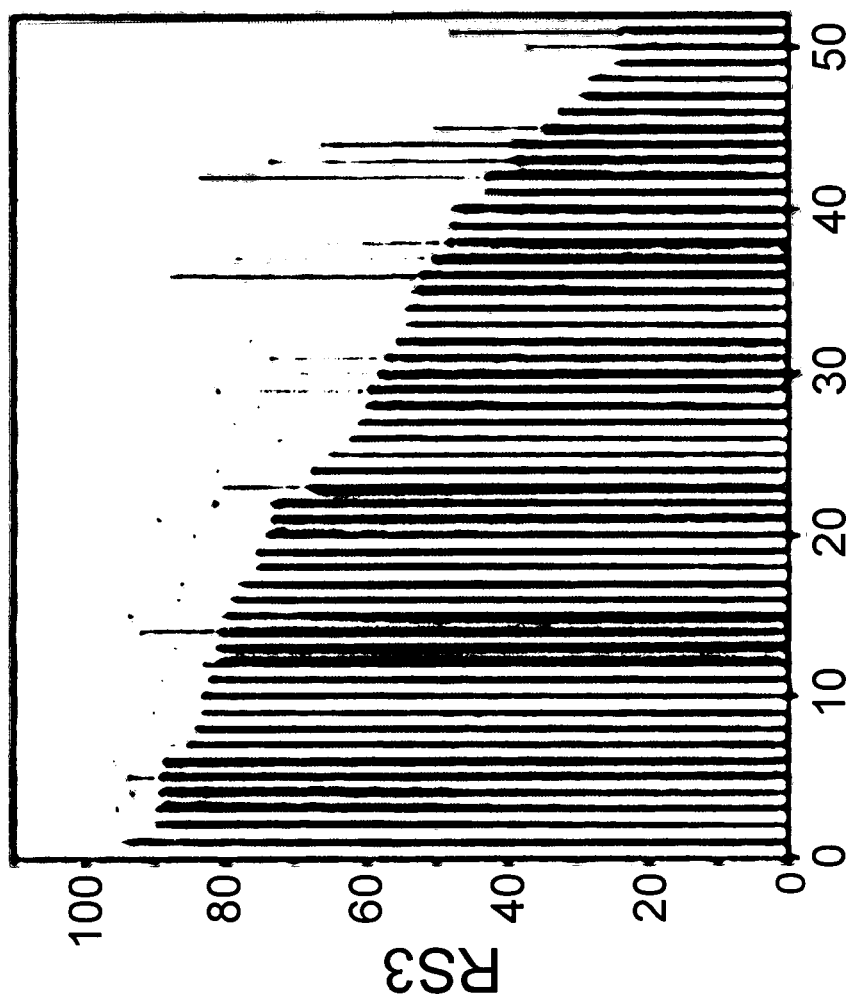
FIGS. 4A-F depict example robustness comparison between 2-stage and growth associated approaches.
Figure 4C:
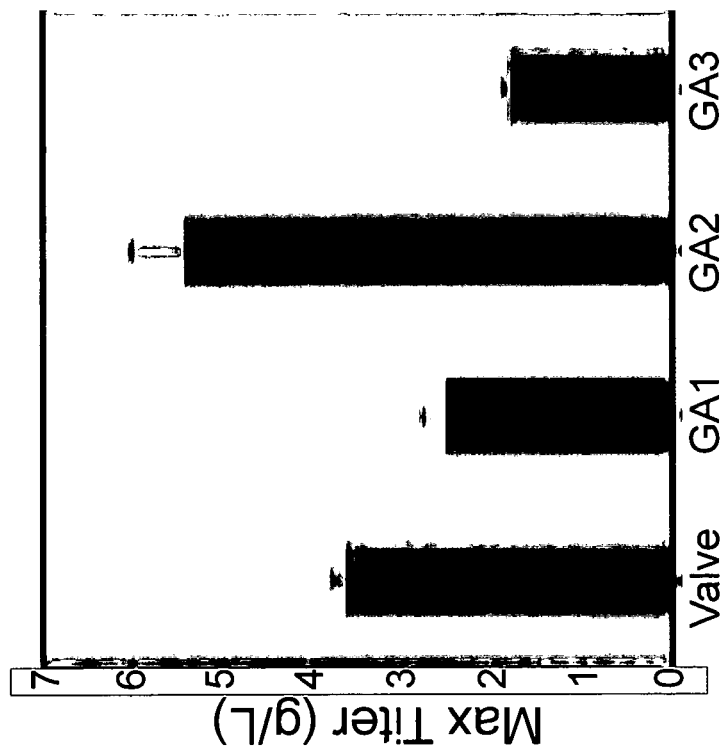
Figure 4B:
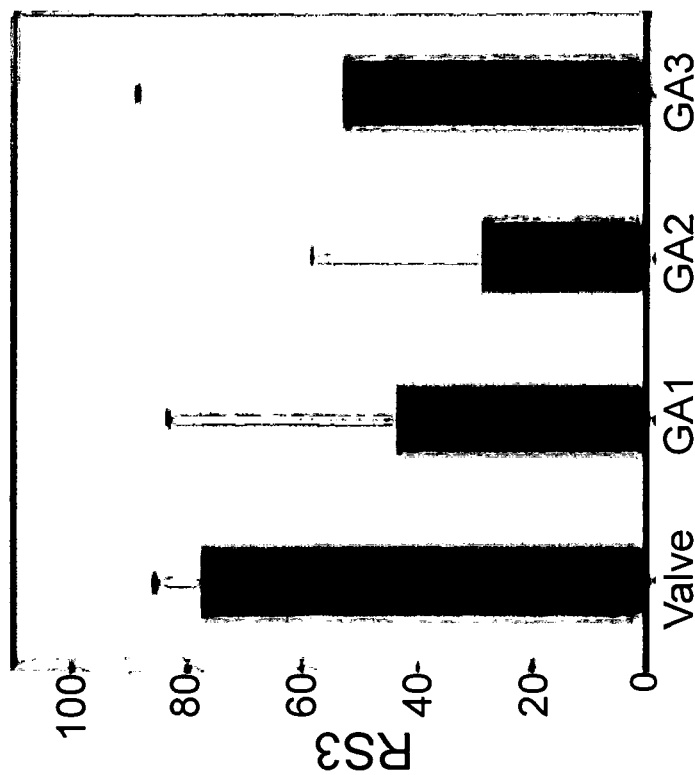
Figure 4D:
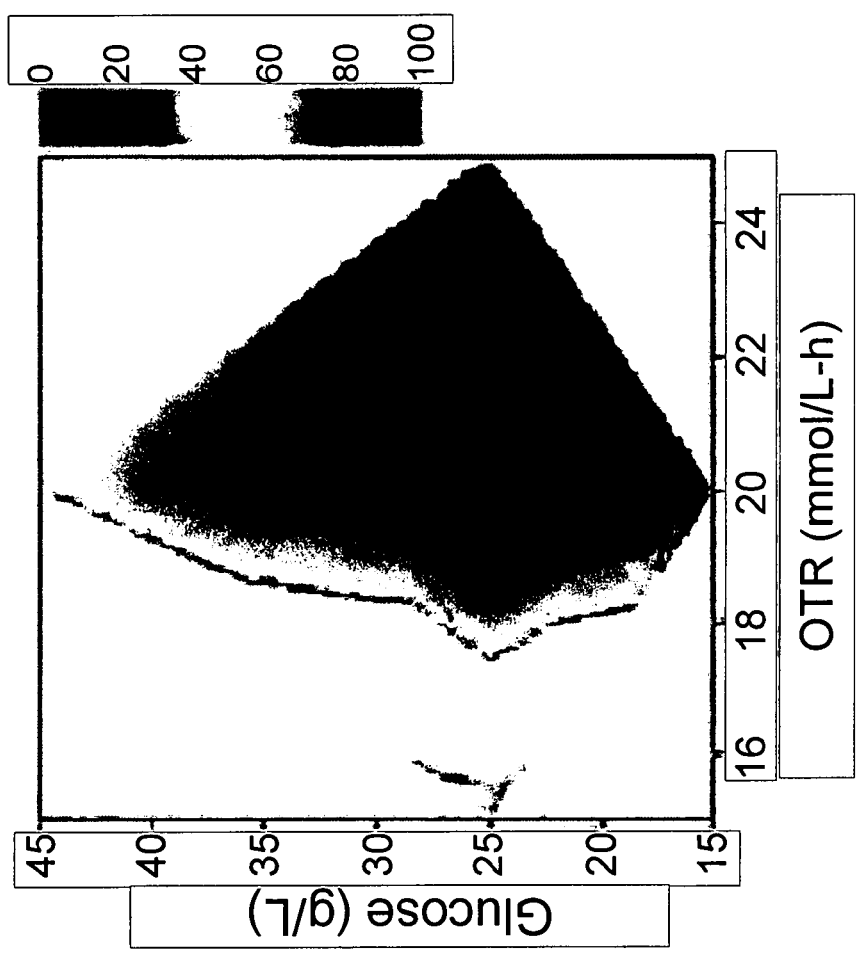
Figure 4E:
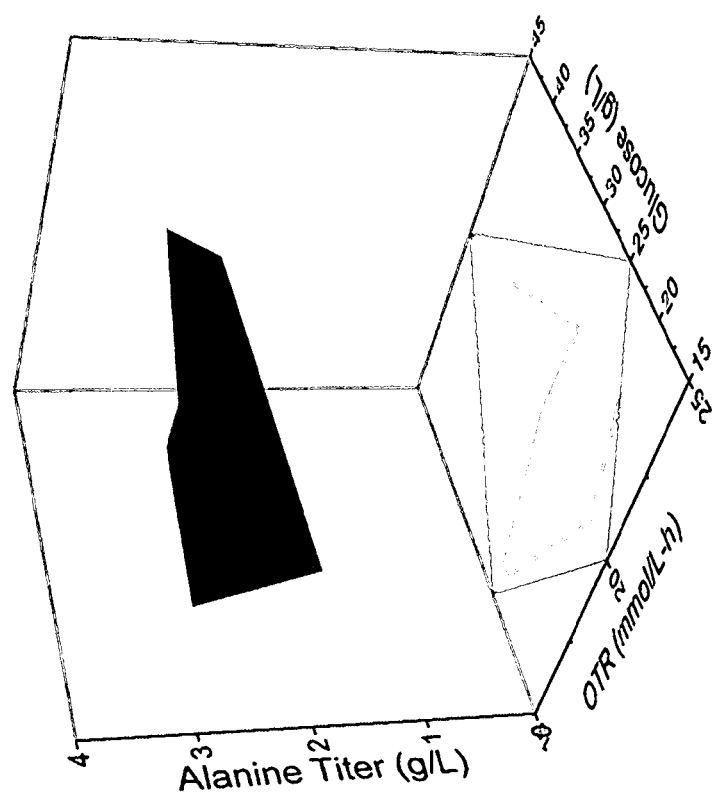
Figure 4F:
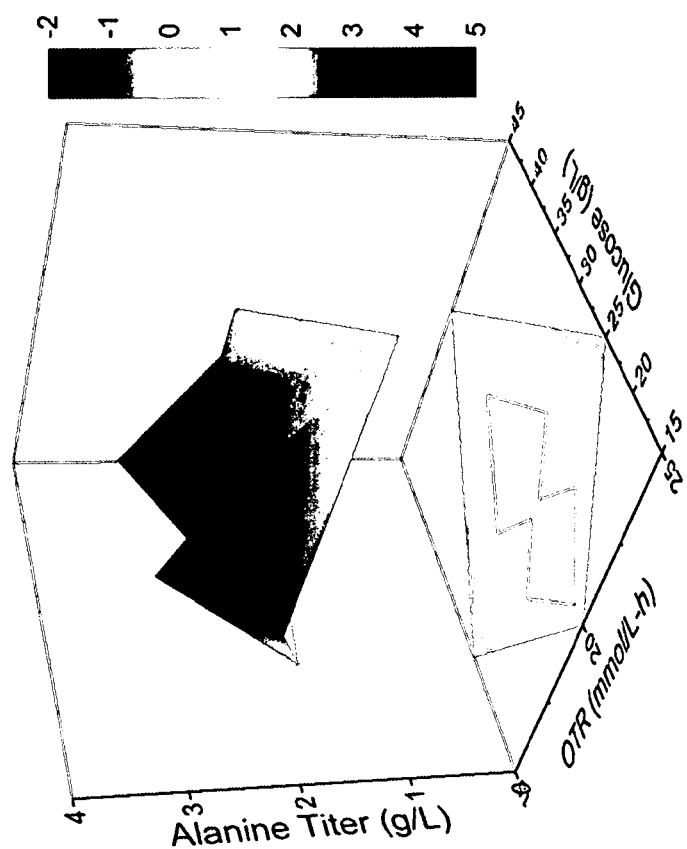

FIGS. 4A-F: Robustness Comparison Between 2-Stage and Growth Associated Approaches. FIG. 4A depicts rank order of the RS3 scores for all alanine strains evaluated, red bars indicate valve alanine strains, and blue bars indicate growth associated (GA) alanine strains. FIG. 4B depicts average RS3 score for "Valve" alanine strains with proteolysis "F" valve, and growth associated alanine strains. FIG. 4C depicts max titer plot for a representative "Valve" alanine (Proteolysis_FGU, Silencing_gltA1), and growth associated alanine strains in micro-fermentation of all conditions evaluated. FIG. 4D depicts process reproducibility for growth associated alanine strains under all conditions evaluated. FIG. 4E depicts robustness and titer for a representative robust "Valve" alanine (Proteolysis_FGU, Silencing_gltA1). FIG. 4F depicts robustness and titer for the GA2 strain. Bottom surface, heat map for the alanine titer normalized to the median of all process conditions assessed, upper surface, alanine titer under all process conditions, the same color scale (alanine titer in g/L) was used for both panels.

Figure 5A:
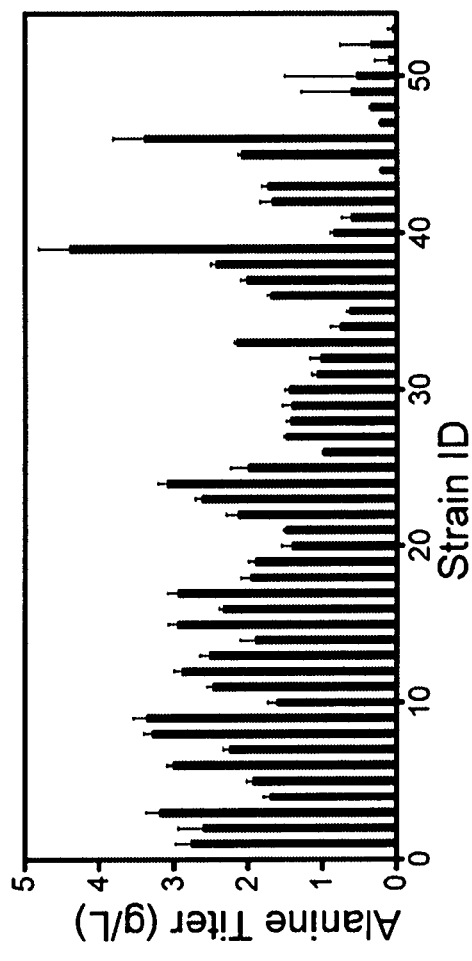
FIGS. 5A-J depict example comparisons of "Valve" and growth associated alanine production in micro-fermentations and 1 L fermentation.
Figure 5B:
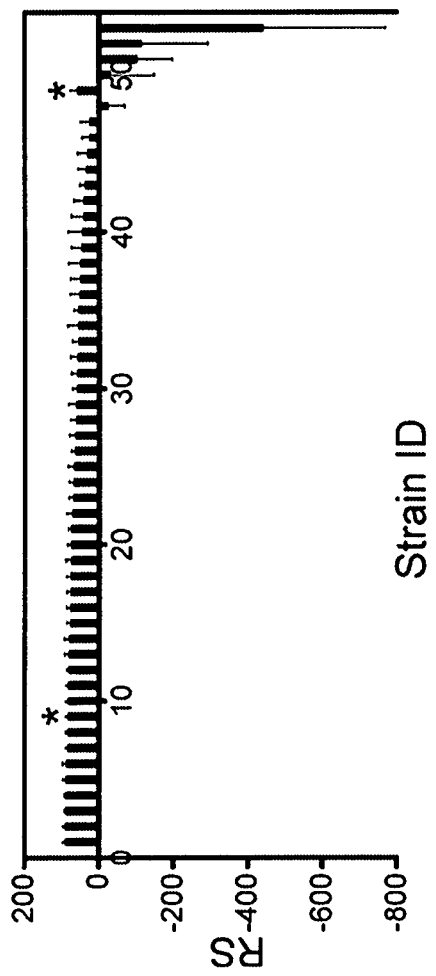
Figure 5C:
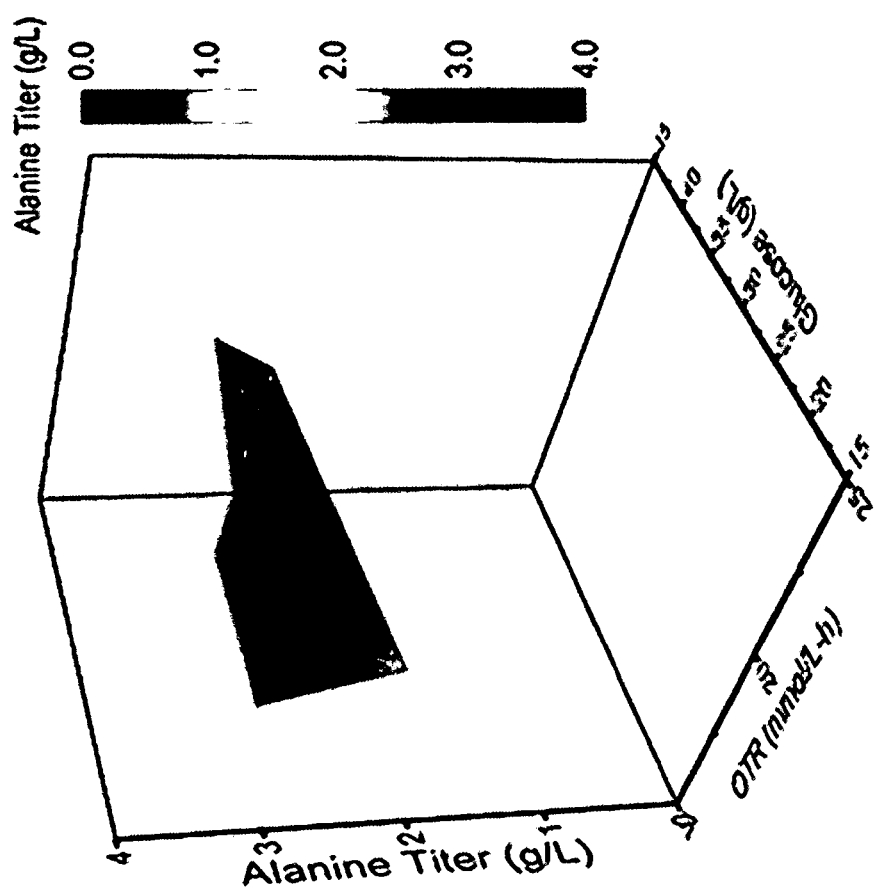
Figure 5D:
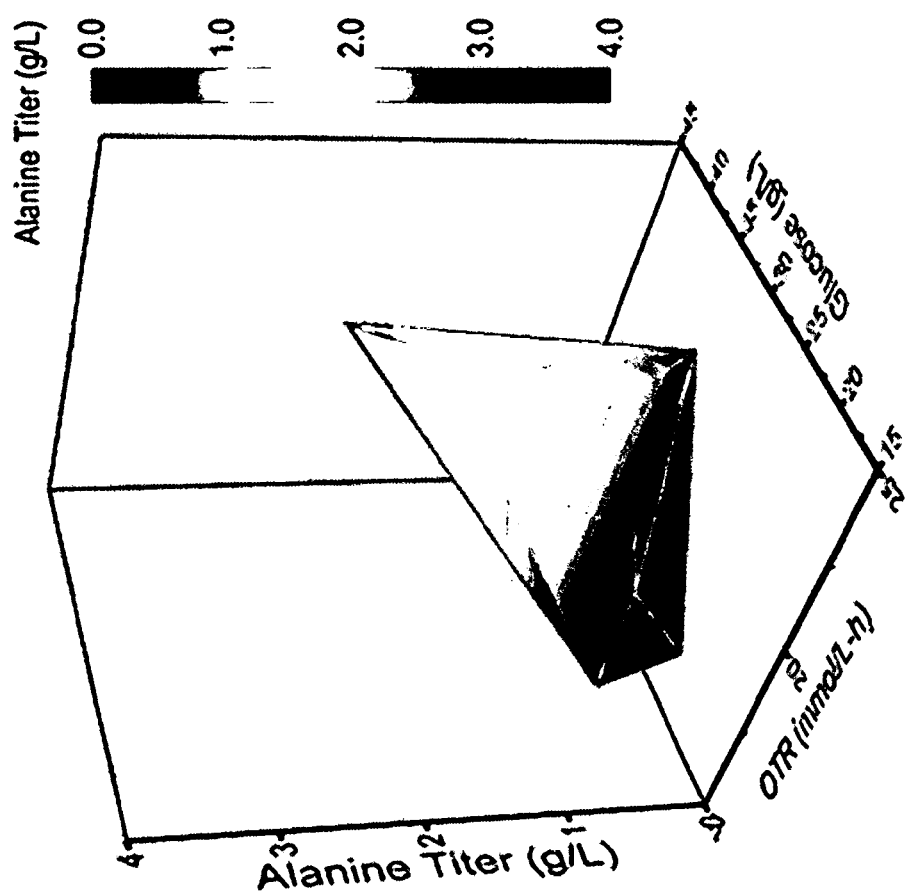
Figure 5E:
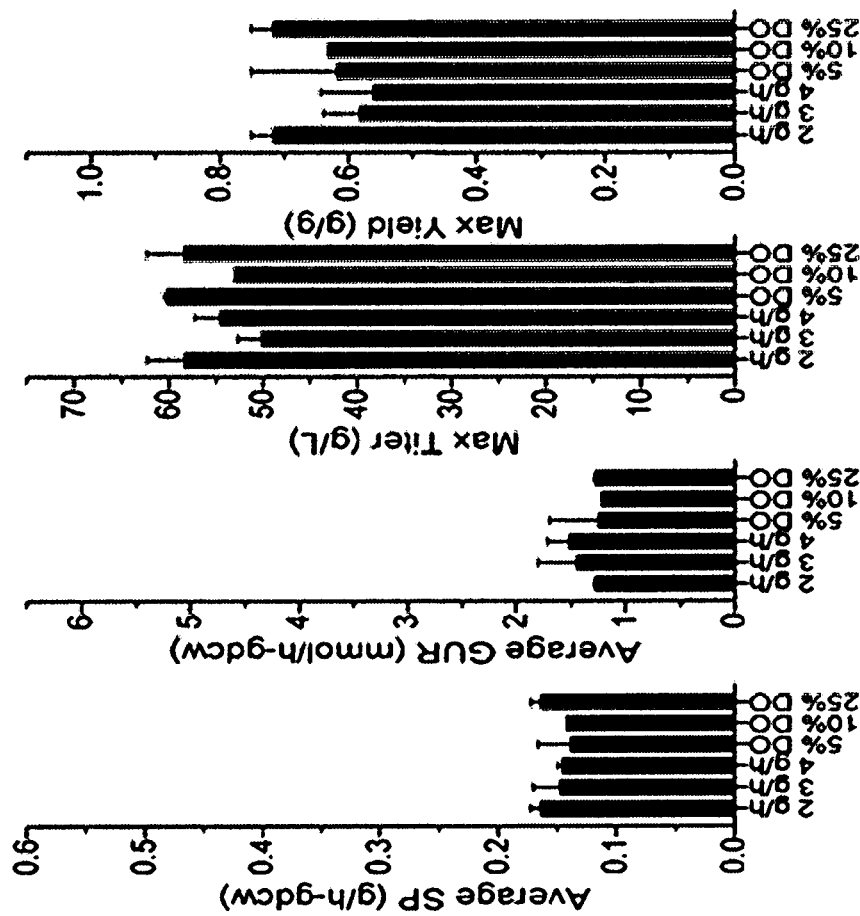
Figure 5F:
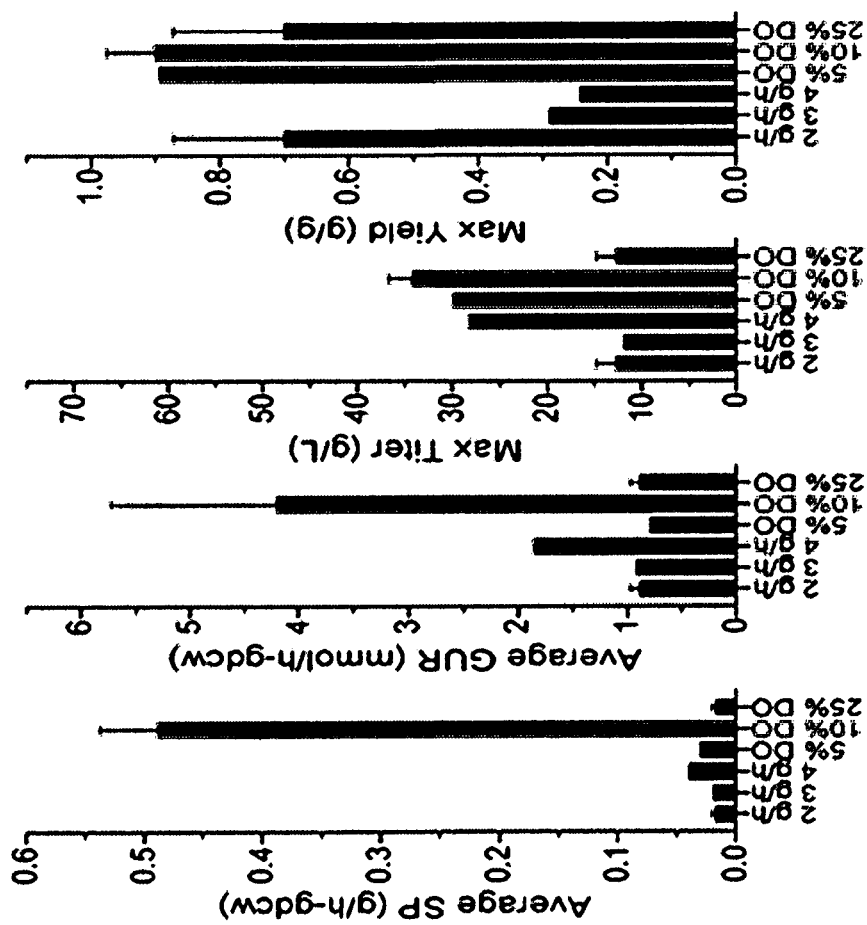
Figure 5G:
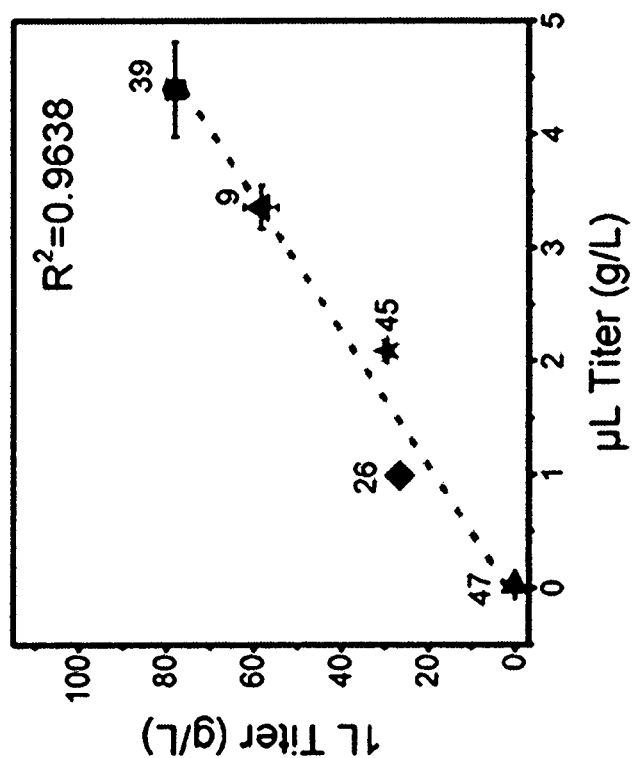
Figure 5H:
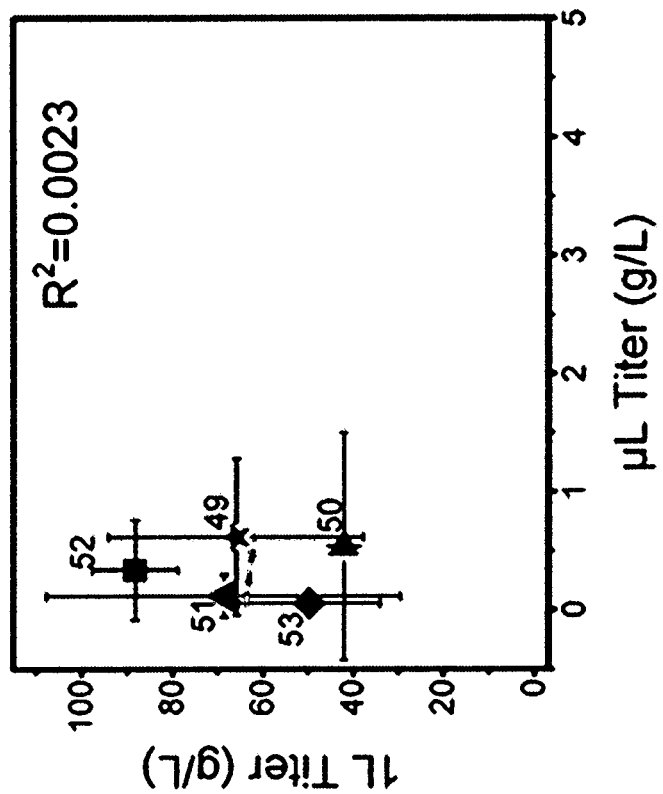
Figure 5I:
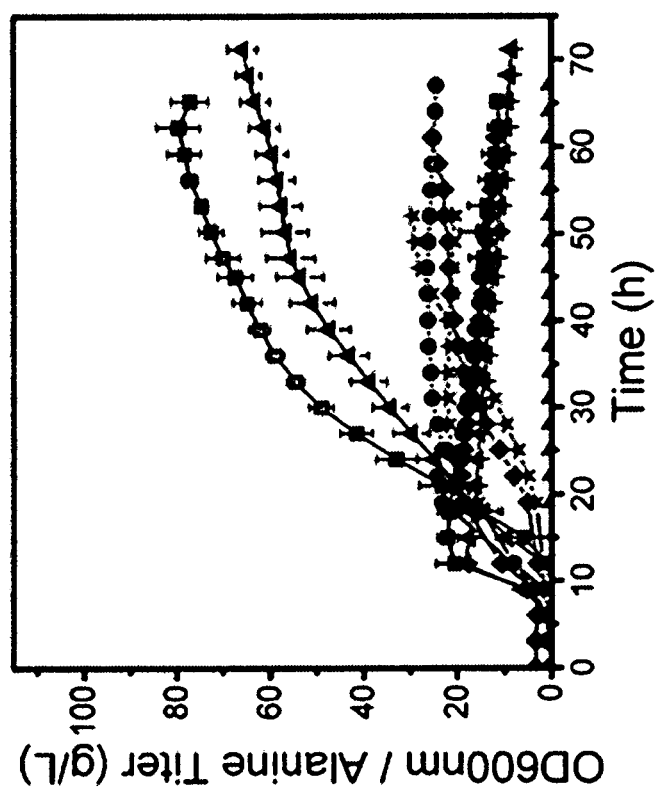
Figure 5J:
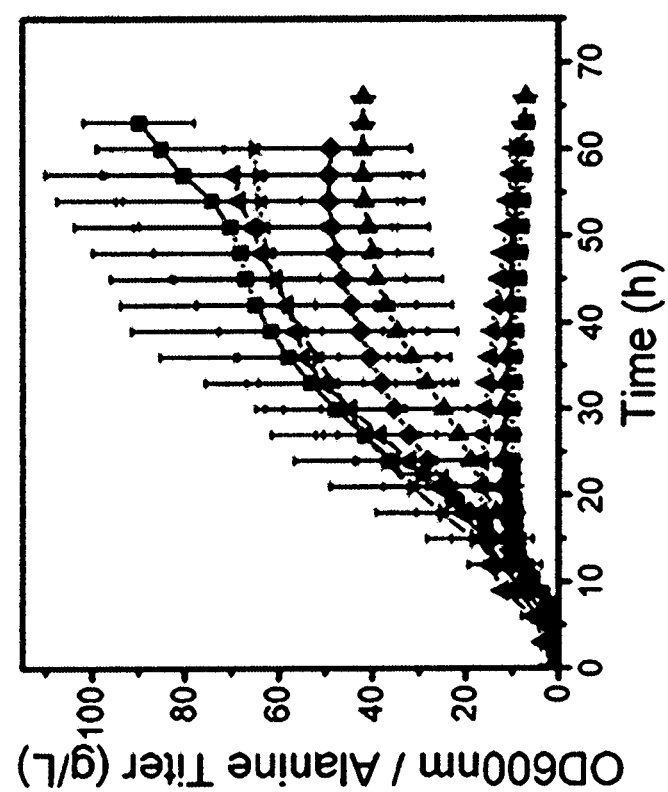

FIGS. 5A-J: Comparisons of "Valve" and growth associated alanine production in micro-fermentations (FIGS. 5A-D) and 1 L fermentation (FIGS. 5E-J). Average alanine titer (FIG. 5A) and robustness score (FIG. 5B) for all strains used for robustness analysis. Average alanine titer in response to different OTR and glucose concentrations for selected "Valve" (FIG. 5C) and growth associated (FIG. 5D) alanine strains. Strains marked by asterisk in (FIG. 5B) were used for this analysis. These two strains were selected for 1 L performance comparison. FIG. 5E and FIG. 5F depicts 1 L performance metrics evaluated, including average specific productivity (SP, g/gdcw-h), average glucose uptake rate (GUR, g/gcdw-h), max titer (g/L), and max yield (g/g). FIG. 5G and FIG. 5H depicts μL to 1 L scalability. 1 L data was standardized to the maximal titer within 50 hours of production. Adequate feed was used for growth associated strains to avoid glucose depletion. FIG. 5I and FIG. 5J depicts 1 L production profiles for all strains used in scalability plot FIG. 5G and FIG. 5H respectively, darker symbols represent growth curves, lighter symbols represent production curves, shape of symbols encode the same strains in FIG. 5G or FIG. 5H.

Figure 6D:
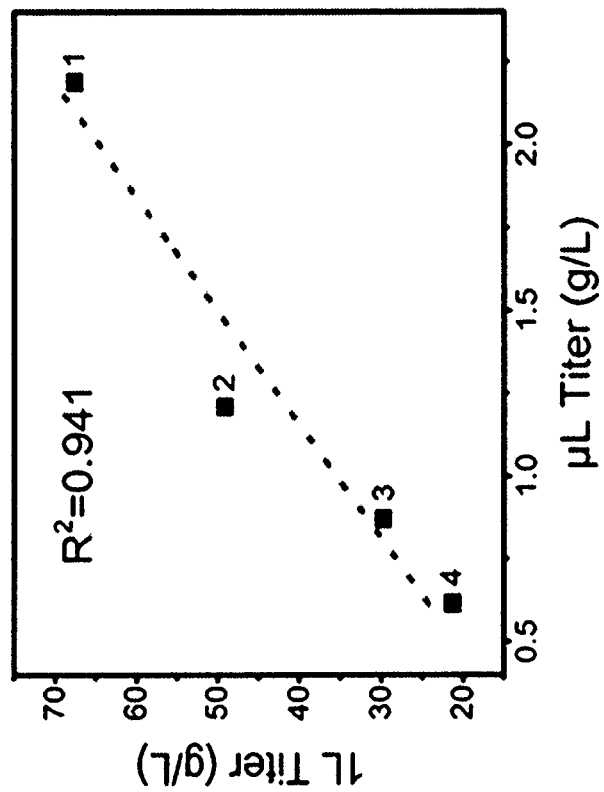
Figure 6E:
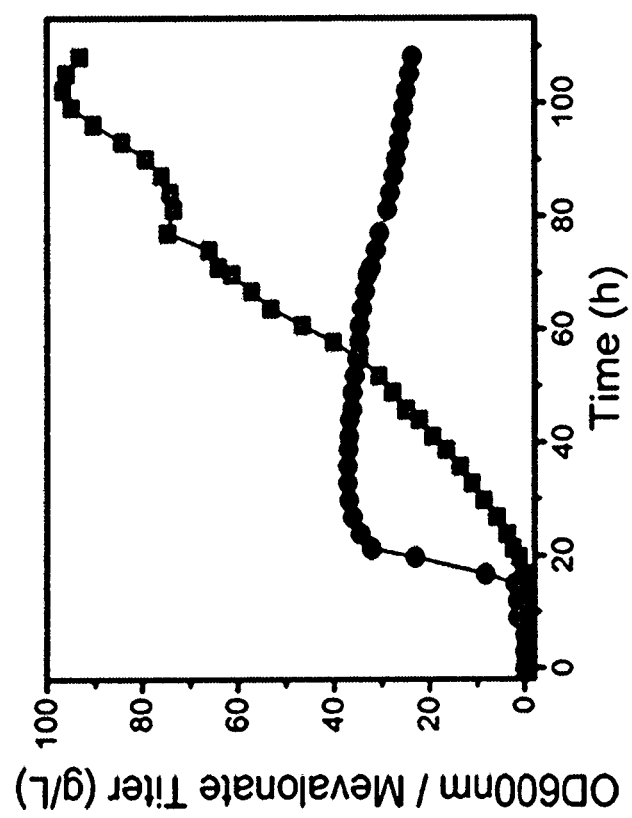
Figure 6F:
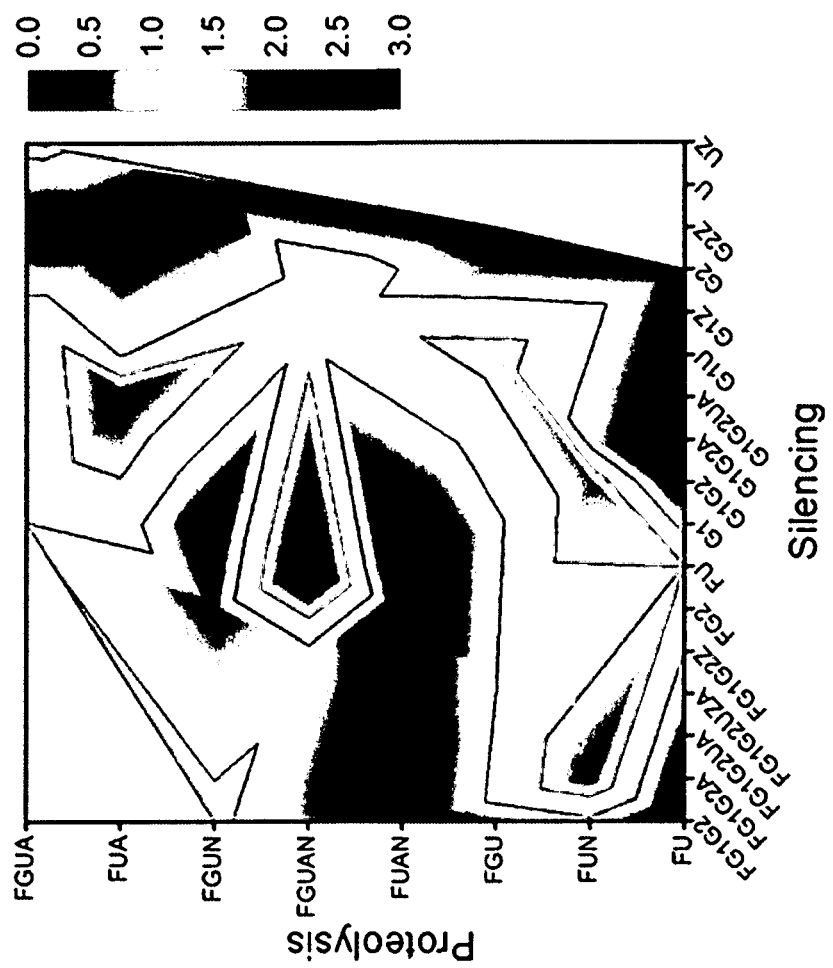
Figure 6G:
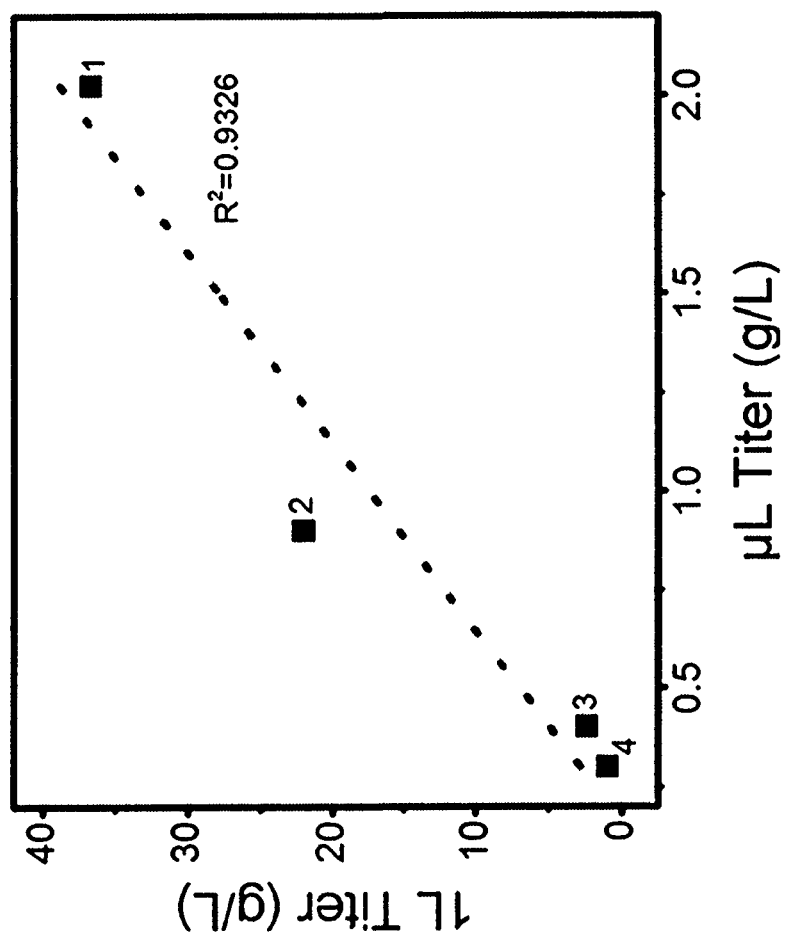
Figure 6H:
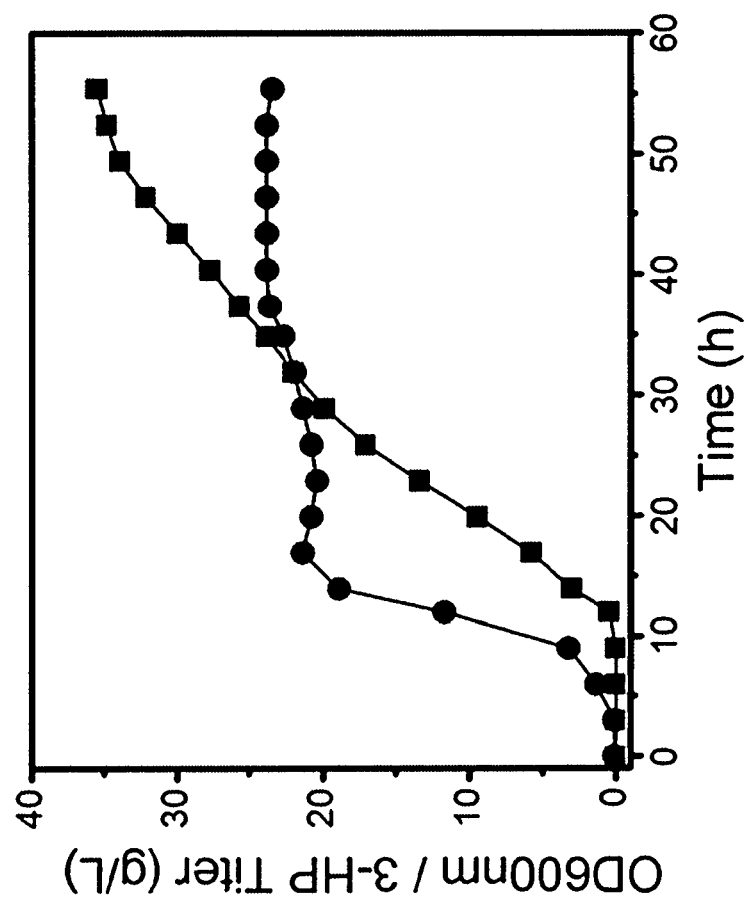

FIG. 6A-E: Mevalonate Production in E. coli utilizing 2-stage Dynamic Control. FIG. 6A depicts Metabolic Pathways and SMVs for mevalonate production. FIG. 6B depicts mevalonate production using several production pathway plasmid variants with varied promoter combinations in the control strain. FIG. 6C depicts micro-fermentation results for a subset of "Valve" strains producing mevalonate, using the best production pathway from FIG. 6B, along with combinations of proteolytic and silencing SMVs. FIG. 6D depicts μL to 1 L scalability for a subset of mevalonate strains evaluated at the 1 L scale. n=3 for μL data and n=1 for 1 L data. The maximal titer within 50 hours of production time was used for the correlation. FIG. 6E depicts production of the best mevalonate strain from FIG. 6D (Silencing of fabI-gltA1-gltA2 ("FG1G2"), Proteolysis of fabI and udhA ("FU")) in 1 L bioreactors. A titer of 97 g/L was observed in 78 hrs of production. Yields during the production stage reached 0.46 g/g (84% of theoretical yield). (Refer to Supplemental Materials, Section 9 for additional details). FIG. 6F depicts micro-fermentation results for a subset of strains producing 3-HP. FIG. 6G depicts μL to 1 L scalability for a subset of 3-HP strains evaluated at the 1 L scale (Supplemental Materials Tables S21 and S22). FIG. 6H depicts production performance for the best 3-HP strains in the 1 L systems, squares, 3-HP/mevalonic acid titer; circles, OD600. Yields during the production stage reached for the 0.46 g/g for mevalonic acid and 0.63 g/g for 3-HP in the highest producers.

FIG. 7: Phosphate depletion promoter characterization. A set of GFP reporter vectors were constructed to assess the expression level of 12 previously identified phosphate regulated promoters. Strains were evaluated continuously for GFP expression in the Biolector™ using a standardized protocol wherein in minimal medium limited for phosphate is used. After Biomass levels reach a peak (not shown for clarity), GFP expression begins. Importantly the current set of promoters enables a large range of expression levels.

FIG. 8: Insulated phosphate depletion promoter characterization. A set of GFP reporter vectors were constructed to assess the expression level of five insulated phosphate regulated promoters in FGM3 media. Strains were evaluated continuously for GFP expression in the Biolector™ using a standardized protocol wherein in minimal medium limited for phosphate is used. After Biomass levels reach a peak (not shown for clarity), GFP expression begins. Importantly the current set of promoters enables a large range of expression levels.

FIG. 9: Insulated constitutive promoter characterization. A set of GFP reporter vectors were constructed to assess the expression level of five insulated constitutive promoters in FGM3 with 40 mM phosphate media. Shaded area represents standard deviations, n=3. Strains were evaluated continuously for GFP expression in the Biolector™ GFP expression was observed only for promoters proA, proB and proD.

Figure 10:
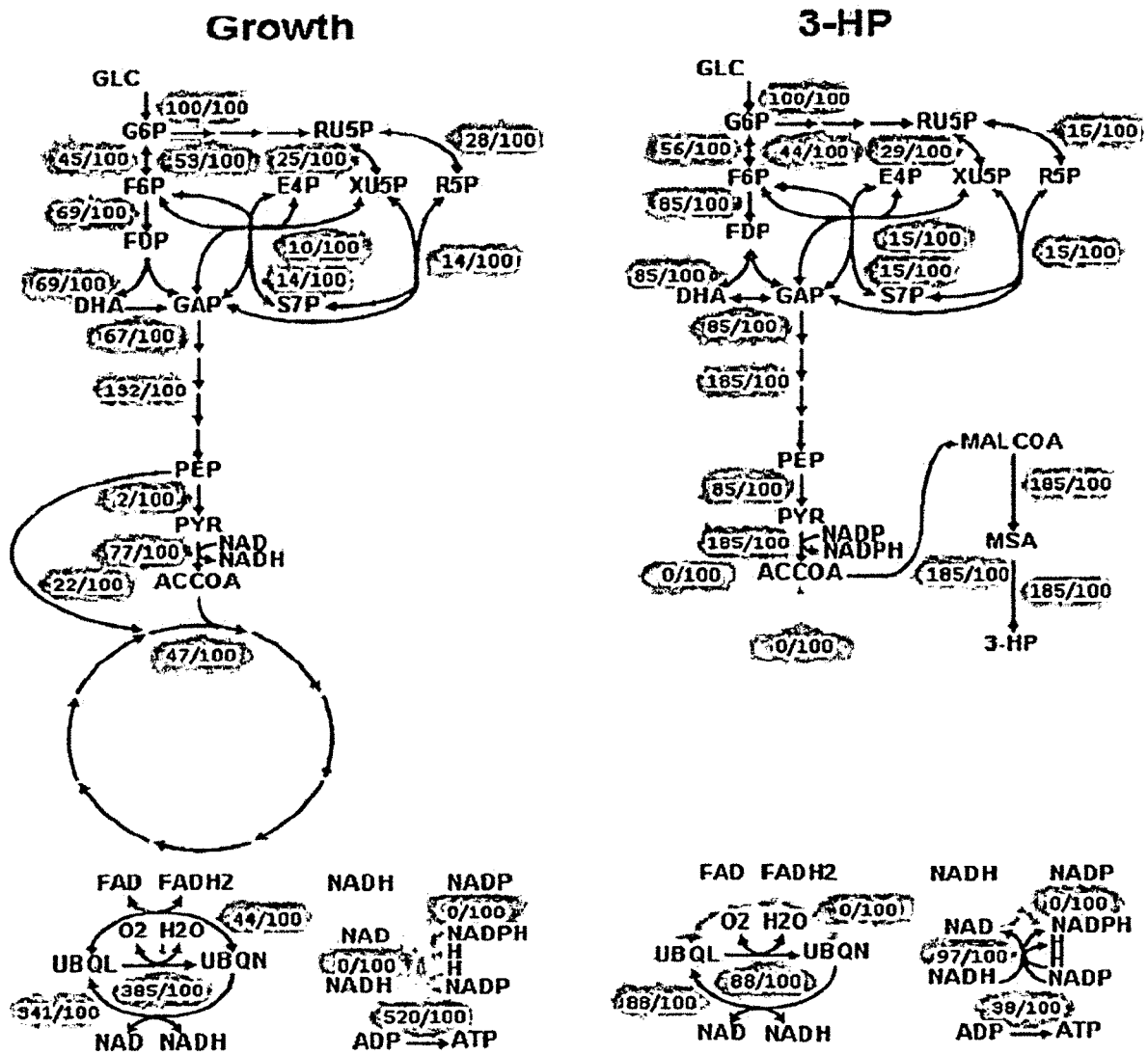
FIG. 10 depicts an example of metabolic modeling results for optimal 3-HP flux in two stage fermentations.

FIG. 10: Metabolic modeling results for optimal 3-HP flux in two stage fermentations. LEFT: Optimized fluxes during the growth stage where biomass production was used as the objective function. RIGHT: Optimized fluxes during the 3-HP production stage where 3-HP production was used as the objective function (biomass production was set to 0). Fluxes are listed as relative ratios or moles of flux through a given reaction per 100 moles of glucose utilized.

FIG. 11: Chromosomal modifications.

Figure 12:
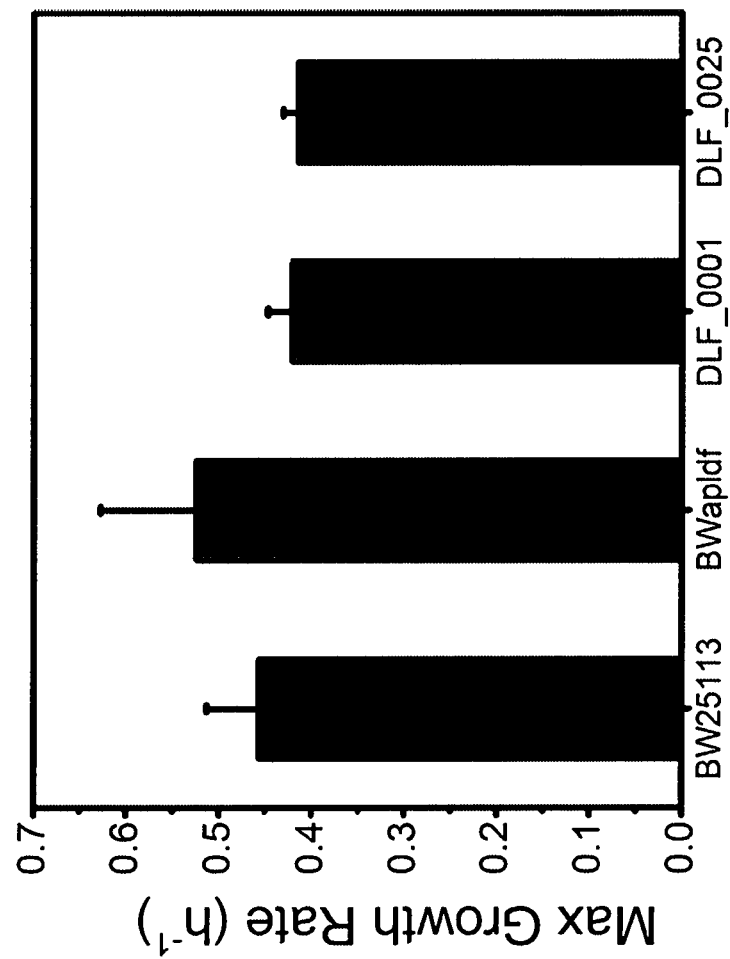
FIG. 12 depicts an example of average maximal growth rates of starting host strains in 1 L FGM10 minimal medium fermentations, n=2.

FIG. 12: Average maximal growth rates of starting host strains in 1 L FGM10 minimal medium fermentations, n=2.

Figure 13B:
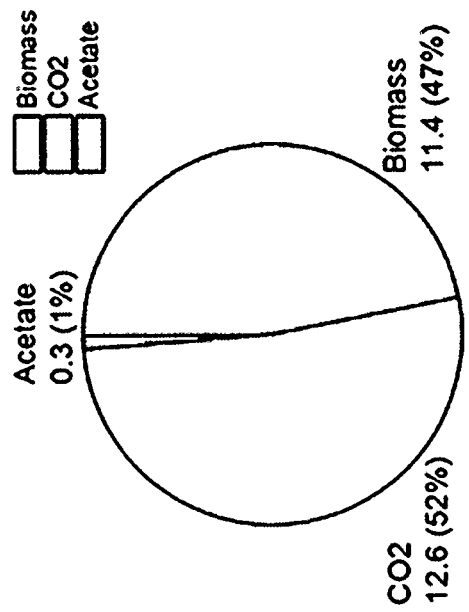
FIG. 13A-E depict examples of distribution of glucose utilized during the growth phase of starting host strains in 1 L standard minimal medium fermentations.
Figure 13A:
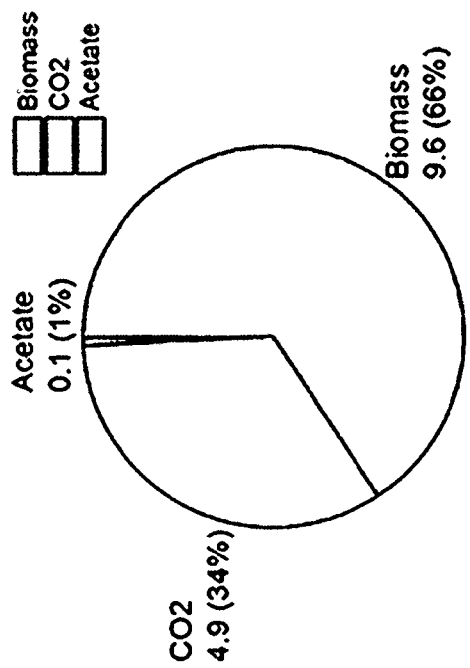
Figure 13C:
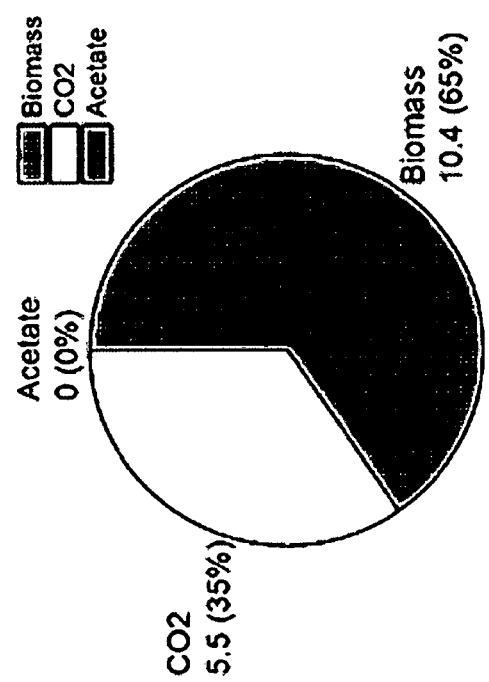
Figure 13D:
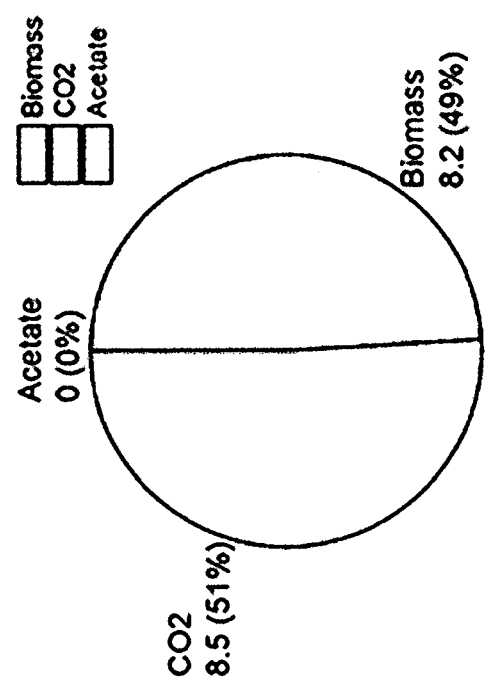
Figure 13E:
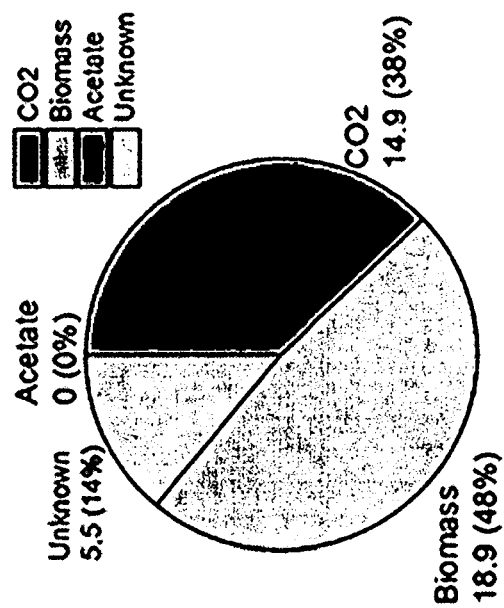

FIG. 13A-E: Distribution of glucose utilized during the growth phase of starting host strains in 1 L standard minimal medium fermentations. Mid exponential and final growth period results are given for DLF_0025 as "production" begins in mid-late exponential phase. Results are averages of duplicate fermentations. FIG. 13A, BW25113; FIG. 13B, BWapldf; FIG. 13C, DLF_0001; FIG. 13D, DLF_0025 at mid-exponential; FIG. 13E, DLF_0025 at end of growth phase. Unit was gram glucose.

Figure 14:
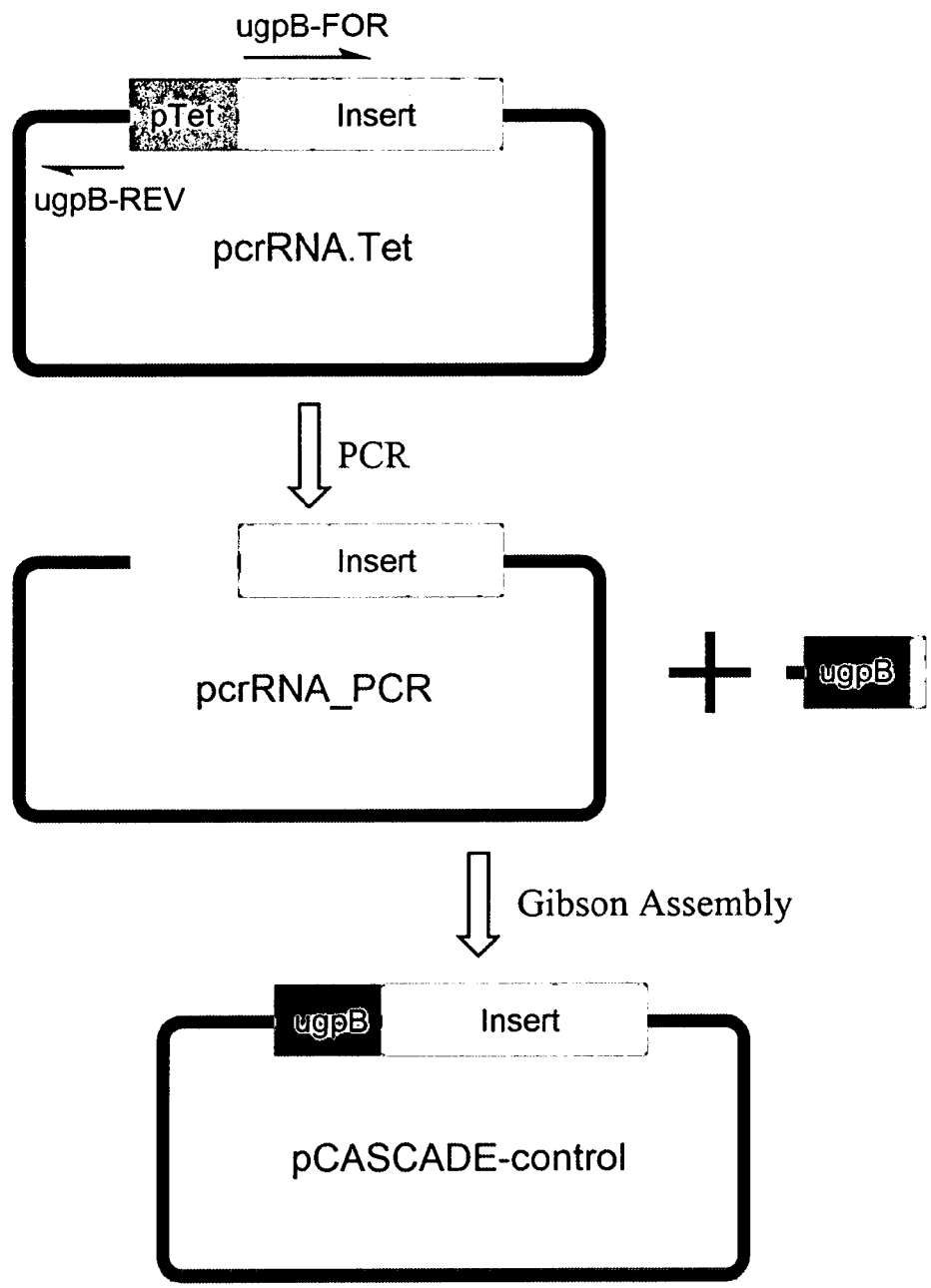
FIG. 14 depicts pCASCADE-control plasmid construction scheme.
Figure 15A:
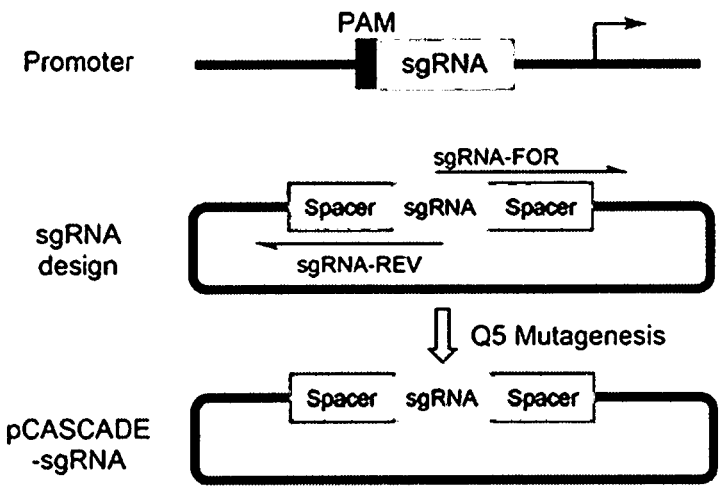
FIGS. 15A-B depict pCASCADE construction scheme.
Figure 15B:
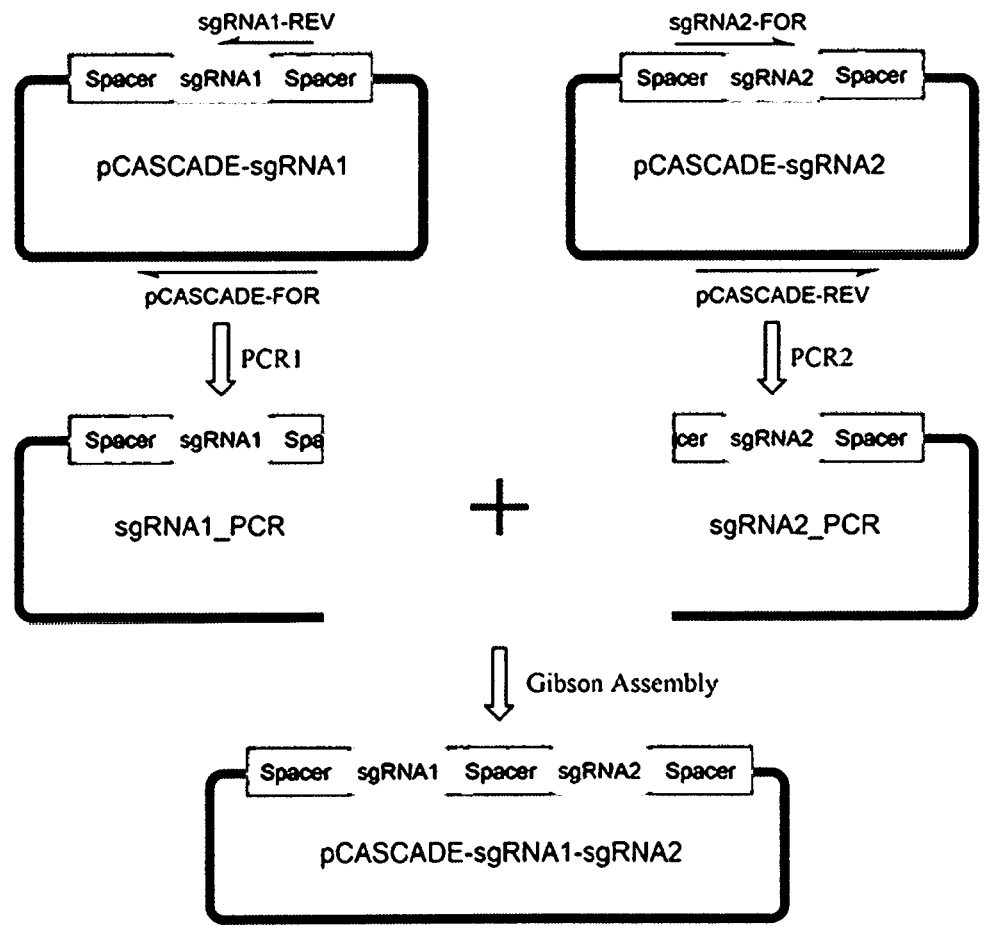

FIG. 14: pCASCADE-control plasmid construction scheme.

FIG. 15A-B: pCASCADE construction scheme. FIG. 15A, single sgRNA cloning;

FIG. 15B, double sgRNA.

FIG. 16A-C: Micro-fermentation process overview. (A) An overview of the high throughput micro-fermentation protocol. Freezer stocks (alternatively colonies may be used) are used to inoculate into SM10++ in 96 well plates. Cultures are grown overnight for 16 hours, harvested by centrifugation, washed with no-phosphate medium and resuspended in no-phosphate medium at target biomass levels. (OD600 nm=1.0). EnzyScreen™ covers and clamps are used to reduce evaporation and enable high oxygen transfer rates. The protocol is implemented with a Tecan Evo liquid handler. (B) Representative overnight growth in a 96 well plates culture, distribution of OD600 for overnight culture was plotted. (C) Representative OD600 distribution after normalization using Tecan Evo liquid handler.

FIG. 17: Micro-fermentation for L-alanine production using different insulated phosphate promoters in DLF_0025 strain.

Figure 18:
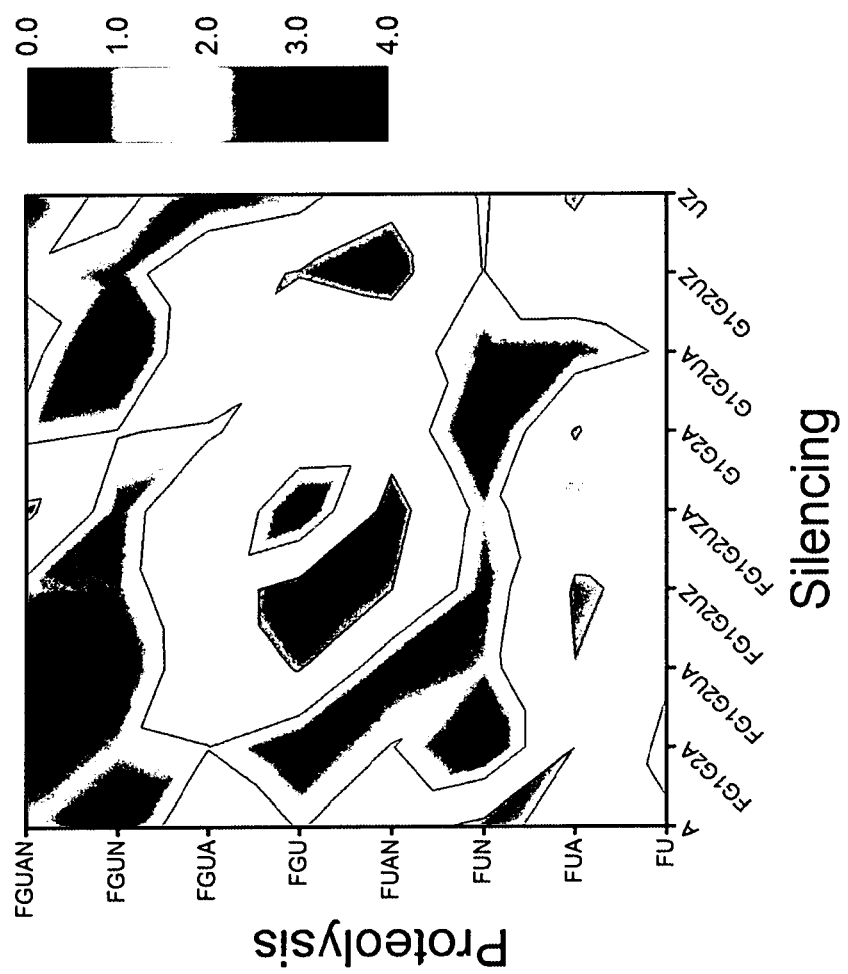
FIG. 18 depicts Heatmap for L-alanine production by gapN/gapA strains.
Figure 19A:
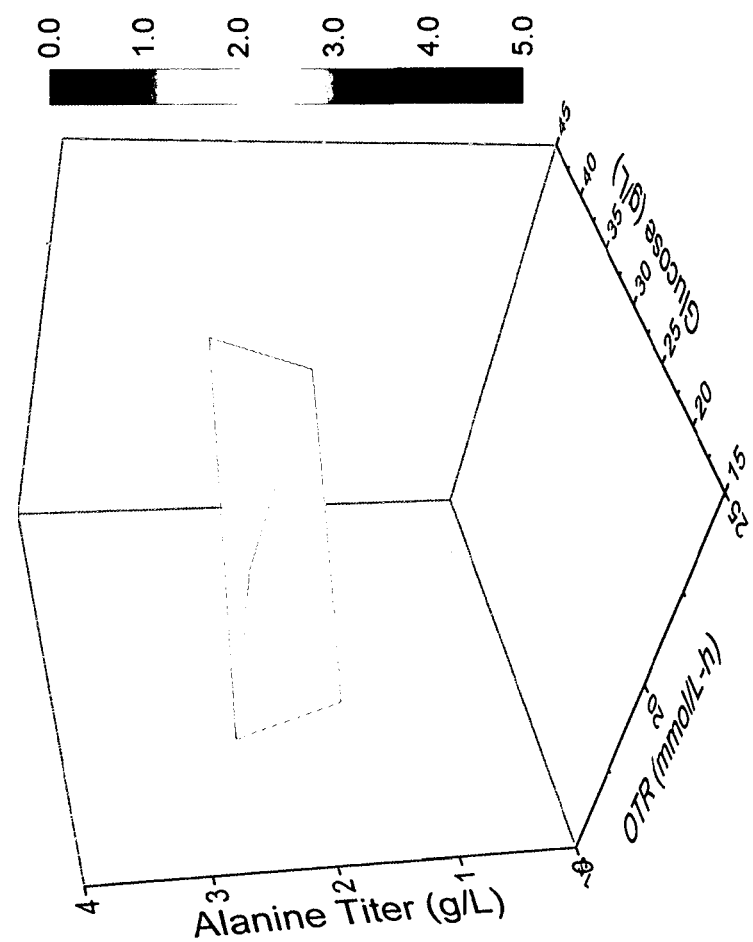
FIGS. 19A-D depict alanine production in response to different OTR and glucose concentration in micro-fermentation for 4 strains evaluated for robustness.
Figure 19B:
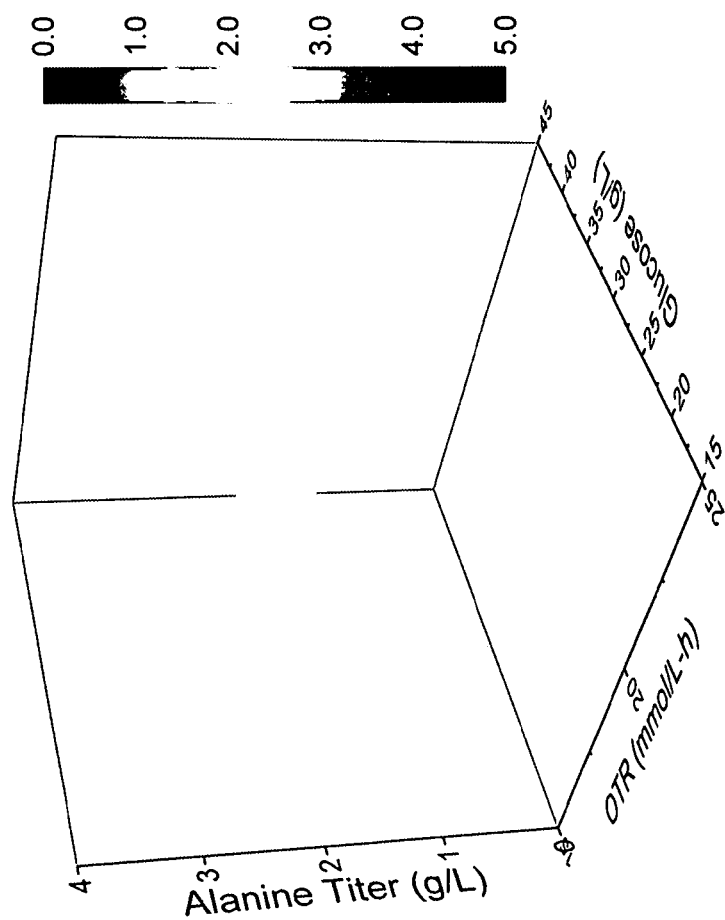
Figure 19C:
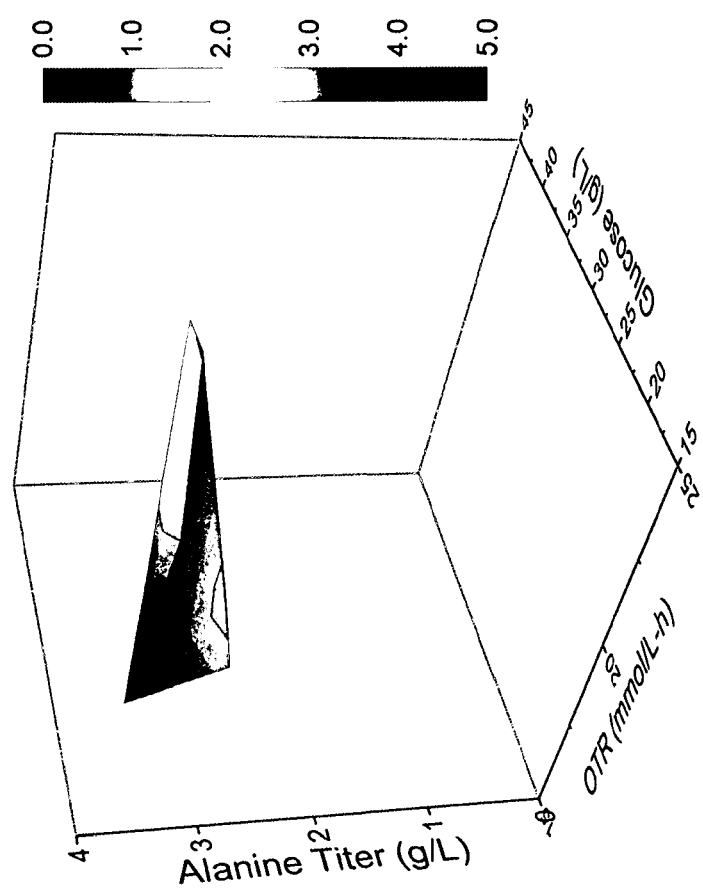
Figure 19D:
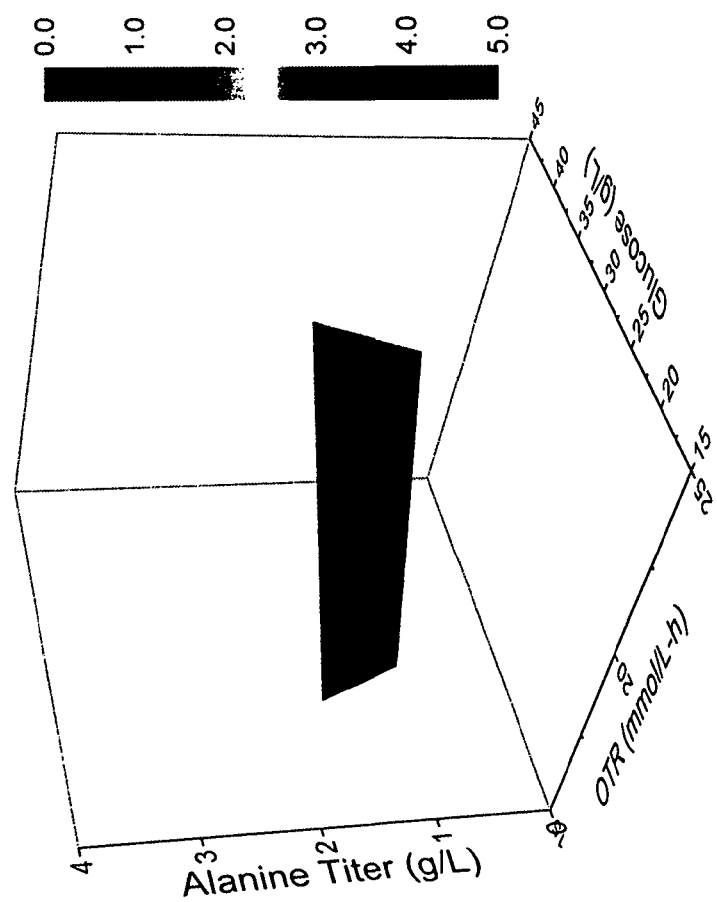
Figure 20A:
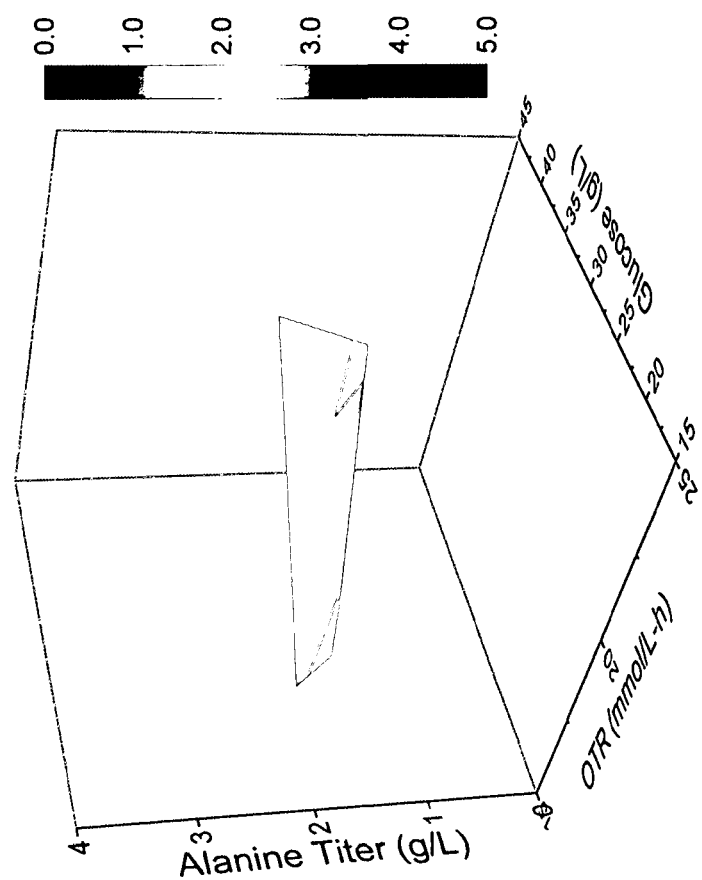
FIGS. 20A-D depict alanine production in response to different OTR and glucose concentration in micro-fermentation for 4 strains evaluated for robustness.
Figure 20B:
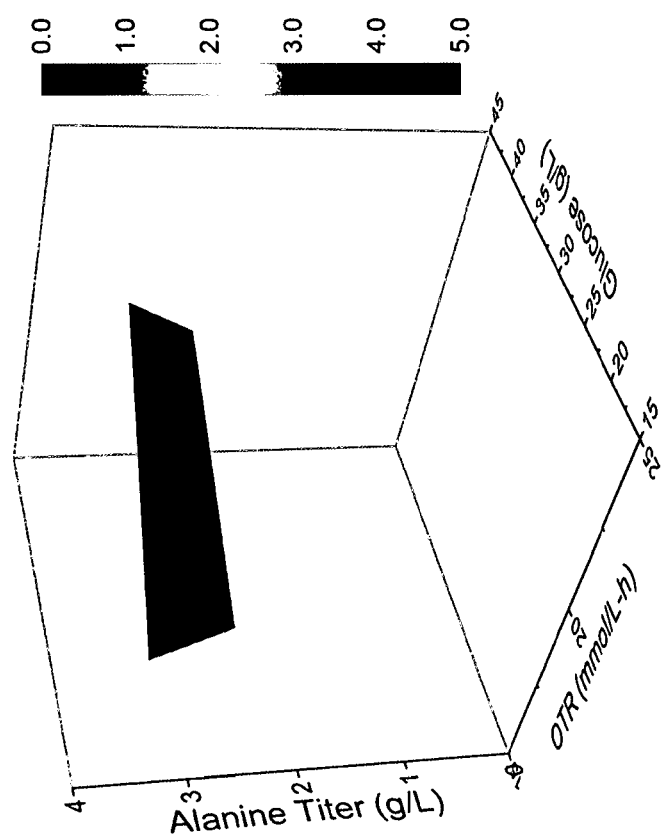
Figure 20C:
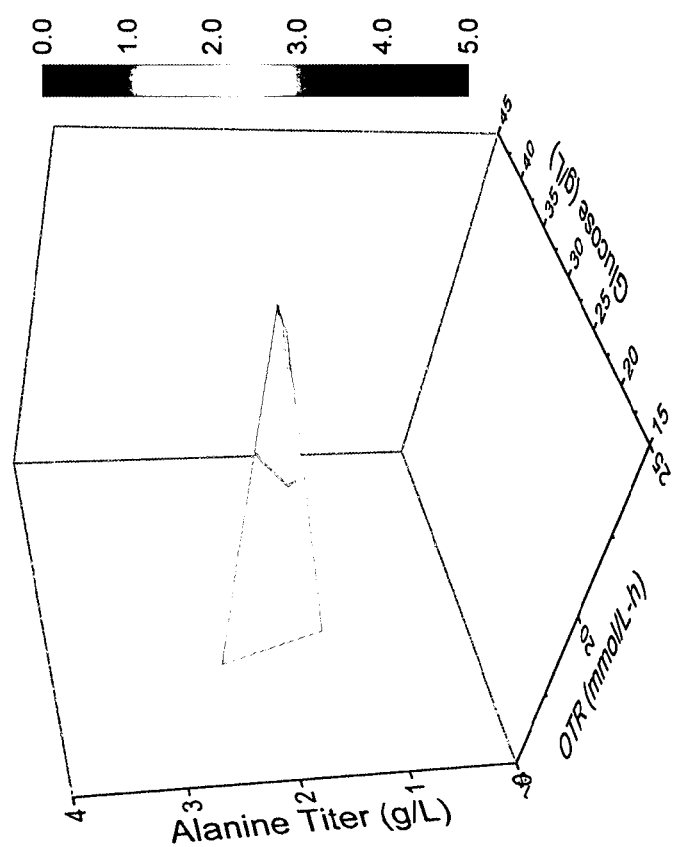
Figure 20D:
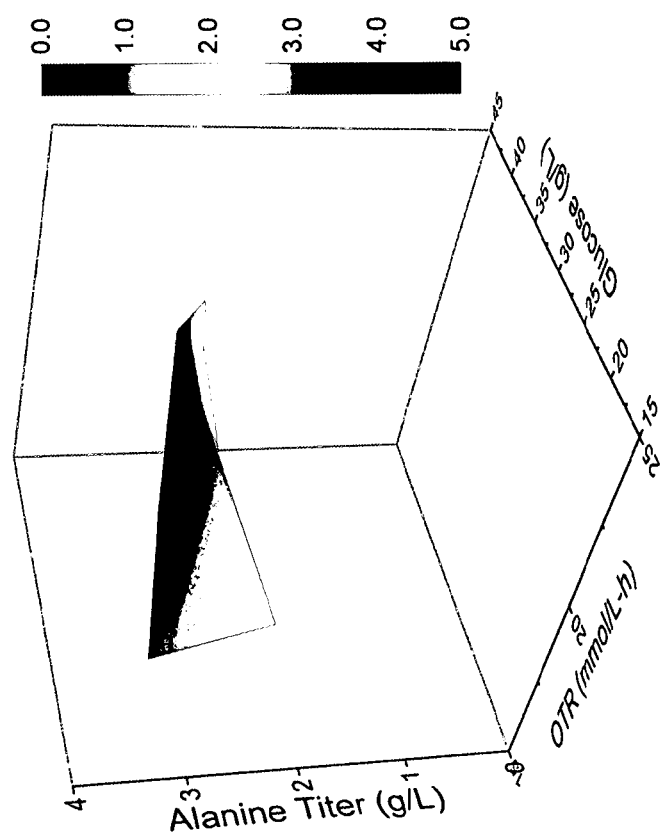
Figure 21A:
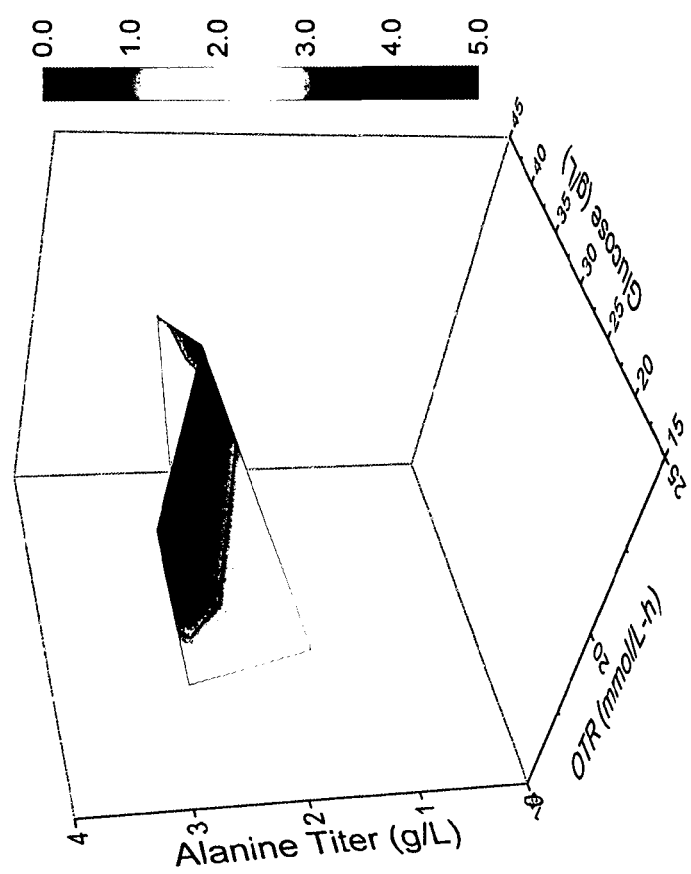
FIGS. 21A-D depict alanine production in response to different OTR and glucose concentration in micro-fermentation for 4 strains evaluated for robustness.
Figure 21B:
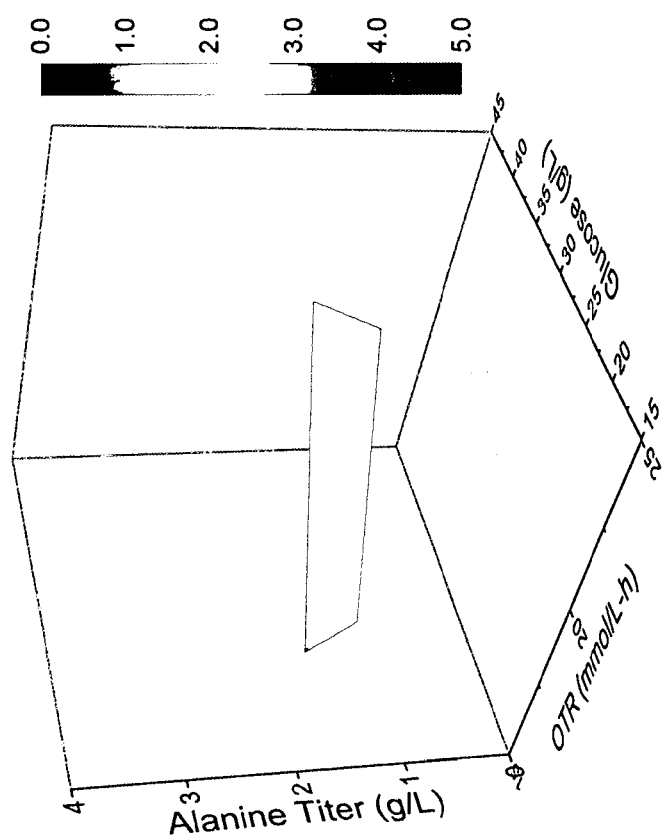
Figure 21C:
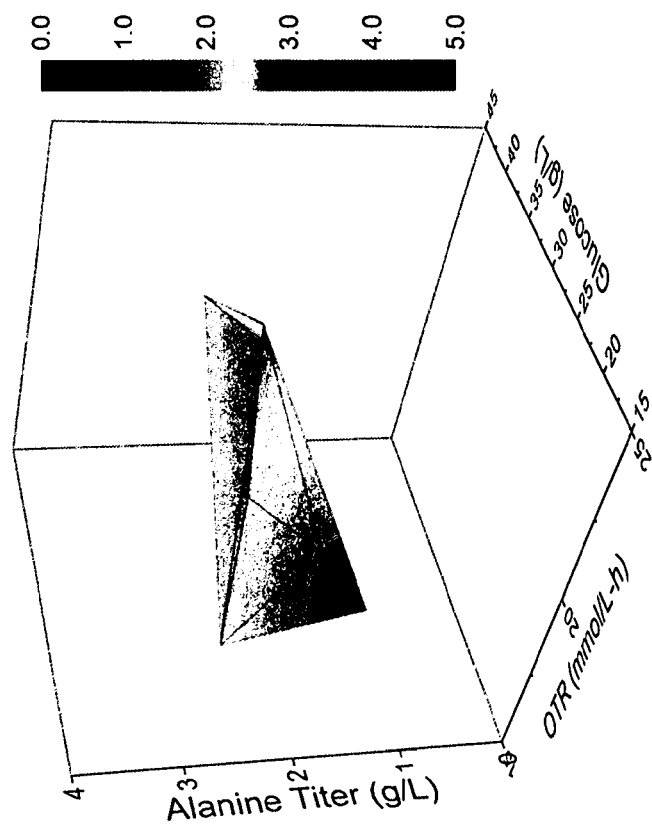
Figure 21D:
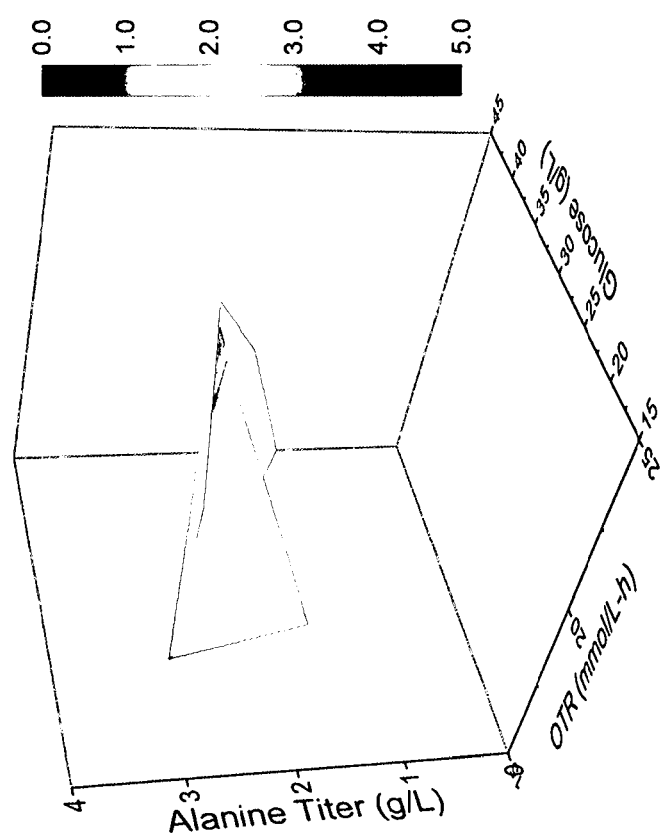
Figure 22A:
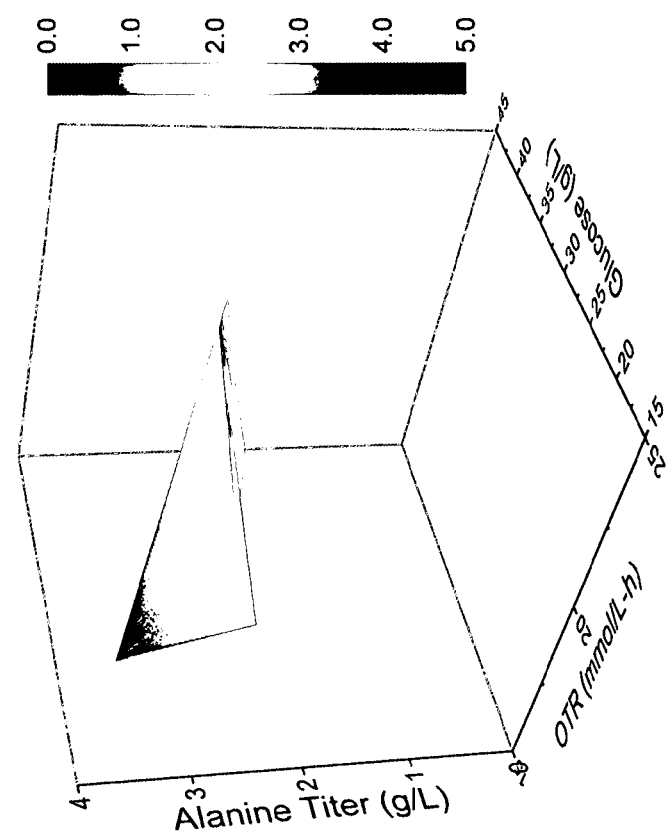
FIGS. 22A-D depict alanine production in response to different OTR and glucose concentration in micro-fermentation for 4 strains evaluated for robustness.
Figure 22B:
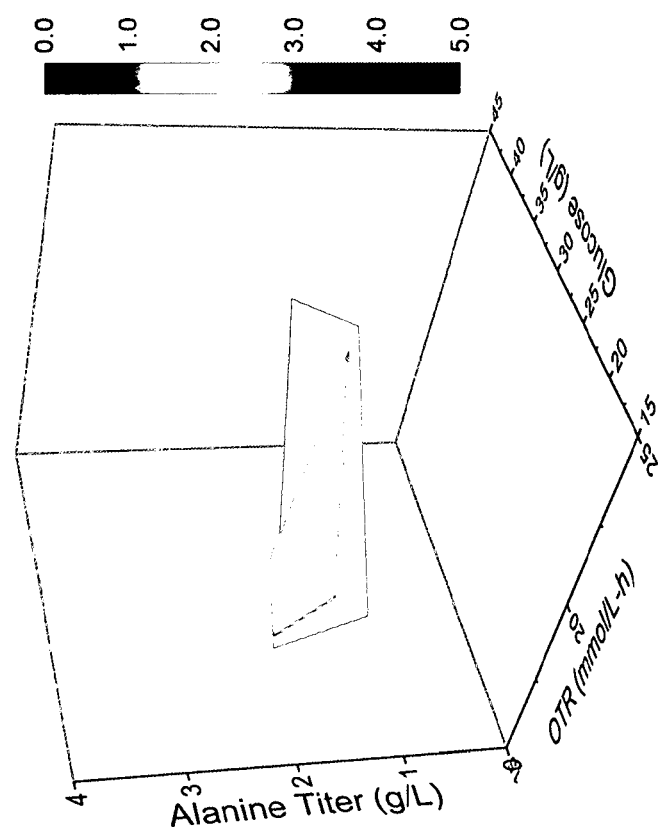
Figure 22C:
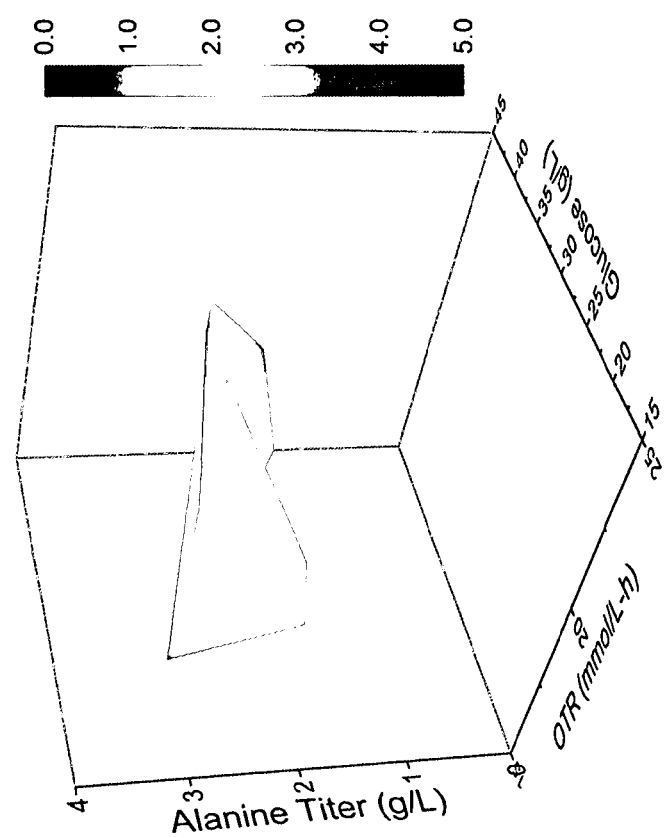
Figure 22D:
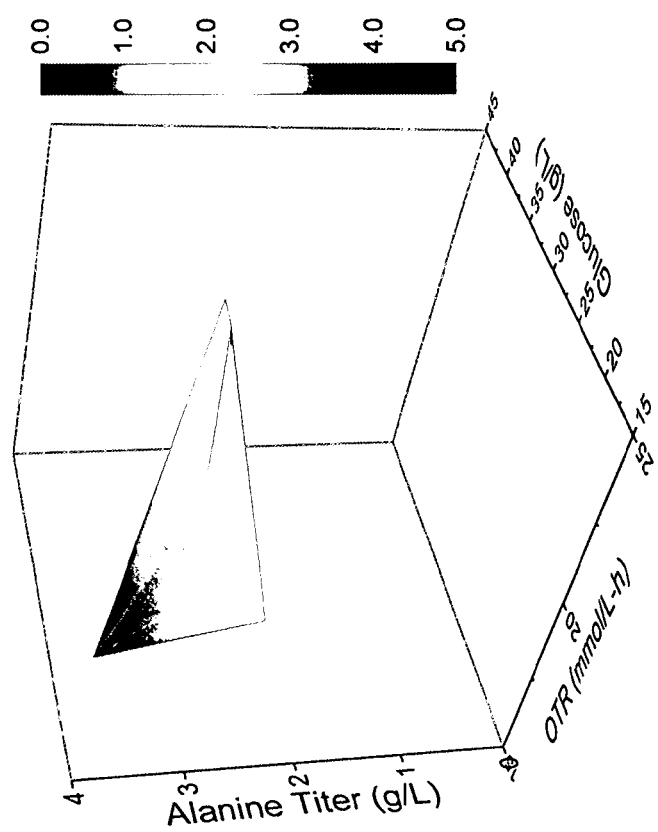
Figure 23A:
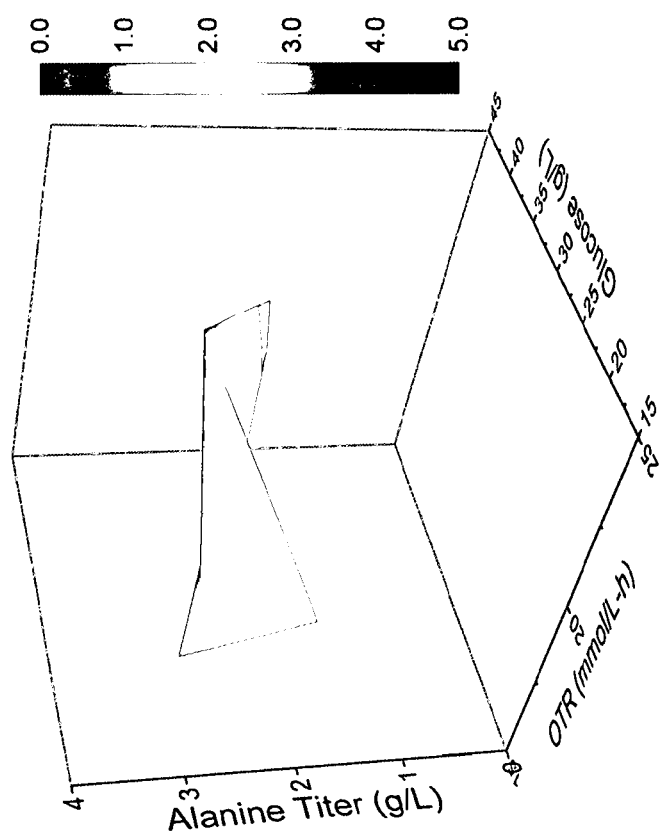
FIGS. 23A-D depict alanine production in response to different OTR and glucose concentration in micro-fermentation for 4 strains evaluated for robustness.
Figure 23B:
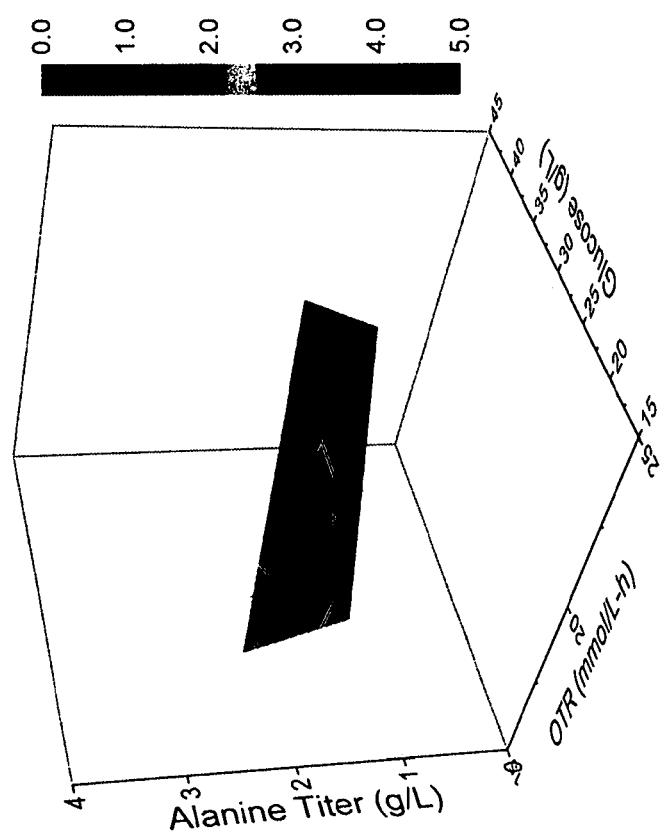
Figure 23C:
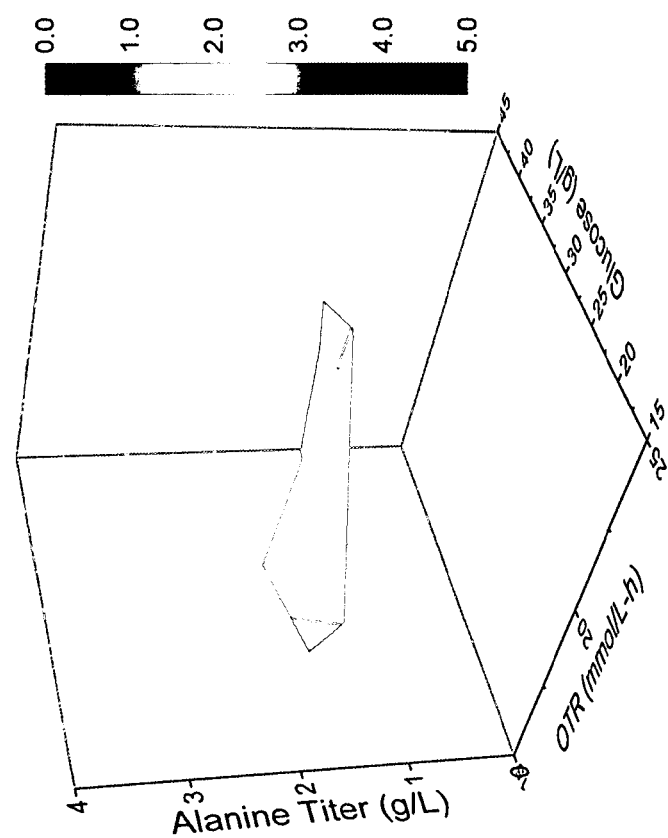
Figure 23D:
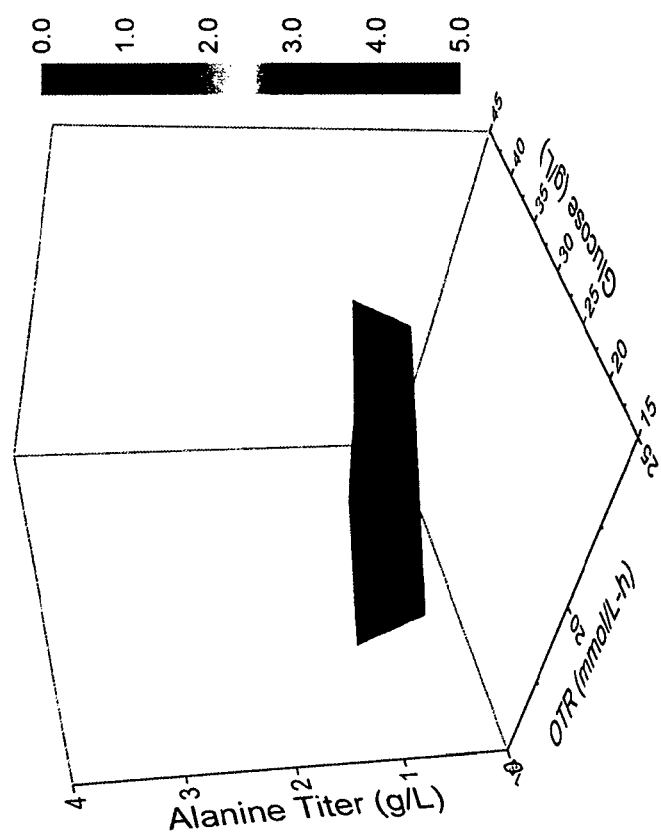
Figure 24A:
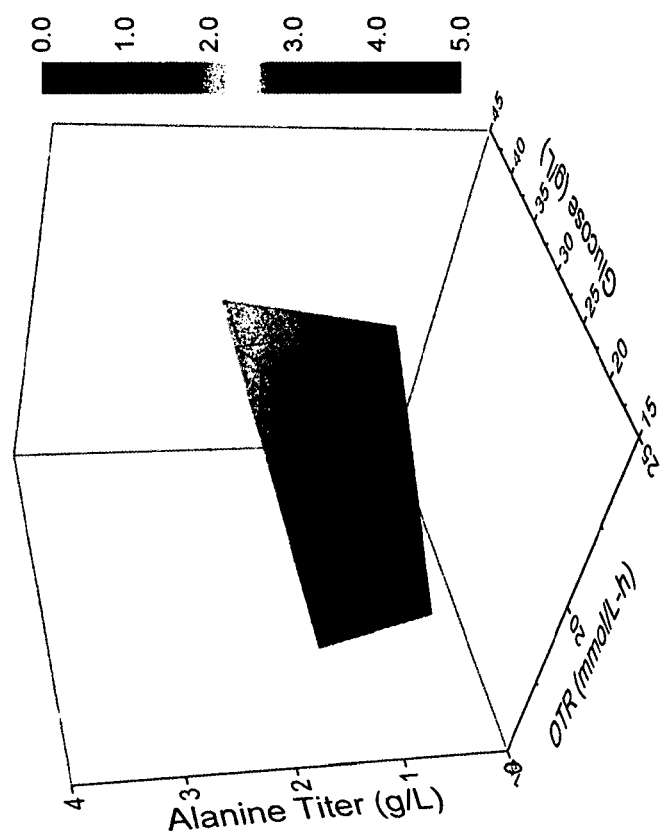
FIGS. 24A-D depict alanine production in response to different OTR and glucose concentration in micro-fermentation for 4 strains evaluated for robustness.
Figure 24B:
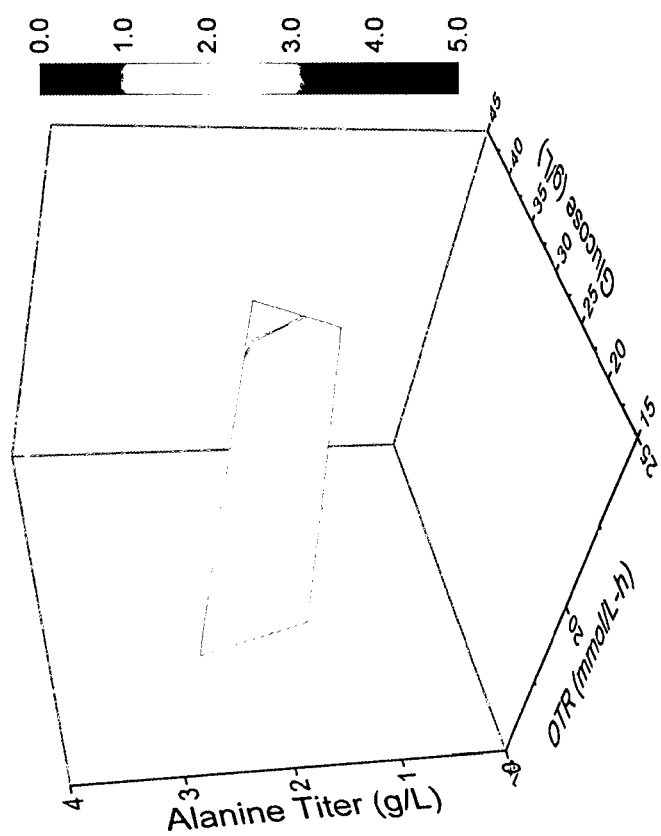
Figure 24C:
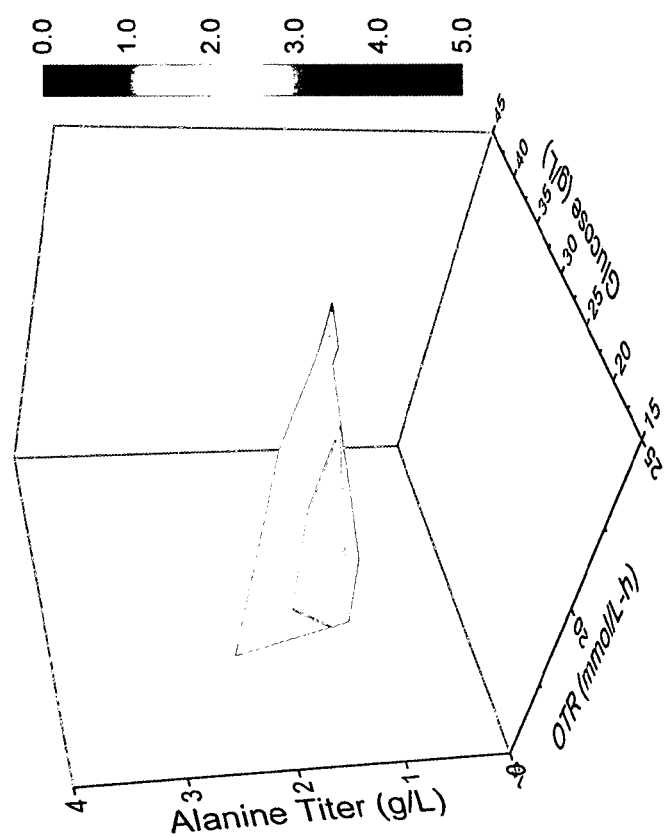
Figure 24D:
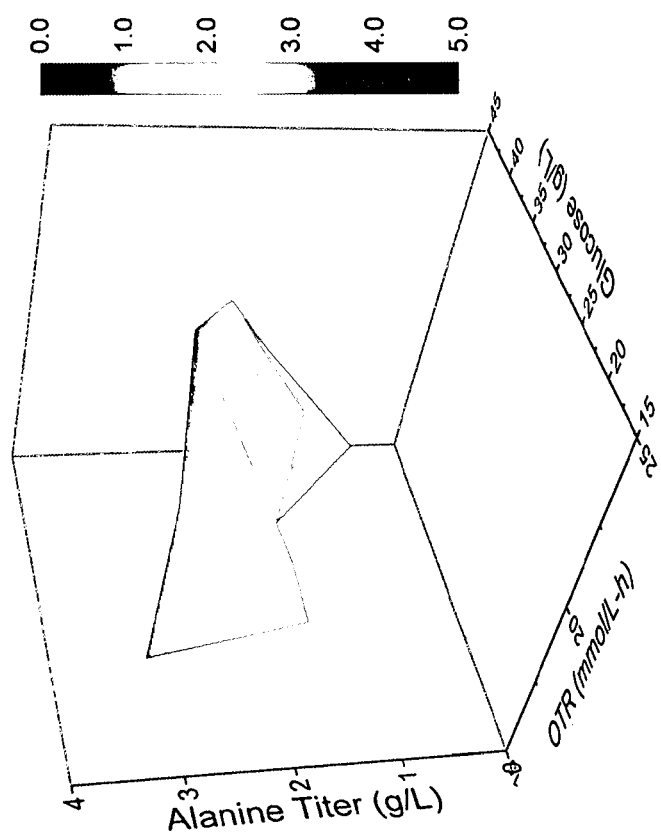
Figure 25A:
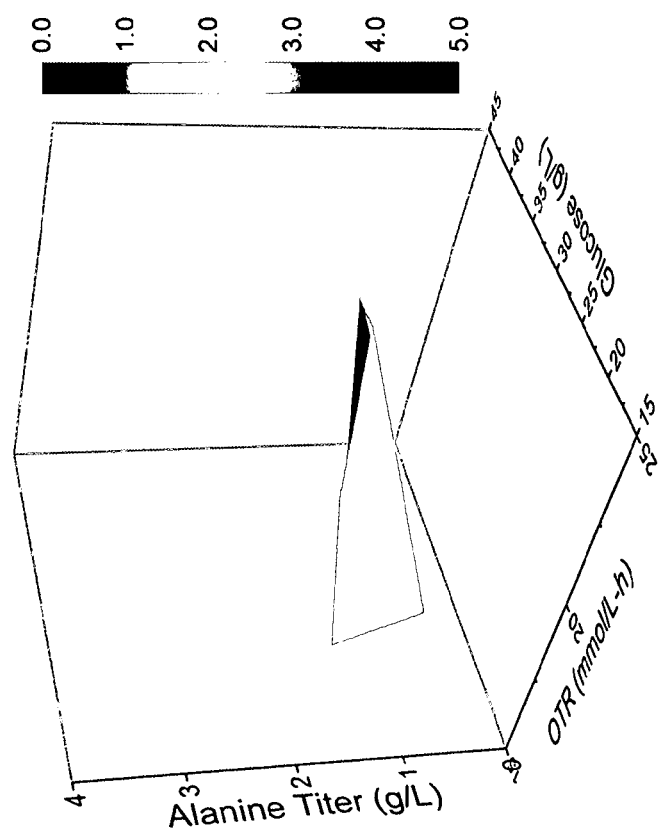
FIGS. 25A-D depict alanine production in response to different OTR and glucose concentration in micro-fermentation for 4 strains evaluated for robustness.
Figure 25B:
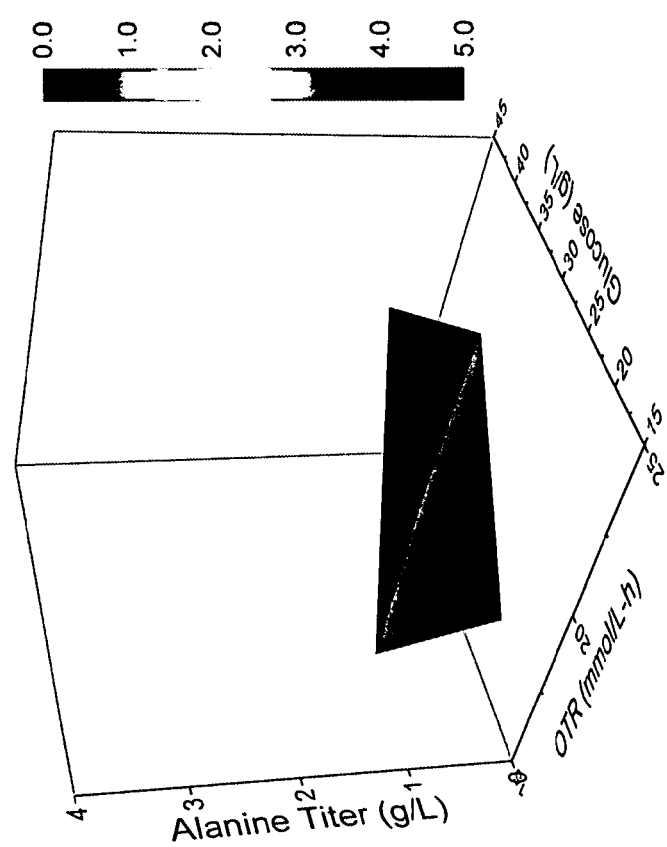
Figure 25C:
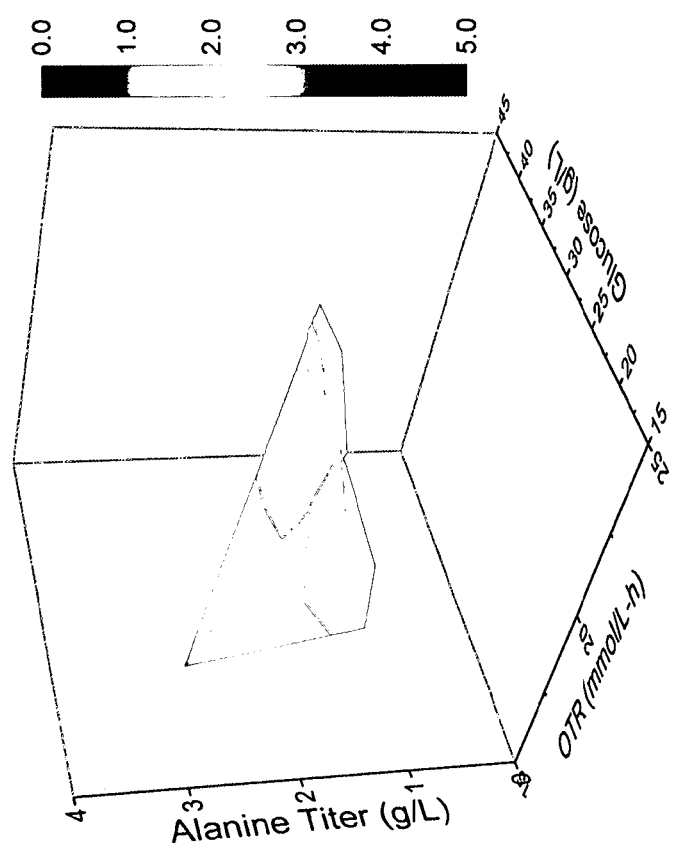
Figure 25D:
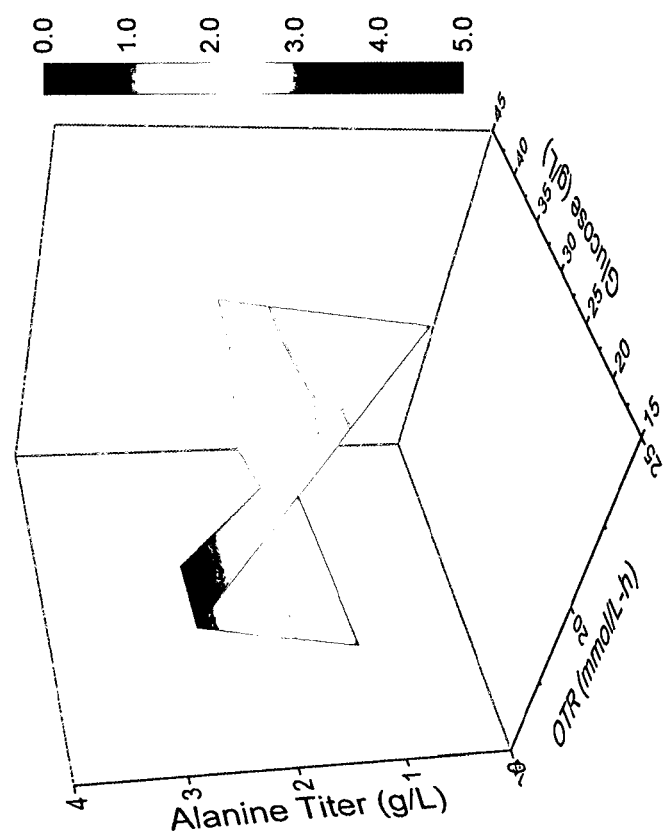
Figure 26A:
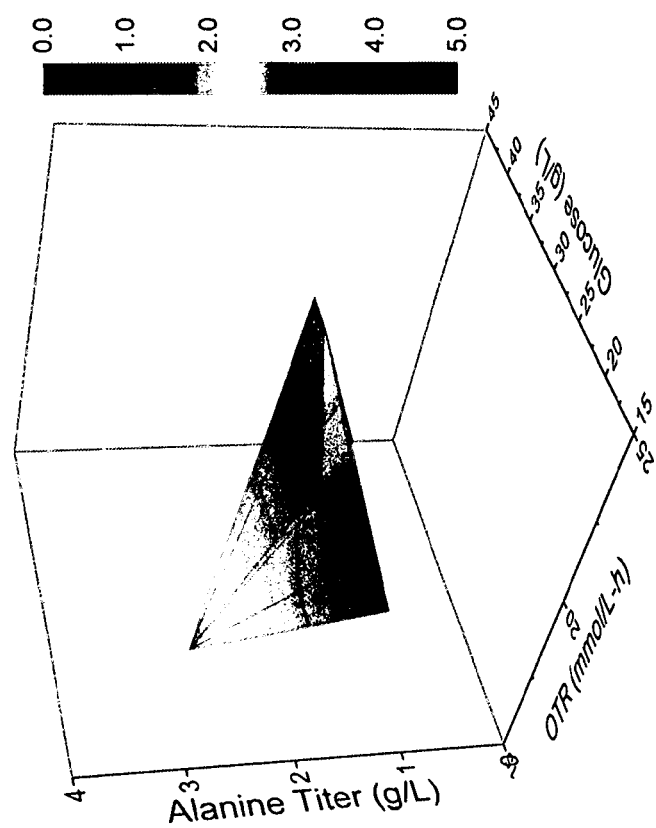
FIGS. 26A-D depict alanine production in response to different OTR and glucose concentration in micro-fermentation for 4 strains evaluated for robustness.
Figure 26B:
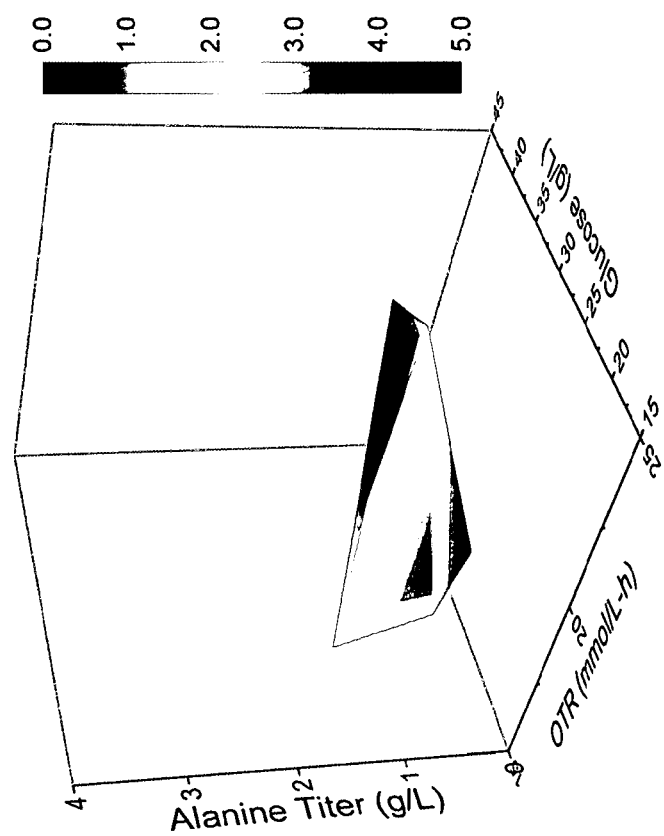
Figure 26C:
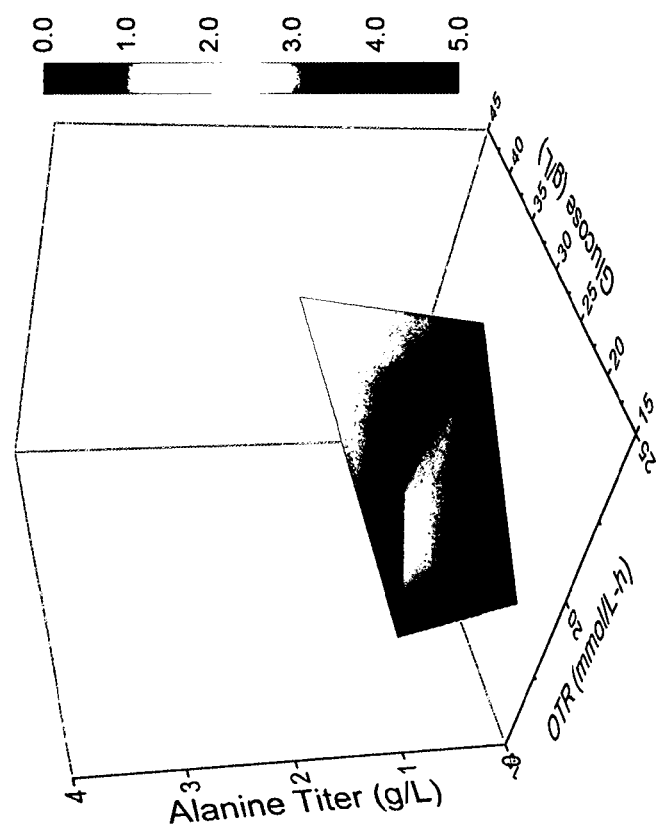
Figure 26D:
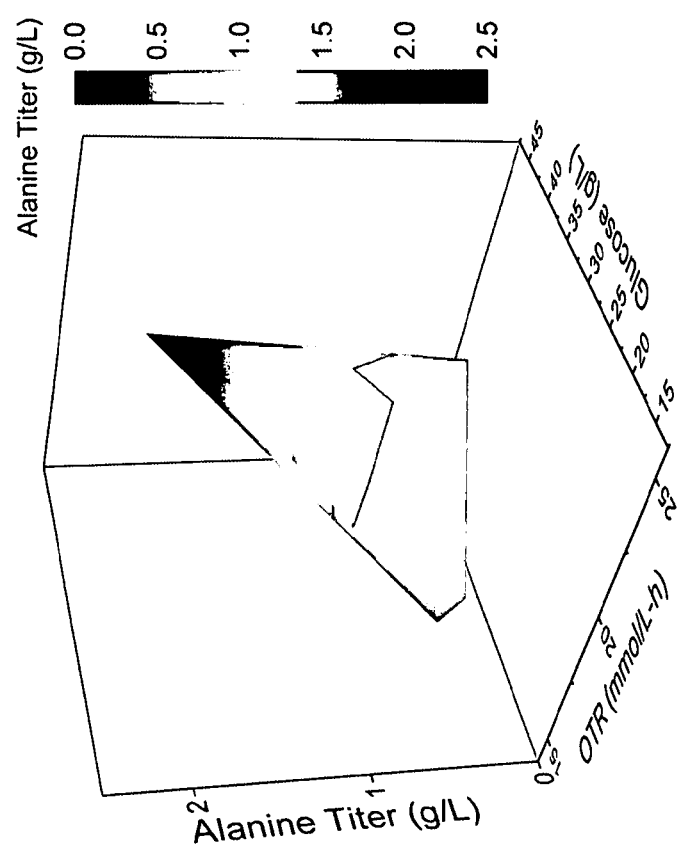
Figure 27B:
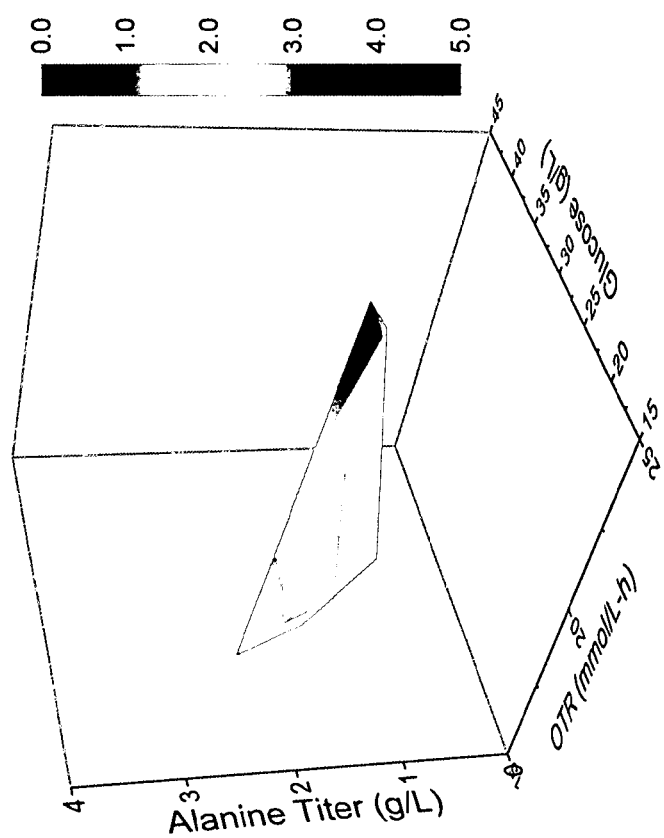
Figure 27C:
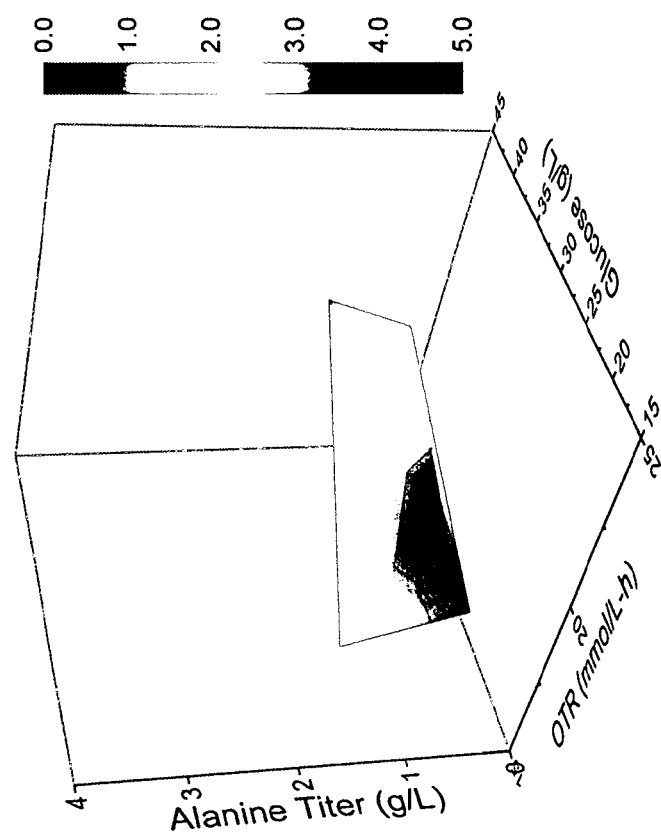
Figure 27D:
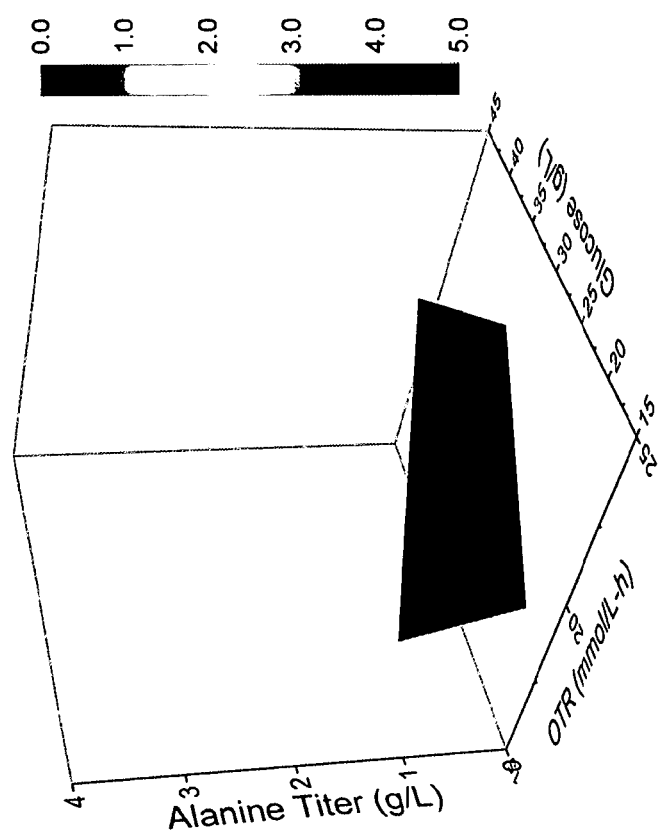
Figure 28A:
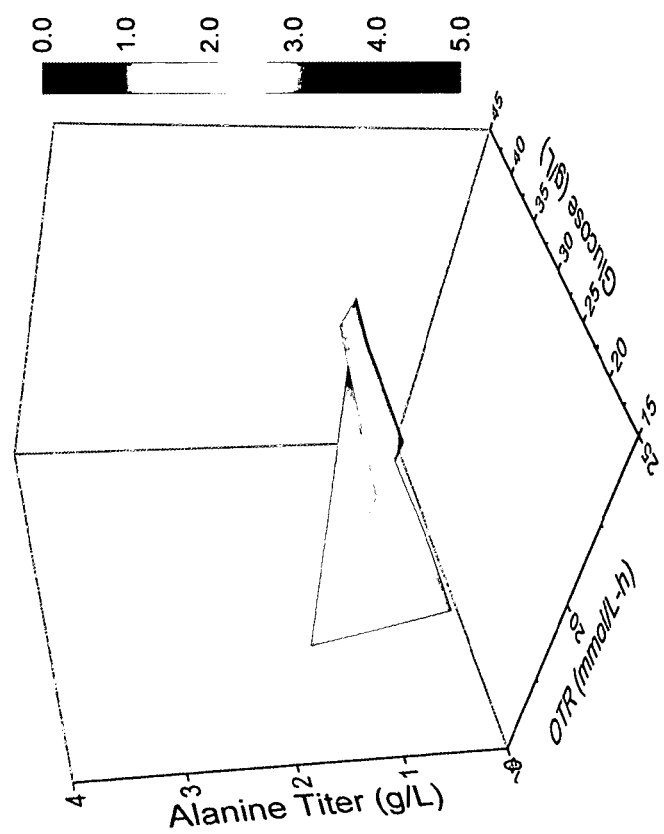
FIGS. 28A-D depict alanine production in response to different OTR and glucose concentration in micro-fermentation for 4 strains evaluated for robustness.
Figure 28B:
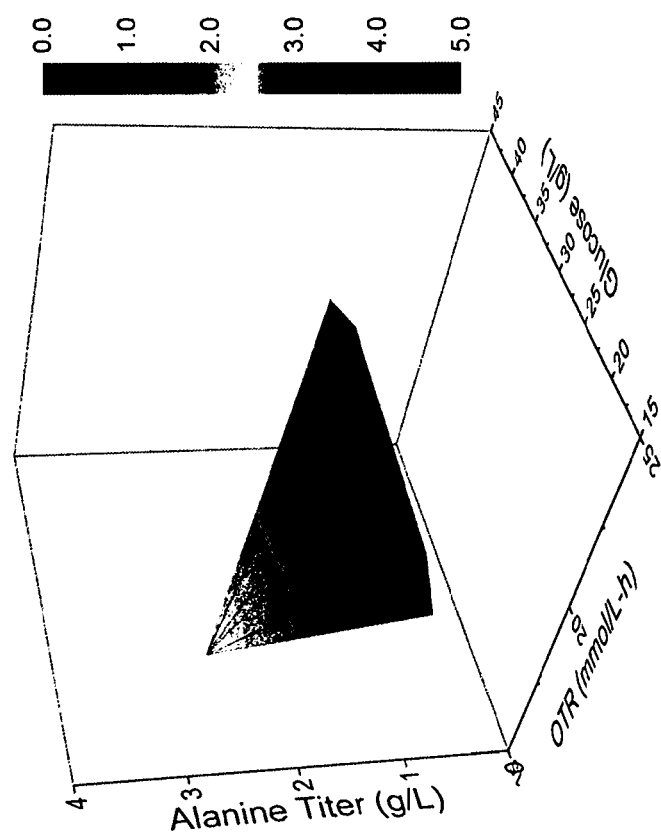
Figure 28C:
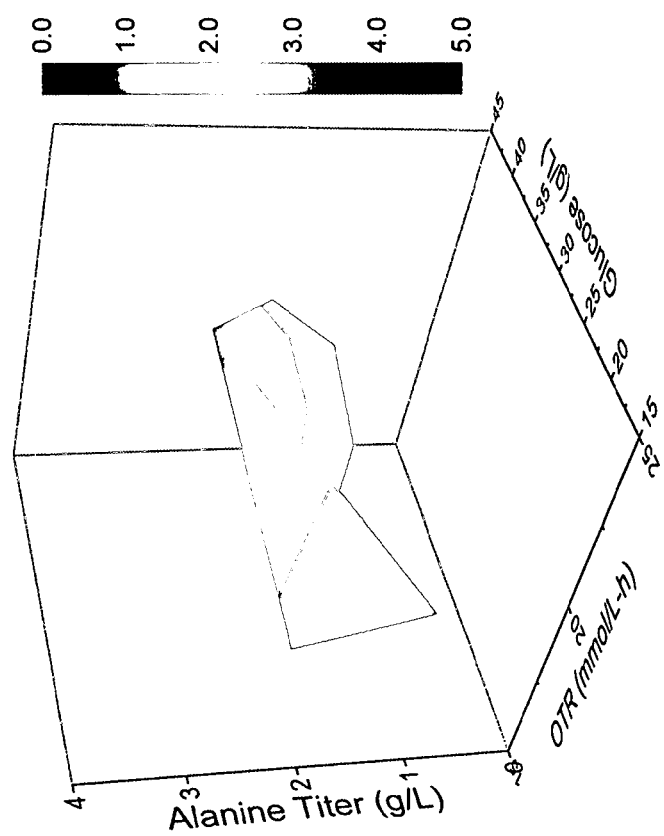
Figure 28D:
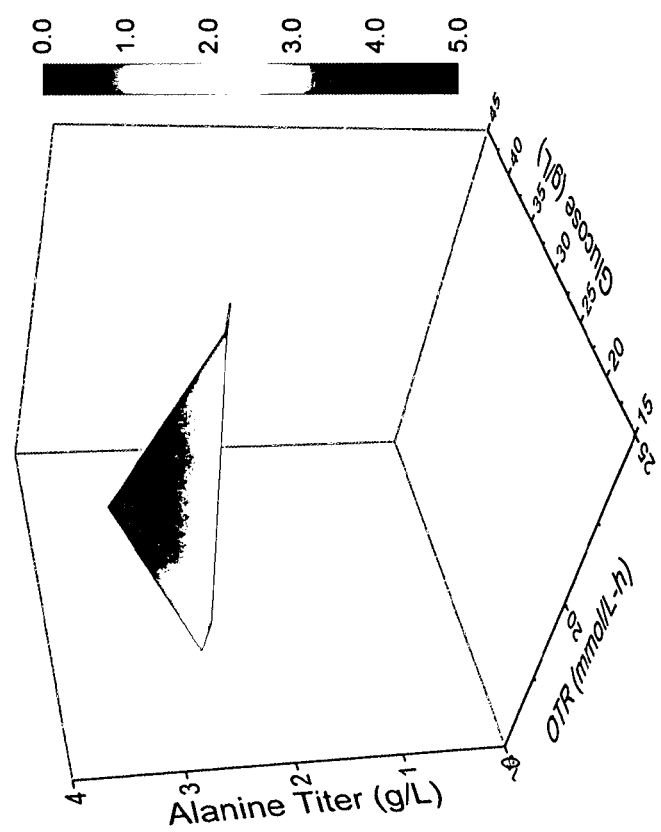
Figure 29A:
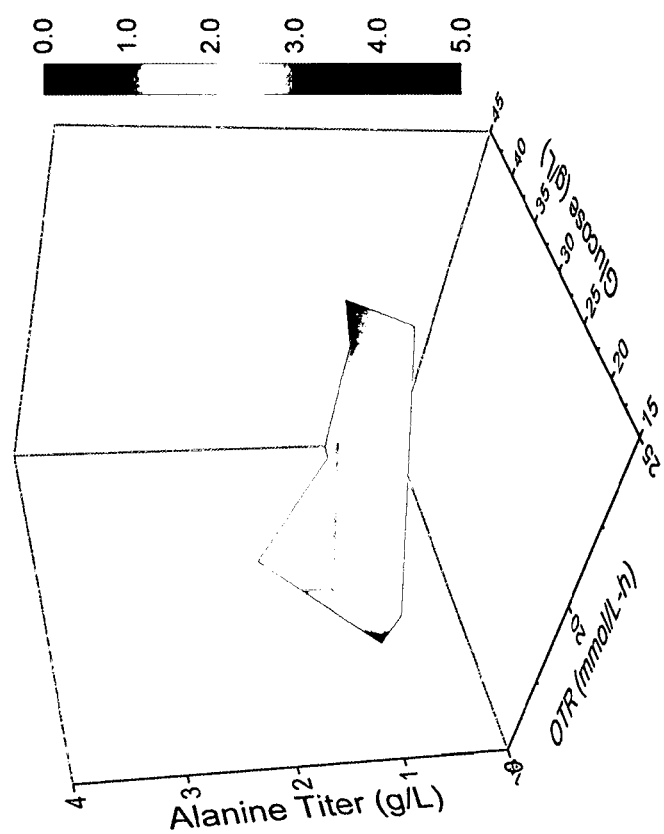
FIGS. 29A-D depict alanine production in response to different OTR and glucose concentration in micro-fermentation for 4 strains evaluated for robustness.
Figure 29B:
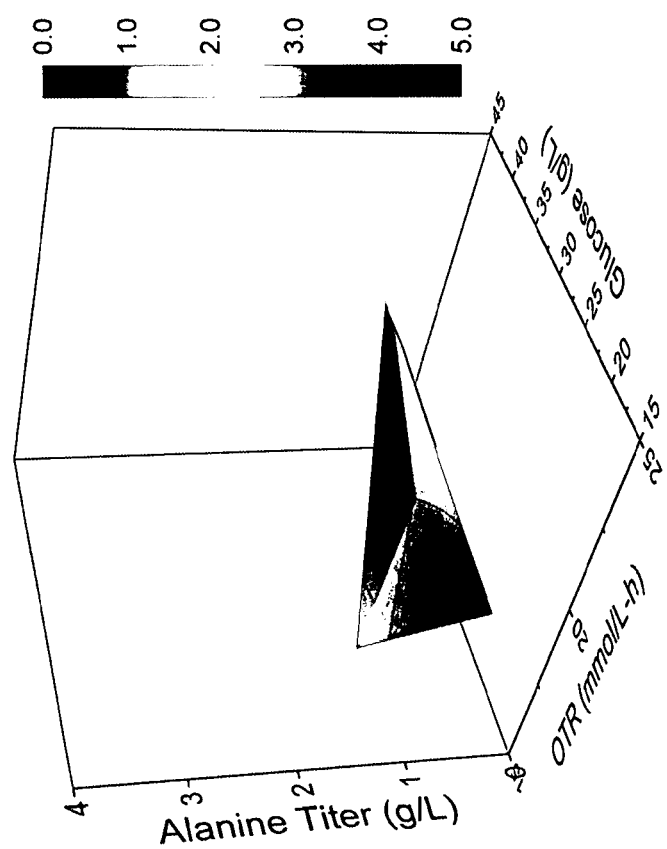
Figure 29C:
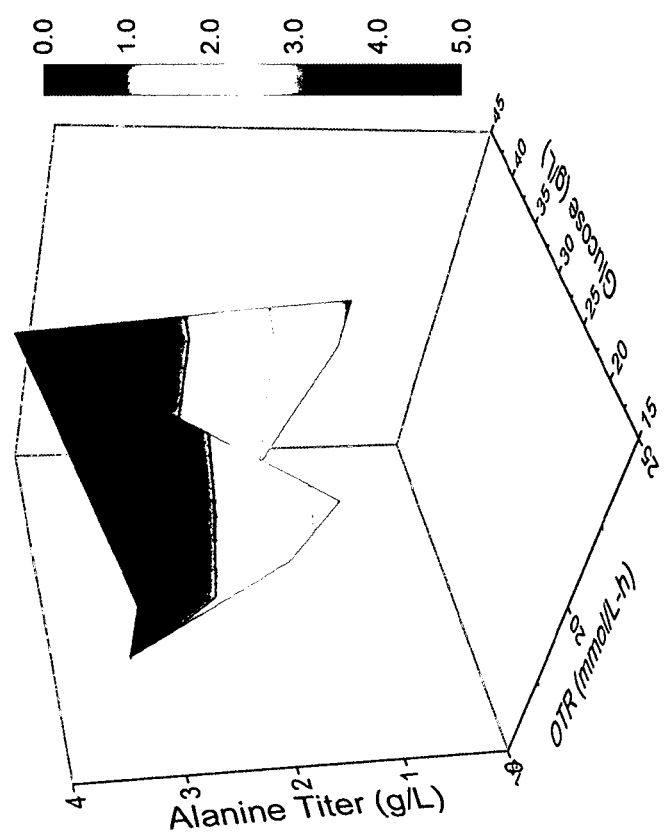
Figure 29D:
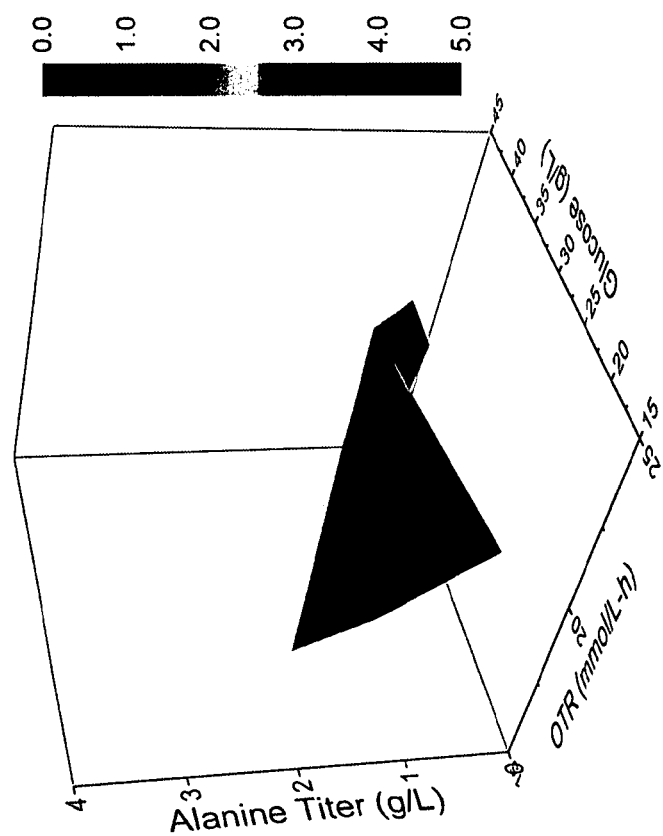
Figure 30A:
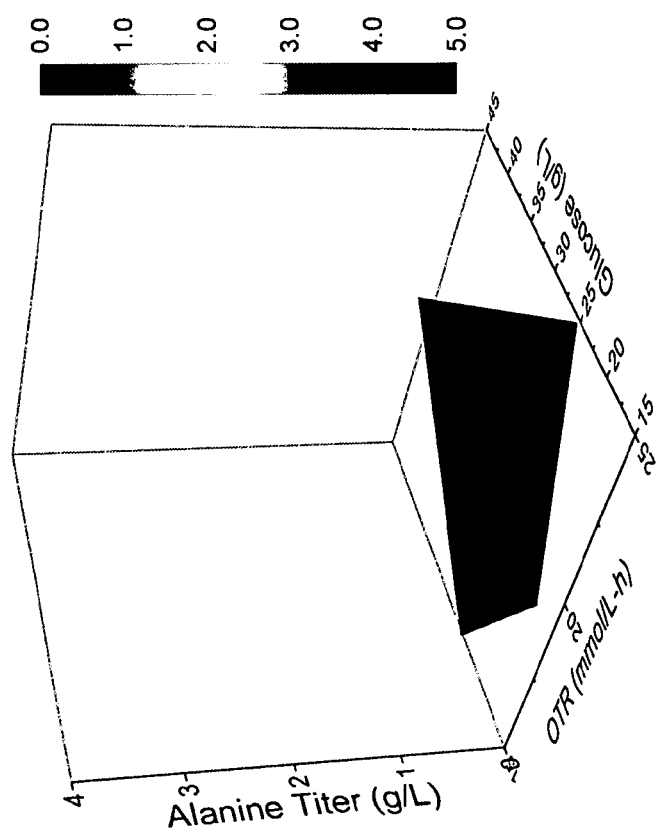
FIGS. 30A-D depict alanine production in response to different OTR and glucose concentration in micro-fermentation for 4 strains evaluated for robustness.
Figure 30B:
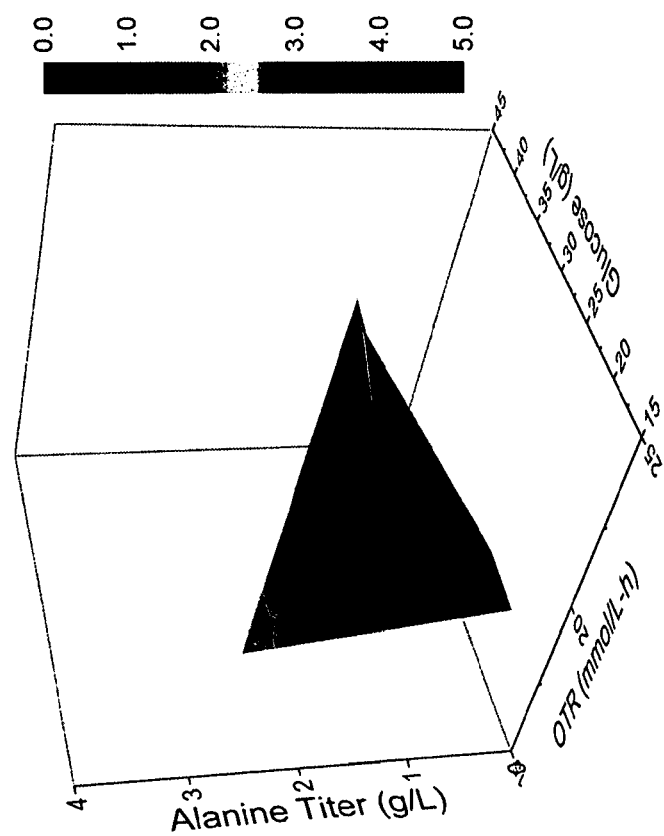
Figure 30C:
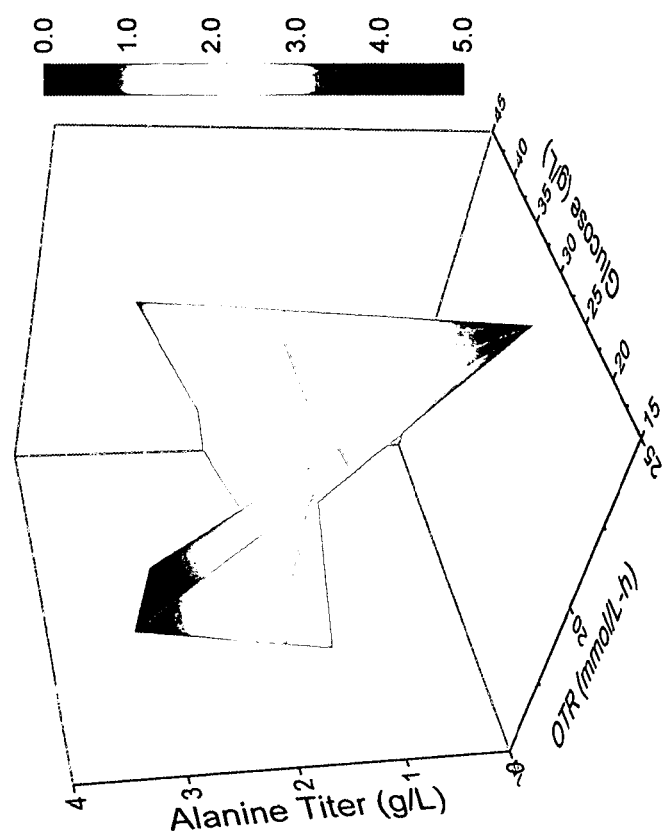
Figure 30D:
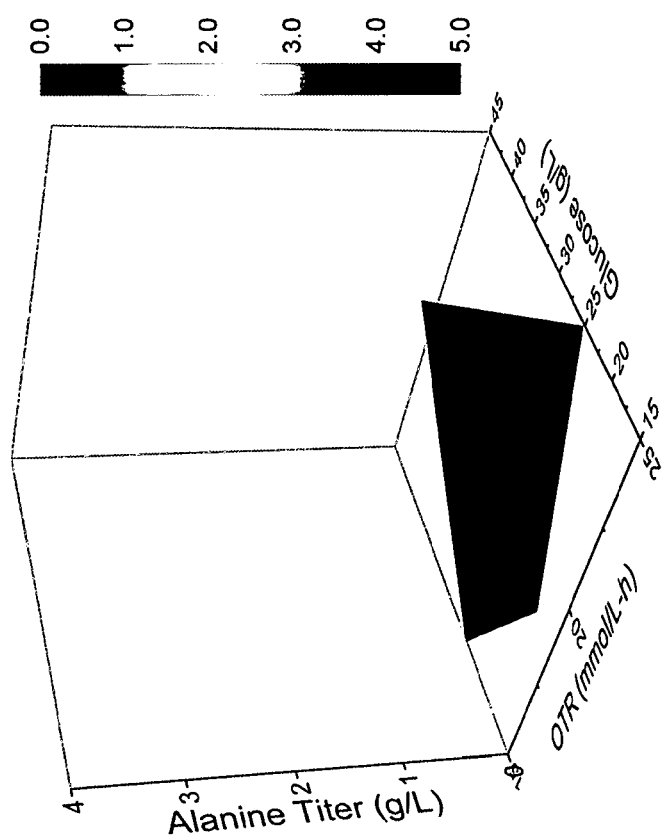
Figure 31A:
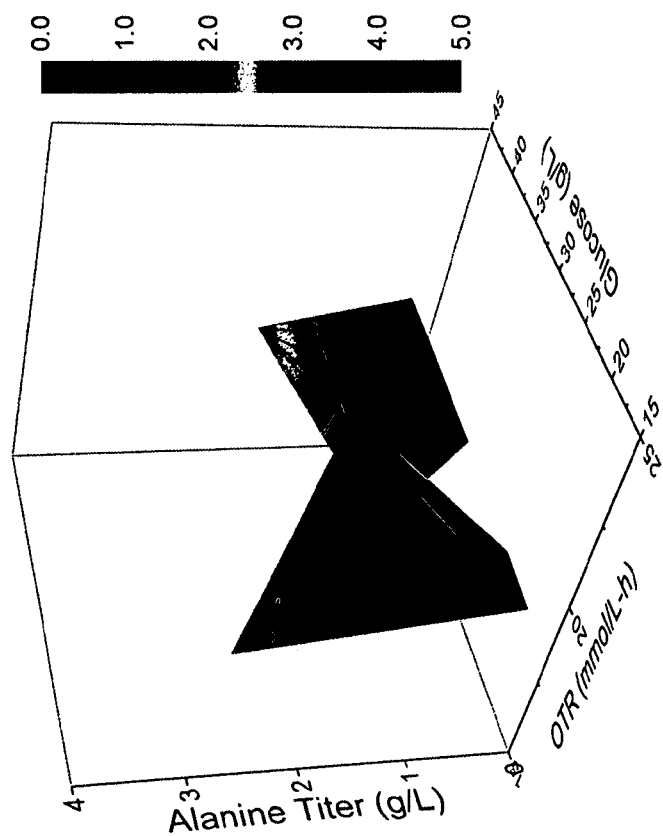
FIGS. 31A-D depict alanine production in response to different OTR and glucose concentration in micro-fermentation for 4 strains evaluated for robustness.
Figure 31B:
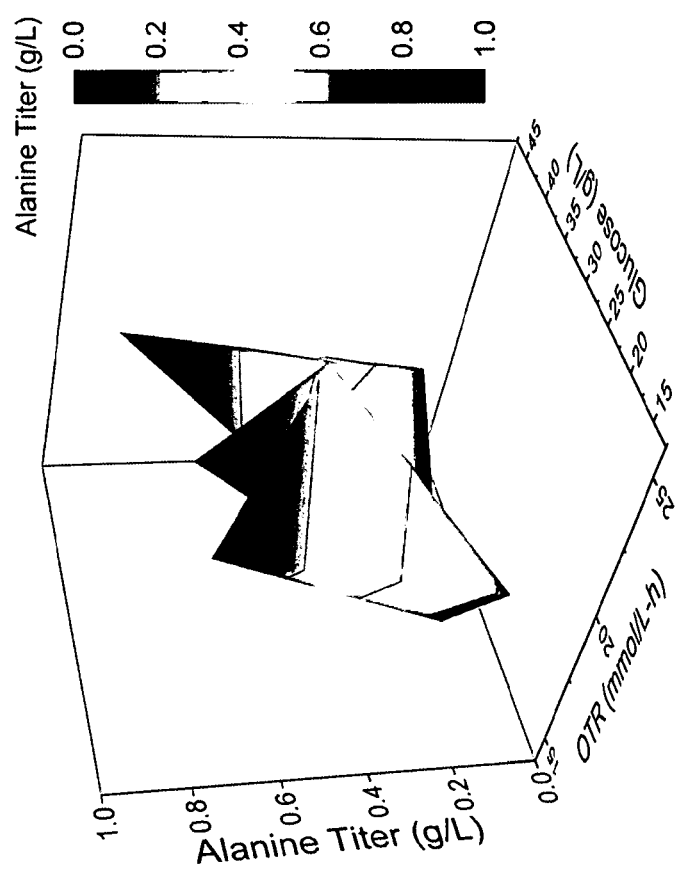
Figure 31C:
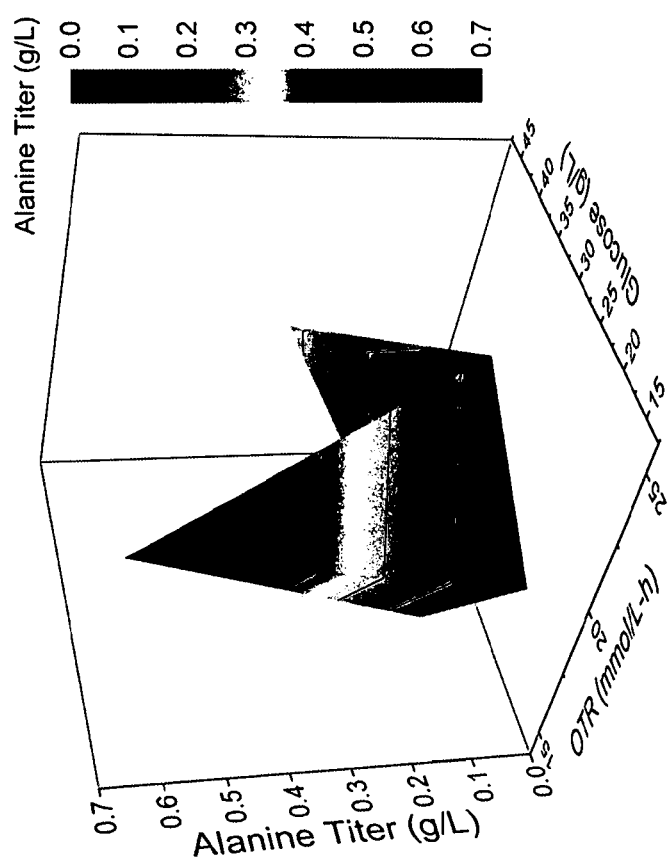
Figure 31D:
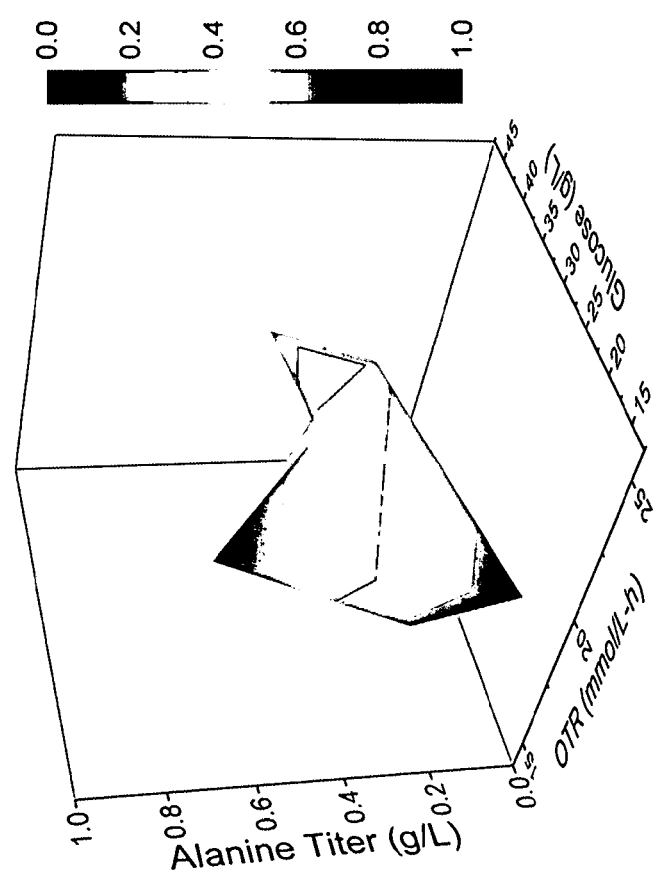

FIG. 18: Heatmap for L-alanine production by gapN/gapA strains.

FIGS. 19A-D: Alanine production in response to different OTR and glucose concentration in micro-fermentation for 4 strains evaluated for robustness.

FIGS. 20A-D: Alanine production in response to different OTR and glucose concentration in micro-fermentation for 4 strains evaluated for robustness.

FIGS. 21A-D: Alanine production in response to different OTR and glucose concentration in micro-fermentation for 4 strains evaluated for robustness.

FIGS. 22A-D: Alanine production in response to different OTR and glucose concentration in micro-fermentation for 4 strains evaluated for robustness.

FIGS. 23A-D: Alanine production in response to different OTR and glucose concentration in micro-fermentation for 4 strains evaluated for robustness.

FIGS. 24A-D: Alanine production in response to different OTR and glucose concentration in micro-fermentation for 4 strains evaluated for robustness.

FIGS. 25A-D: Alanine production in response to different OTR and glucose concentration in micro-fermentation for 4 strains evaluated for robustness.

FIGS. 26A-D: Alanine production in response to different OTR and glucose concentration in micro-fermentation for 4 strains evaluated for robustness.

FIGS. 27A-D: Alanine production in response to different OTR and glucose concentration in micro-fermentation for 4 strains evaluated for robustness.

FIGS. 28A-D: Alanine production in response to different OTR and glucose concentration in micro-fermentation for 4 strains evaluated for robustness.

FIGS. 29A-D: Alanine production in response to different OTR and glucose concentration in micro-fermentation for 4 strains evaluated for robustness.

FIGS. 30A-D: Alanine production in response to different OTR and glucose concentration in micro-fermentation for 4 strains evaluated for robustness.

FIGS. 31A-D: Alanine production in response to different OTR and glucose concentration in micro-fermentation for 4 strains evaluated for robustness.

Figure 32:
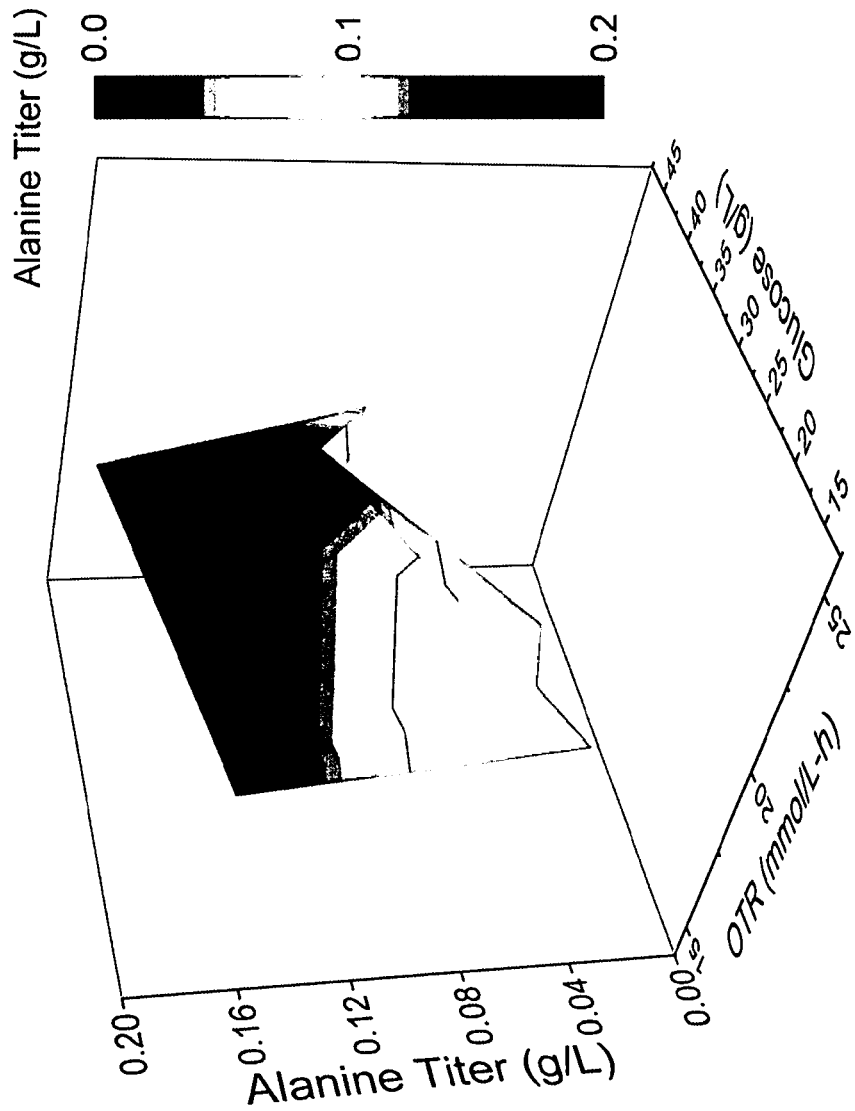
FIG. 32 depicts alanine production in response to different OTR and glucose concentration in micro-fermentation for one strain evaluated for robustness.

FIG. 32: Alanine production in response to different OTR and glucose concentration in micro-fermentation for one strain evaluated for robustness.

Figure 33B:
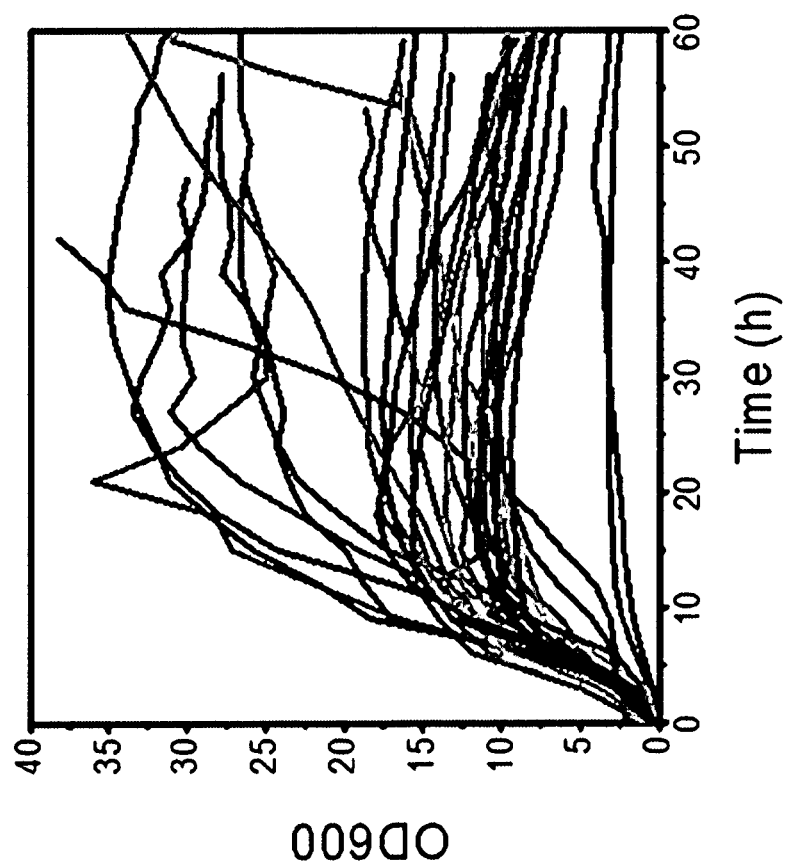

FIGS. 33A-B: Growth profile for all (FIG. 33A) valve and (FIG. 33B) growth associated strains at 1 L scale evaluated in this paper. Growth curves were synced to account for any variations in lag time. Valve strains growth curves were synced to the same mid-exponential point. Growth associated strains growth curves were synced to the same take-off point.

Figure 34:
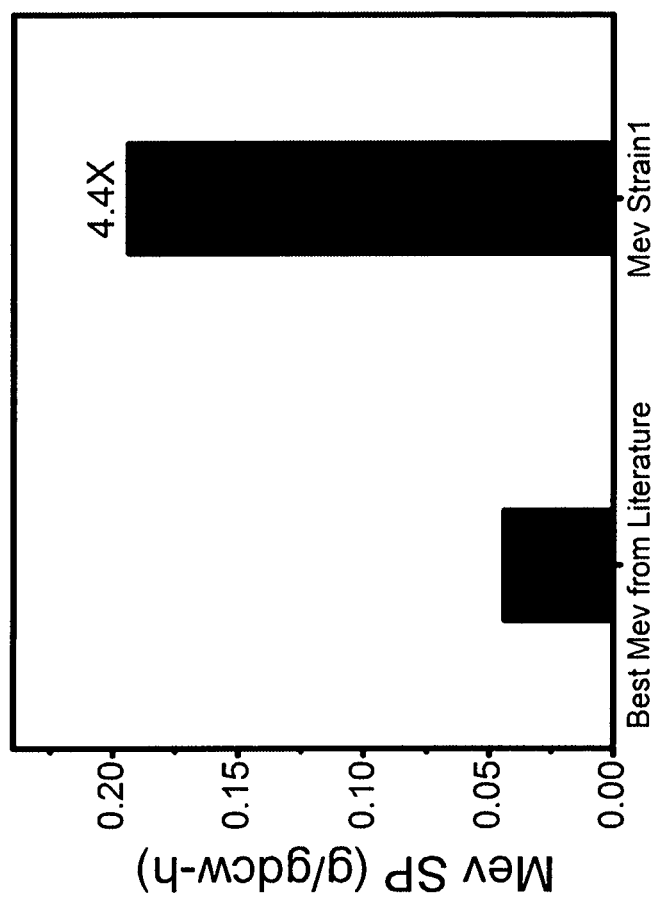
FIG. 34 depicts specific Productivity (SP) comparison for strain with highest mevalonate titer from literature and mevalonate strain 1 evaluated in this work.

FIG. 34: Specific Productivity (SP) comparison for strain with highest mevalonate titer from literature and mevalonate strain 1 evaluated in this work.

Figure 35:
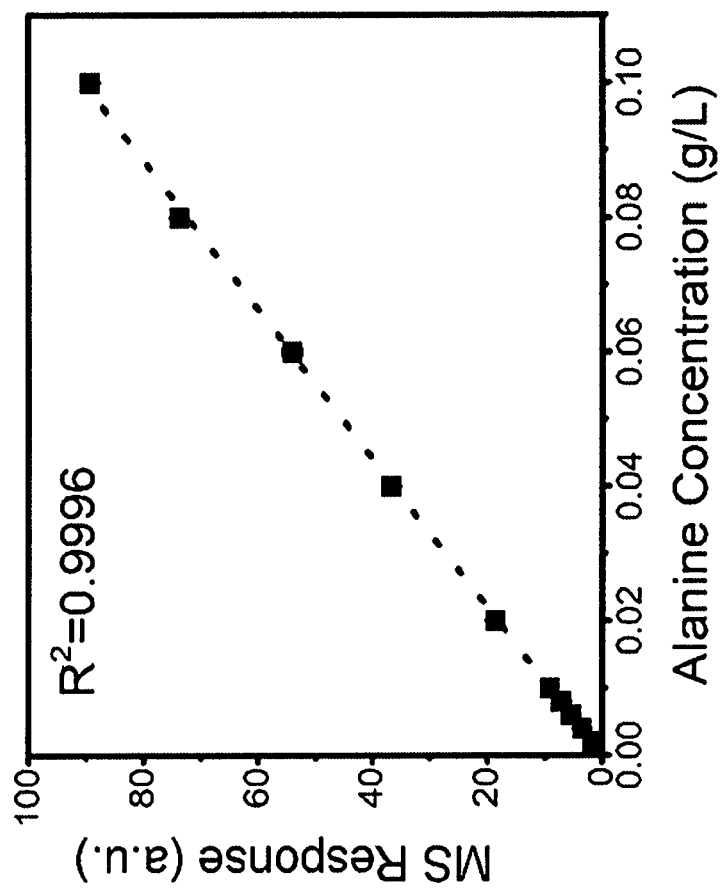
FIG. 35 depicts alanine standard curve from MS measurement. Average and standard deviation for mass spec response from triplicate standard measurement were plotted.

FIG. 35: Alanine standard curve from MS measurement. Average and standard deviation for mass spec response from triplicate standard measurement were plotted.

Figure 36B:
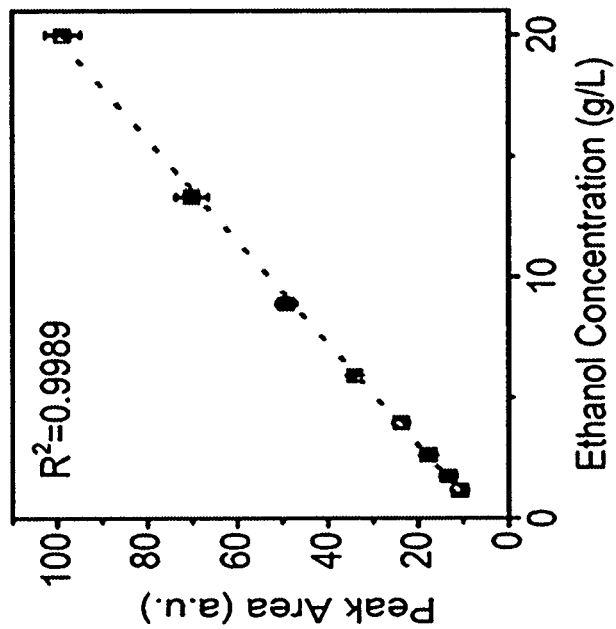
FIGS. 36A-B depict glucose and ethanol standard curves from RI measurement.
Figure 36A:
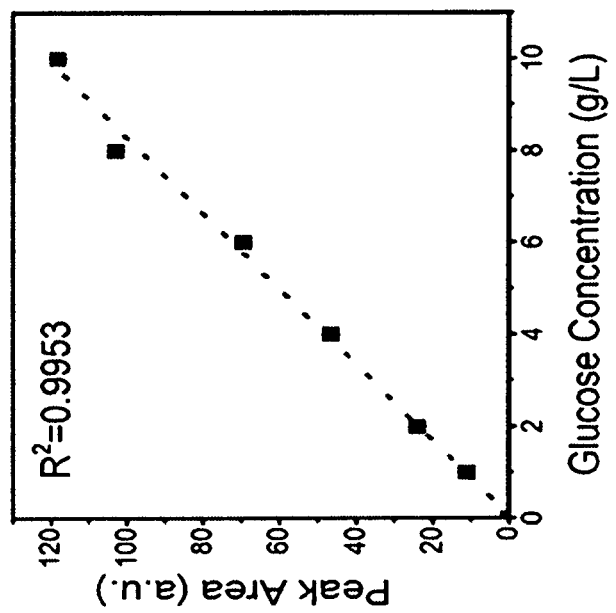

FIGS. 36A-B: Glucose (FIG. 36A) and ethanol (FIG. 36B) standard curves from RI measurement. Average and standard deviation for peak area from triplicate standard measurement were plotted.

Figure 37:
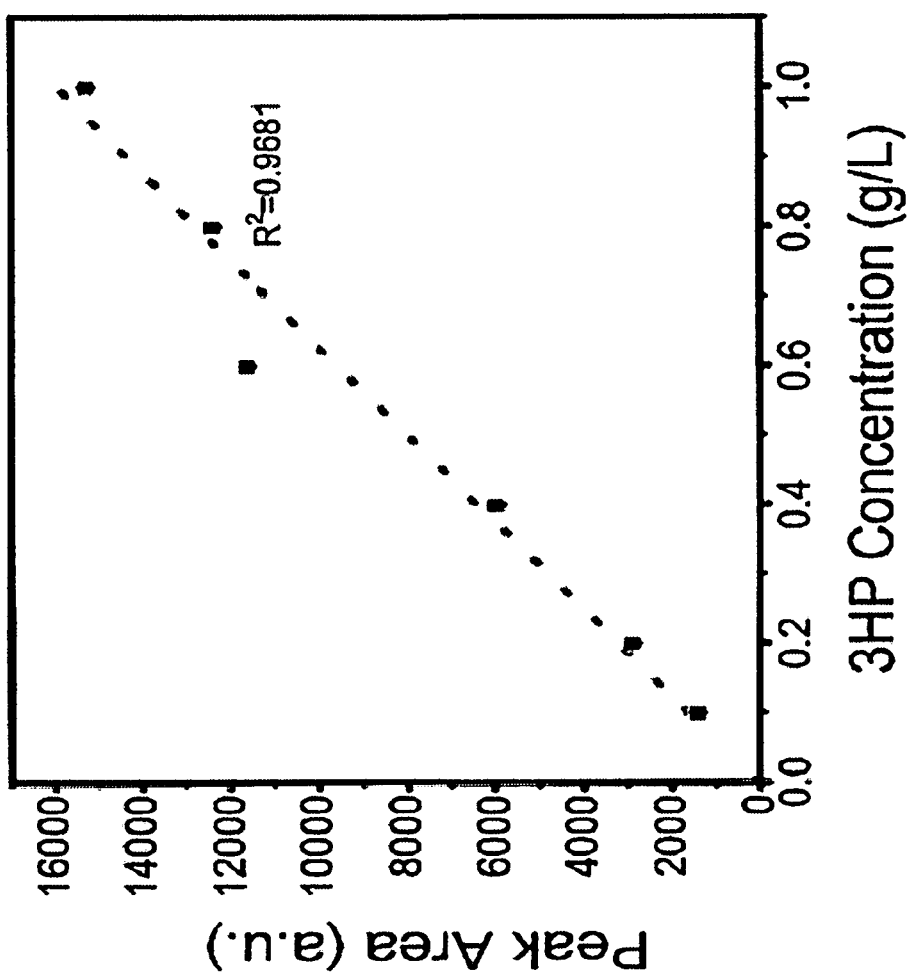
FIG. 37 depicts 3-Hydroxypropionic acid standard curve from TUV measurement.
Figure 38A:
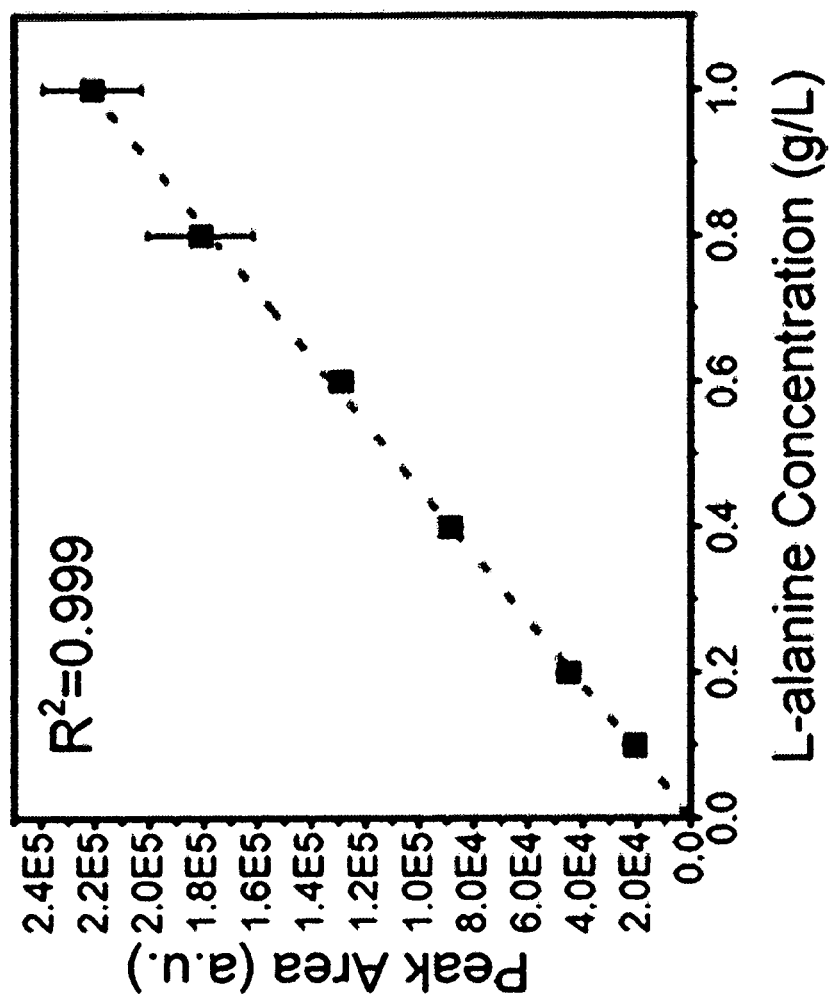
FIGS. 38A-D depict TUV standard curves for L-alanine, D-alanine, mevalonic acid, and mevalonolactone.
Figure 38B:
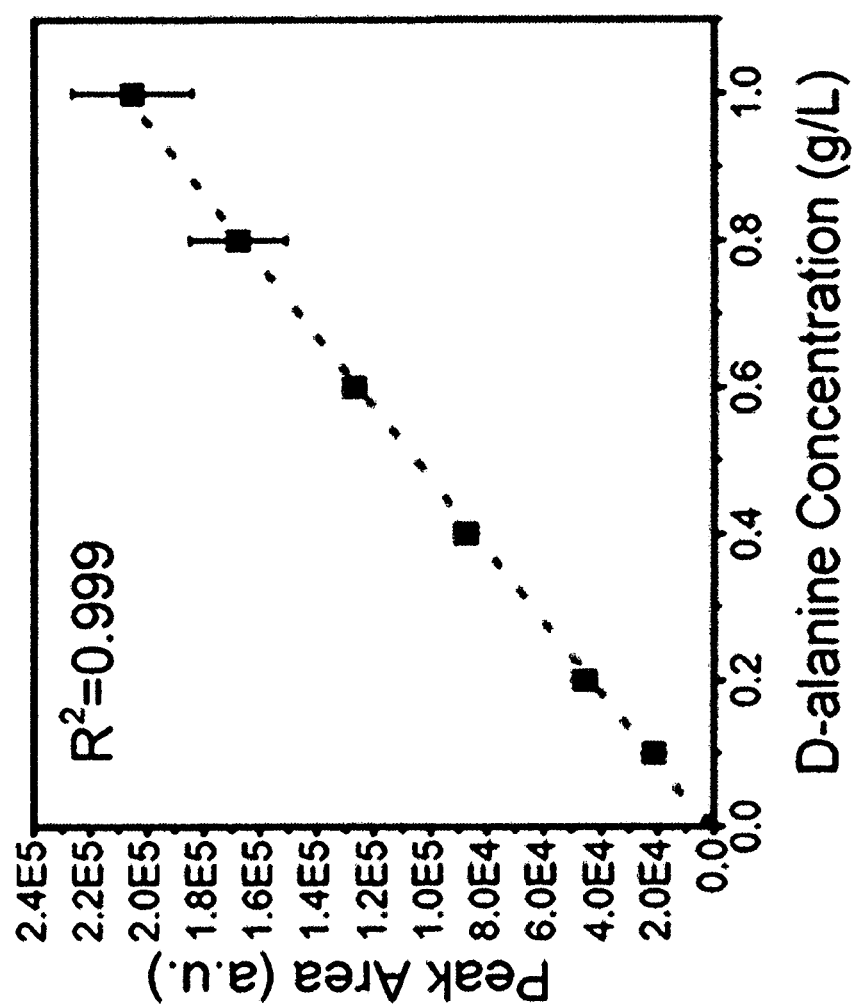
Figure 38C:
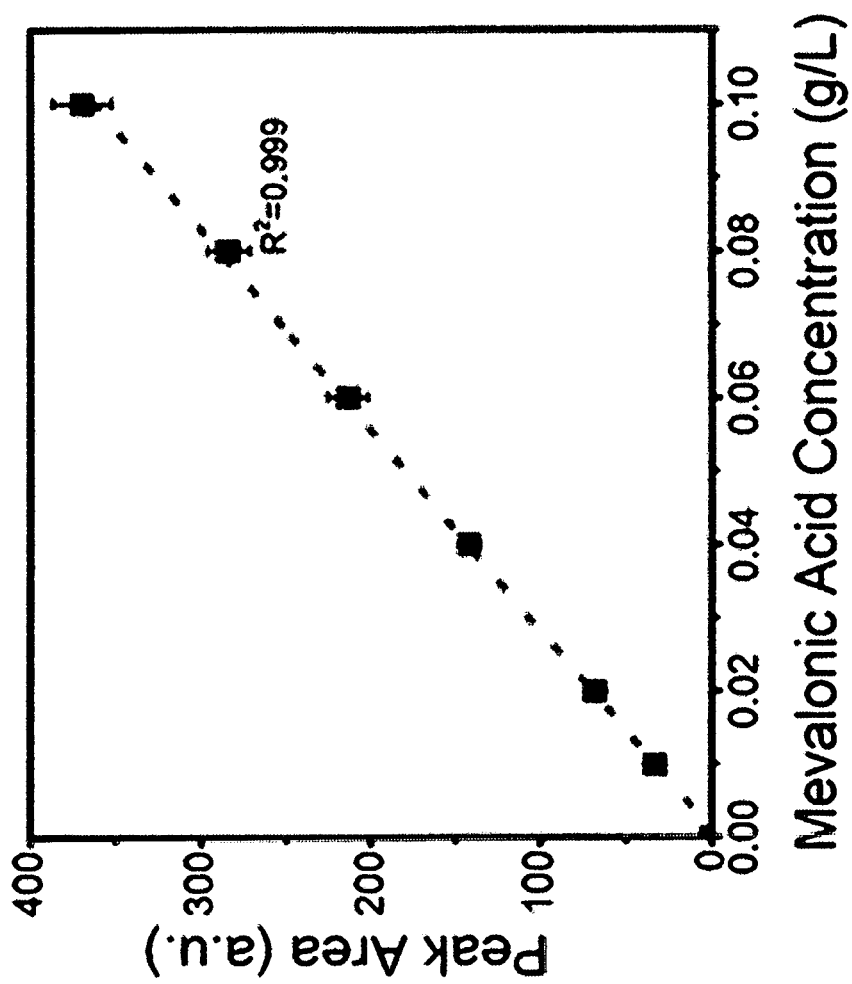
Figure 38D:
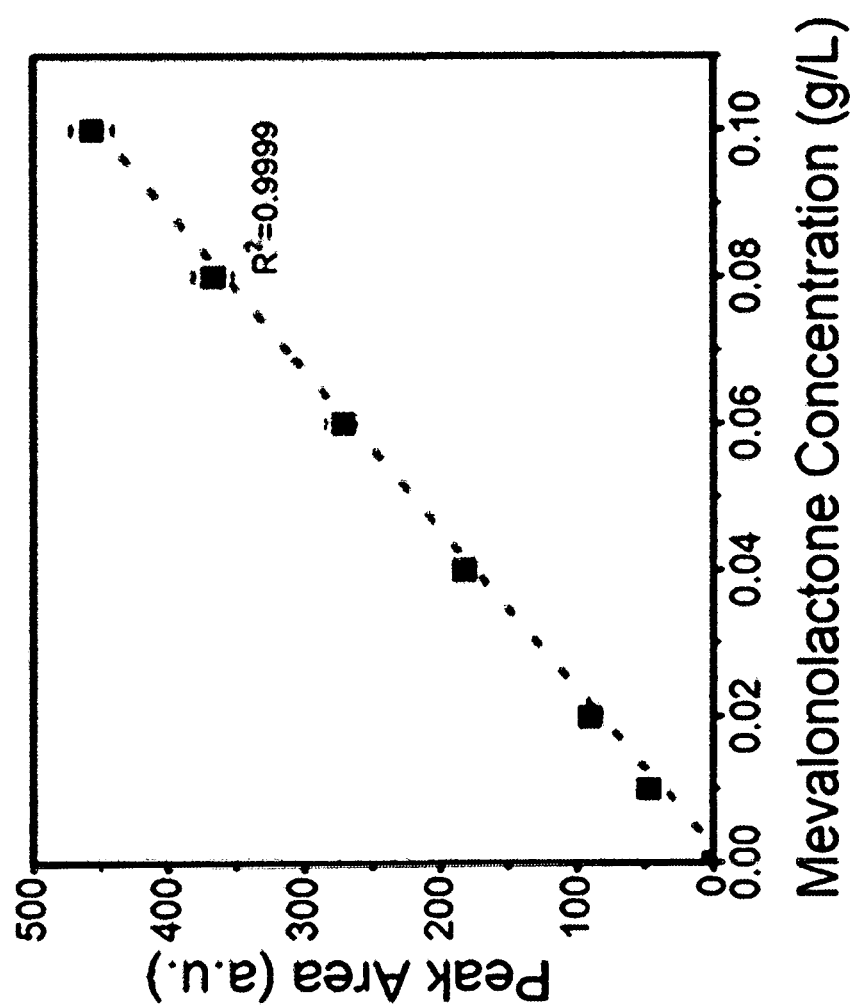

FIG. 37: 3-Hydroxypropionic acid standard curve from TUV measurement. Average and standard deviation for peak area from duplicate standard measurement were plotted.

FIGS. 38A-D: TUV standard curves for (FIG. 38A) L-alanine, (FIG. 38B) D-alanine, (FIG. 38C) mevalonic acid, and (FIG. 38D) mevalonolactone. Average and standard deviation for peak area from triplicate standard measurement were plotted.

REFERENCES

1. Cameron, D. E.; Bashor, C. J.; Collins, J. J., A brief history of synthetic biology. *Nat Rev Microbiol* 2014, 12 (5), 381-90.
2. Cheong, S.; Clomburg, J. M.; Gonzalez, R., Energy- and carbon-efficient synthesis of functionalized small molecules in bacteria using non-decarboxylative Claisen condensation reactions. *Nature biotechnology* 2016, 34 (5), 556-61.
3. Choi, S. Y.; Park, S. J.; Kim, W. J.; Yang, J. E.; Lee, H.; Shin, J.; Lee, S. Y., One-step fermentative production of poly(lactate-co-glycolate) from carbohydrates in *Escherichia coli*. *Nature biotechnology* 2016, 34 (4), 435-40.
4. Jarboe, L. R.; Zhang, X.; Wang, X.; Moore, J. C.; Shanmugam, K. T.; Ingram, L. O., Metabolic engineering for production of biorenewable fuels and chemicals: contributions of synthetic biology. *Journal of biomedicine & biotechnology* 2010, 761042.
5. Lee, J. W.; Na, D.; Park, J. M.; Lee, J.; Choi, S.; Lee, S. Y., Systems metabolic engineering of microorganisms for natural and non-natural chemicals. *Nat Chem Biol* 2012, 8 (6), 536-46.
6. Dellomonaco, C.; Clomburg, J. M.; Miller, E. N.; Gonzalez, R., Engineered reversal of the beta-oxidation cycle for the synthesis of fuels and chemicals. *Nature* 2011, 476 (7360), 355-9.
7. Kim, S.; Clomburg, J. M.; Gonzalez, R., Synthesis of medium-chain length (C6-C10) fuels and chemicals via beta-oxidation reversal in *Escherichia coli*. *J Ind Microbiol Biotechnol* 2015, 42 (3), 465-75.
8. Meadows, A. L.; Hawkins, K. M.; Tsegaye, Y.; Antipov, E.; Kim, Y.; Raetz, L.; Dahl, R. H.; Tai, A.; Mahatdejkul-Meadows, T.; Xu, L.; Zhao, L.; Dasika, M. S.; Murarka, A.; Lenihan, J.; Eng, D.; Leng, J. S.; Liu, C. L.; Wenger, J. W.; Jiang, H.; Chao, L.; Westfall, P.; Lai, J.; Ganesan, S.; Jackson, P.; Mans, R.; Platt, D.; Reeves, C. D.; Saija, P. R.; Wichmann, G.; Holmes, V. F.; Benjamin, K.; Hill, P. W.; Gardner, T. S.; Tsong, A. E., Rewriting yeast central carbon metabolism for industrial isoprenoid production. *Nature* 2016, 537 (7622), 694-697.
9. Yadav, V. G.; De Mey, M.; Lim, C. G.; Ajikumar, P. K.; Stephanopoulos, G., The future of metabolic engineering and synthetic biology: towards a systematic practice. *Metab Eng* 2012, 14 (3), 233-41.
10. Brophy, J. A.; Voigt, C. A., Principles of genetic circuit design. *Nat Methods* 2014, 11 (5), 508-20.
11. Koutinas, M.; Kiparissides, A.; Pistikopoulos, E. N.; Mantalaris, A., Bioprocess systems engineering: transferring traditional process engineering principles to industrial biotechnology. *Comput Struct Biotechnol J* 2012, 3, e201210022.
12. Rodrigo, G.; Jaramillo, A., AutoBioCAD: full biodesign automation of genetic circuits. *ACS Synth Biol* 2013, 2 (5), 230-6.
13. Garst, A. D.; Bassalo, M. C.; Pines, G.; Lynch, S. A.; Halweg-Edwards, A. L.; Liu, R.; Liang, L.; Wang, Z.; Zeitoun, R.; Alexander, W. G.; Gill, R. T., Genome-wide mapping of mutations at single-nucleotide resolution for protein, metabolic and genome engineering. *Nat Biotech* 2017, 35 (1), 48-55.
14. Church, G. M.; Elowitz, M. B.; Smolke, C. D.; Voigt, C. A.; Weiss, R., Realizing the potential of synthetic biology. *Nat Rev Mol Cell Biol* 2014, 15 (4), 289-94.
15. Thomas, S.; Maynard, N. D.; Gill, J., DNA library construction using Gibson Assembly[reg]. *Nat Meth* 2015, 12 (11).
16. Goodwin, S.; McPherson, J. D.; McCombie, W. R., Coming of age: ten years of next-generation sequencing technologies. *Nat Rev Genet* 2016, 17 (6), 333-51.
17. Lynch, M. D.; Warnecke, T.; Gill, R. T., SCALEs: multiscale analysis of library enrichment. *Nat Methods* 2007, 4 (1), 87-93.

18. Zeitoun, R. I.; Garst, A. D.; Degen, G. D.; Pines, G.; Mansell, T. J.; Glebes, T. Y.; Boyle, N. R.; Gill, R. T., Multiplexed tracking of combinatorial genomic mutations in engineered cell populations. *Nat Biotechnol* 2015, 33 (6), 631-7.
19. Crook, N.; Abatemarco, J.; Sun, J.; Wagner, J. M.; Schmitz, A.; Alper, H. S., In vivo continuous evolution of genes and pathways in yeast. *Nat Commun* 2016, 7, 13051.
20. Burg, J. M., Reed, B J., Ye, Z., Cooper, C. B., Moreb, E. A., and Lynch, M. D, Large-Scale Bioprocess Competitiveness: The Potential of Dynamic Metabolic Control in Two-Stage Fermentations. *Current Opinions in Chemical Engineering* 2016, (In Review).
21. Zhang, Y. H., Production of biofuels and biochemicals by in vitro synthetic biosystems: Opportunities and challenges. *Biotechnol Adv* 2015, 33 (7), 1467-83.
22. Dietrich, J. A.; McKee, A. E.; Keasling, J. D., High-throughput metabolic engineering: advances in small-molecule screening and selection. *Annu Rev Biochem* 2010, 79, 563-90.
23. Formenti, L. R.; Norregaard, A.; Bolic, A.; Hernandez, D. Q.; Hagemann, T.; Heins, A. L.; Larsson, H.; Mears, L.; Mauricio-Iglesias, M.; Kruhne, U.; Gernaey, K. V., Challenges in industrial fermentation technology research. *Biotechnol J* 2014, 9 (6), 727-38.
24. Levanon, S. S.; San, K. Y.; Bennett, G. N., Effect of oxygen on the *Escherichia coli* ArcA and FNR regulation systems and metabolic responses. *Biotechnol Bioeng* 2005, 89 (5), 556-64.
25. Logue, J. B.; Findlay, S. E.; Comte, J., Editorial: Microbial Responses to Environmental Changes. *Front Microbiol* 2015, 6, 1364.
26. Garcia-Ochoa, F.; Gomez, E., Bioreactor scale-up and oxygen transfer rate in microbial processes: an overview. *Biotechnol Adv* 2009, 27 (2), 153-76.
27. Waegeman, H.; Beauprez, J.; Moens, H.; Maertens, J.; De Mey, M.; Foulquie-Moreno, M. R.; Heijnen, J. J.; Charlier, D.; Soetaert, W., Effect of iclR and arcA knockouts on biomass formation and metabolic fluxes in *Escherichia coli* K12 and its implications on understanding the metabolism of *Escherichia coli* BL21 (DE3). *BMC Microbiol* 2011, 11, 70.
28. Waegeman, H.; Maertens, J.; Beauprez, J.; De Mey, M.; Soetaert, W., Effect of iclR and arcA deletions on physiology and metabolic fluxes in *Escherichia coli* BL21 (DE3). *Biotechnol Lett* 2012, 34 (2), 329-37.
29. Hemmerich, J.; Adelantado, N.; Barrigon, J. M.; Ponte, X.; Hormann, A.; Ferrer, P.; Kensy, F.; Valero, F., Comprehensive clone screening and evaluation of fed-batch strategies in a microbioreactor and lab scale stirred tank bioreactor system: application on *Pichia pastoris* producing *Rhizopus oryzae* lipase. *Microb Cell Fact* 2014, 13 (1), 36.
30. Ramirez-Vargas, R.; Vital-Jacome, M.; Camacho-Perez, E.; Hubbard, L.; Thalasso, F., Characterization of oxygen transfer in a 24-well microbioreactor system and potential respirometric applications. *J Biotechnol* 2014, 186, 58-65.
31. Huber, R.; Roth, S.; Rahmen, N.; Buchs, J., Utilizing high-throughput experimentation to enhance specific productivity of an *E. coli* T7 expression system by phosphate limitation. *BMC biotechnology* 2011, 11, 22.
32. Lynch, M. D., Into new territory: improved microbial synthesis through engineering of the essential metabolic network. *Curr Opin Biotechnol* 2016, 38, 106-11.
33. McGinness, K. E.; Baker, T. A.; Sauer, R. T., Engineering controllable protein degradation. *Mol Cell* 2006, 22 (5), 701-7.
34. Luo, M. L.; Mullis, A. S.; Leenay, R. T.; Beisel, C. L., Repurposing endogenous type I CRISPR-Cas systems for programmable gene repression. *Nucleic acids research* 2015, 43 (1), 674-81.
35. Qi, L. S.; Larson, M. H.; Gilbert, L. A.; Doudna, J. A.; Weissman, J. S.; Arkin, A. P.; Lim, W. A., Repurposing CRISPR as an RNA-guided platform for sequence-specific control of gene expression. *Cell* 2013, 152 (5), 1173-83.
36. Chubukov, V.; Sauer, U., Environmental dependence of stationary-phase metabolism in *Bacillus subtilis* and *Escherichia coli*. *Applied and environmental microbiology* 2014, 80 (9), 2901-9.
37. Santos-Beneit, F., The Pho regulon: a huge regulatory network in bacteria. *Front Microbiol* 2015, 6, 402.
38. Brouns, S. J.; Jore, M. M.; Lundgren, M.; Westra, E. R.; Slijkhuis, R. J.; Snijders, A. P.; Dickman, M. J.; Makarova, K. S.; Koonin, E. V.; van der Oost, J., Small CRISPR RNAs guide antiviral defense in prokaryotes. *Science* 2008, 321 (5891), 960-4.
39. Jian, J.; Zhang, S. Q.; Shi, Z. Y.; Wang, W.; Chen, G. Q.; Wu, Q., Production of polyhydroxyalkanoates by *Escherichia coli* mutants with defected mixed acid fermentation pathways. *Appl Microbiol Biotechnol* 2010, 87 (6), 2247-56.
40. Grunenfelder, B.; Rummel, G.; Vohradsky, J.; Roder, D.; Langen, H.; Jenal, U., Proteomic analysis of the bacterial cell cycle. *Proc Natl Acad Sci USA* 2001, 98 (8), 4681-6.
41. Hintsche, M.; Klumpp, S., Dilution and the theoretical description of growth-rate dependent gene expression. *J Biol Eng* 2013, 7 (1), 22.
42. Lerchner, A.; Jarasch, A.; Skerra, A., Engineering of alanine dehydrogenase from *Bacillus subtilis* for novel cofactor specificity. *Biotechnol Appl Biochem* 2016, 63 (5), 616-624.
43. Hori, H.; Yoneyama, H.; Tobe, R.; Ando, T.; Isogai, E.; Katsumata, R., Inducible L-alanine exporter encoded by the novel gene ygaW (alaE) in *Escherichia coli*. *Applied and environmental microbiology* 2011, 77 (12), 4027-34.
44. Davis, J. H.; Rubin, A. J.; Sauer, R. T., Design, construction and characterization of a set of insulated bacterial promoters. *Nucleic acids research* 2011, 39 (3), 1131-41.
45. Hedl, M.; Sutherlin, A.; Wilding, E. I.; Mazzulla, M.; McDevitt, D.; Lane, P.; Burgner, J. W., 2nd; Lehnbeuter, K. R.; Stauffacher, C. V.; Gwynn, M. N.; Rodwell, V. W., *Enterococcus faecalis* acetoacetyl-coenzyme A thiolase/3-hydroxy-3-methylglutaryl-coenzyme A reductase, a dual-function protein of isopentenyl diphosphate biosynthesis. *J Bacteriol* 2002, 184 (8), 2116-22.
46. Steussy, C. N.; Robison, A. D.; Tetrick, A. M.; Knight, J. T.; Rodwell, V. W.; Stauffacher, C. V.; Sutherlin, A. L., A structural limitation on enzyme activity: the case of HMG-CoA synthase. *Biochemistry* 2006, 45 (48), 14407-14.
47. Xiong, M.; Schneiderman, D. K.; Bates, F. S.; Hillmyer, M. A.; Zhang, K., Scalable production of mechanically tunable block polymers from sugar. *Proc Natl Acad Sci USA* 2014, 111 (23), 8357-62.
48. Otterstedt, K.; Larsson, C.; Bill, R. M.; Stahlberg, A.; Boles, E.; Hohmann, S.; Gustafsson, L., Switching the mode of metabolism in the yeast *Saccharomyces cerevisiae*. *EMBO Rep* 2004, 5 (5), 532-7.

49. Hubmann, G.; Guillouet, S.; Nevoigt, E., Gpd1 and Gpd2 fine-tuning for sustainable reduction of glycerol formation in *Saccharomyces cerevisiae*. *Applied and environmental microbiology* 2011, 77 (17), 5857-67.
50. Lascaris, R.; Bussemaker, H. J.; Boorsma, A.; Piper, M.; van der Spek, H.; Grivell, L.; Blom, J., Hap4p overexpression in glucose-grown *Saccharomyces cerevisiae* induces cells to enter a novel metabolic state. *Genome Biol* 2003, 4 (1), R3.
51. Mittal, N.; Babu, M. M.; Roy, N., The efficiency of mitochondrial electron transport chain is increased in the long-lived mrg19 *Saccharomyces cerevisiae*. *Aging Cell* 2009, 8 (6), 643-53.
52. Thomas, M. R.; O'Shea, E. K., An intracellular phosphate buffer filters transient fluctuations in extracellular phosphate levels. *Proc Natl Acad Sci USA* 2005, 102 (27), 9565-70.
53. Gray, J. V.; Petsko, G. A.; Johnston, G. C.; Ringe, D.; Singer, R. A.; Werner-Washburne, M., "Sleeping beauty": quiescence in *Saccharomyces cerevisiae*. *Microbiol Mol Biol Rev* 2004, 68 (2), 187-206.
54. Grilly, C.; Stricker, J.; Pang, W. L.; Bennett, M. R.; Hasty, J., A synthetic gene network for tuning protein degradation in *Saccharomyces cerevisiae*. *Mol Syst Biol* 2007, 3, 127.
55. Orth, J. D.; Thiele, I.; Palsson, B. O., What is flux balance analysis? *Nat Biotechnol* 2010, 28 (3), 245-8.
56. Yim, H.; Haselbeck, R.; Niu, W.; Pujol-Baxley, C.; Burgard, A.; Boldt, J.; Khandurina, J.; Trawick, J. D.; Osterhout, R. E.; Stephen, R.; Estadilla, J.; Teisan, S.; Schreyer, H. B.; Andrae, S.; Yang, T. H.; Lee, S. Y.; Burk, M. J.; Van Dien, S., Metabolic engineering of *Escherichia coli* for direct production of 1,4-butanediol. *Nat Chem Biol* 2011, 7 (7), 445-52.
57. Gupta, A.; Reizman, I. M.; Reisch, C. R.; Prather, K. L., Dynamic regulation of metabolic flux in engineered bacteria using a pathway-independent quorum-sensing circuit. *Nature biotechnology* 2017, 35 (3), 273-279.
58. Wang, J.; Yu, H. Q., Biosynthesis of polyhydroxybutyrate (PHB) and extracellular polymeric substances (EPS) by *Ralstonia eutropha* ATCC 17699 in batch cultures. *Appl Microbiol Biotechnol* 2007, 75 (4), 871-8.
59. Xu, P.; Qiao, K.; Ahn, W. S.; Stephanopoulos, G., Engineering *Yarrowia lipolytica* as a platform for synthesis of drop-in transportation fuels and oleochemicals. *Proc Natl Acad Sci US A* 2016,113 (39), 10848-53.
60. Lynch, M. D.; Warnecke, T.; Gill, R. T. Method for Producing 3-Hydroxypropionic Acid and Other Products. Sep. 8, 2011.
61. Qiao, K.; Wasylenko, T. M.; Zhou, K.; Xu, P.; Stephanopoulos, G., Lipid production in *Yarrowia lipolytica* is maximized by engineering cytosolic redox metabolism. *Nat Biotechnol* 2017.
62. Jian, J.; Zhang, S. Q.; Shi, Z. Y.; Wang, W.; Chen, G. Q.; Wu, Q., Production of polyhydroxyalkanoates by *Escherichia coli* mutants with defected mixed acid fermentation pathways. *Appl Microbiol Biotechnol* 2010, 87 (6), 2247-56.
63. Sharan, S. K.; Thomason, L. C.; Kuznetsov, S. G.; Court, D. L., Recombineering: a homologous recombination-based method of genetic engineering. *Nature protocols* 2009, 4 (2), 206-23.
64. Li, X. T.; Thomason, L. C.; Sawitzke, J. A.; Costantino, N.; Court, D. L., Positive and negative selection using the tetA-sacB cassette: recombineering and P1 transduction in *Escherichia coli*. *Nucleic acids research* 2013, 41 (22), e204.
65. Baba, T.; Ara, T.; Hasegawa, M.; Takai, Y.; Okumura, Y.; Baba, M.; Datsenko, K. A.; Tomita, M.; Wanner, B. L.; Mori, H., Construction of *Escherichia coli* K-12 in-frame, single-gene knockout mutants: the Keio collection. *Molecular systems biology* 2006, 2, 2006 0008.
66. van Dijken, J. P.; Bauer, J.; Brambilla, L.; Duboc, P.; Francois, J. M.; Gancedo, C.; Giuseppin, M. L. F.; Heijnen, J. J.; Hoare, M.; Lange, H. C.; Madden, E. A.; Niederberger, P.; Nielsen, J.; Parrou, J. L.; Petit, T.; Porro, D.; Reuss, M.; van Riel, N.; Rizzi, M.; Steensma, H. Y.; Verrips, C. T.; Vindelov, J.; Pronk, J. T., An interlaboratory comparison of physiological and genetic properties of four *Saccharomyces cerevisiae* strains. *Enzyme and Microbial Technology* 2000, 26 (9-10), 706-714.
67. Otterstedt, K.; Larsson, C.; Bill, R. M.; Stahlberg, A.; Boles, E.; Hohmann, S.; Gustafsson, L., Switching the mode of metabolism in the yeast *Saccharomyces cerevisiae*. *EMBO Rep* 2004, 5 (5), 532-7.
68. Wieczorke, R.; Krampe, S.; Weierstall, T.; Freidel, K.; Hollenberg, C. P.; Boles, E., Concurrent knock-out of at least 20 transporter genes is required to block uptake of hexoses in *Saccharomyces cerevisiae*. *FEBS Letters* 1999, 464 (3), 123-128.
69. Gietz, R. D.; Schiestl, R. H., High-efficiency yeast transformation using the LiAc/SS carrier DNA/PEG method. *Nature protocols* 2007, 2 (1), 31-4.
70. Stovicek, V.; Borodina, I.; Forster, J., CRISPR-Cas system enables fast and simple genome editing of industrial *Saccharomyces cerevisiae* strains. *Metabolic Engineering Communications* 2015, 2, 13-22.
71. Labun, K.; Montague, T. G.; Gagnon, J. A.; Thyme, S. B.; Valen, E., CHOPCHOP v2: a web tool for the next generation of CRISPR genome engineering. *Nucleic acids research* 2016, 44 (W1), W272-6.
72. Hoffman, C. S.; Winston, F., A ten-minute DNA preparation from yeast efficiently releases autonomous plasmids for transformation of *Escherichia coli*. *Gene* 1987, 57 (2-3), 267-272.
73. Luo, M. L.; Mullis, A. S.; Leenay, R. T.; Beisel, C. L., Repurposing endogenous type I CRISPR-Cas systems for programmable gene repression. *Nucleic acids research* 2015, 43 (1), 674-81.
74. Davis, J. H.; Rubin, A. J.; Sauer, R. T., Design, construction and characterization of a set of insulated bacterial promoters. *Nucleic acids research* 2011, 39 (3), 1131-41.
75. Smith, J. D.; Suresh, S.; Schlecht, U.; Wu, M.; Wagih, O.; Peltz, G.; Davis, R. W.; Steinmetz, L. M.; Parts, L.; St Onge, R. P., Quantitative CRISPR interference screens in yeast identify chemical-genetic interactions and new rules for guide RNA design. *Genome Biol* 2016, 17, 45.
76. Gilbert, L. A.; Larson, M. H.; Morsut, L.; Liu, Z.; Brar, G. A.; Torres, S. E.; Stern-Ginossar, N.; Brandman, O.; Whitehead, E. H.; Doudna, J. A.; Lim, W. A.; Weissman, J. S.; Qi, L. S., CRISPR-mediated modular RNA-guided regulation of transcription in eukaryotes. *Cell* 2013, 154 (2), 442-51.
77. Sikorski, R. S.; Hieter, P., A system of shuttle vectors and yeast host strains designed for efficient manipulation of DNA in *Saccharomyces cerevisiae*. *Genetics* 1989, 122 (1), 19-27.
78. Duetz, W. A.; Ruedi, L.; Hermann, R.; O'Connor, K.; Buchs, J.; Witholt, B., Methods for intense aeration, growth, storage, and replication of bacterial strains in microtiter plates. *Applied and environmental microbiology* 2000, 66 (6), 2641-6.

79. Duetz, W. A.; Witholt, B., Effectiveness of orbital shaking for the aeration of suspended bacterial cultures in square-deepwell microtiter plates. *Biochem Eng J* 2001, 7 (2), 113-115.
80. Lindemann, C. J.; Singh, M. M.; Ramjit, H. G.; Bell, C.; Ip, D. P., Determination of mevalonolactone in capsules by capillary gas-liquid chromatography. *J Pharm Biomed Anal* 1991, 9 (4), 311-6.
81. Keseler, I. M.; Mackie, A.; Peralta-Gil, M.; Santos-Zavaleta, A.; Gama-Castro, S.; Bonavides-Martinez, C.; Fulcher, C.; Huerta, A. M.; Kothari, A.; Krummenacker, M.; Latendresse, M.; Muniz-Rascado, L.; Ong, Q.; Paley, S.; Schroder, I.; Shearer, A. G.; Subhraveti, P.; Travers, M.; Weerasinghe, D.; Weiss, V.; Collado-Vides, J.; Gunsalus, R. P.; Paulsen, I.; Karp, P. D., EcoCyc: fusing model organism databases with systems biology. *Nucleic acids research* 2013, 41 (Database issue), D605-12.
82. Davis, J. H.; Rubin, A. J.; Sauer, R. T., Design, construction and characterization of a set of insulated bacterial promoters. *Nucleic acids research* 2011, 39 (3), 1131-41.
83. Poo, H.; Song, J. J.; Hong, S.-P.; Choi, Y.-H.; Yun, S. W.; Kim, J.-H.; Lee, S. C.; Lee, S.-G.; Sung, M. H., Novel high-level constitutive expression system, pHCE vector, for a convenient and cost-effective soluble production of human tumor necrosis factor-α. *Biotechnology Letters* 2002, 24 (14), 1185-1189.
84. Baba, T.; Ara, T.; Hasegawa, M.; Takai, Y.; Okumura, Y.; Baba, M.; Datsenko, K. A.; Tomita, M.; Wanner, B. L.; Mori, H., Construction of *Escherichia coli* K-12 in-frame, single-gene knockout mutants: the Keio collection. *Mol Syst Biol* 2006, 2, 2006 0008.
85. Jian, J.; Zhang, S. Q.; Shi, Z. Y.; Wang, W.; Chen, G. Q.; Wu, Q., Production of polyhydroxyalkanoates by *Escherichia coli* mutants with defected mixed acid fermentation pathways. *Appl Microbiol Biotechnol* 2010, 87 (6), 2247-56.
86. van Dijken, J. P.; Bauer, J.; Brambilla, L.; Duboc, P.; Francois, J. M.; Gancedo, C.; Giuseppin, M. L. F.; Heijnen, J. J.; Hoare, M.; Lange, H. C.; Madden, E. A.; Niederberger, P.; Nielsen, J.; Parrou, J. L.; Petit, T.; Porro, D.; Reuss, M.; van Riel, N.; Rizzi, M.; Steensma, H. Y.; Verrips, C. T.; Vindelov, J.; Pronk, J. T., An interlaboratory comparison of physiological and genetic properties of four *Saccharomyces cerevisiae* strains. *Enzyme and Microbial Technology* 2000, 26 (9-10), 706-714.
87. Otterstedt, K.; Larsson, C.; Bill, R. M.; Stahlberg, A.; Boles, E.; Hohmann, S.; Gustafsson, L., Switching the mode of metabolism in the yeast *Saccharomyces cerevisiae*. *EMBO Rep* 2004, 5 (5), 532-7.
88. Luo, M. L.; Mullis, A. S.; Leenay, R. T.; Beisel, C. L., Repurposing endogenous type I CRISPR-Cas systems for programmable gene repression. *Nucleic acids research* 2015, 43 (1), 674-81.
89. Wilde, R. J.; Guest, J. R., Transcript analysis of the citrate synthase and succinate dehydrogenase genes of *Escherichia coli* K12. *J Gen Microbiol* 1986, 132 (12), 3239-51.
90. Charpentier, B.; Branlant, C., The *Escherichia coli* gapA gene is transcribed by the vegetative RNA polymerase holoenzyme E sigma 70 and by the heat shock RNA polymerase E sigma 32. *Journal of Bacteriology* 1994, 176 (3), 830-839.
91. Li, X. T.; Thomason, L. C.; Sawitzke, J. A.; Costantino, N.; Court, D. L., Positive and negative selection using the tetA-sacB cassette: recombineering and P1 transduction in *Escherichia coli*. *Nucleic acids research* 2013, 41 (22), e204.
92. Duetz, W. A.; Ruedi, L.; Hermann, R.; O'Connor, K.; Buchs, J.; Witholt, B., Methods for intense aeration, growth, storage, and replication of bacterial strains in microtiter plates. *Applied and environmental microbiology* 2000, 66 (6), 2641-6.
93. Duetz, W. A.; Witholt, B., Effectiveness of orbital shaking for the aeration of suspended bacterial cultures in square-deepwell microtiter plates. *Biochem Eng J* 2001, 7 (2), 113-115.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A multi-stage fermentation bioprocess for producing a product from a genetically modified *E. coli*, comprising:
   providing a genetically modified *E. coli* having a production pathway for producing a product that is: an amino acid, acetate, acetoin, acetone, acrylic, malate, fatty acid ethyl esters, isoprenoids, glycerol, ethylene glycol, ethylene, propylene, butylene, isobutylene, ethyl acetate, vinyl acetate, 1,4-butanediol, 2,3-butanediol, butanol, isobutanol, sec-butanol, butyrate, isobutyrate, 2-OH-isobutryate, 3-OH-butyrate, ethanol, isopropanol, D-lactate, L-lactate, pyruvate, itaconate, levulinate, glucarate, glutarate, caprolactam, adipic acid, propanol, isopropanol, fused alcohols, 1,2-propanediol, 1,3-propanediol, formate, fumaric acid, propionic acid, succinic acid, valeric acid, maleic acid, or poly-hydroxybutyrate;
   growing the identified genetically modified *E. coli* in a media in a growth phase, the genetically modified *E. coli* comprising:
   i. a production pathway comprising at least one production enzyme for biosynthesis of the product; and
   ii. one or more synthetic metabolic valves for reducing or eliminating flux through multiple metabolic pathways within the genetically modified *E. coli* when the synthetic metabolic valves are induced, the one or more synthetic metabolic valves comprising:
      a) at least one silencing synthetic metabolic valve that silences gene expression of a gene selected from: fabI, gltA, lpd, zwf, and udhA, or
      b) at least one proteolytic synthetic metabolic valve that controls proteolysis of a proteolyzable enzyme selected from: fabI, gltA, lpd, zwf, and udhA;
   transitioning to a productive stationary phase, the transition comprising:
      depletion of a limiting nutrient;
      inducing the one or more synthetic metabolic valves; and
      activation of the production pathway; and
   producing the product.

2. The multi-stage fermentation bioprocess of claim 1, the providing the genetically modified *E. coli* further comprising:
   screening a plurality of genetically modified *E. coli* effective to identify therefrom the genetically modified *E. coli* for the fermentation bioprocess, each of the plurality of genetically modified *E. coli* characterized by a distinct combination of:
   the at least one production enzyme, and
   at least one of the silenceable enzyme and the proteolyzable enzyme.

3. The multi-stage fermentation bioprocess of claim 1, wherein the at least one production enzyme, or a promotor operably linked to a production enzyme is heterologous to a species from which the genetically modified *E. coli* is derived.

4. The multi-stage fermentation bioprocess of claim 1, wherein the product is produced from a metabolite that is: pyruvate, acetolacetate, acetyl-CoA, acetoacetyl-CoA, or malonyl-CoA.

5. The multi-stage fermentation bioprocess of claim 1, the one or more synthetic metabolic valves comprising both:
   the at least one silencing synthetic metabolic valve is characterized by silencing of gene expression of one, two, three, or four genes encoding enzymes, and
   the at least one proteolytic synthetic metabolic valve is characterized by controlled proteolysis of one, two, three, or four enzymes,
   wherein the at least one silencing synthetic metabolic valve and the at least one proteolytic synthetic metabolic valve are the same or different.

6. The multi-stage fermentation bioprocess of claim 1, the *E. coli* further comprising synthetic metabolic valve directed to regulation of a gene encoding a silenceable enzyme or a proteolyzable enzyme are each encoded by: ppc, sucD, aceA, pfkA, lon, rpoS, tktA, tktB, or gapA genes.

7. The multi-stage fermentation bioprocess of claim 1, wherein at least one silencing synthetic metabolic valve is characterized by CRISPR interference of gene expression of a gene that is a fabI, gltA, lpd, zwf, or udhA gene and expression of a CASCADE plasmid comprising an array of guide RNA genes.

8. The multi-stage fermentation bioprocess of claim 1, wherein at least one proteolytic synthetic metabolic valve is characterized by expression of the proteolytic enzyme operably linked to a C-terminal DAS4 peptide tag and controlled proteolysis of a fabI, gltA, ldp, zwf, or udhA enzyme by the synthetic metabolic valve is selective for the tag by clpXP protease upon induction of sspB chaperone protein.

9. The multi-stage fermentation bioprocess of claim 1, wherein the genetically modified E. coli comprises a chromosomal gene deletion of one of the following genes: lactate dehydrogenase (ldhA), phosphate acetyltransferase (pta), pyruvate oxidase (poxB), pyruvateformate lyase (pflB), methylglyoxal synthase (mgsA), acetate kinase (ackA), alcohol dehydrogenase (adhE), a clpXP protease specificity enhancing factor (sspB), an ATPdependent Lon protease (lon), an outer membrane protease (ompT), an arcA transcriptional dual regulator (arcA), or an iclR transcriptional regulator (iclR).

10. The E. coli is characterized by overexpression of a gene resulting in an increase of a NADPH and/or NAD pool in the genetically modified E. coli during the growth phase.

11. The multi-stage fermentation bioprocess of claim 1, wherein transitioning to the productive stationary phase is further modulated by at least one of an artificial chemical inducer including tetracycline, anhydrotetracycline, lactose, isopropyl-beta-D-1-thiogalactopyranoside (IPTG), arabinose, raffinose, and tryptophan or depletion of a limiting nutrient from the E. coli culture media.

12. The multi-stage fermentation bioprocess of claim 1, wherein transitioning to the productive stationary phase further comprises inducing expression of the enzyme of the production pathway.

13. The multi-stage fermentation bioprocess of claim 1, further comprising monitoring an environmental factor of the culture media or culture conditions effective for product production, the environmental factor selected from the group: temperature of the culture media or culture conditions, pH of the culture media, nutrients of the culture media, oxygenation of the culture media, sugar concentration of the culture media, or combinations thereof.

14. A genetically modified E. coli, comprising:
i. a production pathway comprising at least one production enzyme for biosynthesis of a product selected from the group: an amino acid, acetate, acetoin, acetone, acrylic, malate, fatty acid ethyl esters, isoprenoids, glycerol, ethylene glycol, ethylene, propylene, butylene, isobutylene, ethyl acetate, vinyl acetate, 1,4-butanediol, 2,3-butanediol, butanol, isobutanol, sec-butanol, butyrate, isobutyrate, 2-OH-isobutryate, 3-OH-butyrate, ethanol, isopropanol, D-lactate, L-lactate, pyruvate, itaconate, levulinate, glucarate, glutarate, caprolactam, adipic acid, propanol, isopropanol, fused alcohols, 1,2-propanediol, 1,3-propanediol, formate, fumaric acid, propionic acid, succinic acid, valeric acid, maleic acid, or poly-hydroxybutyrate; and
ii. one or more synthetic metabolic valves for reducing or eliminating flux through multiple metabolic pathways within the genetically modified E. coli when the one or more synthetic metabolic valves are induced, the one or more synthetic metabolic valves comprising:
a) at least one silencing synthetic metabolic valve that silences gene expression of a gene encoding at least one silenceable enzyme, or
b) at least one proteolytic synthetic metabolic valve that controls proteolysis of a proteolyzable enzyme; and
wherein growth of the genetically modified E. coli is slowed or stopped and product production is enhanced, as compared to a E. coli lacking the production pathway or synthetic metabolic valve, by inducing the synthetic metabolic valve, and
wherein the silenceable enzyme and the proteolyzable enzyme are each encoded by a gene selected from the group: fabI, gltA, ldp, zwf, or udhA,
wherein growth of the genetically modified microorganism is slowed or stopped by depletion of a limiting nutrient thereby inducing a stationary phase, and product production is enhanced, as compared to a microorganism lacking the production pathway or synthetic metabolic valve, by inducing the synthetic metabolic valve in the stationary phase.

15. The genetically modified E. coli of claim 14, wherein the at least one production enzyme, or a promotor operably linked to the production enzyme, is heterologous to an organism from which the genetically modified E. coli is derived.

16. The genetically modified E. coli of claim 14, the one or more synthetic metabolic valves comprising both:
the at least one silencing synthetic metabolic valve is characterized by silencing of gene expression of one, two, three, or four genes encoding enzymes, and
the at least one proteolytic synthetic metabolic valve is characterized by controlled proteolysis of one, two, three, or four enzymes,
wherein the at least one silencing synthetic metabolic valve and the at least one proteolytic synthetic metabolic valve are the same or different.

* * * * *

UNITED STATES PATENT AND TRADEMARK OFFICE
CERTIFICATE OF CORRECTION

PATENT NO. : 11,268,111 B2
APPLICATION NO. : 16/487542
DATED : March 8, 2022
INVENTOR(S) : Michael David Lynch and Zhixia Ye It is certified that error appears in the above-identified patent and that said Letters Patent is hereby corrected as shown below:

In the Specification

Column 1, Lines 7-12 please replace paragraph entitled "CROSS-REFERENCE" as shown below:
CROSS-REFERENCE
This application is a National Stage Entry of PCT/US18/19040. filed February 21, 2018 which claims the benefit of U.S. Provisional Application No. 62/461,436, filed February 21, 2017, which application is incorporated herein by reference in its entirety.

Signed and Sealed this
Twenty-fourth Day of May, 2022

Katherine Kelly Vidal
*Director of the United States Patent and Trademark Office*

SEQUENCE LISTING

```
<160> NUMBER OF SEQ ID NOS: 204

<210> SEQ ID NO 1
<211> LENGTH: 114
<212> TYPE: DNA
<213> ORGANISM: Escherichia coli

<400> SEQUENCE: 1
tctttctgac accttactat cttacaaatg taacaaaaaa gttatttttc tgtaattcga      60
gcatgtcatg ttaccccgcg agcataaaac gcgtgtgtag gaggataatc tatg           114

<210> SEQ ID NO 2
<211> LENGTH: 160
<212> TYPE: DNA
<213> ORGANISM: Escherichia coli

<400> SEQUENCE: 2
```

```
gtgcgtaatt gtgctgatct cttatatagc tgctctcatt atctctctac cctgaagtga    60
ctctctcacc tgtaaaaata atatctcaca ggcttaatag tttcttaata caaagcctgt   120
aaaacgtcag gataacttct gtgtaggagg ataatctatg                         160

<210> SEQ ID NO 3
<211> LENGTH: 174
<212> TYPE: DNA
<213> ORGANISM: Escherichia coli

<400> SEQUENCE: 3
cgattacgta aagaagttat tgaagcatcc tcgtcagtaa aaagttaatc ttttcaacag    60
ctgtcataaa gttgtcacgg ccgagactta tagtcgcttt gtttttattt tttaatgtat   120
ttgtagtgta ggaggataat ctatggctag caaaggagaa gaacttttca catg         174

<210> SEQ ID NO 4
<211> LENGTH: 154
<212> TYPE: DNA
<213> ORGANISM: Escherichia coli

<400> SEQUENCE: 4
gccacggaaa tcaataacct gaagatatgt gcgacgagct tttcataaat ctgtcataaa    60
tctgacgcat aatgacgtcg cattaatgat cgcaacctat ttattgtgta ggaggataat   120
ctatggctag caaaggagaa gaactttca catg                                154

<210> SEQ ID NO 5
<211> LENGTH: 120
<212> TYPE: DNA
<213> ORGANISM: Escherichia coli

<400> SEQUENCE: 5
agacagtcaa cgcgcttgat agcctggcga agatcatccg atcttcgcct tacactttg    60 tttcacattt ctgtgacata ctatcggatg tgcggtaatt gtataggagg ataatctatg   120

<210> SEQ ID NO 6
<211> LENGTH: 125
<212> TYPE: DNA
<213> ORGANISM: Escherichia coli

<400> SEQUENCE: 6
gctatgccgg actgaatgtc caccgtcagt aatttttata cccggcgtaa ctgccgggtt    60
attgcttgtc acaaaaaagt ggtagactca tgcagttaac tcactgtgta ggaggataat   120
ctatg                                                               125

<210> SEQ ID NO 7
<211> LENGTH: 206
<212> TYPE: DNA
<213> ORGANISM: Escherichia coli

<400> SEQUENCE: 7
catccataaa ttttgcataa ttaatgtaaa gaccaggctc gccagtaacg ctaaattcat    60
ttggctgtaa gcgcggtgtc atccgcgtca ggaaaattaa acagttactt taaaaaatga   120
aaacgtaaaa aggttgggtt tcgatgtatt gacgggtaaa ctttgtcgcc cgctaaacat   180
ttgtttgtgt aggaggataa tctatg                                        206

<210> SEQ ID NO 8
<211> LENGTH: 184
```

```
<212> TYPE: DNA
<213> ORGANISM: Escherichia coli

<400> SEQUENCE: 8
aatcctgctg aaagcacaca gcttttttca tcactgtcat cactctgtca tctttccagt    60
agaaactaat gtcactgaaa tggtgtttta tagttaaata taagtaaata tattgttgca   120
ataaatgcga gatctgttgt acttattaag tagcagcgga agttcgtgta ggaggataat   180
ctat                                                                184

<210> SEQ ID NO 9
<211> LENGTH: 359
<212> TYPE: DNA
<213> ORGANISM: Escherichia coli

<400> SEQUENCE: 9
ctacagagat gacgtgtaga aaatagttac cgatataaat agttacagct aaacgcctga    60
aattacatgt cgagggcact atttaaaaca attttgagga tttccttata ttggtggtta   120
gtacgcatgc aattaaaaat gaaattccgc gaccacaagc caaataaca aacggcaagg    180 agacaaaaat aagcacaaat agccaacacg tcctctgttc actttaaagg gaatcgctga   240
aaaatacgct ctgtttaagg ggattcacct ttctcagaaa gctattccgc ccttttcctg   300
ctgagaaatc gccacattcg gcatgacaac attgtgaaag tgtaggagga taatctatg    359

<210> SEQ ID NO 10
<211> LENGTH: 156
<212> TYPE: DNA
<213> ORGANISM: Escherichia coli

<400> SEQUENCE: 10
accgaactga agcaggatta caccgtggtg atcgtcaccc acaacatgca gcaggctgcg    60
cgttgttccg accacacggc gtttatgtac ctgggcgaat tgattgagtt cagcaacacg   120
gacgatctgt tcaccagtgt aggaggataa tctatg                             156

<210> SEQ ID NO 11
<211> LENGTH: 151
<212> TYPE: DNA
<213> ORGANISM: Escherichia coli

<400> SEQUENCE: 11
aagactttat ctctctgtca taaaactgtc atattcctta catataactg tcacctgttt    60
gtcctatttt gcttctcgta gccaacaaac aatgctttat gagtgtagga ggataatcta   120
tggctagcaa aggagaagaa cttttcacat g                                  151

<210> SEQ ID NO 12
<211> LENGTH: 186
<212> TYPE: DNA
<213> ORGANISM: Escherichia coli

<400> SEQUENCE: 12
agcatggcgt tttgttgcgc gggatcagca agcctagcgg cagttgttta cgcttttatt    60
acagatttaa taaattacca cattttaaga atattattaa tctgtaatat atctttaaca   120
atctcaggtt aaaaactttc ctgttttcaa cgggactctc ccgctggtgt aggaggataa   180
tctatg                                                              186

<210> SEQ ID NO 13
```

```
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
ccaggcatca aataaaacga aaggctcagt cgaaagactg ggcctttcgt tttatctgtt      60
gtttgtcggt gaacgctctc tactagagtc acactggctc accttcgggt gggcctttct     120
gcgtttatac acagctaaca ccacgtcgtc cctatctgct gccctaggtc tatgagtggt     180
tgctggataa cgtgcgtaat tgtgctgatc tcttatatag ctgctctcat tatctctcta     240
ccctgaagtg actctctcac ctgtaaaaat aatatctcac aggcttaata gtttcttaat     300
acaaagcctg taaaacgtca ggataacttc tatattcagg gagaccacaa cggtttccct     360
ctacaaataa ttttgtttaa cttt                                            384

<210> SEQ ID NO 14
<211> LENGTH: 284
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
cgcaaaaaac cccgcttcgg cggggttttt tcgcacgtct ccatcgcttg cccaagttgt      60
gaagcacagc taacaccacg tcgtccctat ctgctgccct aggtctatga gtggttgctg     120
gataacgcca cggaaatcaa taacctgaag atatgtgcga cgagcttttc ataaatctgt     180
cataaatctg acgcataatg acgtcgcatt aatgatcgca acctatttat tatattcagg     240
gagaccacaa cggtttccct ctacaaataa ttttgtttaa cttt                      284

<210> SEQ ID NO 15
<211> LENGTH: 365
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
cgccgaaaac cccgcttcgg cggggttttg ccgcacgtct ccatcgcttg cccaagttgt      60
gaagcacagc taacaccacg tcgtccctat ctgctgccct aggtctatga gtggttgctg     120
gataaccatc cataaatttt gcataattaa tgtaaagacc aggctcgcca gtaacgctaa     180
attcatttgg ctgtaagcgc ggtgtcatcc gcgtcaggaa aattaaacag ttactttaaa     240
aaatgaaaac gtaaaaaggt tgggtttcga tgtattgacg ggtaaacttt gtcgcccgct     300
aaacatttgt ttatattcag ggagaccaca acggtttccc tctacaaata attttgttta     360
acttt                                                                 365

<210> SEQ ID NO 16
<211> LENGTH: 320
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
```

```
aaaaaaaaac cccgcccctg acagggcggg ttttttttta cgtctccatc gcttgcccaa    60
gttgtgaagc acagctaaca ccacgtcgtc cctatctgct gccctaggtc tatgagtggt   120
tgctggataa caccgaactg aagcaggatt acaccgtggt gatcgtcacc cacaacatgc   180
agcaggctgc gcgttgttcc gaccacacgg cgtttatgta cctgggcgaa ttgattgagt   240
tcagcaacac ggacgatctg ttcaccaata ttcagggaga ccacaacggt ttccctctac   300
aaataatttt gtttaacttt                                                320
```

```
<210> SEQ ID NO 17
<211> LENGTH: 350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
cgccgcaaac cccgcccctg acagggcggg tttcgccgc acgtctccat cgcttgccca    60
agttgtgaag cacagctaac accacgtcgt ccctatctgc tgccctaggt ctatgagtgg   120
ttgctggata acaatcctgc tgaaagcaca cagctttttt catcactgtc atcactctgt   180
catctttcca gtagaaacta atgtcactga atggtgttt tatagttaaa tataagtaaa   240
tatattgttg caataaatgc gagatctgtt gtacttatta gtagcagcg gaagttcata   300 ttcagggaga ccacaacggt ttccctctac aaataatttt gtttaacttt              350
```

```
<210> SEQ ID NO 18
<211> LENGTH: 208
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
cgccgaaaac cccgcttcgg cggggttttg ccgcacgtct ccatcgcttg cccaagttgt    60
gaagcacagc taacaccacg tcgtccctat ctgctgccct aggtctatga gtggttgctg   120
gataacttta cgggcatgca taaggctcgt aggctatatt cagggagacc acaacggttt   180
ccctctacaa ataattttgt ttaacttt                                       208
```

```
<210> SEQ ID NO 19
<211> LENGTH: 213
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
aaaaaaaaac cccgcccctg acagggcggg ttttttttta cgtctccatc gcttgcccaa    60
gttgtgaagc acagctaaca ccacgtcgtc cctatctgct gccctaggtc tatgagtggt   120
tgctggataa ctttacgggc atgcataagg ctcgtaatat atattcaggg agaccacaac   180
ggtttccctc tacaaataat tttgtttaac ttt                                 213
```

```
<210> SEQ ID NO 20
<211> LENGTH: 214
<212> TYPE: DNA
<213> ORGANISM: Artificial Sequence
```

-continued

```
<220> FEATURE:
<223> OTHER INFORMATION: Description of Artificial Sequence: Synthetic
      polynucleotide

<400> SEQUENCE: 20
cgccgcaaac cccgcccctg acagggcggg gtttcgccgc acgtctccat cgcttgccca      60
agttgtgaag cacagctaac accacgtcgt ccctatctgc tgccctaggt ctatgagtgg     120
ttgctggata actttacggg catgcataag gctcgtatga tatattcagg gagaccacaa    180
cggtttccct ctacaaataa ttttgtttaa cttt                                  214

<210> SEQ ID NO 21
<211> LENGTH: 208
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
cgcaaaaaac cccgcttcgg cggggttttt tcgcacgtct ccatcgcttg cccaagttgt     60
gaagcacagc taacaccacg tcgtccctat ctgctgccct aggtctatga gtggttgctg    120
gataacttta cgggcatgca taaggctcgt ataatatatt cagggagacc acaacggttt    180
ccctctacaa ataattttgt ttaactttt                                       208

<210> SEQ ID NO 22
<211> LENGTH: 429
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
ccaggcatca aataaaacga aaggctcagt cgaaagactg ggcctttcgt tttatctgtt     60
gtttgtcggt gaacgctctc tactagagtc acactggctc accttcgggt gggcctttct   120
gcgtttatac acagctaaca ccacgtcgtc cctatctgct gccctaggtc tatgagtgg    180 tgctggataa cctccttcac agattcccaa tctcttgtta aataacgaaa aagcatcaat   240
taaaacccat gtctttctat attccagcaa tgttttatag gggacatatt gatgaagatg   300
ggtatcacct tagtgaattg ctataagctg ctcttttttg ttcgtgatat actgataaat   360
tgaattttca cacttcatat tcagggagac cacaacggtt tccctctaca aataattttg   420
tttaacttt                                                            429

<210> SEQ ID NO 23
<211> LENGTH: 76
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
taacaataaa aatgaaaatg atttccacga tacagaaaaa agagactgtc atcctaattt    60
ttgttgacac tctatc                                                     76

<210> SEQ ID NO 24
<211> LENGTH: 75
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 24
tgccactcag gtatgatggg cagaatattg cctctgcccg ccagaaaaag atcaaaggga    60
aaactgtcca tatgc                                                    75

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ccgacaggga ttccatctg                                                19

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tatgacgacc attttgtcta cagttc                                        26

<210> SEQ ID NO 27
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27 ggactttgt acttcctgtt tcgatttagt tggcaattta ggtagcaaac tcctaatttt    60
tgttgacact ctatc                                                    75

<210> SEQ ID NO 28
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ataaaaacgg cgctaaaaag cgccgttttt tttgacggtg gtaaagccga atcaaaggga   60
aaactgtcca tatgc                                                    75

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cctgactgta ctaacggttg ag                                            22
```

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30 tgactttat ggcgttcttt gtttttg                                         27

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ctggtacacg ctgatgaaca cc                                             22

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ctggtcattg ccatttgtgc c                                              21

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gaatcagagc gttccgaccc                                                20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtacgcagtt tgccaacgtg                                                20

<210> SEQ ID NO 35
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
aatagcccgc tgatatcatc gataatacta aaaaacagg gaggctatta tcctaattt     60 tgttgacact ctatc                                                     75

<210> SEQ ID NO 36
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tacagggatc cagttatcaa taagcaaatt catttgttct ccttcatatg atcaaaggga    60
aaactgtcca tatgc                                                     75

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
caagacatgt gtatatcact gtaattc                                        27

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gcgattgcag atttatgatt tgg                                            23

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gcaaaatgct ggctcattg                                                 19

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gaactgaatg gcaaactgac tg                                             22

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tggggatgat cgaccaca                                                        18

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tatcatcctg aaagcgatgg                                                      20

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
atctcaccgt gtgatcgg                                                        18

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
caaaagagat tctgggtatt cact                                                 24

<210> SEQ ID NO 45
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ctgctggaaa ccatgcg                                                         17

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
agagcatgtc gttataggag gtgat                                                25

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
agtactcaac caagtcattc tg                                              22

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gagcatggtg atcttctcag t                                               21

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gcgatgaatg tcttactacg ga                                              22

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gtcgctgggt aatctgcaa                                                  19

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
atcaacgcat atagcgctag cag                                             23

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
actgaagccc agacgatc                                                   18

<210> SEQ ID NO 53
<211> LENGTH: 3527
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53 tcctaattttt tgttgacact ctatcattga tagagttatt ttaccactcc ctatcagtga    60

```
tagagaaaag tgaaatgaat agttcgacaa agatcgcatt ggtaattacg ttactcgatg    120
ccatggggat tggccttatc atgccagtct tgccaacgtt attacgtgaa tttattgctt    180
cggaagatat cgctaaccac tttggcgtat tgcttgcact ttatgcgtta atgcaggtta    240
tctttgctcc ttggcttgga aaaatgtctg accgatttgg tcggcgccca gtgctgttgt    300
tgtcattaat aggcgcatcg ctggattact tattgctggc tttttcaagt gcgctttgga    360
tgctgtattt aggccgtttg ctttcaggga tcacaggagc tactgggct gtcgcggcat     420 cggtcattgc cgataccacc tcagcttctc aacgcgtgaa gtggttcggt tggttagggg    480
caagttttgg gcttggttta atagcggggc ctattattgg tggttttgca ggagagattt    540
caccgcatag tccctttttt atcgctgcgt tgctaaatat tgtcactttc cttgtggtta    600
tgttttggtt ccgtgaaacc aaaaatacac gtgataatac agataccgaa gtaggggttg    660
agacgcaatc gaattcggta tacatcactt tatttaaaac gatgcccatt ttgttgatta    720 tttattttc agcgcaattg ataggccaaa ttcccgcaac ggtgtgggtg ctatttaccg     780
aaaatcgttt tggatggaat agcatgatgg ttggcttttc attagcgggt cttggtcttt    840
tacactcagt attccaagcc tttgtggcag gaagaatagc cactaaatgg ggcgaaaaaa    900
cggcagtact gctcggattt attgcagata gtagtgcatt tgccttttta gcgtttatat    960
ctgaaggttg gttagttttc cctgttttaa ttttattggc tggtggtggg atcgctttac   1020
ctgcattaca gggagtgatg tctatccaaa caaagagtca tcagcaaggt gctttacagg   1080
gattattggt gagccttacc aatgcaaccg gtgttattgg cccattactg tttgctgtta   1140
tttataatca ttcactacca atttgggatg gctggatttg gattattggt ttagcgtttt   1200
actgtattat tatcctgcta tcgatgacct tcatgttaac ccctcaagct caggggagta   1260
aacaggagac aagtgcttag ttatttcgtc accaaatgat gttattccgc gaaatataat   1320
gaccctcttg ataacccaag agcatcacat atacctgccg ttcactatta tttagtgaaa   1380
tgagatatta tgatattttc tgaattgtga ttaaaaaggc aactttatgc ccatgcaaca   1440
gaaactataa aaaatacaga gaatgaaaag aaacagatag atttttttagt tctttaggcc   1500 cgtagtctgc aaatcctttt atgatttct atcaaacaaa agaggaaaat agaccagttg    1560
caatccaaac gagagtctaa tagaatgagg tcgaaaagta aatcgcgcgg gtttgttact   1620
gataaagcag gcaagaccta aatgtgtaa agggcaaagt gtatactttg gcgtcacccc    1680
ttacatattt taggtctttt tttattgtgc gtaactaact tgccatcttc aaacaggagg   1740
gctggaagaa gcagaccgct aacacagtac ataaaaagg agacatgaac gatgaacatc    1800
aaaaagtttg caaaacaagc aacagtatta acctttacta ccgcactgct ggcaggaggc   1860
gcaactcaag cgtttgcgaa agaaacgaac caaaagccat ataaggaaac atacggcatt   1920
tcccatatta cacgccatga tatgctgcaa atccctgaac agcaaaaaaa tgaaaaatat   1980
caagttcctg agttcgattc gtccacaatt aaaaatatct cttctgcaaa aggcctggac   2040
gtttgggaca gctggccatt acaaaacgct gacggcactg tcgcaaacta tcacggctac   2100
cacatcgtct ttgcattagc cggagatcct aaaaaatgcgg atgacacatc gatttacatg   2160
ttctatcaaa aagtcggcga aacttctatt gacagctgga aaaacgctgg ccgcgtcttt   2220
aaagacagcg acaaattcga tgcaaatgat tctatcctaa aagaccaaac acaagaatgg   2280
tcaggttcag ccacatttac atctgacgga aaaatccgtt tattctacac tgatttctcc   2340
ggtaaacatt acggcaaaca aacactgaca actgcacaag ttaacgtatc agcatcagac   2400
```

```
agctctttga acatcaacgg tgtagaggat tataaatcaa tctttgacgg tgacggaaaa    2460
acgtatcaaa atgtacagca gttcatcgat gaaggcaact acagctcagg cgacaaccat    2520
acgctgagag atcctcacta cgtagaagat aaaggccaca atacttagt atttgaagca     2580 aacactggaa ctgaagatgg ctaccaaggc gaagaatctt tatttaacaa agcatactat    2640
ggcaaaagca catcattctt ccgtcaagaa agtcaaaaac ttctgcaaag cgataaaaaa    2700
cgcacggctg agttagcaaa cggcgctctc ggtatgattg agctaaacga tgattacaca    2760
ctgaaaaaag tgatgaaacc gctgattgca tctaacacag taacagatga aattgaacgc    2820
gcgaacgtct ttaaaatgaa cggcaaatgg tacctgttca ctgactcccg cggatcaaaa    2880
atgacgattg acggcattac gtctaacgat atttacatgc ttggttatgt ttctaattct    2940
ttaactggcc catacaagcc gctgaacaaa actggccttg tgttaaaaat ggatcttgat    3000
cctaacgatg taacctttac ttactcacac ttcgctgtac ctcaagcgaa aggaaacaat    3060
gtcgtgatta caagctatat gacaaacaga ggattctacg cagacaaaca atcaacgttt    3120
gcgccaagct tcctgctgaa catcaaaggc aagaaaacat ctgttgtcaa agacagcatc    3180
cttgaacaag gacaattaac agttaacaaa taaaaacgca aaagaaaatg ccgatattga    3240
ctaccggaag cagtgtgacc gtgtgcttct caaatgcctg attcaggctg tctatgtgtg    3300
actgttgagc tgtaacaagt tgtctcaggt gttcaatttc atgttctagt tgctttgttt    3360
tactggtttc acctgttcta ttaggtgtta catgctgttc atctgttaca ttgtcgatct    3420
gttcatggtg aacagcttta aatgcaccaa aaactcgtaa aagctctgat gtatctatct    3480
tttttacacc gttttcatct gtgcatatgg acagttttcc ctttgat              3527
```

<210> SEQ ID NO 54
<211> LENGTH: 70
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 54

```
aaatgatttc cacgatacag aaaaaagaga ctgtcatggg cagaatattg cctctgcccg    60
ccagaaaaag                                                            70
```

<210> SEQ ID NO 55
<211> LENGTH: 70
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 55

```
ctgtttcgat ttagttggca atttaggtag caaactcggc tttaccaccg tcaaaaaaaa    60
cggcgctttt                                                            70
```

<210> SEQ ID NO 56
<211> LENGTH: 476
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 56

```
caagacatgt gtatatcact gtaattcgat atttatgagc agcatcgaaa aatagcccgc    60
tgatatcatc gataatacta aaaaaacagg gaggctatta ccaggcatca aataaaacga   120
aaggctcagt cgaaagactg ggcctttcgt tttatctgtt gtttgtcggt gaacgctctc   180
tactagagtc acactggctc accttcgggt gggccttttct gcgtttatat ctttctgaca   240
ccttactatc ttacaaatgt aacaaaaaag ttattttttct gtaattcgag catgtcatgt   300
taccccgcga gcataaaacg cgtgtgtagg aggataatct tgacggcta gctcagtcct   360 aggtacagtg ctagccatat gaaggagaac aaatgaattt gcttattgat aactggatcc   420
ctgtacgccc gcgaacggg gggaaagtcc aaatcataaa tctgcaatcg ctatac       476
```

<210> SEQ ID NO 57
<211> LENGTH: 974
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
caagacatgt gtatatcact gtaattcgat atttatgagc agcatcgaaa aatagcccgc    60
tgatatcatc gataatacta aaaaaacagg gaggctatta ccaggcatca aataaaacga   120
aaggctcagt cgaaagactg ggcctttcgt tttatctgtt gtttgtcggt gaacgctctc   180
tactagagtc acactggctc accttcgggt gggccttttct gcgtttatat ctttctgaca   240
ccttactatc ttacaaatgt aacaaaaaag ttattttttct gtaattcgag catgtcatgt   300
taccccgcga gcataaaacg cgtgtgtagg aggataatct atggatttgt cacagctaac   360
accacgtcgt ccctatctgc tgcgtgcatt ctatgagtgg ttgctggata accagctcac   420
gccgcacctg gtggtggatg tgacgctccc tggcgtgcag gttcctatgg aatatgcgcg   480
tgacgggcaa atcgtactca acattgcgcc gcgtgctgtc ggcaatctgg aactggcgaa   540
tgatgaggtg cgctttaacg cgcgctttgg tggcattccg cgtcaggttt ctgtgccgct   600
ggctgccgtg ctggctatct acgcccgtga aaatggcgca ggcacgatgt ttgagcctga   660
agctgcctac gatgaagata ccagcatcat gaatgatgaa gaggcatcgg cagacaacga   720
aaccgttatg tcggttattg atggcgacaa gccagatcac gatgatgaca ctcatcctga   780
cgatgaacct ccgcagccac cacgcggtgg tcgaccggga ttacgcgttg tgaagtaatt   840
gacggctagc tcagtcctag gtacagtgct agccatatga aggagaacaa atgaatttgc   900
ttattgataa ctggatccct gtacgcccgc gaacgggg gaaagtccaa atcataaatc   960
tgcaatcgct atac                                                    974
```

<210> SEQ ID NO 58
<211> LENGTH: 970
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

```
ctattgaaga tgtgggtaac tctgcggcat tcctgtgctc cgatctctct gccggtatct    60
ccggtgaagt ggtccacgtt gacggcggtt tcagcattgc tgcaatgaac gaactcgaac   120
tgaaagcggc caacgatgaa actattctg aaaactatgc ggatgcgtct taataggaag   180
ttcctattct ctagaaagta taggaacttc cgaatccatg tgggagttta ttcttgacac   240
```

```
agatatttat gatataataa ctgagtaagc ttaacataag gaggaaaaac atatgttacg      300
cagcagcaac gatgttacgc agcagggcag tcgccctaaa acaaagttag gtggctcaag      360
tatgggcatc attcgcacat gtaggctcgg ccctgaccaa gtcaaatcca tgcgggctgc      420
tcttgatctt ttcggtcgtg agttcggaga cgtagccacc tactcccaac atcagcggaa      480
ctccgattac ctcgggaact tgctccgtag taagacattc atcgcgcttg ctgccttcga      540
ccaagaagcg gttgttggcg ctctcgcggc ttacgttctg cccaagtttg agcagccgcg      600
tagtgagatc tatatctatg atctcgcagt ctccggcgag caccggaggc agggcattgc      660
caccgcgctc atcaatctcc tcaagcatga ggccaacgcg cttggtgctt atgtgatcta      720
cgtgcaagca gattacggtg acgatcccgc agtggctctc tatacaaagt tgggcatacg      780
ggaagaagtg atgcactttg atatcgaccc aagtaccgcc acctaagaag ttcctattct      840
ctagaaagta taggaacttc cgttctgttg gtaaagatgg gcggcgttct gccgcccgtt      900
atctctgtta tacctttctg atatttgtta tcgccgatcc gtctttctcc ccttcccgcc      960
ttgcgtcagg                                                             970

<210> SEQ ID NO 59
<211> LENGTH: 2000
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
tctccaaagc ggccaacgat gaaaactatt ctgaaaacta tgcggatgcg tcttgattga       60
cagctagctc agtcctaggt ataatgctag caactttaaa attaaagagg tatatattaa      120
tgactaagca atataagaat tacgtaaatg gggagtggaa gctttcggag aatgaaatta      180
agatctatga accagccagt ggggcggaat tggggtcagt cccggcaatg tccactgaag      240
aagttgacta tgtctacgcc tcggccaaaa aagcgcagcc agcatggcgc tcgctttcct      300
atattgagcg tgcggcttat ttgcacaaag tcgcagacat cctgatgcgt gacaaggaga      360
aaattggagc ggtattgtcc aaggaagtag cgaaaggcta caaatccgca gtatcggagg      420
tcgtccgcac cgccgagatt attaattatg cggccgaaga agggcttcgc atggagggtg      480
aggtcttgga gggcggcagt tttgaggcgg catccaagaa aaaaatcgct gtcgtccgtc      540
gcgagccggt gggacttgtg cttgctatta gtccgttcaa ttaccccgtg aatctggccg      600
gctccaagat tgcccctgca ctgatcgcgg gcaatgtaat cgcttttaaa ccaccgaccc      660
aaggatcgat tagtggactt cttttagcgg aggcgtttgc ggaggcaggt cttcagccgt      720
gcgtattcaa taccatcacg gggcgtggaa gtgaaatcgg ggattacatc gtggagcacc      780
aggcagtaaa tttcatcaac ttcacggggt ccacggggat cggggagcgt atcggtaaga      840
tggctgggat gcgtccgatc atgttggaac ttggcggcaa ggatagtgcg attgtgctgg      900
aagacgcaga cttggaattg acagctaaaa acattatcgc tggagccttc gggtatagtg      960
gtcaacgttg cacggcagtt aagcgcgttc ttgttatgga agtgtcgcg gatgaattgg     1020 tcgagaagat tcgcgagaaa gtgttagctc ttacgattgg aaatccagag gacgatgctg     1080
acatcactcc attgatcgac acgaaatccg cggattacgt cgaggggctg atcaacgacg     1140
cgaacgataa gggagcagcg gctttgaccg agatcaaacg cgaggggaac ctgatctgcc     1200
cgattctttt tgacaaagtc acaactgaca tgcgcttggc atgggaagaa cccttcggcc     1260
```

```
cagtcttgcc tattatccgc gttactagcg tagaggaagc aattgaaatt tccaataaat    1320
ccgaatatgg gttgcaagcg agtatcttta ctaacgattt tccacgtgcc tttggtattg    1380
cggaacagtt agaagtcggg acagttcaca tcaacaacaa gacgcagcgc gggacagata    1440
acttcccctt tttgggagca agaagtctg ggctggaat ccaaggggtg aaatactcca    1500
tcgaagccat gacgacggtg aagagcgttg tttttgacat caagtaaaac ataaggagga    1560
aaaacagatg gcgaaactga cctcggcggt tccggttctg acggcacgtg atgtggcggg    1620
cgcggttgaa ttttggacgg atcgtctggg cttcagtcgt gattttgtgg aagatgactt    1680
cgcaggcgtg gttcgcgatg acgtcaccct gtttatttcc gcagttcagg atcaagtcgt    1740
gccggacaac acgctggctt gggtgtgggt tcgtggcctg gatgaactgt atgcggaatg    1800
gagcgaagtt gtctctacca atttccgtga cgcgagcggt ccggccatga cggaaatcgg    1860
cgaacagccg tggggtcgcg aatttgctct gcgtgacccg gctggcaact gtgtccattt    1920
cgtggctgaa gaacaagatt gagttgagat gacactgtga tctaaaaaga gcgacttcgg    1980
tcgctctttt ttttacctga                                                 2000
```

<210> SEQ ID NO 60
<211> LENGTH: 2000
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 60

```
acgaaaccgg ttactccaac aaagttctgg acctgatcgc tcacatctcc aaatgattga      60
cagctagctc agtcctaggt ataatgctag caactttaaa attaaagagg tatatattaa     120
tgactaagca atataagaat tacgtaaatg gggagtggaa gctttcggag aatgaaatta     180
agatctatga accagccagt ggggcggaat tgggtcagt cccggcaatg tccactgaag     240
aagttgacta tgtctacgcc tcggccaaaa aagcgcagcc agcatggcgc tcgcttttcct    300 atattgagcg tgcggcttat ttgcacaaag tcgcagacat cctgatgcgt gacaaggaga     360
aaattggagc ggtattgtcc aaggaagtag cgaaaggcta caaatccgca gtatcggagg     420
tcgtccgcac cgccgagatt attaattatg cggccgaaga agggcttcgc atggagggtg     480
aggtcttgga gggcggcagt tttgaggcgg catccaagaa aaaaatcgct gtcgtccgtc     540
gcgagccggt gggacttgtg cttgctatta gtccgttcaa ttaccccgtg aatctggccg     600
gctccaagat tgcccctgca ctgatcgcgg gcaatgtaat cgcttttaaa ccaccgaccc     660
aaggatcgat tagtggactt cttttagcgg aggcgtttgc ggaggcaggt cttccagccg     720
gcgtattcaa taccatcacg gggcgtggaa gtgaaatcgg ggattacatc gtggagcacc     780
aggcagtaaa tttcatcaac ttcacgggtt ccacggggat cggggagcgt atcggtaaga     840
tggctgggat gcgtccgatc atgttggaac ttggcggcaa ggatagtgcg attgtgctgg     900
aagacgcaga cttggaattg acagctaaaa acattatcgc tggagccttc gggtatagtg     960
gtcaacgttg cacggcagtt aagcgcgttc ttgttatgga aagtgtcgcg gatgaattgg    1020
tcgagaagat tcgcgagaaa gtgttagctc ttacgattgg aaatccagag gacgatgctg    1080
acatcactcc attgatcgac acgaaatccg cggattacgt cgaggggctg atcaacgacg    1140
cgaacgataa gggagcagcg gctttgaccg agatcaaacg cgaggggaac ctgatctgcc    1200
cgattctttt tgacaaagtc acaactgaca tgcgcttggc atgggaagaa cccttcggcc    1260
```

```
cagtcttgcc tattatccgc gttactagcg tagaggaagc aattgaaatt tccaataaat      1320
ccgaatatgg gttgcaagcg agtatcttta ctaacgattt tccacgtgcc tttggtattg      1380
cggaacagtt agaagtcggg acagttcaca tcaacaacaa gacgcagcgc gggacagata      1440
acttcccctt tttgggagca agaagtctg gggctggaat ccaaggggtg aaatactcca       1500
tcgaagccat gacgacggtg aagagcgttg tttttgacat caagtaaaac ataaggagga      1560
aaaacagatg gcgaaactga cctcggcggt tccggttctg acggcacgtg atgtggcggg      1620
cgcggttgaa ttttggacgg atcgtctggg cttcagtcgt gattttgtgg aagatgactt      1680
cgcaggcgtg gttcgcgatg acgtcaccct gtttatttcc gcagttcagg atcaagtcgt      1740
gccggacaac acgctggctt gggtgtgggt tcgtggcctg gatgaactgt atgcggaatg      1800
gagcgaagtt gtctctacca atttccgtga cgcgagcggt ccggccatga cggaaatcgg      1860
cgaacagccg tggggtcgcg aatttgctct gcgtgacccg gctggcaact gtgtccattt      1920
cgtggctgaa gaacaagatt gagttgagat gacactgtga tctaaaagaa gcgacttcgg      1980
tcgctctttt ttttacctga                                                 2000
```

<210> SEQ ID NO 61
<211> LENGTH: 907
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
tctaccgatt tcaacggcga agtttgcact tccgtgttcg atgctaaagc tggtatcgct       60
ctgaacgaca acttcgtgaa actggtatcc tggtacgaca acgaaaccgg ttactccaac      120
aaagttctgg acctgatcgc tcacatctcc aaagcggcca acgatgaaaa ctattctgaa      180
aactatgcga atgcgtcttg atcctgacgg atggcctttt tgcgtttcta caaactcttt      240
ttgtttattt ttctaaatac attcaaatat gtatccgctc atgagacaat aaccctgata      300
aatgcttcaa taatattgaa aaaggaagag taatggcgaa actgacctcg gcggttccgg      360
ttctgacggc acgtgatgtg gcgggcgcgg ttgaattttg gacggatcgt ctgggcttca      420
gtcgtgattt tgtggaagat gacttcgcag gcgtggttcg cgatgacgtc accctgttta      480
tttccgcagt tcaggatcaa gtcgtgccgg acaacacgct ggcttgggtg tgggttcgtg      540
gcctggatga actgtatgcg gaatggagcg aagttgtctc taccaatttc cgtgacgcga      600
gcggtccggc catgacggaa atcggcgaac agccgtgggg tcgcgaattt gctctgcgtg      660
acccggctgg caactgtgtc catttcgtgg ctgaagaaca agattgagtt gagatgacac      720
tgtgatctaa aagagcgac ttcggtcgct ctttttttta cctgataaaa tgaagttaaa       780
ggactgcgtc atgattaaga aaattttgc ccttccggtc atcgaacaaa tctcccctgt       840
cctctcccgt cgtaaactgg atgaactgga cctcattgtg gtcgatcatc cccaggtaaa      900
agcctct                                                               907
```

<210> SEQ ID NO 62
<211> LENGTH: 1421
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

```
gtattccgtc ttccatgttc accgtcattt tcgcaatggc acgtaccgtt ggctggatcg      60
cccactggag cgaaatgcac agtgacggta tgaagattgc ccgtccgcgt cagctgtata     120
caggatatga aaacgcgac tttaaaagcg atatcaagcg tgcggccaac gatgaaaact     180
attctgaaaa ctatgcggat gcgtcttaat agtcctgacg gatggccttt tgcgtttct     240
acaaactctt tttgtttatt tttctaaata cattcaaata tgtatccgct catgagacaa     300
taaccctgat aaatgcttca ataatattga aaaggaaga gtatgagtat tcaacatttc     360
cgtgtcgccc ttattccctt ttttgcggca ttttgccttc ctgttttgc tcacccagaa      420
acgctggtga agtaaaaga tgctgaagat cagttgggtg cacgagtggg ttacatcgaa      480
ctggatctca acagcggtaa gatccttgag agttttcgcc ccgaagaacg ttttccaatg     540
atgagcactt ttaaagttct gctatgtggc gcggtattat cccgtgttga cgccgggcaa     600
gagcaactcg gtcgccgcat acactattct cagaatgact tggttgagta ctcaccagtc     660
acagaaaagc atcttacgga tggcatgaca gtaagagaat tatgcagtgc tgccataacc     720
atgagtgata acactgcggc caacttactt ctgacaacga tcggaggacc gaaggagcta     780
accgcttttt tgcacaacat gggggatcat gtaactcgcc ttgatcgttg ggaaccggag     840
ctgaatgaag ccataccaaa cgacgagcgt gacaccacga tgcctacagc aatggcaaca     900
acgttgcgca aactattaac tggcgaacta cttactctag cttcccggca acaattaata     960
gactggatgg aggcggataa agttgcagga ccacttctgc gctcggccct tccggctggc    1020
tggtttattg ctgataaatc tggagccggt gagcgtgggt ctcgcggtat cattgcagca    1080
ctggggccag atggtaagcc ctcccgtatc gtagttatct acacgacggg gagtcaggca    1140
actatggatg aacgaaatag acagatcgct gagataggtg cctcactgat taagcattgg    1200
taactgtcag actaatggtt gattgctaag ttgtaaatat tttaacccgc cgttcatatg    1260
gcgggttgat ttttatatgc ctaaacacaa aaaattgtaa aaataaaatc cattaacaga    1320
cctatataga tatttaaaaa gaatagaaca gctcaaatta tcagcaaccc aatactttca    1380
attaaaaact tcatggtagt cgcatttata accctatgaa a                         1421
```

<210> SEQ ID NO 63
<211> LENGTH: 1078
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 63

```
accgtcattt tcgcaatggc acgtaccgtt ggctggatcg cccactggag cgaaatgcac      60
agtgacggta tgaagattgc ccgtccgcgt cagctgtata caggatatga aaacgcgac     120
tttaaaagcg atatcaagcg tgcggccaac gatgaaaact attctgaaaa ctatgcggat     180
gcgtcttaat cctgacggat ggccttttg cgttctaca aactctttt gtttattt       240
ctaaatacat tcaaatatgt atccgctcat gagacaataa ccctgataaa tgcttcaata     300
atattgaaaa aggaagagta tgactgaata caagcccacg gtacgcttgg cgacgcgcga     360
cgatgttccc cgcgctgttc gtacattagc tgcggccttt gcagattacc cagcgacgcg     420
ccataccgtc gatccggacc gccatatcga gcgtgtcaca gaattgcagg aacttttctt     480
aactcgcgtg ggccttgaca tcggaaaggt ctgggtggct gacgatggcg ctgcagtggc     540
```

```
tgtttggacc actccggaga gtgtagaggc tggtgcagtg ttcgccgaaa ttggtcctcg      600
tatggccgaa ttaagtggaa gtcgtctggc agcccaacaa caaatggaag ggttgcttgc      660
gccccaccgt ccgaaagaac ccgcgtggtt ccttgccacc gttggagtaa gcccagatca      720
ccaggggaag ggtttaggat ctgccgtagt tttaccaggt gtggaggcag cagaacgtgc      780
gggagttccg gccttccttg agacgtcggc gccgcgcaat ttaccgtttt acgaacgtct      840
tggattcacc gttacggcgg acgtggaggt gccggaggga ccccgtactt ggtgtatgac      900
tcgtaaaccg ggagcctgat aatggttgat tgctaagttg taaatatttt aacccgccgt      960
tcatatggcg ggttgatttt tatatgccta aacacaaaaa attgtaaaaa taaaatccat     1020
taacagacct atatagatat ttaaaaagaa tagaacagct caaattatca gcaaccca      1078

<210> SEQ ID NO 64
<211> LENGTH: 869
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
gtattccgtc ttccatgttc accgtcattt tcgcaatggc acgtaccgtt ggctggatcg       60
cccactggag cgaaatgcac agtgacggta tgaagattgc ccgtccgcgt cagctgtata      120
caggatatga aaacgcgac tttaaaagcg atatcaagcg tgcggccaac gatgaaaact       180
attctgaaaa ctatgcggat gcgtcttaat agttgacaat taatcatcgg catagtatat      240
cggcatagta taatacgact cactatagga gggccatcat ggccaagttg accagtgccg      300
ttccggtgct caccgcgcgc gacgtcgccg gagcggtcga gttctggacc gaccggctcg      360
ggttctcccg ggacttcgtg gaggacgact cgccggtgt ggtccgggac gacgtgaccc       420
tgttcatcag cgcggtccag gaccaggtgg tgccggacaa caccctgcc tgggtgtggg       480 tgcgcggcct ggacgagctg tacgccgagt ggtcggaggt cgtgtccacg aacttccggg      540
acgcctccgg gccggccatg accgagatcg cgagcagcc gtgggggcgg gagttcgccc       600
tgcgcgaccc ggccggcaac tgcgtgcact tgtggcaga ggagcaggac tgaggataag       660
taatggttga ttgctaagtt gtaaatattt taacccgccg ttcatatggc gggttgattt      720
ttatatgcct aaacacaaaa aattgtaaaa ataaaatcca ttaacagacc tatatagata      780
tttaaaaaga atagaacagc tcaaattatc agcaacccaa tactttcaat taaaaacttc      840
atggtagtcg catttataac cctatgaaa                                         869

<210> SEQ ID NO 65
<211> LENGTH: 1000
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
gcggcgagct gctgggtgaa atcggcctgg caatcgaaat gggttgtgat gctgaagaca       60
tcgcactgac catccacgcg cacccgactc tgcacgagtc tgtgggcctg gcggcagaag      120
tgttcgaagg tagcattacc gacctgccga acccgaaagc gaagaagaag gcggccaacg      180
atgaaaacta ttctgaaaac tatgcggatg cgtcttaata gcgaatccat gtgggagttt      240
attcttgaca cagatattta tgatataata actgagtaag cttaacataa ggaggaaaaa      300
```

```
catatgttac gcagcagcaa cgatgttacg cagcagggca gtcgccctaa aacaaagtta      360
ggtggctcaa gtatgggcat cattcgcaca tgtaggctcg gccctgacca agtcaaatcc      420
atgcgggctg ctcttgatct tttcggtcgt gagttcggag acgtagccac ctactcccaa      480
catcagccgg actccgatta cctcgggaac ttgctccgta gtaagacatt catcgcgctt      540
gctgccttcg accaagaagc ggttgttggc gctctcgcgg cttacgttct gcccaagttt      600
gagcagccgc gtagtgagat ctatatctat gatctcgcag tctccggcga gcaccggagg      660
cagggcattg ccaccgcgct catcaatctc ctcaagcatg aggccaacgc gcttggtgct      720
tatgtgatct acgtgcaagc agattacggt gacgatcccg cagtggctct ctatacaaag      780
ttgggcatac gggaagaagt gatgcacttt gatatcgacc caagtaccgc cacctaattt      840
ttcgtttgcc ggaacatccg gcaattaaaa aagcggctaa ccacgccgct ttttttacgt      900
ctgcaattta cctttccagt cttcttgctc cacgttcaga gagacgttcg catactgctg      960
accgttgctc gttattcagc ctgacagtat ggttactgtc                          1000

<210> SEQ ID NO 66
<211> LENGTH: 852
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
tctgggtatt cactgctttg gcgagcgcgc tgccgaaatt attcatatcg gtcaggcgat       60
tatggaacag aaaggtggcg gcaacactat tgagtacttc gtcaacacca cctttaacta      120
cccgacgatg gcggaagcct atcgggtagc tgcgttaaac ggtttaaacc gcctgtttgc      180
ggccaacgat gaaaactatt ctgaaaacta tgcggatgcg tcttaatagt tgacaattaa      240
tcatcggcat agtatatcgg catagtataa tacgactcac tataggaggg ccatcatgaa      300
gaccttcaac atctctcagc aggatctgga gctggtggag gtcgccactg agaagatcac      360
catgctctat gaggacaaca agcaccatgt cggggcggcc atcaggacca agactgggga      420
gatcatctct gctgtccaca ttgaggccta cattggcagg gtcactgtct gtgctgaagc      480
cattgccatt gggtctgctg tgagcaacgg gcagaaggac tttgacacca ttgtggctgt      540
caggcacccc tactctgatg aggtggacag atccatcagg gtggtcagcc cctgtggcat      600
gtgcagagag ctcatctctg actatgctcc tgactgcttt gtgctcattg agatgaatgg      660
caagctggtc aaaaccacca ttgaggaact catcccoctc aagtacacca ggaactaaag      720
taaaacttta tcgaaatggc catccattct tgcgcggatg gcctctgcca gctgctcata      780
gcggctgcgc agcggtgagc caggacgata aaccaggcca atagtgcggc gtggttccgg      840
cttaatgcac gg                                                         852

<210> SEQ ID NO 67
<211> LENGTH: 898
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
gaagtggaag aagcctggaa atgggtagac tccattactg aggcgtgggc gatggacaat       60
```

```
gatgcgccga aaccgtatca ggccggaacc tggggacccg ttgcctcggt ggcgatgatt      120
acccgtgatg gtcgttcctg gaatgagttt gaggcggcca acgatgaaaa ctattctgaa      180
aactatgcgg atgcgtctta atagttgaca attaatcatc ggcatagtat atcggcatag      240
tataatacga ctcactatag gagggccatc atgaagacct tcaacatctc tcagcaggat      300
ctggagctgg tggaggtcgc cactgagaag atcaccatgc tctatgagga caacaagcac      360
catgtcgggg cggccatcag gaccaagact ggggagatca tctctgctgt ccacattgag      420
gcctacattg gcagggtcac tgtctgtgct gaagccattg ccattgggtc tgctgtgagc      480
aacgggcaga aggactttga caccattgtg gctgtcaggc acccctactc tgatgaggtg      540
gacagatcca tcagggtggt cagcccctgt ggcatgtgca gagagctcat ctctgactat      600
gctcctgact gctttgtgct cattgagatg aatggcaagc tggtcaaaac caccattgag      660
gaactcatcc ccctcaagta caccaggaac taaagtaata tctgcgctta tcctttatgg      720
ttattttacc ggtaacatga tcttgcgcag attgtagaac aattttttaca ctttcaggcc      780 tcgtgcggat tcacccacga ggcttttttt attacactga ctgaaacgtt tttgccctat      840
gagctccggt tacaggcgtt tcagtcataa atcctctgaa tgaaacgcgt tgtgaatc        898

<210> SEQ ID NO 68
<211> LENGTH: 1181
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
gcgtgcgcac catgacggtg gggaccgtct cgatggatat gctagcggtc gatttaacgc       60
cttgcccgca ggcgggtatt ggtacgccgg ttgagctgtg gggcaaggag atcaaaattg      120
atgatgtcgc cgccgctgcc ggaacggtgg gctatgagtt gatgtgcgcg ctggcgctac      180
gcgtcccggt tgtgacggtg gcggccaacg atgaaaacta ttctgaaaac tatgcggatg      240
cgtcttaatc ctgacggatg gccttttttgc gtttctacaa actcttttttg tttattttttc      300 taaatacatt caaatatgta tccgctcatg agacaataac cctgataaat gcttcaataa      360
tattgaaaaa ggaagagtat gactgaatac aagcccacgg tacgcttggc gacgcgcgac      420
gatgttcccc gcgctgttcg tacattagct gcggcctttg cagattaccc agcgacgcgc      480
catacggtcg atccggaccg ccatatcgag cgtgtcacag aattgcagga acttttctta      540
actcgcgtgg gccttgacat cggaaaggtc tgggtggctg acgatggcgc tgcagtggct      600
gtttggacca ctccggagag tgtagaggct ggtgcagtgt tcgccgaaat tggtcctcgt      660
atggccgaat taagtggaag tcgtctggca gcccaacaac aaatggaagg ttgcttgcg       720 ccccaccgtc cgaaagaacc cgcgtggttc cttgccaccg ttggagtaag cccagatcac      780
caggggaagg gtttaggatc tgccgtagtt ttaccaggtg tggaggcagc agaacgtgcg      840
ggagttccgg ccttccttga cgtcggcg ccgcgcaatt taccgtttta cgaacgtctt        900
ggattcaccg ttacggcgga cgtggaggtg ccggagggac cccgtacttg gtgtatgact      960
cgtaaaccgg gagcctgata acttgttgta agccggatcg gaggcaacgt cttctgggtg     1020
caaaaaaatc atccatccgg ctggtcagca actgtagttg ttaatgtgac agagccattg     1080
cccatgatag tgtccattaa aaggatggac actatttccc cggaacctga actcaccgca     1140
caggcgttct acataaaacg cttacgcttc attgttgact c                         1181
```

<210> SEQ ID NO 69
<211> LENGTH: 92
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 69
tcgagttccc cgcgccagcg gggataaacc gttgattata ataaccgttt atctgttcgt      60
atcgagttcc ccgcgccagc ggggataaac cg                                    92

<210> SEQ ID NO 70
<211> LENGTH: 59
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
gtttatctgt tcgtatcgag ttccccgcgc cagcggggat aaaccgaaaa aaaaacccc       59

<210> SEQ ID NO 71
<211> LENGTH: 60
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
ggttattata atcaacggtt tatccccgct ggcgcgggga actcgaggtg gtaccagatc      60

<210> SEQ ID NO 72
<211> LENGTH: 92
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 72
tcgagttccc cgcgccagcg gggataaacc ggtttttgta attttacagg caacctttta     60
ttcgagttcc ccgcgccagc ggggataaac cg                                    92

<210> SEQ ID NO 73
<211> LENGTH: 59
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
caggcaacct tttattcgag ttccccgcgc cagcggggat aaaccgaaaa aaaaacccc       59

<210> SEQ ID NO 74
<211> LENGTH: 60
<212> TYPE: DNA
<213> ORGANISM: Artificial Sequence
<220> FEATURE:
<223> OTHER INFORMATION: Description of Artificial Sequence: Synthetic primer

<400> SEQUENCE: 74

```
taaaattaca aaaaccggtt tatccccgct ggcgcgggga actcgaggtg gtaccagatc      60
```

<210> SEQ ID NO 75
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75

```
tcgagttccc cgcgccagcg gggataaacc gaaaagcata taatgcgtaa aagttatgaa      60
gttcgagttc cccgcgccag cggggataaa ccg                                  93
```

<210> SEQ ID NO 76
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76

```
gcgtaaaagt tatgaagttc gagttccccg cgccagcggg gataaaccga aaaaaaaacc      60
cc                                                                    62
```

<210> SEQ ID NO 77
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77

```
attatatgct tttcggttta tccccgctgg cgcggggaac tcgaggtggt accagatct       59
```

<210> SEQ ID NO 78
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78

```
tcgagttccc cgcgccagcg gggataaacc gtattgacca attcattcgg gacagttatt      60
agttcgagtt ccccgcgcca gcggggataa accg                                 94
```

<210> SEQ ID NO 79
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79

```
gggacagtta ttagttcgag ttccccgcgc cagcgggat aaaccgaaaa aaaaacccc       59
```

<210> SEQ ID NO 80
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gaatgaattg gtcaatacgg tttatccccg ctggcgcggg gaactcgagg tggtaccaga    60
tct                                                                  63

<210> SEQ ID NO 81
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
tcgagttccc cgcgccagcg gggataaacc gagtggttgc tggataactt tacgggcatg    60
ctcgagttcc ccgcgccagc ggggataaac cg                                  92

<210> SEQ ID NO 82
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
aactttacgg gcatgctcga gttccccgcg ccagcgggga taaaccgaaa aaaaaacccc    60

<210> SEQ ID NO 83
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
atccagcaac cactcggttt atccccgctg gcgcggggaa ctcgaggtgg taccagatct    60

<210> SEQ ID NO 84
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
tcgagttccc cgcgccagcg gggataaacc gttaccattc tgttgctttt atgtataaga    60
atcgagttcc ccgcgccagc ggggataaac cg                                  92

<210> SEQ ID NO 85
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ttttatgtat aagaatcgag ttccccgcgc cagcggggat aaaccgaaaa aaaaacccc     59

<210> SEQ ID NO 86
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gcaacagaat ggtaacggtt tatccccgct ggcgcgggga actcgaggtg gtaccagatc    60

<210> SEQ ID NO 87
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
tcgagttccc cgcgccagcg gggataaacc gctcgtaaaa gcagtacagt gcaccgtaag    60
atcgagttcc ccgcgccagc ggggataaac cg                                  92

<210> SEQ ID NO 88
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
cagtgcaccg taagatcgag ttccccgcgc cagcggggat aaaccgaaaa aaaaacccc     59

<210> SEQ ID NO 89
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
tactgctttt acgagcggtt tatccccgct ggcgcgggga actcgaggtg gtaccagatc    60

<210> SEQ ID NO 90
<211> LENGTH: 154
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
tcgagttccc cgcgccagcg gggataaacc gttgattata ataaccgttt atctgttcgt    60
atcgagttcc ccgcgccagc ggggataaac cgaaaagcat ataatgcgta aaagttatga   120
agttcgagtt ccccgcgcca gcggggataa accg                               154

<210> SEQ ID NO 91
<211> LENGTH: 36
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 91
gcgccagcgg ggataaaccg aaaagcatat aatgcg                                36

<210> SEQ ID NO 92
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
cttgcccgcc tgatgaatgc tcatccgg                                        28

<210> SEQ ID NO 93
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ccggatgagc attcatcagg cgggcaag                                        28

<210> SEQ ID NO 94
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
cggtttatcc ccgctggcgc ggggaactcg atacgaacag ataaacggtt attataatc     59

<210> SEQ ID NO 95
<211> LENGTH: 155
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
tcgagttccc cgcgccagcg gggataaacc gttgattata ataccgtttt atctgttcgt     60
atcgagttcc ccgcgccagc ggggataaac cgtattgacc aattcattcg ggacagttat    120
tagttcgagt tccccgcgcc agcggggata aaccg                               155

<210> SEQ ID NO 96
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gcgccagcgg ggataaaccg tattgaccaa ttcattc                              37

<210> SEQ ID NO 97
<211> LENGTH: 28
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 97
cttgcccgcc tgatgaatgc tcatccgg                                         28

<210> SEQ ID NO 98
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ccggatgagc attcatcagg cgggcaag                                         28

<210> SEQ ID NO 99
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
cggtttatcc ccgctggcgc ggggaactcg atacgaacag ataaacggtt attataatc      59

<210> SEQ ID NO 100
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
tcgagttccc cgcgccagcg gggataaacc gttgattata ataaccgttt atctgttcgt      60
atcgagttcc ccgcgccagc ggggataaac cgttaccatt ctgttgcttt tatgtataag    120
aatcgagttc cccgcgccag cggggataaa ccg                                  153

<210> SEQ ID NO 101
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
gcgccagcgg ggataaaccg ttaccattct gttg                                  34

<210> SEQ ID NO 102
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
cttgcccgcc tgatgaatgc tcatccgg                                         28

<210> SEQ ID NO 103
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
ccggatgagc attcatcagg cgggcaag                                         28

<210> SEQ ID NO 104
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
cggtttatcc ccgctggcgc ggggaactcg atacgaacag ataaacggtt attataatc       59

<210> SEQ ID NO 105
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
tcgagttccc cgcgccagcg gggataaacc gttgattata ataaccgttt atctgttcgt      60
atcgagttcc ccgcgccagc ggggataaac cgctcgtaaa agcagtacag tgcaccgtaa     120
gatcgagttc cccgcgccag cggggataaa ccg                                  153

<210> SEQ ID NO 106
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
gcgccagcgg ggataaaccg ctcgtaaaag                                       30

<210> SEQ ID NO 107
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
cttgcccgcc tgatgaatgc tcatccgg                                         28

<210> SEQ ID NO 108
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
ccggatgagc attcatcagg cgggcaag                                         28
```

<210> SEQ ID NO 109
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
cggtttatcc ccgctggcgc ggggaactcg atacgaacag ataaacggtt attataatc          59

<210> SEQ ID NO 110
<211> LENGTH: 156
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
tcgagttccc cgcgccagcg gggataaacc gaaaagcata taatgcgtaa aagttatgaa          60
gttcgagttc cccgcgccag cggggataaa ccgtattgac caattcattc gggacagtta         120
ttagttcgag ttccccgcgc cagcggggat aaaccg                                   156

<210> SEQ ID NO 111
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gcgccagcgg ggataaaccg tattgaccaa ttcattc                                   37

<210> SEQ ID NO 112
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
cttgcccgcc tgatgaatgc tcatccgg                                             28

<210> SEQ ID NO 113
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
ccggatgagc attcatcagg cgggcaag                                             28

<210> SEQ ID NO 114
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
cggtttatcc ccgctggcgc ggggaactcg aacttcataa cttttac                47

<210> SEQ ID NO 115
<211> LENGTH: 154
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115
tcgagttccc cgcgccagcg gggataaacc gaaaagcata taatgcgtaa aagttatgaa      60
gttcgagttc cccgcgccag cggggataaa ccgttaccat tctgttgctt ttatgtataa     120
gaatcgagtt ccccgcgcca gcggggataa accg                                 154

<210> SEQ ID NO 116
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
gcgccagcgg ggataaaccg ttaccattct gttg                                 34

<210> SEQ ID NO 117
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
cttgcccgcc tgatgaatgc tcatccgg                                        28

<210> SEQ ID NO 118
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
ccggatgagc attcatcagg cgggcaag                                        28

<210> SEQ ID NO 119
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
cggtttatcc ccgctggcgc ggggaactcg aacttcataa cttttac                47

<210> SEQ ID NO 120
<211> LENGTH: 154
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 120
tcgagttccc cgcgccagcg gggataaacc gaaaagcata taatgcgtaa aagttatgaa    60
gttcgagttc cccgcgccag cggggataaa ccgctcgtaa aagcagtaca gtgcaccgta   120
agatcgagtt ccccgcgcca gcggggataa accg                               154

<210> SEQ ID NO 121
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
gcgccagcgg ggataaaccg ctcgtaaaag                                     30

<210> SEQ ID NO 122
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
cttgcccgcc tgatgaatgc tcatccgg                                       28

<210> SEQ ID NO 123
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
ccggatgagc attcatcagg cgggcaag                                       28

<210> SEQ ID NO 124
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
cggtttatcc ccgctggcgc ggggaactcg aacttcataa cttttac                  47

<210> SEQ ID NO 125
<211> LENGTH: 155
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
tcgagttccc cgcgccagcg gggataaacc gtattgacca attcattcgg gacagttatt    60
agttcgagtt ccccgcgcca gcggggataa accgttacca ttctgttgct tttatgtata   120
agaatcgagt tccccgcgcc agcggggata aaccg                              155

<210> SEQ ID NO 126
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
gcgccagcgg ggataaaccg ttaccattct gttg                                  34

<210> SEQ ID NO 127
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
cttgcccgcc tgatgaatgc tcatccgg                                         28

<210> SEQ ID NO 128
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
ccggatgagc attcatcagg cgggcaag                                         28

<210> SEQ ID NO 129
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
cggtttatcc ccgctggcgc ggggaactcg aactaataac tgtc                       44

<210> SEQ ID NO 130
<211> LENGTH: 155
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130
tcgagttccc cgcgccagcg gggataaacc gtattgacca attcattcgg gacagttatt      60
agttcgagtt ccccgcgcca gcgggataa accgctcgta aaagcagtac agtgcaccgt      120
aagatcgagt tccccgcgcc agcggggata aaccg                                155

<210> SEQ ID NO 131
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
gcgccagcgg ggataaaccg ctcgtaaaag                                30

<210> SEQ ID NO 132
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
cttgcccgcc tgatgaatgc tcatccgg                                  28

<210> SEQ ID NO 133
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
ccggatgagc attcatcagg cgggcaag                                  28

<210> SEQ ID NO 134
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
cggtttatcc ccgctggcgc ggggaactcg aactaataac tgtc                44

<210> SEQ ID NO 135
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135
tcgagttccc cgcgccagcg gggataaacc gttaccattc tgttgctttt atgtataaga      60
atcgagttcc ccgcgccagc ggggataaac cgctcgtaaa agcagtacag tgcaccgtaa     120
gatcgagttc cccgcgccag cggggataaa ccg                                  153

<210> SEQ ID NO 136
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
gcgccagcgg ggataaaccg ctcgtaaaag                                30

<210> SEQ ID NO 137
<211> LENGTH: 28
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 137
cttgcccgcc tgatgaatgc tcatccgg                                         28

<210> SEQ ID NO 138
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
ccggatgagc attcatcagg cgggcaag                                         28

<210> SEQ ID NO 139
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
cggtttatcc ccgctggcgc ggggaactcg attcttatac ataaaagc                   48

<210> SEQ ID NO 140
<211> LENGTH: 217
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140
tcgagttccc cgcgccagcg gggataaacc gttgattata ataaccgttt atctgttcgt      60
atcgagttcc ccgcgccagc ggggataaac cgaaaagcat ataatgcgta aaagttatga    120
agttcgagtt ccccgcgcca gcggggataa accgtattga ccaattcatt cgggacagtt    180
attagttcga gttccccgcg ccagcgggga taaaccg                             217

<210> SEQ ID NO 141
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
gcgccagcgg ggataaaccg tattgaccaa ttcattc                               37

<210> SEQ ID NO 142
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
cttgcccgcc tgatgaatgc tcatccgg                                         28
```

<210> SEQ ID NO 143
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
ccggatgagc attcatcagg cgggcaag                                          28

<210> SEQ ID NO 144
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
cggtttatcc ccgctggcgc ggggaactcg aacttcataa cttttac                     47

<210> SEQ ID NO 145
<211> LENGTH: 217
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145
tcgagttccc cgcgccagcg gggataaacc gaaaagcata taatgcgtaa aagttatgaa       60
gttcgagttc cccgcgccag cggggataaa ccgtattgac caattcattc gggacagtta      120
ttagttcgag ttccccgcgc cagcggggat aaaccggttt ttgtaatttt acaggcaacc      180
ttttattcga gttccccgcg ccagcgggga taaaccg                               217

<210> SEQ ID NO 146
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
gcgccagcgg ggataaaccg gttttgtaa ttttacaggc                              40

<210> SEQ ID NO 147
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
cttgcccgcc tgatgaatgc tcatccgg                                          28

<210> SEQ ID NO 148
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 148
ccggatgagc attcatcagg cgggcaag                                          28

<210> SEQ ID NO 149
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
cggtttatcc ccgctggcgc ggggaactcg aactaataac tgtc                        44

<210> SEQ ID NO 150
<211> LENGTH: 217
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 150
tcgagttccc cgcgccagcg gggataaacc gaaaagcata taatgcgtaa aagttatgaa       60
gttcgagttc cccgcgccag cggggataaa ccgtattgac caattcattc gggacagtta      120
ttagttcgag ttccccgcgc cagcggggat aaaccgttac cattctgttg cttttatgta      180
taagaatcga gttccccgcg ccagcgggga taaaccg                               217

<210> SEQ ID NO 151
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
gcgccagcgg ggataaaccg ttaccattct gttg                                   34

<210> SEQ ID NO 152
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
cttgcccgcc tgatgaatgc tcatccgg                                          28

<210> SEQ ID NO 153
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
ccggatgagc attcatcagg cgggcaag                                          28

<210> SEQ ID NO 154
<211> LENGTH: 44
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 154
cggtttatcc ccgctggcgc ggggaactcg aactaataac tgtc                    44

<210> SEQ ID NO 155
<211> LENGTH: 217
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 155
tcgagttccc cgcgccagcg gggataaacc gaaaagcata taatgcgtaa aagttatgaa   60
gttcgagttc cccgcgccag cggggataaa ccgtattgac caattcattc gggacagtta  120
ttagttcgag ttccccgcgc cagcggggat aaaccgctcg taaaagcagt acagtgcacc  180
gtaagatcga gttccccgcg ccagcgggga taaaccg                           217

<210> SEQ ID NO 156
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
gcgccagcgg ggataaaccg ctcgtaaaag                                    30

<210> SEQ ID NO 157
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
cttgcccgcc tgatgaatgc tcatccgg                                      28

<210> SEQ ID NO 158
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
ccggatgagc attcatcagg cgggcaag                                      28

<210> SEQ ID NO 159
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
cggtttatcc ccgctggcgc ggggaactcg aactaataac tgtc                    44
```

<210> SEQ ID NO 160
<211> LENGTH: 278
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 160
tcgagttccc cgcgccagcg gggataaacc gttgattata ataaccgttt atctgttcgt    60
atcgagttcc ccgcgccagc ggggataaac cgaaaagcat ataatgcgta aaagttatga   120
agttcgagtt ccccgcgcca gcggggataa accgtattga ccaattcatt cgggacagtt   180
attagttcga gttccccgcg ccagcgggga taaaccggtt tttgtaattt tacaggcaac   240
cttttattcg agttccccgc gccagcgggg ataaaccg                           278

<210> SEQ ID NO 161
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
gcgccagcgg ggataaaccg gtttttgtaa ttttacaggc                          40

<210> SEQ ID NO 162
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
cttgcccgcc tgatgaatgc tcatccgg                                       28

<210> SEQ ID NO 163
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
ccggatgagc attcatcagg cgggcaag                                       28

<210> SEQ ID NO 164
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
cggtttatcc ccgctggcgc ggggaactcg aactaataac tgtc                     44

<210> SEQ ID NO 165
<211> LENGTH: 278
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 165
tcgagttccc cgcgccagcg gggataaacc gttgattata ataaccgttt atctgttcgt      60
atcgagttcc ccgcgccagc ggggataaac cgaaaagcat ataatgcgta aaagttatga     120
agttcgagtt ccccgcgcca gcggggataa accgtattga ccaattcatt cgggacagtt    180
attagttcga gttccccgcg ccagcgggga taaaccgtta ccattctgtt gcttttatgt    240
ataagaatcg agttccccgc gccagcgggg ataaaccg                              278

<210> SEQ ID NO 166
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
gcgccagcgg ggataaaccg tattgaccaa ttcattc                               37

<210> SEQ ID NO 167
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
cttgcccgcc tgatgaatgc tcatccgg                                         28

<210> SEQ ID NO 168
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
ccggatgagc attcatcagg cgggcaag                                         28

<210> SEQ ID NO 169
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
cggtttatcc ccgctggcgc ggggaactcg aacttcataa cttttac                    47

<210> SEQ ID NO 170
<211> LENGTH: 278
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 170

```
tcgagttccc cgcgccagcg gggataaacc gttgattata ataaccgttt atctgttcgt    60
atcgagttcc ccgcgccagc ggggataaac cgaaaagcat ataatgcgta aaagttatga   120
agttcgagtt ccccgcgcca gcggggataa accgtattga ccaattcatt cgggacagtt   180
attagttcga gttccccgcg ccagcgggga taaaccgctc gtaaaagcag tacagtgcac   240
cgtaagatcg agttccccgc gccagcgggg ataaaccg                           278

<210> SEQ ID NO 171
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
gcgccagcgg ggataaaccg tattgaccaa ttcattc                             37

<210> SEQ ID NO 172
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
cttgcccgcc tgatgaatgc tcatccgg                                       28

<210> SEQ ID NO 173
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
ccggatgagc attcatcagg cgggcaag                                       28

<210> SEQ ID NO 174
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
cggtttatcc ccgctggcgc ggggaactcg aacttcataa cttttac                  47

<210> SEQ ID NO 175
<211> LENGTH: 278
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 175
tcgagttccc cgcgccagcg gggataaacc gaaaagcata taatgcgtaa aagttatgaa    60
gttcgagttc cccgcgccag cggggataaa ccgtattgac caattcattc gggacagtta   120
ttagttcgag ttccccgcgc cagcggggat aaaccgttac cattctgttg cttttatgta   180
```

```
taagaatcga gttccccgcg ccagcgggga taaaccggtt tttgtaattt tacaggcaac    240
cttttattcg agttccccgc gccagcgggg ataaaccg                            278
```

<210> SEQ ID NO 176
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176

```
gcgccagcgg ggataaaccg gttttttgtaa ttttacaggc                         40
```

<210> SEQ ID NO 177
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177

```
cttgcccgcc tgatgaatgc tcatccgg                                       28
```

<210> SEQ ID NO 178
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178

```
ccggatgagc attcatcagg cgggcaag                                       28
```

<210> SEQ ID NO 179
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179

```
cggtttatcc ccgctggcgc ggggaactcg attcttatac ataaaagc                 48
```

<210> SEQ ID NO 180
<211> LENGTH: 278
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 180

```
tcgagttccc cgcgccagcg gggataaacc gaaaagcata taatgcgtaa aagttatgaa    60
gttcgagttc cccgcgccag cggggataaa ccgtattgac caattcattc gggacagtta   120
ttagttcgag ttccccgcgc cagcgggggat aaaccgttac cattctgttg cttttatgta   180
taagaatcga gttccccgcg ccagcgggga taaaccgctc gtaaaagcag tacagtgcac   240
cgtaagatcg agttccccgc gccagcgggg ataaaccg                           278
```

<210> SEQ ID NO 181

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
gcgccagcgg ggataaaccg ctcgtaaaag                                         30

<210> SEQ ID NO 182
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
cttgcccgcc tgatgaatgc tcatccgg                                          28

<210> SEQ ID NO 183
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
ccggatgagc attcatcagg cgggcaag                                          28

<210> SEQ ID NO 184
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
cggtttatcc ccgctggcgc ggggaactcg attcttatac ataaaagc                    48

<210> SEQ ID NO 185
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 185
tcgagttccc cgcgccagcg gggataaacc gttgattata ataaccgttt atctgttcgt       60
atcgagttcc ccgcgccagc ggggataaac cgaaaagcat ataatgcgta aaagttatga      120
agttcgagtt ccccgcgcca gcggggataa accgtattga ccaattcatt cgggacagtt      180
attagttcga gttccccgcg ccagcgggga taaaccgtta ccattctgtt gcttttatgt      240
ataagaatcg agttccccgc gccagcgggg ataaaccggt ttttgtaatt ttacaggcaa      300
ccttttattc gagttccccg cgccagcggg gataaaccg                             339

<210> SEQ ID NO 186
<211> LENGTH: 40
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 186
gcgccagcgg ggataaaccg gttttttgtaa ttttacaggc                               40

<210> SEQ ID NO 187
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
cttgcccgcc tgatgaatgc tcatccgg                                            28

<210> SEQ ID NO 188
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
ccggatgagc attcatcagg cgggcaag                                            28

<210> SEQ ID NO 189
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
cggtttatcc ccgctggcgc ggggaactcg attcttatac ataaaagc                      48

<210> SEQ ID NO 190
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 190
tcgagttccc cgcgccagcg gggataaacc gttgattata taaccgttt atctgttcgt          60 atcgagttcc ccgcgccagc ggggataaac cgaaaagcat ataatgcgta aaagttatga       120
agttcgagtt ccccgcgcca gcggggataa accgtattga ccaattcatt cgggacagtt       180
attagttcga gttccccgcg ccagcgggga taaaccgtta ccattctgtt gcttttatgt       240
ataagaatcg agttccccgc gccagcgggg ataaaccgct cgtaaaagca gtacagtgca       300
ccgtaagatc gagttccccg cgccagcggg gataaaccg                              339

<210> SEQ ID NO 191
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191

```
gcgccagcgg ggataaaccg ctcgtaaaag                                      30
```

<210> SEQ ID NO 192
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192

```
cttgcccgcc tgatgaatgc tcatccgg                                        28
```

<210> SEQ ID NO 193
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193

```
ccggatgagc attcatcagg cgggcaag                                        28
```

<210> SEQ ID NO 194
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194

```
cggtttatcc ccgctggcgc ggggaactcg attcttatac ataaaagc                  48
```

<210> SEQ ID NO 195
<211> LENGTH: 400
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 195

```
tcgagttccc cgcgccagcg gggataaacc gttgattata ataaccgttt atctgttcgt     60
atcgagttcc ccgcgccagc ggggataaac cgaaaagcat ataatgcgta aaagttatga    120
agttcgagtt ccccgcgcca gcggggataa accgtattga ccaattcatt cgggacagtt    180
attagttcga gttccccgcg ccagcgggga taaaccgtta ccattctgtt gcttttatgt    240
ataagaatcg agttccccgc gccagcgggg ataaaccgct cgtaaaagca gtacagtgca    300
ccgtaagatc gagttccccg cgccagcggg gataaaccgg tttttgtaat tttacaggca    360
acctttattt cgagttcccc gcgccagcgg ggataaaccg                          400
```

<210> SEQ ID NO 196
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196

```
gcgccagcgg ggataaaccg gttttgtaa ttttacaggc                            40
```

<210> SEQ ID NO 197
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
cttgcccgcc tgatgaatgc tcatccgg                                          28

<210> SEQ ID NO 198
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
ccggatgagc attcatcagg cgggcaag                                          28

<210> SEQ ID NO 199
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
cggtttatcc ccgctggcgc ggggaactcg atcttacggt gcactgtac                   49

<210> SEQ ID NO 200
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 200
tcgagttccc cgcgccagcg gggataaacc gttaccattc tgttgctttt atgtataaga       60
atcgagttcc ccgcgccagc ggggataaac cgctcgtaaa agcagtacag tgcaccgtaa      120
gatcgagttc cccgcgccag cggggataaa ccg                                   153

<210> SEQ ID NO 201
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
gcgccagcgg ggataaaccg ctcgtaaaag                                        30

<210> SEQ ID NO 202
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 202
cttgcccgcc tgatgaatgc tcatccgg                                          28

<210> SEQ ID NO 203
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
ccggatgagc attcatcagg cgggcaag                                          28

<210> SEQ ID NO 204
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
cggtttatcc ccgctggcgc ggggaactcg attcttatac ataaaagc                    48
```